US011547382B2

(12) United States Patent
Berger et al.

(10) Patent No.: US 11,547,382 B2
(45) Date of Patent: Jan. 10, 2023

(54) NETWORKED ULTRASOUND SYSTEM AND METHOD FOR IMAGING A MEDICAL PROCEDURE USING AN INVASIVE PROBE

(71) Applicant: Teratech Corporation, Burlington, MA (US)

(72) Inventors: Noah Berger, Sudbury, MA (US); Michael Brodsky, Brookline, MA (US); Mark Laforest, Acton, MA (US); Alice M. Chiang, Wayland, MA (US); William M. Wong, Milton, MA (US); Xingbai He, Belmont, MA (US); Peter P. Chang, Burlington, MA (US)

(73) Assignee: Teratech Corporation, Burlington, MA (US)

( * ) Notice: Subject to any disclaimer, the term of this patent is extended or adjusted under 35 U.S.C. 154(b) by 553 days.

(21) Appl. No.: 13/846,231

(22) Filed: Mar. 18, 2013

(65) Prior Publication Data

US 2014/0051984 A1    Feb. 20, 2014

Related U.S. Application Data

(63) Continuation of application No. 10/386,360, filed on Mar. 11, 2003, now abandoned, which is a
(Continued)

(51) Int. Cl.
*A61B 8/08* (2006.01)
*A61B 8/00* (2006.01)
(Continued)

(52) U.S. Cl.
CPC .......... *A61B 8/0841* (2013.01); *A61B 8/0866* (2013.01); *A61B 8/0883* (2013.01);
(Continued)

(58) Field of Classification Search
CPC ..... A61B 10/04; A61B 18/02; A61B 19/2203; A61B 19/5244; A61B 8/0808;
(Continued)

(56) References Cited

U.S. PATENT DOCUMENTS

| 4,070,905 A | 1/1978 | Kossoff |
| 4,140,022 A | 2/1979 | Maslak |

(Continued)

FOREIGN PATENT DOCUMENTS

| EP | 1016875 A2 | 7/2000 |
| JP | 2000-316865 A | 11/2000 |

(Continued)

OTHER PUBLICATIONS

U.S. Appl. No. 10/094,950, filed Mar. 11, 2002, Granted.
(Continued)

*Primary Examiner* — Amanda Lauritzen Moher
(74) *Attorney, Agent, or Firm* — McCarter & English, LLP; Thomas O. Hoover

(57) ABSTRACT

A hand-held ultrasound system includes integrated electronics within an ergonomic housing. The electronics includes control circuitry, beamforming and circuitry transducer drive circuitry. The electronics communicate with a host computer using an industry standard high speed serial bus. The ultrasonic imaging system is operable on a standard, commercially available, user computing device without specific hardware modifications, and is adapted to interface with an external application without modification to the ultrasonic imaging system to allow a user to gather ultrasonic data on a standard user computing device such as a PC, and employ the data so gathered via an independent external application without requiring a custom system, expensive hardware modifications, or system rebuilds. An integrated interface program allows such ultrasonic data to be invoked
(Continued)

by a variety of such external applications having access to the integrated interface program via a standard, predetermined platform such as visual basic or c++.

44 Claims, 63 Drawing Sheets

Related U.S. Application Data continuation-in-part of application No. 10/354,946, filed on Jan. 30, 2003, now Pat. No. 9,402,601.

(51) Int. Cl.

| | |
|---|---|
| G01S 15/89 | (2006.01) |
| G01S 7/52 | (2006.01) |
| A61B 34/30 | (2016.01) |
| A61B 34/20 | (2016.01) |
| A61B 10/04 | (2006.01) |
| A61B 18/02 | (2006.01) |
| A61M 5/00 | (2006.01) |
| A61M 25/01 | (2006.01) |
| A61N 5/10 | (2006.01) |

(52) U.S. Cl.
CPC .......... *A61B 8/4427* (2013.01); *A61B 8/4444* (2013.01); *A61B 8/4483* (2013.01); *A61B 8/461* (2013.01); *A61B 8/463* (2013.01); *A61B 8/467* (2013.01); *A61B 8/52* (2013.01); *A61B 8/546* (2013.01); *A61B 8/56* (2013.01); *A61B 8/565* (2013.01); *A61B 8/58* (2013.01); *A61B 10/04* (2013.01); *A61B 18/02* (2013.01); *A61B 34/20* (2016.02); *A61B 34/30* (2016.02); *A61M 5/00* (2013.01); *A61M 25/0108* (2013.01); *A61N 5/1039* (2013.01); *G01S 7/5208* (2013.01); *G01S 7/52025* (2013.01); *G01S 7/52079* (2013.01); *G01S 15/892* (2013.01); *G01S 15/899* (2013.01); *A61B 8/0808* (2013.01); *A61B 8/4472* (2013.01); *A61B 8/465* (2013.01); *G01S 7/52055* (2013.01); *G01S 15/8918* (2013.01); *G01S 15/8979* (2013.01)

(58) Field of Classification Search
CPC ... A61B 8/0841; A61B 8/0866; A61B 8/0883; A61B 8/4427; A61B 8/4444; A61B 8/4472; A61B 8/4483; A61B 8/461; A61B 8/463; A61B 8/52; A61B 8/546; A61B 8/56; A61B 8/565; A61B 8/58; A61M 25/0108; A61M 5/00; A61N 5/1039; G01S 15/8918; G01S 15/892; G01S 15/8979; G01S 15/899; G01S 7/52025; G01S 7/52055; G01S 7/52
See application file for complete search history.

(56) References Cited

U.S. PATENT DOCUMENTS

| | | | |
|---|---|---|---|
| 4,159,462 A | 6/1979 | Rocha et al. | |
| 4,310,907 A | 1/1982 | Tachita et al. | |
| 4,319,489 A | 3/1982 | Yamaguchi et al. | |
| 4,344,327 A | 8/1982 | Yoshikawa et al. | |
| 4,368,643 A | 1/1983 | Tachita et al. | |
| 4,573,477 A | 3/1986 | Namekawa et al. | |
| 4,582,065 A | 4/1986 | Adams | |
| 4,622,977 A | 11/1986 | Namekawa et al. | |
| 4,664,122 A | 5/1987 | Yano | |
| 4,759,375 A | 7/1988 | Namekawa | |
| 4,852,577 A | 8/1989 | Smith et al. | |
| 4,896,283 A | 1/1990 | Hunt et al. | |
| 4,937,797 A | 6/1990 | Snyder et al. | |
| 4,949,259 A | 8/1990 | Hunt et al. | |
| 4,962,667 A | 10/1990 | Ogawa et al. | |
| 4,976,702 A * | 12/1990 | Andrews | A61M 5/3243 604/198 |
| 5,123,415 A | 6/1992 | Daigle | |
| 5,148,810 A | 9/1992 | Maslak et al. | |
| 5,235,986 A | 8/1993 | Maslak et al. | |
| 5,261,408 A | 11/1993 | Maslak et al. | |
| 5,291,893 A * | 3/1994 | Slayton | A61B 8/12 600/444 |
| 5,295,485 A * | 3/1994 | Shinomura | A61B 8/06 600/443 |
| 5,379,771 A | 1/1995 | Kawasaki et al. | |
| 5,383,457 A | 1/1995 | Cohen | |
| 5,526,816 A | 6/1996 | Arditi | |
| 5,553,620 A | 9/1996 | Snider et al. | |
| 5,590,658 A | 1/1997 | Chiang et al. | |
| 5,603,323 A | 2/1997 | Pflugrath et al. | |
| 5,609,155 A | 3/1997 | Guracar | |
| 5,615,679 A | 4/1997 | Ri et al. | |
| 5,680,536 A | 10/1997 | Tyuluman | |
| 5,685,307 A | 11/1997 | Holland et al. | |
| 5,690,114 A * | 11/1997 | Chiang | A61B 8/4236 600/447 |
| 5,715,823 A | 2/1998 | Wood et al. | |
| 5,718,228 A | 2/1998 | Hiruta et al. | |
| 5,722,412 A | 3/1998 | Pflugrath et al. | |
| 5,758,649 A | 6/1998 | Iwashita et al. | |
| 5,763,785 A | 6/1998 | Chiang | |
| 5,774,876 A | 6/1998 | Woolley et al. | |
| 5,795,297 A | 8/1998 | Daigle | |
| 5,798,461 A | 8/1998 | Banta, Jr. et al. | |
| 5,817,024 A | 10/1998 | Ogle et al. | |
| 5,839,442 A | 11/1998 | Chiang et al. | |
| 5,851,186 A | 12/1998 | Wood et al. | |
| 5,853,367 A * | 12/1998 | Chalek | G06F 9/5055 128/916 |
| 5,855,556 A | 1/1999 | Shirai | |
| 5,860,930 A | 1/1999 | Guracar | |
| 5,891,030 A | 4/1999 | Johnson et al. | |
| 5,893,363 A | 4/1999 | Little et al. | |
| 5,897,498 A * | 4/1999 | Canfield, II | A61B 5/0002 600/437 |
| 5,904,652 A | 5/1999 | Gilbert et al. | |
| 5,928,169 A * | 7/1999 | Schatzle | A61B 8/4494 600/439 |
| 5,957,846 A | 9/1999 | Chiang et al. | |
| 5,961,610 A | 10/1999 | Kelly et al. | |
| 5,964,709 A | 10/1999 | Chiang et al. | |
| 5,971,923 A | 10/1999 | Finger | |
| 5,986,662 A * | 11/1999 | Argiro | G06T 11/00 345/419 |
| 6,032,120 A | 2/2000 | Rock et al. | |
| 6,063,030 A | 5/2000 | Vara et al. | |
| 6,101,407 A | 8/2000 | Groezinger | |
| 6,106,468 A | 8/2000 | Dowdell | |
| 6,106,472 A | 8/2000 | Chiang et al. | |
| 6,111,816 A | 8/2000 | Chiang et al. | |
| 6,126,608 A | 10/2000 | Kemme et al. | |
| 6,135,961 A | 10/2000 | Pflugrath et al. | |
| 6,139,496 A | 10/2000 | Chen et al. | |
| 6,139,498 A | 10/2000 | Katsman et al. | |
| 6,142,946 A | 11/2000 | Hwang et al. | |
| 6,159,150 A | 12/2000 | Yale et al. | |
| 6,198,283 B1 | 3/2001 | Foo et al. | |
| 6,203,499 B1 * | 3/2001 | Imling | A61B 8/0833 600/461 |
| 6,210,327 B1 | 4/2001 | Brackett et al. | |
| 6,216,539 B1 * | 4/2001 | Johnson | G01N 29/14 73/40.5 A |
| 6,217,519 B1 | 4/2001 | Grund et al. | |
| 6,251,073 B1 | 6/2001 | Imran et al. | |
| 6,306,089 B1 | 10/2001 | Coleman et al. | |
| 6,337,481 B1 | 1/2002 | Stearns et al. | |
| 6,368,279 B1 | 4/2002 | Liu | |
| 6,379,306 B1 | 4/2002 | Washburn et al. | |

(56) References Cited

U.S. PATENT DOCUMENTS

| | | | |
|---|---|---|---|
| 6,381,557 B1 | 4/2002 | Babula et al. | |
| 6,464,636 B1 | 10/2002 | Kinicki et al. | |
| 6,475,146 B1 | 11/2002 | Frelburger et al. | |
| 6,511,426 B1 | 1/2003 | Hossack et al. | |
| 6,514,201 B1 * | 2/2003 | Greenberg | A61B 5/7475 600/437 |
| 6,519,632 B1 * | 2/2003 | Brackett | A61B 8/00 600/437 |
| 6,530,887 B1 | 3/2003 | Gilbert et al. | |
| 6,537,219 B2 | 3/2003 | Poland et al. | |
| 6,547,730 B1 * | 4/2003 | Lin | A61B 5/0456 600/437 |
| 6,569,097 B1 | 5/2003 | McMorrow et al. | |
| 6,603,494 B1 | 8/2003 | Banks et al. | |
| 6,629,926 B1 | 10/2003 | Finger et al. | |
| 6,669,633 B2 | 12/2003 | Brodsky et al. | |
| 6,733,448 B2 | 5/2004 | Kelly et al. | |
| 6,734,880 B2 | 5/2004 | Chang et al. | |
| 6,783,493 B2 | 8/2004 | Chiang et al. | |
| 6,839,762 B1 | 1/2005 | Yu et al. | |
| 6,869,401 B2 | 3/2005 | Gilbert et al. | |
| 6,969,352 B2 | 11/2005 | Chiang et al. | |
| 7,110,583 B2 | 9/2006 | Yamauchi | |
| 7,115,093 B2 | 10/2006 | Halmann et al. | |
| 7,162,439 B2 | 1/2007 | Panelli | |
| 7,171,255 B2 | 1/2007 | Holupka et al. | |
| 7,201,715 B2 | 4/2007 | Burdette et al. | |
| 7,331,925 B2 * | 2/2008 | McMorrow | A61B 8/00 600/437 |
| 7,549,961 B1 | 6/2009 | Hwang | |
| 7,606,861 B2 | 10/2009 | Killcommons et al. | |
| 9,402,601 B1 | 8/2016 | Berger et al. | |
| 2001/0050087 A1 * | 12/2001 | Weissman | A61B 8/56 128/899 |
| 2002/0007119 A1 * | 1/2002 | Pelissier | G01S 15/8979 600/443 |
| 2002/0037919 A1 * | 3/2002 | Hunter | A61K 31/437 514/449 |
| 2002/0102023 A1 | 8/2002 | Yamauchi | |
| 2002/0156864 A1 * | 10/2002 | Kniest | H04L 67/04 709/217 |
| 2003/0028113 A1 | 2/2003 | Gilbert et al. | |
| 2003/0073894 A1 | 4/2003 | Chiang et al. | |
| 2003/0083563 A1 * | 5/2003 | Katsman | A61B 8/468 600/407 |
| 2003/0088182 A1 | 5/2003 | He et al. | |
| 2003/0115018 A1 | 6/2003 | Sharma et al. | |
| 2003/0125629 A1 | 7/2003 | Ustuner | |
| 2003/0176787 A1 | 9/2003 | Gilbert et al. | |
| 2003/0212327 A1 | 11/2003 | Wang et al. | |
| 2003/0233046 A1 | 12/2003 | Ferguson et al. | |
| 2004/0015079 A1 | 1/2004 | Berger et al. | |
| 2004/0030227 A1 | 2/2004 | Littrup et al. | |
| 2004/0158146 A1 | 8/2004 | Mate et al. | |
| 2004/0260790 A1 * | 12/2004 | Balloni | A61B 5/055 709/219 |
| 2005/0033108 A1 | 2/2005 | Sawyer | |
| 2005/0228281 A1 | 10/2005 | Nefos | |
| 2006/0067469 A1 | 3/2006 | Dooley et al. | |
| 2006/0100509 A1 | 5/2006 | Wright et al. | |
| 2008/0161686 A1 | 7/2008 | Halmann | |
| 2009/0054781 A1 | 2/2009 | Stonefield et al. | |
| 2009/0112089 A1 | 4/2009 | Barnard et al. | |
| 2009/0198132 A1 | 8/2009 | Pelissier et al. | |
| 2010/0305444 A1 | 12/2010 | Fujii et al. | |
| 2011/0125022 A1 | 5/2011 | Lazebnik | |
| 2013/0184587 A1 | 7/2013 | Eom et al. | |
| 2016/0338676 A1 | 11/2016 | Berger et al. | |
| 2017/0105706 A1 | 4/2017 | Berger et al. | |

FOREIGN PATENT DOCUMENTS

| | | |
|---|---|---|
| WO | 1997/01768 A2 | 1/1997 |
| WO | 1998/28631 A2 | 7/1998 |
| WO | 1998/34294 A2 | 8/1998 |
| WO | 1999/58044 A1 | 11/1999 |
| WO | 1999/59472 A1 | 11/1999 |
| WO | 2000/33231 A2 | 6/2000 |
| WO | 2000/60522 A2 | 10/2000 |
| WO | 2000/79300 A1 | 12/2000 |
| WO | 2001/22115 A1 | 3/2001 |
| WO | 2005/053664 A2 | 6/2005 |
| WO | 2006/040697 A1 | 4/2006 |
| WO | 2010/051587 A1 | 5/2010 |

OTHER PUBLICATIONS

U.S. Appl. No. 10/227,187, filed Aug. 23, 2002, Granted.
U.S. Appl. No. 10/386,360, filed Mar. 11, 2003, Published.
U.S. Appl. No. 10/354,946, filed Jan. 30, 2003, Granted.
U.S. Appl. No. 15/225,211, filed Aug. 1, 2016, Published.
U.S. Appl. No. 14/995,175, filed Jan. 13, 2016, Published.
Khuri-Yakub et al., Capacitive micromachined ultrasonic transducers for medical imaging and therapy. J Micromech Microeng. May 2011;21(5):54004-54014.
Strassberg, Despite Threats from USB and Firewire, IEEE 488 ain't down yet. EDN Electrical Design News. EDN, Electrical Design News. Jul. 1998 43(15):67-80.

* cited by examiner

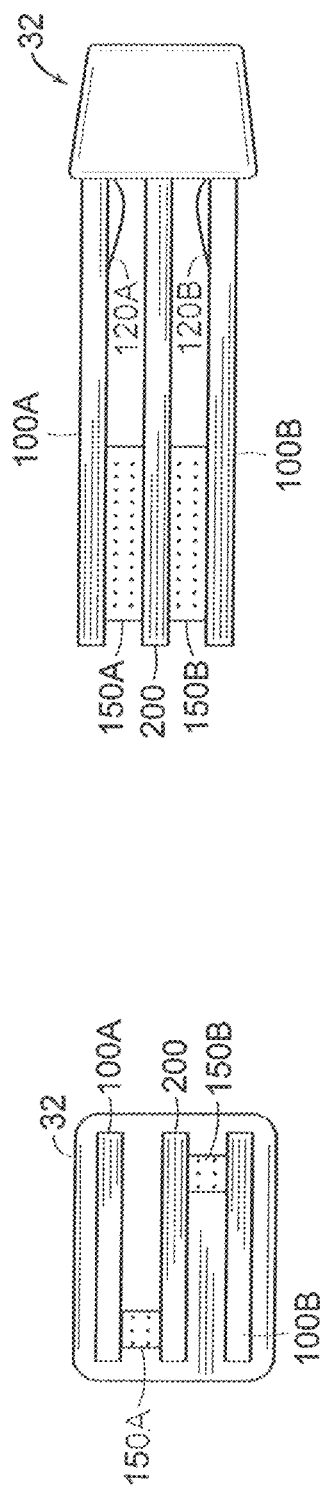
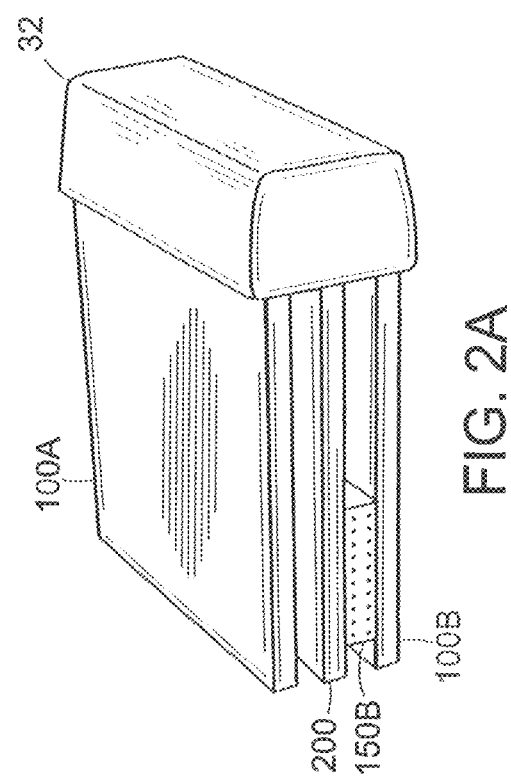
FIG. 2C
FIG. 2A
FIG. 2B

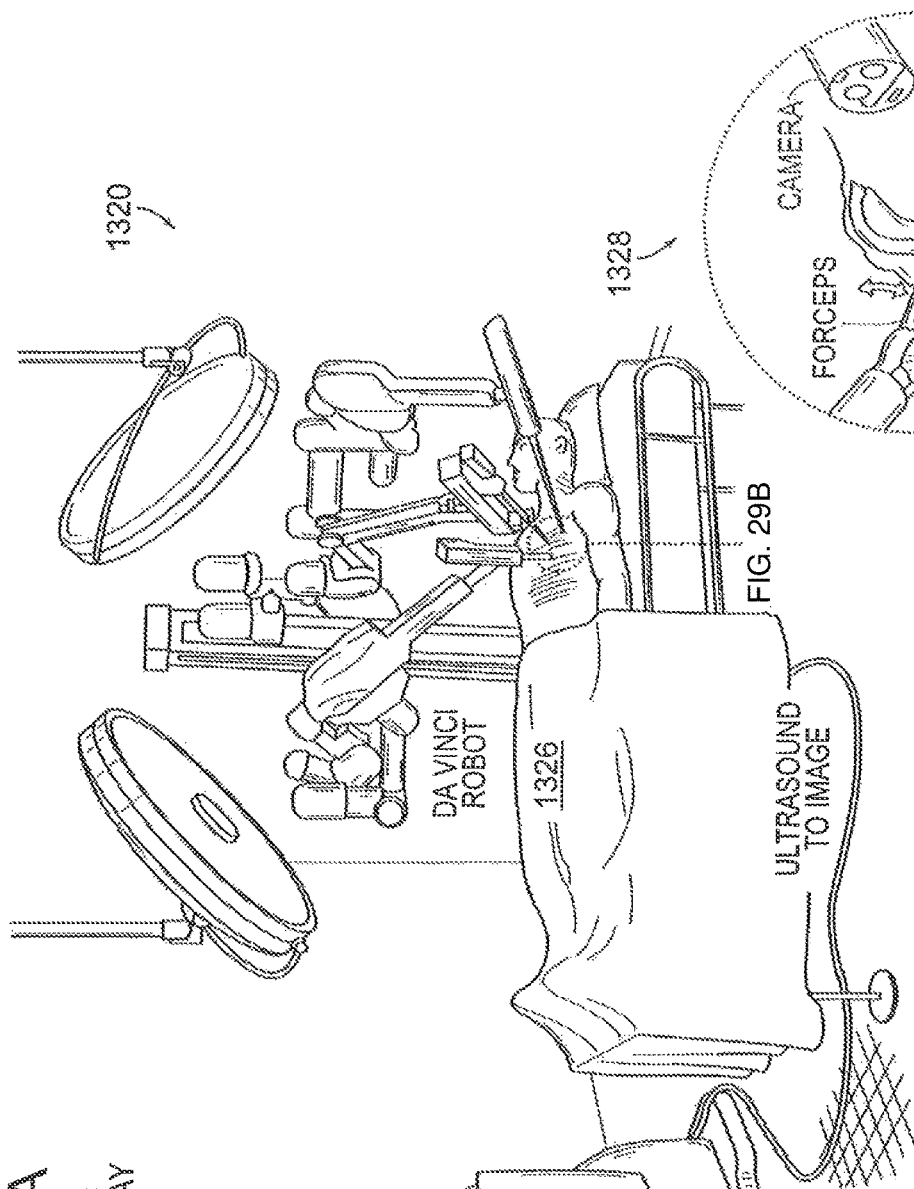

*1620*

| Image Display | Patient Info |

Patient Identification Information

Last: [First] [Middle]

Patient ID: [ ]

DOB: [ / / ▽]

Gender: ☐ M  ☐ F

Comment: [ ▽]

Exam Location & Clinician Information

Site: [ ▽]

Clinician: [ ▽]

Exam Selection

Exam: [ABDOMINAL ▽]

[Save]  [New Patient]  [Cancel]  [Help]

Comment: | 4TH FOLLOW-UP |
2ND FOLLOW-UP
4TH FOLLOW-UP
NO HEALTH CARE COVERAGE
OB EXAM BASED ON REFERRAL
REFERRAL FROM DR. HARRIS Exam Location
Site:
Clinician: | GEORGE RICE |

Exam Selection
Exam: | CARDIAC |

| Depth | 12 ▽ |

Focus

Gain

TGC 6
7
8
9
10
11
12
13
14
15
16
17
18
19
20
21
22
23
24

FIG. 47C

NETWORKED ULTRASOUND SYSTEM AND METHOD FOR IMAGING A MEDICAL PROCEDURE USING AN INVASIVE PROBE

CROSS REFERENCES TO RELATED APPLICATIONS

This application is a continuation of U.S. application Ser. No. 10/386,360 filed Mar. 11, 2003, which is continuation-in-part of U.S. application Ser. No. 10/354,946 filed Jan. 30, 2003, the entire contents of the above applications being incorporated herein by reference in their entirety.

BACKGROUND OF THE INVENTION

Conventional ultrasound imaging systems typically include a hand-held probe coupled by cables to a large rack-mounted console processing and display unit. The probe typically includes an array of ultrasonic transducers which transmit ultrasonic energy into a region being examined and receive reflected ultrasonic energy returning from the region. The transducers convert the received ultrasonic energy into low-level electrical signals which are transferred over the cable to the processing unit. The processing unit applies appropriate beam forming techniques to combine the signals from the transducers to generate an image of the region of interest.

Typical conventional ultrasound systems include a transducer array each transducer being associated with its own processing circuitry located in the console processing unit. The processing circuitry typically includes driver circuits which, in the transmit mode, send precisely timed drive pulses to the transducer to initiate transmission of the ultrasonic signal. These transmit timing pulses are forwarded from the console processing unit along the cable to the scan head. In the receive mode, beamforming circuits of the processing circuitry introduce the appropriate delay into each low-level electrical signal from the transducers to dynamically focus the signals such that an accurate image can subsequently be generated.

SUMMARY OF THE INVENTION

In accordance with a preferred embodiment of the invention, provides for further improvements in portable ultrasound medical imaging systems developed for use with personal computers. In one embodiment the control circuitry and beamforming circuitry are localized in a portable assembly. Such an integrated package simplifies the cable requirements of the assembly, without adding significant weight.

Traditional ultrasonic imaging systems have been dedicated systems having specialized hardware for processing the large amounts of data generated by ultrasonic transducers providing input to such systems. These imaging systems tend to be unwieldy, expensive, and difficult to upgrade. Further, since dedicated systems have specialized components, it is difficult to employ the gathered ultrasound data in other contexts, such as by downloading to another application for processing and/or operations which are unavailable on the native dedicated system. Accordingly, it is beneficial to provide an ultrasonic imaging system operable on a standard, commercially available, user computing device without specific hardware modifications, and adapted to interface with an external application without modification to the ultrasonic imaging system. In this manner, a user may gather ultrasonic data on a standard user computing device such as a personal computer (PC), and employ the data so gathered via an independent external application without requiring a custom system, expensive hardware modifications, or system rebuilds.

A system and method for gathering ultrasonic data on a standard user computing device and employing the data via an integrated interface program allows such ultrasonic data to be invoked by a variety of external applications having access to the integrated interface program via a standard, predetermined platform such as visual basic or c++.

The system provides external application integration in an ultrasonic imaging system by defining an ultrasonic application server for performing ultrasonic operations. An integrated interface program with a plurality of entry points into the ultrasonic application server is defined. The entry points are operable to access each of the ultrasonic operations. An external application sends a command indicative of at least one of the ultrasonic operations. The command is transmitted via the integrated interface program to the ultrasonic application server. Concurrently, at periodic intervals, raw ultrasonic data indicative of ultrasonic image information is received by the ultrasonic application server over a predetermined communication interface. A result corresponding to the command is computed by the ultrasonic application server, and transmitted to the external application by the integrated interface program.

An embodiment of the invention includes a probe having a plurality of circuit boards or circuit panels that are mounted within a generally rectangular cavity within a hand-held housing. The circuit panels each have one or more integrated circuits and are mounted in planes that are parallel to one another. These integrated circuits can be fabricated using a standard CMOS process that support voltage levels between 3.3 V and 200 V.

A particular embodiment of the invention utilizes two or three circuit boards or panels, a center panel having a center system controller and a communication link to an external processor. The center panel can be mounted between a pair of surrounding panels, each including a memory and a beamforming circuit. The system accommodates the use of different probe elements and can employ a variable power supply that is adjusted to different levels for different probes. Also, it is desirable to use a variable clock generator so that different frequencies can be selected for different probes.

Another preferred embodiment of the invention provides a small probe that is connected by a first cable to an interface-housing. The interface housing can contain the beamformer device and associated circuits and is a small light weight unit that can be held in one hand by the user while the other hand manipulates the probe. The probe can be any of several conventional probes that can be interchangeably connected by cable to the interface housing. Alternatively, the interface housing can be worn on the body of the user with a strap, on the forearm or the waist with a belt, for example, or in a pocket of the user. A preferred embodiment using such an interface can include two or three circuit boards as described in greater detail herein. The interface housing is connected to a personnel computer by standard FireWire or serial bus connection.

In another preferred embodiment, the probe incorporating the beamformer, or the probe with the interface housing can be connected to a wearable personal computer. In this embodiment, the computer performing scan conversion, post signal processing or color doppler processing is located in a housing worn by the user, such as on the forearm, on the waist or in a pocket. A power supply board can be inserted into the probe, into the interface housing or in another external pod and can include a DC-DC converter. The display system can also include a head mounted display. A hand-held controller can be connected to the computer or interface by wire or wireless connection.

A preferred embodiment of the invention can utilize certain safety features including circuits that check the power supply voltage level, that test every channel of the beamformer and assists in setting gain levels, that counts pulses per second and automatically shuts off the system to prevent over-radiating of the patient.

Another preferred embodiment of the invention employs the use of dedicated controls that the user can employ to perform specific tasks during a patient study. These controls are readily accessible and intuitive in use. These controls provide for freezing or unfreezing of the image on the display, for recording an image in electronic memory, to measure distances in two dimensions using a marker or caliper and a "set" function fix two markers or calipers on screen, a track ball, touchpad or other manually manipulated element to control the marker, a time gain compensation control, such as 8 slide pots, to correct for sound attenuation in the body, scale or depth control to provide a zoom feature and for selection of focal zones.

The system can be employed with a number of probe systems and imaging methods. These include the generation of color Doppler, power Doppler and spectral density studies. These studies can be aided by the use of contrast agents that are introduced into the body during a study to enhance the response to ultrasound signals. Such agents can also include medications that are acoustically released into the body when they are activated by specific acoustic signals generated by the probe transducer array.

In accordance with another aspect of the present invention, a system for ultrasonic imaging includes a probe and a computing device. The probe has a transducer array, control circuitry and a digital communication control circuit. The control circuitry includes a transmit/receive module, beamforming module and a system controller. A computing device connects to the digital communication control circuit of the probe with a communication interface. The computer processes display data.

The communication interface between the probe and the computing device is a wireless interface in several embodiments. In an embodiment, the wireless interface is a radio frequency (RF) interface. In another embodiment, the wireless interface is an infrared interface (IR). In an alternative embodiment, the communication interface between the probe and the computing device is a wired link.

In a preferred embodiment, the beamforming module is a charge domain processor beamforming module. The control circuitry has a pre-amp/time-gain compensation (TGC) module.

A supplemental display device is connected to the computing device by a second communication interface. The supplemental display device is a computing device in several embodiments. At least one of the communication interfaces can be a wireless interface.

In an embodiment, the communication between the probe and the computing device is a wireless interface. The second communication interface between the supplemental display device and the computing device is wireless. In an embodiment, the second communication interface includes a hub to connect a plurality of secondary supplemental devices.

In another preferred embodiment, the ultrasonic imaging system includes a handheld probe system which is in communication with a remotely located computing device. The computing device can be a handheld portable information device such as a personal digital assistant provided by Compaq or Palm, Inc. The communication link between the probe and the computing device is a wireless link such as, but not limited to, IEEE 1394 (FireWire). The computing device may be used for controlling, monitoring or displaying ultrasonic imaging data.

A method of controlling an ultrasonic imaging system from a unitary operating position facilitates ultrasonic image processing by defining ultrasonic imaging operations and defining a range of values corresponding to each of the ultrasonic imaging operations. An operator then selects, via a first control, one of the ultrasonic imaging operations, and then selects, via a second control, a parameter in the range of values corresponding to the selected ultrasonic imaging operation. The ultrasonic imaging system applies the selected ultrasonic imaging operation employing the selected parameter. In this manner, the operator produces the desired ultrasonic image processing results by employing both the first control and the second control from a common operating position from one hand, thereby allowing the operator to continue scanning with a free hand while continuing to control the ultrasonic imaging system.

The ultrasonic imaging system is controlled from a control keypad accessible from one hand of the operator, or user. The other hand of the operator may therefore be employed in manipulating an ultrasonic probe attached to the ultrasonic imaging system for gathering ultrasonic data employed in the ultrasonic imaging operations. The first control allows qualitative selection of the various ultrasonic imaging operations which may be invoked using the system. The second control allows quantitative selection of parameters along a range to be employed in the ultrasonic operation. The range of parameters may be a continuum, or may be a series of discrete values along the range. The control keypad includes two keys for scrolling through the qualitative ultrasonic operations, and two keys for selecting the quantitative parameters along the corresponding range.

The ultrasonic imaging system in accordance with preferred embodiments may be used for patient monitoring systems such as bedside monitoring system, pacemaker monitoring, for providing image guided implants, and pacemaker implantation. Further, preferred embodiments of the systems of the present invention may be used for cardiac rhythm management, for radiation therapy systems and for image guided surgery, such as, but not limited to, image guided neurosurgery, breast biopsy and computer enabled surgery.

The ultrasonic imaging operations which may be invoked include scanning operations, to be applied to live, real time ultrasonic image gathering, and processing operations, which may be applied to live or frozen ultrasonic images. Typical scanning ultrasonic imaging operations which are known to those skilled in the art and which may be applied by the ultrasonic imaging system include size, depth, focus, gain, Time Gain Compensation (TGC) and TGC lock. Typical processing ultrasonic imaging operations include view, inversion, palette, smoothing, persistence, map, and contrast.

Preferred embodiments of the present invention include control and data transfer methods that allow a third party Windows® based application to control, for example, a portable Windows® based ultrasound system by running the ultrasound application as a background task, sending control commands to the ultrasound application server and receiving images (data) in return. Further, the embodiment configures a portable ultrasound Windows® based application as a server of live ultrasound image frames supplying another Windows® based-application that acts as a client. This client application receives these ultrasound image frames and processes them further. In addition, an alternate embodiment configures the portable ultrasound Windows® based application as a server, interacting with a third party client application via two communication mechanisms, for example, a component object model (COM) automation interface used by third party, hereinafter referred to as an external application or a client to startup and control the portable ultrasound Windows® based application and a high-speed shared memory interface to deliver live ultrasound images.

A preferred embodiment includes and configures a shared memory interface to act as a streaming video interface between a portable Windows® based Ultrasound application and another third party Windows® based application. This streaming video interface is designed to provide ultrasound images to a third party client in real-time.

A preferred embodiment allows the third party Windows® based application to control the flow rate of images from the portable ultrasound Windows® based application through the shared memory interface within the same PC platform and the amount of memory required to implement this interface. These controls consist of a way to set the number of image buffers, the size of each buffer and the rate of image transfer. This flow rate control can be set for zero data loss thus ensuring that every frame is delivered to the third party Windows® based application from the ultrasound system, or minimum latency thus delivering the latest frame generated by the ultrasound system to the third party Windows® based application first.

A preferred embodiment formats the ultrasound image frame such that probe, spatial, and temporal information can be interpreted by the third party Windows® based application as it retrieves the images (generated by the portable ultrasound Windows® based application) from the shared memory interface. The actual image data passed between the server (i.e. portable ultrasound application) and the client application (third party Windows® based application) is a Microsoft® device independent bitmap (DIB) with 8 bit pixels and a 256 entry color table. The image frame also contains a header that provides the following additional information, for example, but not limited to, Probe Type, Probe Serial Number, Frame Sequence Number, Frame Rate, Frame Timestamp, Frame Trigger Timestamp, Image Width (in pixels), Image Height (in pixels), Pixel Size (in X and Y), Pixel Origin (x, y location of the first pixel in image relative to the Transducer Head, and Direction (spatial direction along or across each line of the image).

Further, the preferred embodiment controls the shared memory interface used to transfer ultrasound images between a Windows® based portable ultrasound system and a third party Windows® based system through the use of ActiveX controls. The Windows® based portable ultrasound application contains an ActiveX control that transfers a frame into the shared memory and sends out a Windows® Event (that includes a pointer to the frame just written) to the third party Windows® based application. This third party application has a similar ActiveX control that receives this Event and pulls the image frame out of shared memory.

In accordance with a preferred embodiment the present invention includes a method for providing streaming video in an ultrasonic imaging system including providing an ultrasonic application server having at least one ultrasonic operation and corresponding ultrasonic data. The method further includes sending, from an external application, a command indicative of one of the ultrasonic operations, executing in the ultrasonic application server, a result corresponding to the commands and sending data from the ultrasonic server to the external application. A shared memory is in communication with the ultrasonic application server and the external application. The method further includes an integrated interface program having a plurality of entry points into the application server, transmitting via the integrated interface program a command to the ultrasonic application server, receiving over a predetermined communication interface, ultrasonic data indicative of ultrasonic image formation and transmitting the result to the external application via the integrated interface program.

The integrated interface program is adapted to transmit real-time imaging data including ultrasonic imaging for radiation therapy planning and treatment, minimally invasive and robotic surgery methods including biopsy procedures, invasive procedures such as catheter introduction for diagnostic and therapeutic angiography, fetal imaging, cardiac imaging, vascular imaging, imaging during endoscopic procedures, imaging for telemedicine applications, imaging for veterinary applications, cryotherapy and ultrasound elastography.

In preferred embodiments, the streaming video includes radio frequency data, real-time image data and transformation parameters. The external application can reside on the same computing device as the ultrasonic application server or be resident on a different computing device. The external application communicates with the ultrasonic application server using a control program using a component object model automation interface and a shared memory interface.

The command in the method for providing streaming video includes operations selected from the group consisting of an ultrasound application initialization/shutdown functions such as, for example, start ultrasound application, load preset files, exit application; ultrasound setup functions such as, for example, set shared memory parameters, initialize-communication to shared memory, set image frame size, set shared memory size, set transfer priority (for low latency, high throughput, or first in, first out), set image resolution and format; and ultrasound image capture functions such as, for example, freeze live data, fetch live data, and resume live imaging.

The ultrasonic-application server includes a graphical user interface having image control presets which are operable to store image settings. The image settings include application controls such as, for example, image mode, patient name, patient ID; B-mode controls, for example, size, depth, focus, TGC, change examination type; M-mode controls, for example, sweep speed, scan line position; image quality controls, for example, brightness, contrast, invert, palette, smoothing persistence; and Doppler controls; for example, color region of interest, pulse repetition rate, wall filter, steering angle, color gain, color invert, color priority, color baseline and line density control.

In a preferred embodiment, in certain applications such as angiographic monitoring, it is desirable for the system user to remain visually focussed on the patient and not be distracted by the need to view a display outside the user's field of view. For such applications, a display can be integrated into the probe housing and/or the interface housing.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

BRIEF DESCRIPTION OF THE DRAWINGS

FIGS. 2A-2C illustrate a particular embodiment of packaging integrated probe electronics.

FIGS. 29A-29B are exploded views illustrating a robotic imaging and surgical system integrating the ultrasound system in accordance with a preferred embodiment of the present invention.

FIG. 29C is a diagram illustrating a robotic imaging and surgical system integrating the ultrasound system in accordance with a preferred embodiment of the present invention.

FIG. 43 illustrates a view of patient-information screen in a graphical user interface in accordance with a preferred embodiment of the present invention.

FIG. 44 illustrates further interface buttons in a patient interface screen in accordance with a preferred embodiment of the present invention.

FIG. 45 illustrates a view of a screen for adding a new patient in a graphical user interface in accordance with a preferred embodiment of the present invention.

FIGS. 47A-47H illustrate the control interfaces for adjusting a B-mode image in a graphical user interface in accordance with a preferred embodiment of the present invention.

DETAILED DESCRIPTION OF THE INVENTION

Figure 1:
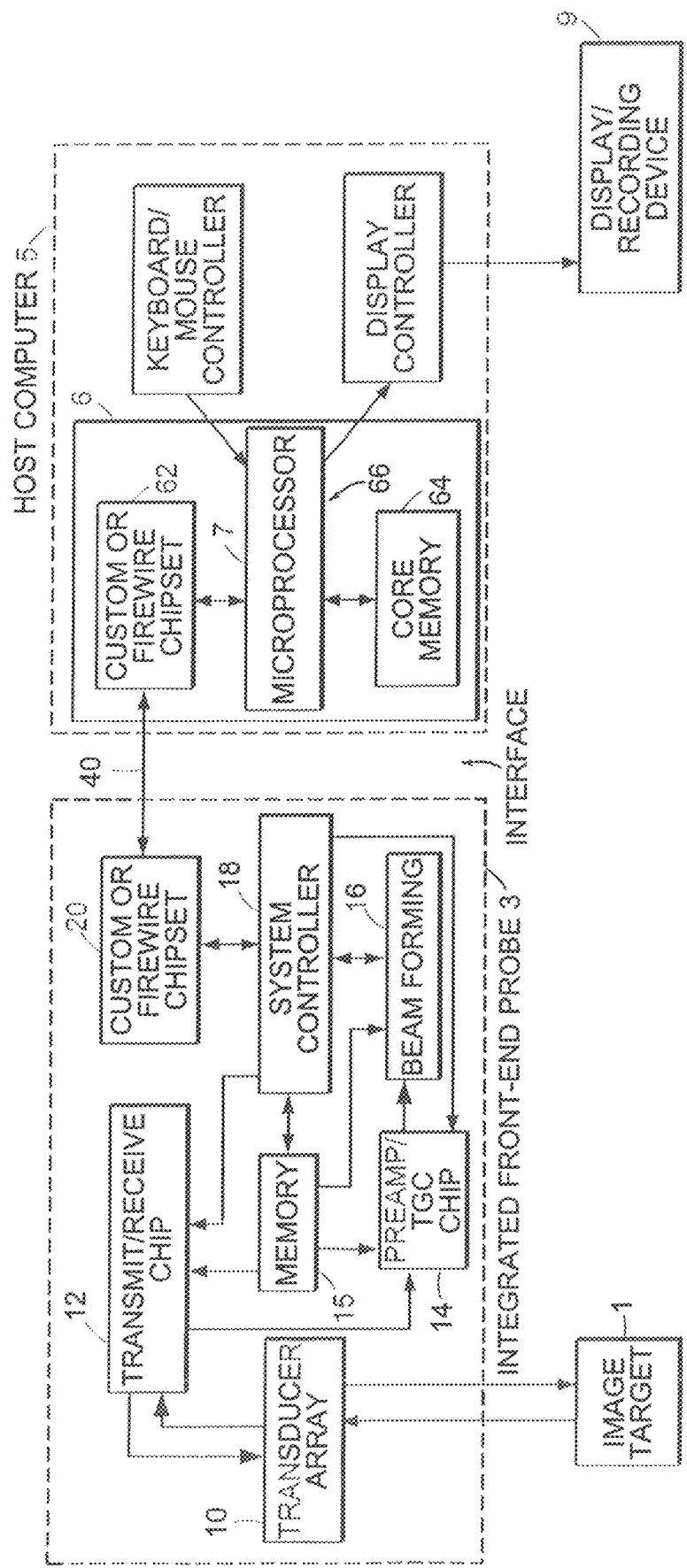
FIG. 1 is a schematic block diagram of an integrated probe system.

FIG. 1 is a schematic block diagram of an integrated probe system. Illustrated are a target object 1, a front-end probe 3, and a host computer 5, and a supplemental display/recording device 9. The front-end probe 3 integrates a transducer array 10 and control circuitry into a single hand-held housing. The control circuitry includes a transmit/receive module 12, a pre-amp/time-gain compensation (TGC) module 14, a charge domain processor (CDP) beamforming module 16, and a system controller 18. Memory 15 stores program instructions and data. The CDP beamformer integrated circuit 16 includes a computational capacity that can be used to calculate the delay coefficients used in each channel. The probe 3 interfaces with the host-computer 5 over a communications link 40, which can follow a standard high-speed communications protocol, such as the FireWire (IEEE 1394 Standards Serial Interface) or fast (e.g., 200 Mbits/second or faster) Universal Serial Bus (USB 2.0) protocol. The standard communication link to the personal computer operates at least at 100 Mbits/second or higher, preferably at 200 Mbits/second, 400 Mbits/second or higher. Alternatively, the link 40 can be a wireless connection such as an infrared (IR) link. The probe 3 thus includes a communications chipset 20.

The components in the portable ultrasound system require a continuous source of data for correct operation. For instance, the beamformer 16 requires steering data, the transmit circuitry 12 requires data to instruct it where to focus the next pulse and when to fire, and the TGC 14 needs to know what gain level is appropriate at the given time. Additionally, further information may be required synchronous to the scanning operation to control how the beamformed data is sent back to the host. For instance, a DATA-VALID signal can be helpful to reduce the amount of data that the host 5 actually has to process. Along with data, the various parts of the ultrasound system relies on common synchronization for the system to work in harmony. For example, the transmitter must be fired at an exact time with respect to when the beamformer is looking at a particular position.

Engineering goals of the ultrasonic probe include small size, thermal management, low-power consumption, and the capability and flexibility to allow efficient high resolution imaging as well as calibration and experimentation. The small size and low-power operation implies dense storage. The capability and flexibility entails the ability to use irregular firing sequences, concurrent reprogramming and use for seamless adaptive beamforming modes, as well as full flexibility to perform debugging and complete-set imaging. Ergonomic, economic portable design also requires a cost-effective, non-encumbering connection between the scan head 3 and the PC host 5. A general description of the probe system can be found in International Application PCT/US96/11166, filed on Jun. 28, 1996, in U.S. application Ser. No. 08/981,427 filed on Dec. 29, 1997 now U.S. Pat. No. 5,964,709 issued on Oct. 12, 1999, in U.S. application Ser. No. 08/599,816 filed on Feb. 12, 1996 now U.S. Pat. No. 5,690,114 issued on Nov. 25, 1997, in U.S. application Ser.

Nos. 08/496,804 and 08/496,805 both filed on Jun. 29, 1995, now U.S. Pat. Nos. 5,590,658 and 5,839,442, respectively, issued Jan. 7, 1997 and Nov. 24, 1998, respectively, and further embodiments are described in U.S. application Ser. No. 09/364,699 filed Jul. 30, 1999, now U.S. Pat. No. 6,292,433 issued on Sep. 18, 2001, in International Application No. PCT/US98/02291 filed on Feb. 3, 1998, and in U.S. application Ser. No. 09/447,144 filed on Nov. 23, 1999 now U.S. Pat. No. 6,379,304 issued on Apr. 30, 2002, in International Application No. PCT/US97/24291 filed on Dec. 23, 1997 the above patents and applications being incorporated herein by reference in their entirety.

Additional factors of interest include ease, speed, and low-cost of design and manufacturing. These factors motivate the use of a Field Programmable Gate Array (FPGA) architecture. Additionally, they involve the use of a design that can be extended easily to diverse applications.

FIGS. 2A-2C illustrate a particular embodiment of integrated probe electronics. FIG. 2A is a perspective view showing a transducer array housing 32, an upper circuit board 100A, a lower circuit board 100B, and a central circuit board 200. Also shown is a lower Molex connector 150B carrying data and signal lines between a central circuit board 200 and the lower circuit board 100B. The transducer array housing 32 can be a commercially available unit having a pair of flexible cable connectors 120A, 120B (See FIG. 2C) connected to the upper board 100A and lower board 100B, respectively, with strain relief FIG. 2B is a back-end view of the probe, which also shows an upper Molex connector 150A. FIG. 2C is a side-view of the probe. Using 8 mm high Molex connectors 150A, 150B, the entire stack has a thickness of approximately 30 mm or less, with this particular embodiment being about 21 mm.

Small size is achieved through the use of modern fabrication and packaging techniques. For example, by exploiting modern semiconductor fabrication techniques, numerous circuit functions can be integrated onto single chips. Furthermore, the chips can be mounted using space-saving packaging, such as chip on-board technology. As technology improves, it is expected that the size of the electronic components will decrease further.

More functionality can be included within the hand-held probe such as a wireless IEEE 1394 connection to the personal computer. A display can be mounted directly on the hand-held probe, for example, to provide a more usable and user-friendly instrument.

Figure 3A:
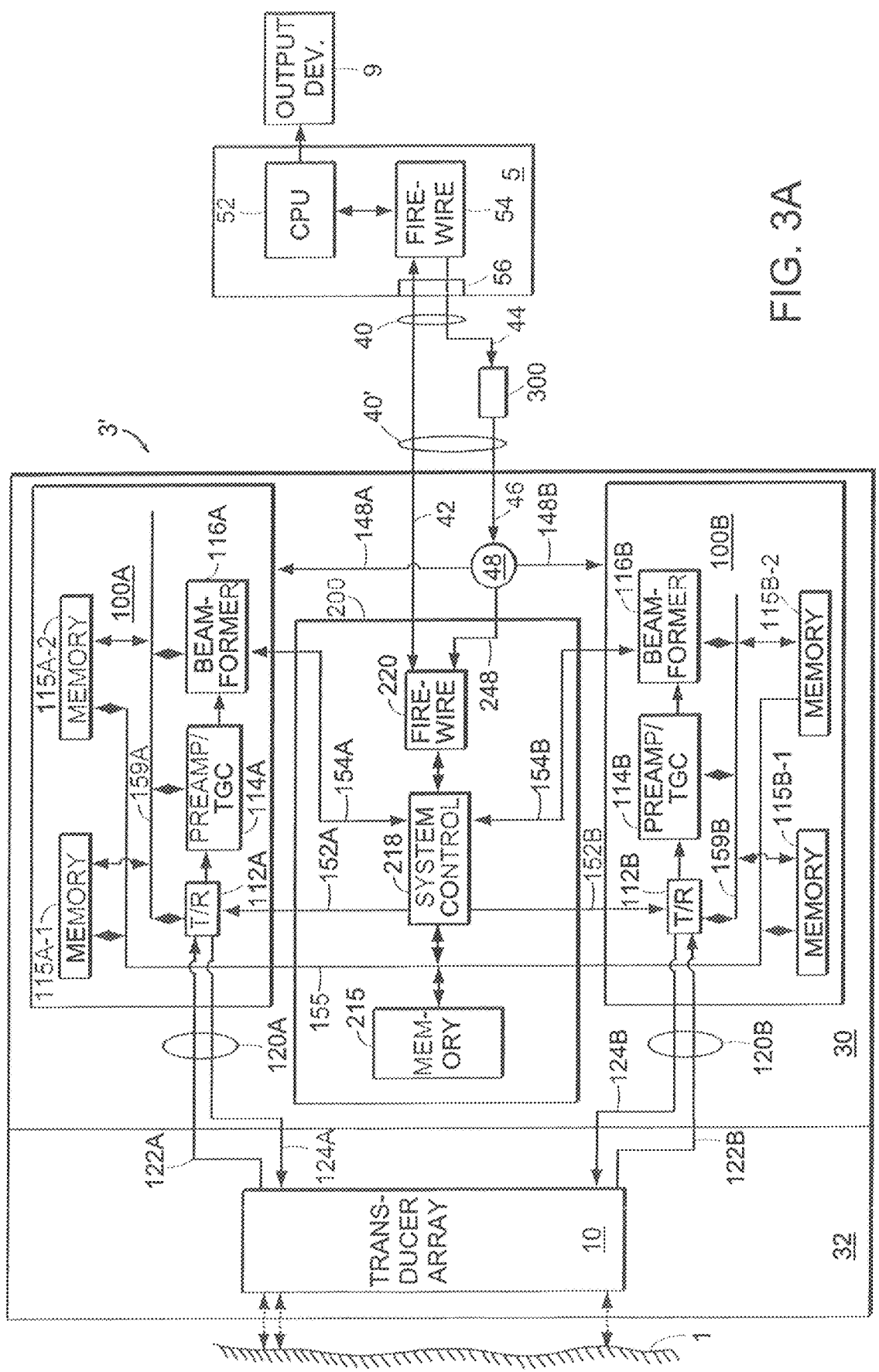
FIG. 3A is a schematic block diagram of a particular embodiment of an integrated probe system.

FIG. 3A is a schematic block diagram of a particular embodiment of an integrated probe system. The host computer 5 can be a commercially available personal computer having a microprocessor CPU 52 and a communications chipset 54. A communications cable 40 is connected through a communications port 56 to the communications chipset 54.

The front-end probe 3' includes a transducer head 32, which can be an off-the-shelf commercial product, and an ergonomic hand-held housing 30. The transducer head 32 houses the transducer array 10. The housing 30 provides a thermally and electrically insulated molded plastic handle that houses the beamforming and control circuitry.

The beamforming circuitry, as shown, can be embodied in a pair of analog circuit boards 100A, 100B. Each analog circuit board 100A, 100B includes a respective transmit/receive chip 112A, 112B; a preamp/TGC chip 114A, 114B; a beamformer chip 116A, 116B; all of which are interconnected with a pair of the memory chips 115A-1, 115B-1, 115A-2, 115B-2 via an operational bus 159A, 159B. In a particular embodiment of the invention, the memory chips are Video Random Access Memory (VRAM) chips and the operational bus is 32 bits wide. Furthermore, preamp/TGC chips 114 and beamformer chips 116 operate on 32 channels simultaneously. The transmit/receive chips 112 include a 64 channel driver and a 64-to-32 demultiplexer.

Figure 4A:
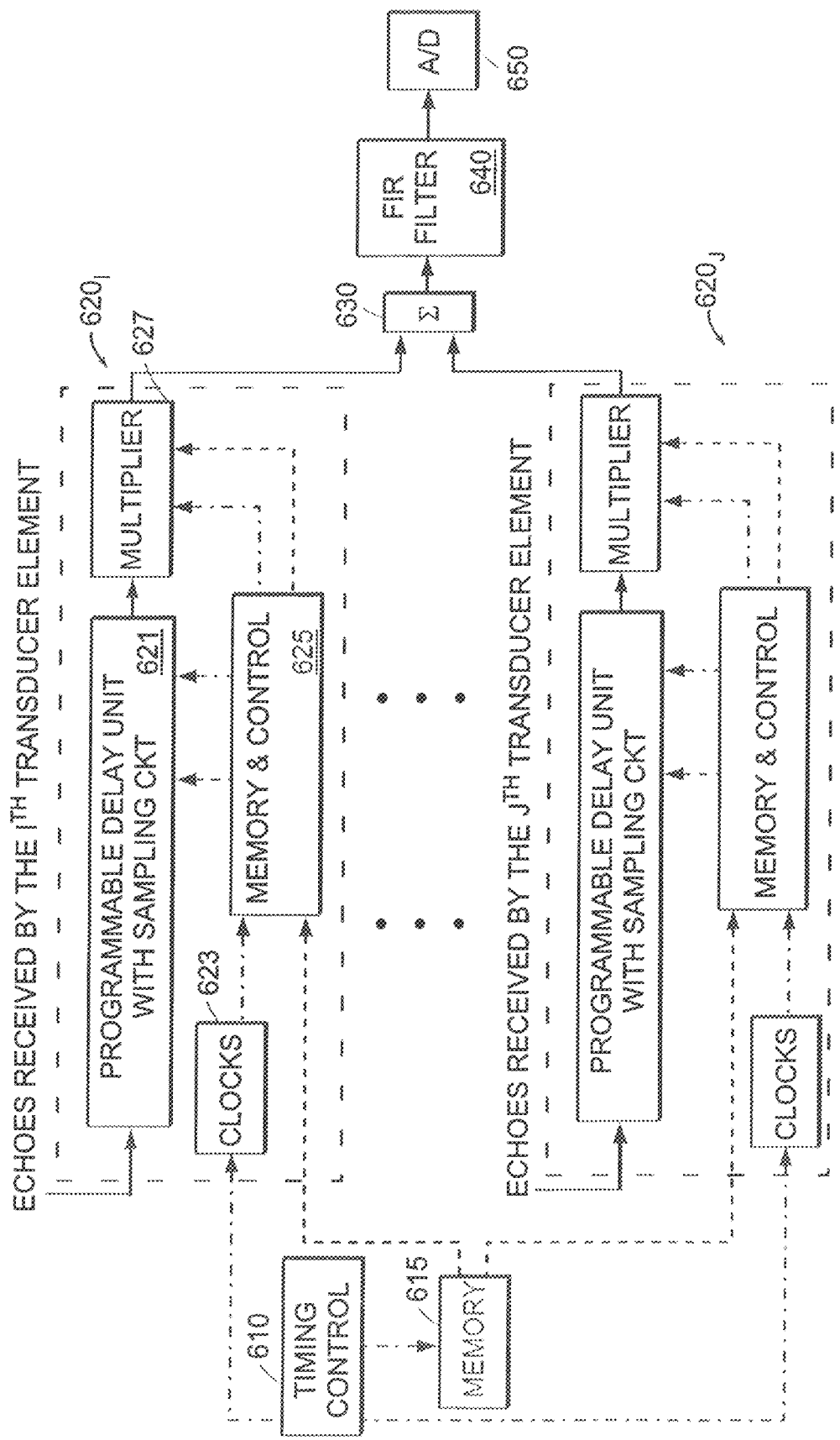
FIG. 4A is a block diagram of a particular 1-dimensional time-domain beamformer.

FIG. 4A is a block diagram of a particular 1-dimensional time-domain beamformer. The beamformer 600 features 32-channel programmable apodized delay lines. In addition, the beamformer 600 can include an on-chip output bandpass filtering and analog-to-digital conversion.

As illustrated in FIG. 4A, the beamformer 600 includes a plurality of single channel beamforming processors 620 subscript I, . . . , 620 subscript J. imaging signals are represented by solid leader lines, digital data is represented by dashed leader lines, and clock and control signals are illustrated by alternating dot and dash leader lines. A timing controller 610 and memory 615 interface with the single channel beamforming processors 620. Each single channel beamforming processor includes clock circuitry 623, memory and control circuitry 625, a programmable delay unit with sampling circuitry 621, in a multiplier circuit 627.

Each programmable delay unit 621 receives an imaging signal echo E from a respective transducer element. The outputs from the single channel beamforming processors 620 are added in a summer 630. A frequency impulse response (FIR) filter 640 processes the resulting imaging signal, which is digitized by the analog-to-digital (A/D) converter 650. In a particular embodiment of the invention, both the FIR filter 640 and the A/D converter 650 are fabricated on chip with the beamforming processors 620.

The choice of a Field Programmable Gate Array (FPGA) implementation as well as extensibility for ease of modification, points to the use of VRAMs for the memory modules. VRAM is a standard Dynamic RAM (DRAM) with an additional higher-speed serial access port. While DRAM has two basic operations, for example, read and write memory location, VRAM adds a third operation: transfer block to serial readout register. This transfers a block (typically 128 or 256 words) of data to the serial readout register which can then be clocked out at a constant rate without further tying up the DRAM core. Thus refresh, random access data read/write, and sequential readout can operate concurrently. Alternate embodiments may include a synchronous Dynamic Ram (synchDRAM) memory.

In the probe 3', dual-ported operation is beneficial so the data loading performed by the host 5 can be decoupled from data sent to memory modules. A modular architecture which allows additional VRAMs to be added in order to obtain additional bandwidth is useful, particularly when the exact data rate requirements may change. Using wide memories, the data does not have to be buffered before going to the various destination modules in the system. A particular embodiment uses five 256K word by 16 bit VRAMs which yields a total of 80 output lines. If fewer output lines are required, fewer VRAMs can be used. If more output lines are required, only very minor modifications to the controller have to be made.

The downside is that VRAM is lower density than other varieties of DRAM. Currently only 512 Kbyte VRAM chips are available. Synchronous DRAM (SDRAM) is 2 Mbyte/chip, but expects buffering of all data from the memory to the various destination modules because it is not continuous. The use of SDRAM implies that the modules accept data bursts instead of continuous data. Additionally, more buffering of host-data can be used or else concurrent readout and loading may not be possible. Using a multiple data rate feature in the controller can reduce the storage requirements making VRAM a first embodiment. However, a further preferred embodiment uses SDRAM to provide further improvements in the speed and capacity of the system.

The control circuitry, as shown in FIG. 3A, is embodied in a digital circuit board 200. The digital circuit board 200 includes a FireWire chipset 220, a system control chip 218 to control the scan head, and a memory chip 215. In a particular embodiment of the invention, the memory chip 215 is a VRAM chip and the system control chip 218 is interconnected to the various memory chips 115, 215 over a control bus 155, which in this particular application is 16 bits wide.

As illustrated, the system control chip 218 provides scan head control signals to be transmit/receive chips 112A, 112B over respective signal lines 152A, 152B. The transmit/receive chips 112A, 112B energize the transducer array 10 over transmit lines 124A, 124B. Received energy from the transducer array 10 is provided to the transmit/receive chips 112A, 112B over receive lines 122A, 122B. The received signals are provided to the pre-amp/TOC chips 114A, 114B. After being amplified, the signals are provided to the beamformer chips 116A, 116B. Control signals are exchanged between the beamformer and the system controller over signal lines 154A, 154B to adjust the scan beam.

The five VRAM chips 115A-1, 115A-2, 115B-1, 115B-2, 215 serve to supply the real-time control data needed by the various operating modules. The term "operating modules" refers to the different parts of the system that require control data—namely the beamformers 116A, 116B, transmit/receive chips 112A, 112B, and preamp/TGC chips 114A, 114B. The system controller 218 maintains proper clocking and operation of the VRAM to assure continuous data output. Additionally, it generates clocks and control signals for the various operating modules of the system so that they know when the data present at the DRAM serial port output is for them. Finally, it also interfaces with the host (PC) 5 via a PC communications protocol (e.g., FireWire or high speed bus) to allow the host 5 to write data into the VRAM.

Some of the VRAMs are shared by multiple modules. The 64-bit output of four VRAMs 115A-1, 115A-2, 115B-1, 115B-2 is used by both the transmit module as well as the beamformer. This is not a problem, because typically only one requires data at any given time. Additionally, the transmit module chip uses relatively less data and thus it is wasteful to have to dedicate entire VRAMs for transmit operations. In order to allow the VRAM data to be shared by multiple modules, codes are embedded in the VRAM data that the controller deciphers and asserts the appropriate MODCLOCK line.

The fifth VRAM 215 is used to generate data that is not shared by multiple modules. For example, it is convenient to put the control for the TGC here because that data is required concurrently with beamformer data. It can also be useful to have one dedicated control bit which indicates when valid data is available from the beamformer and another bit indicating frame boundaries. Thus, because the location of the data in the VRAM corresponds to the position in the frame scanning sequence, additional bits are synchronized with the operation of the system. CCD clock enable signals can also be generated to gate the CCD clock to conserve power. Lastly, the VRAM can be used to generate test data for a D/A converter to test the analog circuitry with known waveforms.

As the system is reduced in size, the number of VRAMs may be reduced. In a SDRAM system clocked twice as fast, the four shared VRAM chips may be merged into two SDRAM chips in a 128 line system, for example.

The data sent to the beamformer and transmit modules are bit-serial within a channel; with all channels being available in parallel. For the transmit module, two transmit channels share each bit line with alternating clocks strobing in data for the two channels. All per channel transmit module coefficients (such as start time) are presented bit-serially.

The data in the VRAM is organized into runs. A run consists of a one word header, which is interpreted by the VRAM controller, followed by zero or more actual data words which are used by the various modules. The headers (see Table 1) specify where the data in the run is destined, how fast it should be clocked out, and how many values there are in the run. (Note that the run destination is only for the data coming out of the 4 VRAMs. The bits coming out of the controller VRAM always have the same destinations.) The headers are also used to encode the special instructions for Jump, Pause, and End described below.

TABLE 1

| | VRAM Instruction Data Format (Only top VRAM matters) | | | | | | | | | | | | | | | |
|---|---|---|---|---|---|---|---|---|---|---|---|---|---|---|---|---|
| | Bit Position | | | | | | | | | | | | | | | |
| Command | 15 | 14 | 13 | 12 | 11 | 10 | 9 | 8 | 7 | 6 | 5 | 4 | 3 | 2 | 1 | 0 |
| Data | Mod | Sel (2-7) | | Rate | | Length | | | | | | | | | | |
| Pause | 0 | 0 | 1 | Rate (not 0 1) | | Pause Count | | | | | | | | | | |
| Wait | 0 | 0 | 1 | 0 | 1 | 0 | 0 | 0 | 0 | 0 | 0 | 0 | 0 | 0 | 0 | 1 |
| Jump | 0 | 0 | 0 | 0 | 0 | 0 | Jump Addr/0x100 | | | | | | | | | |
| End | 0 | 0 | 0 | 0 | 0 | 1 | X | X | X | X | X | X | X | X | X | X |

The data in the VRAM are read out basically sequentially but some variations are allowed to reduce the memory requirements and facilitate system operation based on several observations about how the ultrasound system operates.

The first observation is that the peak control data rate requirements are far higher than the average rates needed. This is because, during close zone imaging, the focus may be updated at every clock to maintain maximal sharpness. However, for deep zones approaching the far field, the focusing parameters need not vary very quickly. Thus the data may be supplied at a lower rate. This is accomplished by the use of a 2-bit RATE field associated with each run (see Table 2). The RATE field allows the specified run to be clocked out at either the full system clock rate (which can be 8-32 MHZ), one-half, one-quarter, or one-eighth of that rate.

TABLE 1

Rate Field Definitions

| Rate | | Data Meaning | Pause Length |
|---|---|---|---|
| Bit 12 | Bit 11 | | |
| 0 | 0 | New Data Every Clock | PauseCount Clock |
| 0 | 1 | New Data Every Other Clock | PauseCount*2 Clocks |
| 1 | 0 | New Data Every 4 Clocks | PauseCount* Clocks |
| 1 | 1 | New Data Every 8 Clocks | PauseCount*8 Clocks |

The next observation is that there are often large gaps during which time data is not required. After a transmit pulse is fired into a deep zone, a relatively large amount of time can pass before its echo is received and the beamformer is activated. Thus it is advantageous to not have to waste VRAM space for work time periods. For this reason, explicit pause commands are allowed. When the system controller 218 receives a pause command, it waits the specified number of clock cycles before reading the next word in the VRAM memory. The PAUSECOUNT is an 11 bit number which can take on the range 1-2047. This is additionally scaled by the RATE field to allow pauses of up to 16376 (2047*8) system clock cycles. Note that the RATE field can only take on the values 0, 2 and 3 because a pause of RATE 1 is interpreted as a wait command, described next. This is not a problem, however, because typically only RATE 0 is used for maximum wait accuracy (to within one clock) and RATE 3 is used for maximum wait time (up to 16376 clock cycles).

Because the data from the beamformer 116 has to be sent back to the host 5 over a bandwidth-constrained link, buffering and flow-control are required to prevent data loss. The buffering is achieved by a 16K by 18 FIFO while the flow control is achieved by feeding the FIFO fullness indication back to the system controller 218. In this way, if the FIFO becomes too full, the scanning stops until the FIFO has been emptied. However, the scanning should not stop arbitrarily because it is timed with the propagation of the sound waves. Thus explicit synchronization points can be inserted into the code, and at these points the controller waits until the FIFO is empty enough to proceed safely. The wait command is used to indicate these synchronization points. The wait command causes the controller to wait until the WAITPROCEED line is high. In one embodiment, this is connected (via the aux FPGA) to the "not half-full" indicator on the FIFO. Thus the wait commands can be placed at least every 8K data-generating cycles to assure that data overflow cannot occur. Because this is greater than one ultrasound line, it still allows multi-line interleaving to be used.

The next command is the jump command. This allows non-sequential traversal through the VRAM memory. This is employed so that the VRAM memory can be modified concurrently with the readout operation and also to make it easier to add and remove variable size control sequences. To understand why this is useful, consider the following example: Imagine that one wants to change the data in VRAM locations 512-1023 while continuing operation of the scanning using the other locations. If the host were to just modify locations 512-1023, there is no guarantee that they will not be used exactly when they are in the middle of being modified. Thus the data would be in an indeterminate state and can lead to an erroneous sequence. However, if location 512 is first modified to be a jump to location 1024, and locations to 513-1023 are then modified to their new values, and location 512 is then finally modified to its new value, this race condition cannot occur. (Assuming that it is not reading locations 513-1023 at the start of the modifications but blank regions can be left to get around this.) Additionally "subroutines" (which can only be used once per scan due to the fact that the return is coded as an absolute jump) can be used to allow easy change of the scan sequence.

A jump always takes 128 cycles to execute because the system controller has to load this new start address into the VRAMs and transfer the new row of data to the serial shift register. This typically takes only about 25 cycles; but because other parts of the system controller may have access to the VRAM (such as the refresh dr host controller), a safe upper bound is used to maintain a fixed delay.

The last command is the end command. This is used at the end of the sequence for a frame to tell the system controller that the frame has completed. The controller then stops fetching instructions until it is restarted (from location 0) by host if it is in single-frame mode. If it is in continuous mode then it will start immediately on the next 0.5 frame. (After 128 cycles required for the implied jump 0).

Figure 5A:
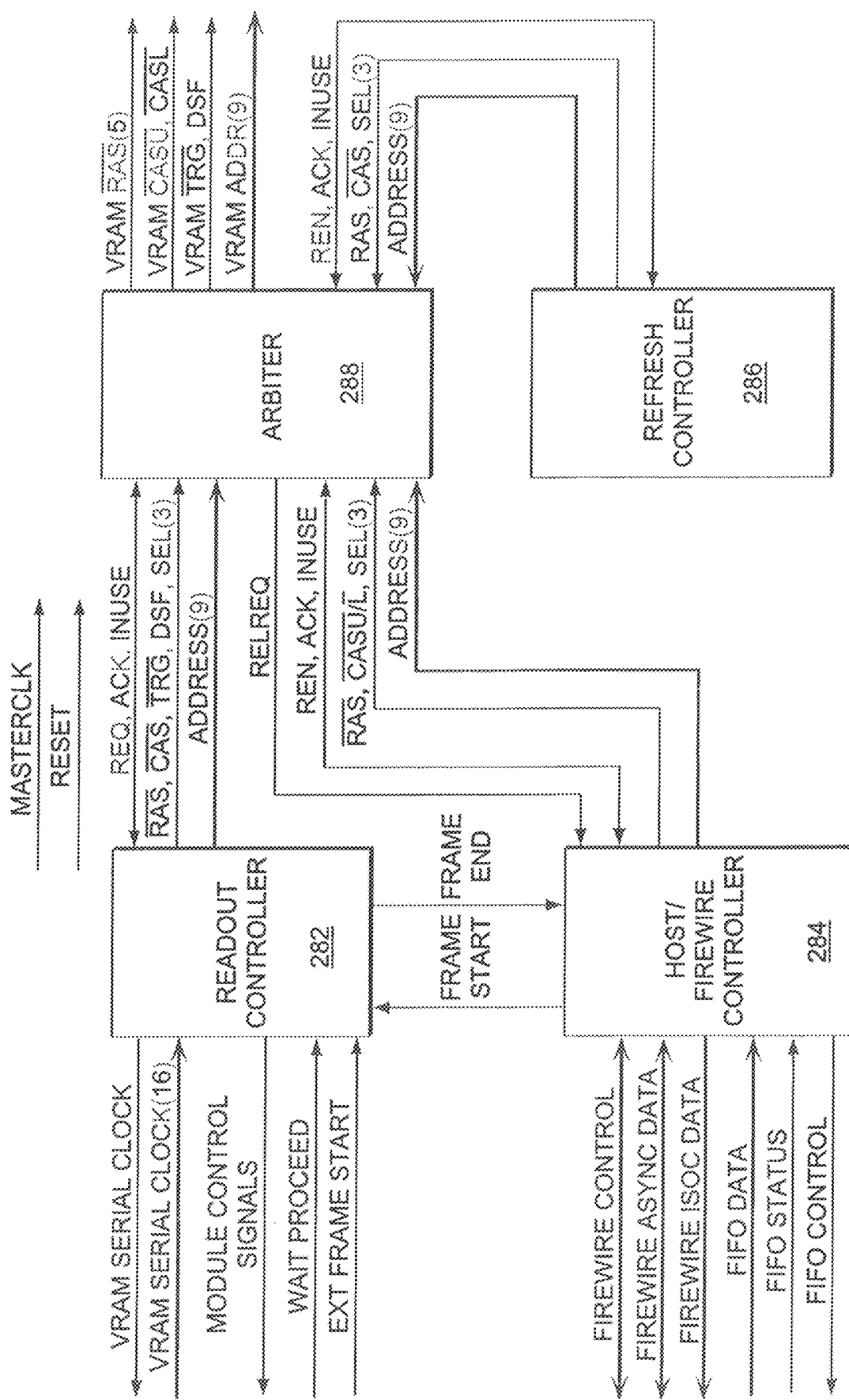
FIG. 5A is a functional block diagram of the system controller of FIG. 3.

FIG. 5A is a functional block diagram of the architecture of the system controller of FIG. 3A. The system controller 218 has four basic parts: a readout controller 282, a host controller 284, the refresh controller 286, and the Arbiter 288. The first three support the three basic operations on the VRAM: reading out data, writing in of data at host'S request, and refreshing the DRAM core. The arbiter 288 is responsible for merging the requests of the first three sections into one connection to the VRAM's DRAM core. Only one of the first three sections can have control at a given time, so the explicitly request control and wait until this request is acknowledged by the arbiter 288. They also must tell the arbiter 288 when they are still using the DRAM so that the arbiter knows not to grant it to one of the other sections. This is done via the INUSE lines.

Additionally the arbiter 288 sends the host controller 284 a RELREQ or relinquish request signal to ask the host controller 284 to give up ownership of the DRAM core because some other section wants it. Note that only the host 284 controller needs to be asked to relinquish the bus because the readout controller 284 and refresh controller 286 both only use the DRAM core for fixed short intervals. The host controller 284, however, can hold on to the DRAM as long as there is data coming over the FireWire to be written into the DRAM, so it needs to be told when to temporarily stop transferring data.

Note that the serial section of the VRAMs is not multiplexed—it is always controlled by the readout controller 282. The VRAM serial data also only goes to the readout controller 282.

The readout controller 282 controls the sequencing of the data out the VRAMs' serial access ports. This involves parsing the data headers to determine what locations should be read, clocking the VRAM Serial Clock at the correct time, driving the module control lines, and also arranging for the proper data from the VRAM's DRAM core to be transferred into the serial access memory.

The host controller 284 is the part of the VRAM Controller that interfaces to the host 5 via FireWire to allow the host to write into the VRAM. When the host wants to write into the VRAM, it sends asynchronous packets specifying which VRAM and which addresses to modify as well as the new data to write. The host controller 284 then asks the arbiter 288 for access to the VRAM. When the DRAM core is not in use by either the readout 282 or refresh 286 controller, the arbiter 288 grants control to the host controller 284. The host controller 284 then takes care of address and control signal generation. When the whole packet has been decoded, the host controller 284 releases its request line giving up the DRAM control, allowing the other two sections to use it.

The refresh controller 286 is responsible for periodically generating refresh cycles to keep the DRAM core of the VRAM from losing its data. The refresh controller 286 has its own counter to keep track of when it needs to request a refresh. Once it gains access to the VRAMs via the arbiter 288, it generates one refresh cycle for each of the VRAMs sequentially. This reduces the amount of spikes on the DRAM power supply lines as compared to refreshing all 5 VRAMs in parallel.

The REFRATE inputs control how many system clock cycles occur between refresh cycles. (See Table 3.) This is compensate for different system clock rates. Additionally, refresh may be disabled for debugging purposes.

TABLE 3

Refresh Rate Definitions

| RefRate1 | RefRate0 | System clock cycles between refresh cycles | Minimum System Clock to achieve 16 μs refresh rate |
|---|---|---|---|
| 0 | 0 | 128 | 8 MHZ |
| 0 | 1 | 256 | 16 MHZ |
| 1 | 0 | 512 | 32 MHZ |
| 1 | 1 | No Refresh | ∞ |

The arbiter controls 288 the access to the VRAM by the Readout, Host, and Refresh Controller 282, 284, 286 sections. Only one section may have access to the DRAM port of the VRAM at any given time. The arbiter 288 does not reassign control of the VRAM to another section until the section with control relinquishes it by deasserting its IN_USE line. The sections are prioritized with the Readout Controller 282 getting the highest priority and the host controller 284 getting the lowest priority. The reasoning is that if the readout controller 282 needs access to the VRAM, but does not get it, then the system may break down as the serial output data will be incorrect. The refresh controller 286 can tolerate occasional delay, although it should not happen much. Finally, the host controller 284 can potentially tolerate very long delays because the host can be kept waiting without too many consequences except that the writing of the VRAM may take longer.

A highly capable, yet cost-effective and physically non-encumbering connection between the scan head and host computer is possible using the FireWire standard (also known as IEEE 1394). The FireWire standard is used for multimedia equipment and allows 100-200 Mbps and preferably in the range of 400-800 Mbps operation over an inexpensive 6 wire cable. Power is also provided on two of the six wires so that the FireWire cable is the only necessary electrical connection to the probe head. A power source such as a battery or IBE1394 hub can be used. The FireWire protocol provides both isochronous communication for transferring high-rate, low-latency video data as well as asynchronous, reliable communication that can be used for configuration and control of the peripherals as well as obtaining status information from them. Several chipsets are available to interface custom systems to the FireWire bus. Additionally, PCI-to-FireWire chipsets and boards are currently available to complete the other and of the head-to-host connection. CardBus-to-FireWire boards can also be used.

Although the VRAM controller directly controls the ultrasound scan head, higher level control, initialization, and data processing and display comes from a general purpose host such as a desktop PC, laptop, or palmtop computer. The display can include a touchscreen capability. The host writes the VRAM data via the VRAM Controller. This is performed both at initialization as well as whenever any parameters change (such as number or positions of zones, or types of scan head) requiring a different scanning pattern. During routine operation when data is just being continually read from the scan head with the same scanning parameters, the host need not write to the VRAM. Because the VRAM controller also tracks where in the scan pattern it is, it can perform the packetization to mark frame boundaries in the data that goes back to the host. The control of additional functions such as power-down modes and querying of buttons or dial on the head can also be performed via the FireWire connection.

Although FireWire chipsets manage electrical and low-level protocol interface to the FireWire interface, the system controller has to manage the interface to the FireWire chipset as well as handling higher level FireWire protocol issues such as decoding asynchronous packets and keeping frames from spanning isochronous packet boundaries.

Asynchronous data transfer occurs at anytime and is asynchronous with respect to the image data. Asynchronous data transfers take the form of a write or read request from one node to another. The writes and reads are to a specific range of locations in the target node's address space. The address space can be 48 bits. The individual asynchronous packet lengths are limited to 1024 bytes for 200 Mbps operation. Both reads and writes are supported by the system controller. Asynchronous writes are used to allow the host to modify the VRAM data as well as a control word in the controller which can alter the operation mode. Asynchronous reads are used to query a configuration ROM (in the system controller FPGA) and can also be used to query external registers or I/O such as a "pause" button. The configuration ROMs contain a querible "unique ID" which can be used to differentiate the probe heads as well as allow node-lockings of certain software features based on a key.

Using isochronous transfers, a node reserves a specified amount of bandwidth, and it gets guaranteed low-overhead bursts of link access every 1/8000 second. All image data from the head to the host is sent via isochronous packets. The FireWire protocol allows for some packet-level synchronization and additional synchronization is built into the system controller.

The asynchronous write request packets are sent from the host to the probehead in order to:

a) Configure the Link Layer controller chip (TI GPLynx or TI GP2 Lynx)

b) Control the system controller FPGA c) Write sequencing data into the VRAM

Both the "Asynchronous Write Request with Block Payload" or the "Asynchronous Write Request with Quadlet Payload" forms can be used. The later simply restricts the payload to one quadlet (4 bytes). The formats of the two packets are shown in Table 4 and Table 5. Note that these are how the packets are passed on by the TI LINK controller chip. The difference between this and the format over the wire is that the CRCs are stripped and the speed code (spd) and acknowledgment code (ackSent) are appended to the end. The Adaptec API and device driver take care of assembling the packets.

TABLE 4

Asynchronous Write Request with Quadlet Payload as Delivered by TI LINK chip

| Word | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 |
|---|---|---|---|---|---|---|---|---|---|---|---|---|---|---|---|---|---|---|---|---|---|---|---|---|---|---|---|---|---|---|---|
| 1 | | | | | | | | | | | | | | | | | destinationOffsetHi | | | | | | | | | | | | | | |
| 2 | | | | | | | | | | | | | | | | | | | | | | | | | | | | | | | |
| 3 | | | | | Data 1 | | | | | | | | | | | | Data 2 | | | | | | | | | Data 3 | | | | | |
| 4 | | | | | | | | | spd | | | | | | | | | | | | | | | | | | | | | ackSent | |

Bit (bit 0 is MSB)

TABLE 5

Asynchronous Write Request with Block Payload as Delivered by TI LINK chip

Bit (bit 0 is MSB)

| Word | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 |
|---|---|---|---|---|---|---|---|---|---|---|---|---|---|---|---|---|---|---|---|---|---|---|---|---|---|---|---|
| 0 | | | | | | | | | | | tLabel | | | | rt | | | tCode = 1 | | | | | priority | | | | |
| 1 | | | | | | | | | | | | | | destinationOffsetHi | | | | | | | | | | | | | |
| 2 | | | | | | | | | | | | | | | | | | | | | | | | | | | |
| 3 | | | | | | | | | | | | | | | | | | extendedTcode | | | | | | | | | |
| 4 | | | | | Data 1 | | | | | | | | | Data 2 | | | | | | | | | Data 3 | | | | |
| 5 | | | | | Data 5 | | | | | | | | | Data 6 | | | | | | | | | Data 7 | | | | |
| 6 | | | | | ... | | | | | | | | | ... | | | | | | | | | ... | | | | |
| 3 + N/4 | | | | | Data N − 3 | | | | | | | | | Data N − 2 | | | | | | | | | Data N − 1 | | | | |
| 4 | | | | | | | | | spd | | | | | | | | | | | | | | | | | ackSent | |

The destinationID field holds the node ED of the destination which is the probe head FireWire controller. The physical layer chip can use this to determine if the packet is for it. The system controller can ignore this field. The tLabel field is used to match requests and responses. For write requests, this does not matter and can be ignored. The rt is the retry code used at link and/or phy level. It is not used by the system controller. The tCode field is the transaction code which determines what type of packet it is. In particular 0 is for quadlet write requests and 1 is for block write requests. The system controller parses this field to determine what type of packet it is. Currently only tCode values of 0 and 1 are recognized. The priority field is used by the PHY chip only and id ignored by the system controller. It is used in, i.e. in selecting which unit on the interface is to receive a particular packet of data.

Next, the destinationOffsetHi and destinationOffsetLo fields form the 48 but destination start address. This indicates within the node what the data should be used for. The system controller used the dtinationOffsetHi to determine the function as shown in Table 6. Note that only the 3 least significant bits of the destinationOffsetHi field are currently examined. The spd field indicates the speed at which the data was sent while the ackSent field is use to indicate status by saying how the LINK chip acknowledged the packet.

TABLE 6

| destinationOffsetHi values | |
|---|---|
| destinationOffsetHi | Meaning |
| 0 | Write VRAM 0 |
| 1 | Write VRAM 1 |
| 2 | Write VRAM 2 |
| 3 | Write VRAM 3 |

TABLE 6-continued

| destinationOffsetHi values | |
|---|---|
| destinationOffsetHi | Meaning |
| 4 | Write VRAM 4 |
| 5 | Write ISO packet Length Register |
| 6 | Write System Controller Mode Word |
| 7 | Wrote to LINK chip |

As can be seen, destinationOffsetHi values of 0-4 correspond to writing the VRAMs. In this case the destinationOffsetLow is set to the byte address to start writing. This is twice the standard VRAM address which is typically formed in 16-bit words. Note also that the start address (destinationOffsetLow) and the length (dataLength) can both be multiples of 4 such that all operations are quadlet aligned. The payload data is little endian and thus need not be converted if written by an Intel PC host. The length (dataLength) must additionally be between 4 and 128 bytes due to the size of the GPLynx FIFO. The total FIFO size is 200 bytes, but 72 bytes are dedicated to the asynchronous transmit FIFO required for read responses.

A destinationOffsetHi value of 5 signifies that the system controller ISO Packet Length register is to be written. The ISO Packet Length has to be set in the controller to allow it to correctly format the ISO packets back to the host via FireWire. An explicit counter in the system controller is used due to the fact that the TI GPLynx chip does not assert the end-of-packet indication until one word too late. Note that the ISO Packet length also has to be set in the LINK chip. The value written is the number of 16-bit words in the ISO Packet length which also has to be set in the LINK chip. The value written is the number of 16-bit words in the ISO packet (i.e. bytes/2) and it is written in little endian order because it is only interpreted by system controller and not the LINK chip.

Specifying a destinationOffsetHi value of 6 signifies that the system controller mode word is to be modified. Currently only the least significant 16 bits are used out of each quadlet and all quadlets go to the same place so writing multiple values just causes the system controller mode word to be rewritten. Please note that the payload data is again little endian. (Putting these two facts together yields that the first two out of every four bytes are used and the second two are ignored.) The definition of the system controller Mode Word is given in Table 7.

TABLE 7

| System Controller Mode Word Bit (bit 31 is MSB) | | | | | | | | |
|---|---|---|---|---|---|---|---|---|
| 31-36 | 15-8 | 7 | 6 | 5 | 4 | 3 | 2 | 1 | 0 |
| unused | BOF Word | unused | unused | Abort Frame | Single Frame | Run | Extra 2 | Extra 1 | Data Loop-back |

The BOF Word field is used to set the value that the system controller will put in the high byte of the first word of an isochronous packet to indicate the beginning of frame. The BOF word field can be set to some value that is not likely to occur in typical data. This not crucial, however, because choosing a BOF word that occurs in the data will make it more likely to miss incorrect frame synchronization but will never cause false alarms where it thinks it is mis-synchronized but is really correctly synchronized. The initial value upon reset is 80 hex.

The AbortFrame, SingleFrame, and Run bits are used to control the system operation. Their use is shown in Table 8. The data FIFO is never allowed to fully empty so an entire frame can not be read out until part of the next one is the queue.

TABLE 8

Use of AbortFrame, SingleFrame, and Run bits in System Controller Mode Word

| Abort Frame | Single Frame | Run | Meaning |
|---|---|---|---|
| 1 | 0 | 0 | Abort an current frame and wait |
| 0 | 1 | 0 | Start a single new frame |
| 0 | 0 | 1 | Keep scanning new frames |
| 0 | 0 | 0 | Let any current frame complete |

The DataLoopback bit is used to control whether the data that is read back from the host comes from A/D or from one of the VRAMs. (Currently this is VRAM 1.) This second option can used for test purposes to test the digital data generation and collection without testing the beamformer and A/D conversion. A 0 in the DataLoopback bit indicates normal operation of reading from A/D while a 1 means that it should get data from the VRAM.

The Extra1 and Extra2 bits are available for general use. They are latched by the system controller and currently brought out on pins called EXTRACLOCK0 and EXTRACLOCK1 but can be used for any purpose.

Finally setting destinationOffsetHi to 7 indicates that the data in the asynchronous packet be written back to the FireWire Link chip. This allows any of the TI TSB12LV31's (or 32's) registers to be modified by the host. This can be used to configure and enable the Isochronous data transmit. The destinationOffsetLow specifies the first register to write. Because the registers are all 4-bytes in size and must be written in their entirety, destinationOffsetLow and dataLength must both be multiples of 4. Multiple consecutive registers can be written with a single packet. Note that the data is big-endian because the TSB12LV31 is designed as big-endian. This byte-swapping must be performed by the Intel PC host.

Read request packets are used to asynchronously read data from the probehead. This currently only consists of configuration ROM data (see below) but can be easily used for other types of data such as status information or button indications.

The Adaptec device drivers send Asynchronous Read Requests in response to explicit application requests as well as to interrogate the node's FireWire configuration ROM in response to a SendPAPICommand of P_GET_DEV_INFO or after a bus reset or when an application tries to obtain a handle to a node.

Asynchronous read requests can either be of the quadlet or block variety as with the asynchronous write requests. The formats are shown in Table 9 and Table 10. They are similar to the write request formats.

TABLE 9

Asynchronous Read Request with Quadlet Payload as Delivered by TI LINK chip

| | Bit (bit 0 is MSB) | | | | | | | | | | | | | | | | | | | | | | | | | | |
|---|---|---|---|---|---|---|---|---|---|---|---|---|---|---|---|---|---|---|---|---|---|---|---|---|---|---|---|
| Word | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 |
| 0 | | | | | | | | | | | | | | tLabel | | | | rt | | tCode = 4 | | | | priority | | | |
| 1 | | | | | | | | | | | | | | | | | | destinationOffsetHi | | | | | | | | | |
| 2 | | | | | | | | | | | | | | | | | | | | | | | | | | | |
| 4 | | | | | | | spd | | | | | | | | | | | | | | | | | | ackSent | | |

TABLE 10

Asynchronous Read Request with Quadlet Payload as Delivered by TI LINK chip

| Word | Bit (bit 0 is MSB) |
|------|---------------------|
| 0 | tLabel (14–19), rt (22–23), tCode = 5 (24–27), priority (28–31) |
| 1 | destinationOffsetHi |
| 2 | |
| 3 | extendedTcode |
| 4 | spd, ackSent |

As with the asynchronous write packets, the destinationOffsetHi and destinationOffsetLow determine what is being requested. The high addresses are defined for use as Control and Status Registers and the configuration ROM while the lower address are for more general purpose use. In particular, the FireWire configuration ROM starts at destinationOffsetHi=0xffff, and destinationOffsetLow=0xf0000400, for example.

When the system controller receives a Quadlet or Block Read Request packet from the TI LINK chip's General Receive FIFO, it formulates a Quadlet or Block Read Response packet and places it in the LINK chip's Asynchronous Transmit FIFO. The format of these packets (as placed in the Asynchronous Transmit FIFO) is shown in Table 11 and Table 12.

packet was invalid or unsupported. In this case, if the request was a block request then the dataLength of the response packet must be 0 and no data should be included. A resp_type_error is returned if the dataLength or destinationOffsetLow of the request packet were not multiples of 4 or if the dataLength was not between 4 and 32 (for block packets). This is because the TI chip's asynchronous transmit FIFO is configured to be 12 quadlets (for 8 payload quadlets +4 quadlet header) so that the receive FIFO can be 36 quadlets in order to allow 128 byte payload write packets. The longest request the Adaptec device drivers should request is 8 quadlets because that is the length of the configuration ROM. In any case, it is assumed that if a long transfer failed, it falls back to a smaller request.

TABLE 11

Asynchronous Read Response with Quadlet Payload as Expected by TI LINK chip

| Word | Bit (bit 0 is MSB) |
|------|---------------------|
| 0 | spd (14–17), tLabel (18–23), rt (24–25), tCode = 6 (26–27)... priority (28–31) |
| 1d | rCode (10–15), reserved = 0 (24–27) |
| 2 | |
| 3 | Data 1, Data 2, Data 3 |

TABLE 12

Asynchronous Read Response with Block Payload as Expected by TI LINK chip

| Word | Bit (bit 0 is MSB) |
|------|---------------------|
| 0 | spd, tLabel, rt, tCode = 7, priority |
| 1 | rCode, reserved = 0 |
| 2 | |
| 3 | extendedTcode |
| 4 | Data 1, Data 2, Data 3 |
| 5 | Data 5, Data 6, Data 7 |
| ... | ... |
| 3 + N/4 | Data N − 3, Data N − 2, Data N − 1 |

The spd, tLabel, rt, and priority values are copied from the request packet. The destinationID is taken from the sourceID of the request packet. Note that all packet CRCs are generated by the TI LINK chip and are thus note included the data that the system controller must generate. (The ROM CRCs do have to be computed explicitly off-line.) The rCode field is used to indicate the status of the reply. In particular, 0 means resp_complete indicating all is well. A value of 6 means resp_type_error indicating that some field of the The FireWire specification expects each FireWire node to have a configuration ROM that contains various details about the device, its requirements, and its capabilities. This ROM is to be queried via Read Request packets. There are two types of ROM implementations: a minimal ROM and a general ROM. The former has only one quadlet (4-byte) piece of data indicating a 24-bit vendor DD. The general ROM has many other fields, and many which are optional ranging from the ASCII name of the vendor and device to its power consumption and how to access its capabilities.

One of the required fields in a general ROM is a node unique ID. This consists of the 24-bit vendor ID and a 40-bit chip ID. The 40-bit chip-ID is up to the vendor to assign such that all nodes have unique values. The node unique ID's are required to keep a consistent handle on the device if the FireWire bus is reset or reconfigured during operation. When a device is first opened, the application reads its configuration ROM and determines if it wants to work with it. If so it records its node unique ID and opens a connection to the device via that node unique ID. This is then at any given time mapped to its FireWire ID (16-bit) by the host adapter and its device driver. If the topology changes or a FireWire bus reset occurs, the node's FireWire ID can change, however the node unique ID will not. Thus, in such an event, the adapter automatically determines the new FireWire ID and continues. Thus for smooth operation, particularly with multiple heads attached to the system, implementing node unique IDs and the configuration ROM is required.

The configuration ROM is divided into several sections. The sections of particular interest are the first word, which defines the length and CRC of the ROM, the next 4 words comprising the Bus_Info_Block, which gives some fixed 1394—specific information (such as Node Unique ID), and the last 3 words representing the Root Directory which is a set of key-value tagged entries. Only the two required key-value pairs are included the ROM built into the FPGA. An 8-word ROM that can be used is shown in Table 13.

then use the Sync field to assure proper frame alignment. However, the TI GPLynx Controller chip only supports frame-level granularity of when to send packets and not packet level so when the System Controller tells the FireWire link chip it has data, it must be prepared to send a whole frame of data. Because the FIFO is much smaller than a frame, a sage option is to reduce the effective FireWire frame size to one packet. Then a specific Beginning of Frame (BOF) code in the high byte of the first word of every ultrasound frame and force the start of ultrasound frames to occur at the beginning of FireWire frames (and packets) and do frame-level synchronization in the Ultrasound application software. For efficiency, a full ultrasound frame of data can still be read in one FireWire call (and hence one interrupt).

There are three steps in setting up for Isochronous head-to-host data transfers. These initialization steps need only be performed once per probe initialization.

The first step is to reserve isochronous bandwidth. This reservation causes a central record of the request (in the FireWire isochronous cycle manager node) to be kept to assure that the total bandwidth allocated does not exceed the total bandwidth of the link. For example, this reservation is achieved using the Adaptec API BusConfig 0 command with Cmd field set to P_ALLOCATE_RESOURCE. A requested payload in bytes is passed in. This can be the amount of data desired in every 1/8000 second. Setting this value too high simply wastes reserved bandwidth on the FireWire interface which is not a problem if there is only one device. Setting this value too low may constrain the head-to-host data rate.

TABLE 13

| | Fire Wire Configuration ROM built into FPGA | | | |
| --- | --- | --- | --- | --- |
| | Bit (bit 0 is MSB) | | | |
| Word 5 6 7 8 9 10 11 12 13 14 15 | 16 17 18 19 20 | 21 22 23 | 24 25 26 27 | 28 29 30 31 |
| 0 crc_length = 0x07 | | rom_crc_value = 0xfbc8 | | |
| 1 0x33 ("3") | 0x39 ("9") | | | 0x34 ("4") |
| 2 cyc_clk_acc = 0xff | max_rec = 6 | | reserve = 0x000 | |
| 3 | | | chip_is_hi = 0 | |
| 4 | | | | |
| 5 | | | Root_Dir_CRC = 0xbc8e | |
| 6 | module_vendor_id = 1234567 (0x12d687) | | | |
| 7 | node_capabilities = 0x000000 | | | |

Isochronous packets are used for the probehead-to-host communication of beamformed data. This is conceptually a stream of 16-bit numbers punctuated by frame markers. The frame markers are important to keep in sync with where in the frame the data corresponds. While some ultrasound systems use elaborate frame and line markers embedded in the data, the integrated system can use a single auxiliary bit, which is not sent as part of the data, to mark frame boundaries. Line boundaries can be derived by knowing the VRAM sequencing program.

While asynchronous packets can be sent at will and do not have any guarantee of bandwidth availability, isochronous packets can be used as low-overhead way to send a guaranteed rate of data. Once a peripheral reserves a specified amount of bandwidth, it gets guaranteed bursts of link access every 1/8000 second. All data from the head to the host is sent via isochronous packets. Because isochronous packets are limited to 1/8000 second, this is a frame of data. The FireWire specification describes the use of synchronization bits which can be used to tag each isochronous packet with a 4 bit SYNC code. The Adaptec FireWire-to-PCI bridge can No overflows or data loss are likely to occur, the scanning may simply proceed slower. The resource allocation call will return both an isochronous channel number as well as the payload size granted. This payload size granted may be less than that requested if part of the link has already been reserved.

The next step is to set the system controller ISO packet length word to tell how long of an ISO packet to expect.

The final step is to initialize the probehead LINK chip. This is done via the writeback to LINK chip asynchronous packets described above. In particular, initializing registers 54h, 58h, and 5ch is necessary. The probehead can then be told to start sequencing and the data will flow back.

If multiple probes are connected to the system then the isochronous bandwidth reservation can take place once but at any given time, only one probe's isochronous transmission (as well as its sequencing) is enabled.

As previously described, isochronous data transfers are used to deliver the probe head data to the host. Maintaining frame synchronization is necessary. The FireWire will support sub-frame packetization of about 3000 bytes but it is up to the system controller to implement frame synchronization on top of this. Synchronization is achieved via two methods:

1. The high byte of the first word in the first packet of a frame is set to the Beginning of Frame (BOF) code. (This can be set in the system controller Mode word).

2. All frames are padded to consume a whole number of packets.

When these two are combined, they guarantee that frame synchronization will be maintained if the correct number of packets are read at a time and the resynchronization can be effected by just scanning the high-byte of the first word of each packet in the data stream.

An example packetization is shown in Table 14. This depicts 4 packets of 4 words (8 bytes) apiece showing one complete ultrasound frame and the first packet of the next frame. The ultrasound frame size is 10 words. As can be seen, the Hi byte of the first word is set to the BOF code. This can be examined to assure that proper synchronization has been maintained. The data is then split into the three packets 1-3. Because the frame ends in the middle of packet 3, the end of packet 3 is padded with the BOF code in the high word. Importantly, this means that the first word of the fourth packet will be the first word of the second frame even though the ultrasound frame size is not a multiple of the packet size.

TABLE 14

Example Packetization of Isochronous Head-to-Host Data

| Packet | Word | Lo Byte | Hi Byte |
|---|---|---|---|
| 1 | 1 | Data 1 Lo | BOF |
| (Frame 1) | 2 | Data 2 Lo | Data 2 Hi |
| | 3 | Data 3 Lo | Data 3 Hi |
| | 4 | Data 4 Lo | Data 4 Hi |
| 2 | 1 | Data 5 Lo | Data 5 Hi |
| (Frame 1) | 2 | Data 6 Lo | Data 6 Hi |
| | 3 | Data 7 Lo | Data 7 Hi |
| | 4 | Data 8 Lo | Data 8 Hi |
| 3 | 1 | Data 9 Lo | Data 9 Hi |
| (Frame 1) | 2 | Data 10 Lo | Data 10 Hi |
| | 3 | Data 1 Lo | BOF |
| | 4 | Data 1 Lo | BOF |
| 4 | 1 | Data 1 Lo | BOF |
| (Frame 2) | 2 | Data 3 Lo | Data 2 Hi |
| | 3 | Data 3 Lo | Data 3 Hi |
| | 4 | | |

The TSB 12LV31 (or 32) performs packetization of the isochronous data but informs the system controller of packet boundaries via the ISORST signal The system controller then uses this to reset its internal word-to-byte multiplexer as well as packetization circuitry. If it receives a frame marker from the FIFO then stops clocking data out of the FIFO until it receive a ISORST pulse.

The module interface defines how the various modules in the system are controlled by the VRAM controller. There are two types of modules, those that receive data from the four VRAMs which are shared (two on each analog board), and those that receive data from the VRAM on the digital board, (via the VRAM controller) which is dedicated. The two types of modules use different control signals to synchronize their operation.

Figure 5B:
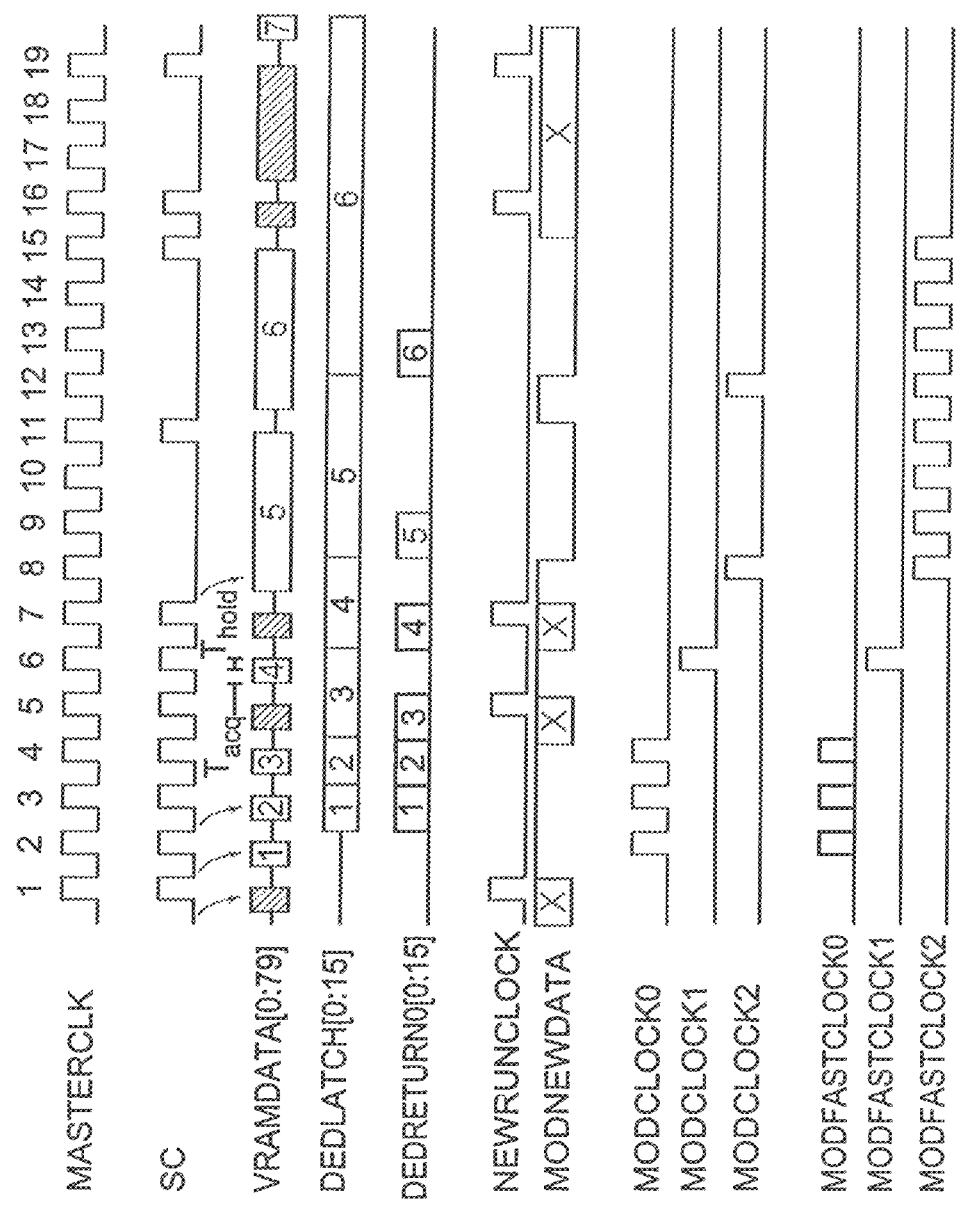
FIG. 5B schematically illustrates a timing diagram for the control of modules in the system.

Much of the timing depends on the speed of the runs of the module (shared/dedicated VRAM usage.) FIG. 5B shows typical timing for the different module interfacing modes for a typical program sequence.

As previously stated, VRAMDATA, the data from the loopback VRAM, control the execution. The diagonal shaded boxes denote header data used by the VRAM controller while the shaded boxes denote module data in FIG. 5B. The data in the four other VRAMs go to the modules. The data from the first VRAM is looped back into the system controller and then used for dedicated data supply for things like the TGC, feedback control, etc.

In clocks 1-4 in FIG. 5B a run of data at a rate 1/1 destined for module 0. The header is clocked out at clock 1. The pulse of NEWRUNCLOCK at clock 1 lets the modules know that the next clock will be the first in a run. They thus reset their internal run-related state if necessary. The data is clocked out during clocks 2, 3, and 4. Since the data is destined for module 0, the MODCLOCK0 is pulsed once per new data word. Module 0 should latch the data at VRAMDATA on the rising edge of MODCLOCK0.

Note that the access and hold times of the VRAM ($T_{acc}$ and $T_{hold}$, in FIG. 5B) must be observed carefully. Since the access time of the VRAM is 15 ns-25 ns depending on the speed grade the hold time can be as low as 4 ns, this does not leave a lot of margin when operating at data no earlier than $T_{clk}$-$T_{acc}$ before the rising edge of their module clock. (Any skew between SC and the MODCLOCK tightens this bound accordingly but due to the way the VRAM controller was designed to generate both signals as gated clocks from the same MASTERCLK the skew is minimal assuming that the loading conditions are not too dissimilar) given a master clock frequency of 33 MHz and the fast VRAM, this gives 15 ns slack. Using the slower VRAMs gives 5 ns slack.

The modules accepting data at the full rate must additionally make sure that they do not latch the data more than $T_{hold}$ after the rising clock. This is because the same clock is used to retrieve the next words from the VRAM Thus in general modules should make sure to delay the data inputs at least as much as they delay the clock inputs to effectively clock at or before the rising edge of their module clock. This second constraint does not exist when 1/2, 1/4, or 1/8 rate data is used.

Since the first example is of 1/1 rate data, the MODULEFASTCLOCK0 signal follows the MODULECLOCK0 line. They will only differ when 1/2, 1/4, or 1/8 rate data is used.

Clocks 7-15 show a run of length 2 at rate 1/4 destined for Module 2. Thus new data will be clocked out of the VRAMs only once every $4^{th}$ master clock. Here MODULEFASTCLOCK2 will exhibit different behavior than MODULECLOCK2. Again the NEWRUNCLOCK at clock 7 signals that a new run is beginning on the next clock cycle. During clock 7, the VRAM controller has latched the header data indicating that the next run is for module 2 at a rate of 1/4. Also during clock 7, the VRAM generates the module data that the module will use. At clock 8, a MODCLOCK2 occurs, telling module 2 to latch in and use the VRAM's data. Note that the data will present until the master clock before the next MODCLOCK2.

Although MODCLOCK2 is only clocked once per new data word; MODULEFASTCLOCK2 is clocked once per master clock for the duration of the run. This is useful for modules, such as the beamformer which may only need data at a lower rate but need to perform computation at the full rate. The MODNEWDATA signal can also be used by modules using the MODFASTCLOCK lines to determine on which of the fast clocks new data has been presented.

Clocks 16-18 show the result of a pause command. Here the NEWRUNCLOCK is sequenced as usual but no MODCLOCK or MODFASTCLOCK is generated.

Figure 4B:
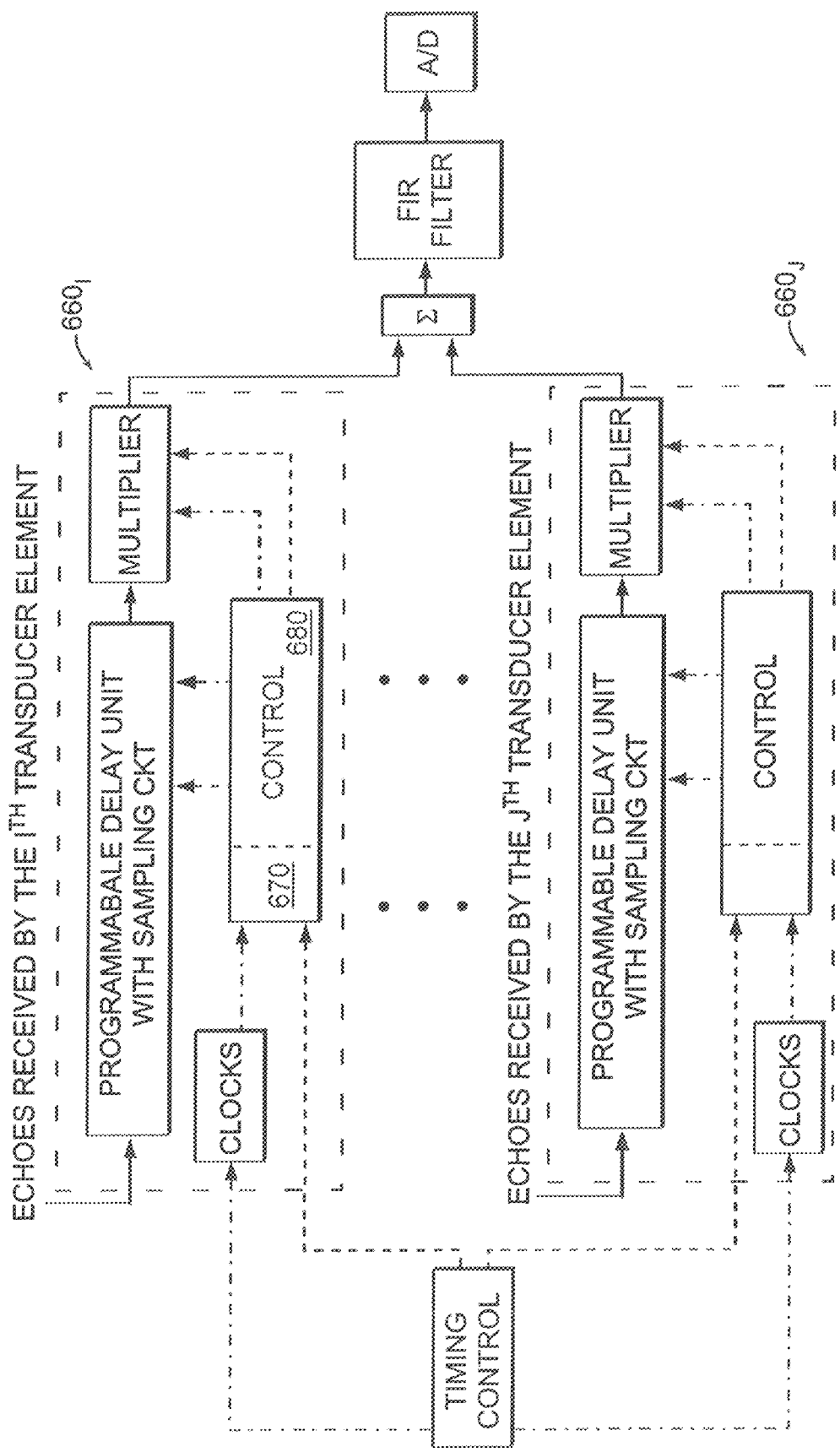
FIG. 4B illustrates another preferred embodiment of a beamformer in accordance with the invention.

As noted above, the particular embodiment was chosen based on a number of criteria, including simplicity of implementation using an FPGA. This motivated the use of VRAMs. An ASIC interface using more dense SDRAM requires at least some buffering, but this can be built into the controller, or alternatively; with the beamformer, T/R circuit or amplifier modules. In this way they receive bursts of data ss opposed to the simple synchronous, continuous data that the above system supplies. The benefit is that SDRAMs are more dense and can provide data at higher rates, which reduces the parts count. Such a configuration is shown in FIG. 4B, for example, in which the 64 or 128 channel ($660_i$-$660_j$) system is configured on one or two printed circuit boards. In this two board system, the T/R circuit and the preamplifier/TGC circuit are fabricated in a single integrated circuit and are placed on one board with a CDP beamformer that is formed as a second integrated circuit. The beamformer control circuits can include the calculation of weighted inputs with processor 670. The memory for this system is either a SDRAM or VRAM located on the second board along with the system controller and the digital communication control circuit.

Returning to FIG. 3A, the standard FireWire cable 40 includes a plurality of FireWire signal lines 42 and a FireWire power line 44. In order to provide the necessary voltages, the FireWire power line 44 is fed to an inline DC-DC converter 300. The DC-DC converter 300 generates the necessary voltages and provides them over a plurality of power lines 46. These new power lines 46 are repackaged with the FireWire signal lines 42 in a custom cable 40'. In the probe housing 3', the FireWire signal lines 42 are connected to the FireWire chipset 220 and the custom power lines 46 are connected to a power distributor 48, which filters and distributes the various voltages over respective internal voltage lines 148A, 148B, 248. In addition, the power distributor 48 may perform additional DC-DC conversions, as described in more detail below.

The transmit/receive control chip is needed to interface with the transducer array. In a transmit mode, the chip can provide delays to the high-voltage driving pulses applied to each of the selected transducer elements such that the transmitted pulses will be coherently summed on the image place at the required transmit focus point. In a receive mode, it provides connection of the reflected sound waves received by a selected element to its corresponding amplifier. The functions of a multi-channel transmit/receive chip can be separated into two parts: a core function which provide low-voltage transmit/receive control and a buffer function which level shifts the low-voltage transmit/receive control into high voltage and directly interfaces with the transducer array. The core function of the transmit/receive chip includes a global counter which broadcasts a master clock and bit values to each channel processor; a global memory which controls transmit frequency, pulse number, pulse sequence and transmit/receive select; a local comparator which provides delay selection for each channel. For example, for a 60 MHZ clock and a 10 bit global counter, it can provide each channel with up to 17 μs delay; a local frequency counter which provides programmable transmit frequency; a local pulse counter which provides different pulse sequences. For example, a 7-bit counter can provide programmable transmitted pulse lengths from one pulse up to 128 pulses; a locally programmable phase selector which provides sub-clock delay resolution. For example, for a 60 MHz master clock and a two-to-one phase selector provides 8 ns delay resolution.

While typically the period of the transmit-chip clock determines the delay resolution, a technique called programmable subclock delay resolution allows the delay resolution to be more precise than the clock period. With programmable subclock delay resolution, the output of the frequency counter is gated with a phase of the clock that is programmable on a per-channel basis. In the simplest form, a two-phase clock is used and the output of the frequency counter—is either gated with the asserted or Deasserted clock. Alternatively, multiple skewed clocks can be used. One per channel can be selected and used to gate the coarse timing signal from the frequency counter.

Figure 3C:
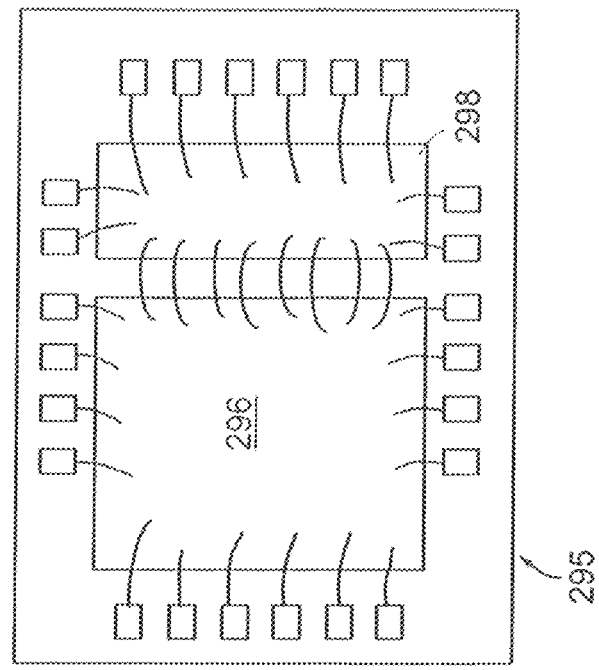
FIGS. 3B and 3C illustrate embodiments of the transmit/receive circuit.
Figure 3B:
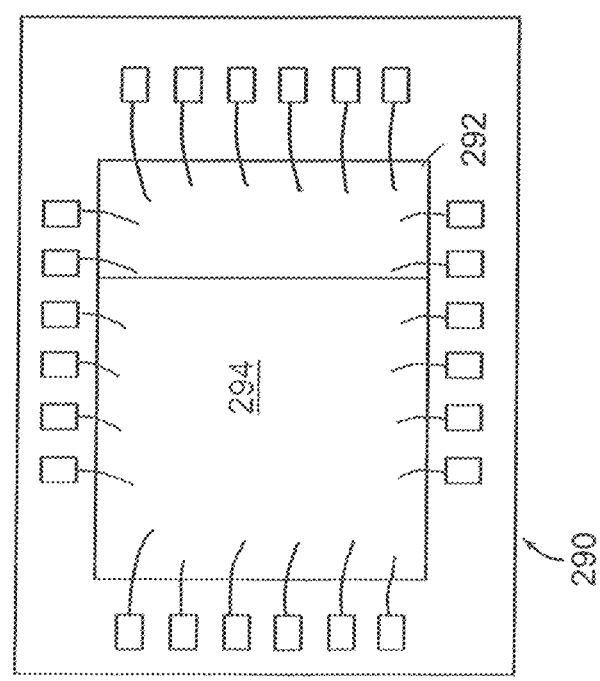

As can be seen in FIG. 3B, a semiconductor process that can support both high-voltage and low-voltage operations is ideally matched for a single-chip solution to the transmit/receive chip described above. The core function of the transmit/receive chip can be implemented on low-voltage transistors to reduce power consumption. The level-shifting function can be implemented on high-voltage transistors to provide the necessary-driving pulses to the transducer array. However, only selected semiconductor processes can make the integration of both high-voltage (buffer 292) and low-voltage transistors (294) on one chip 290 possible. As a result, the high/low voltage process has been so far offered only with 0.8-to-1 um-design-rules. With these design rules, a 64-channel transmit/receive chip can easily be integrated on a single chip in less than 1 cm$^2$ chip area.

In order to save power and silicon area, a multi-chip module 295 can be used to implement a transmit/receive chip. For example, a deep-sub-micron process can be used to implement the core function 296 of the module, and a separate process can be used to implement the buffer 298 function. As shown in FIG. 3C, the multi-chip set can be mounted in a single package to realize the transmit/receive control function. With multi-chip module approach, a 128-channel transmit/receive controller can easily be integrated on one package.

Figure 3D:
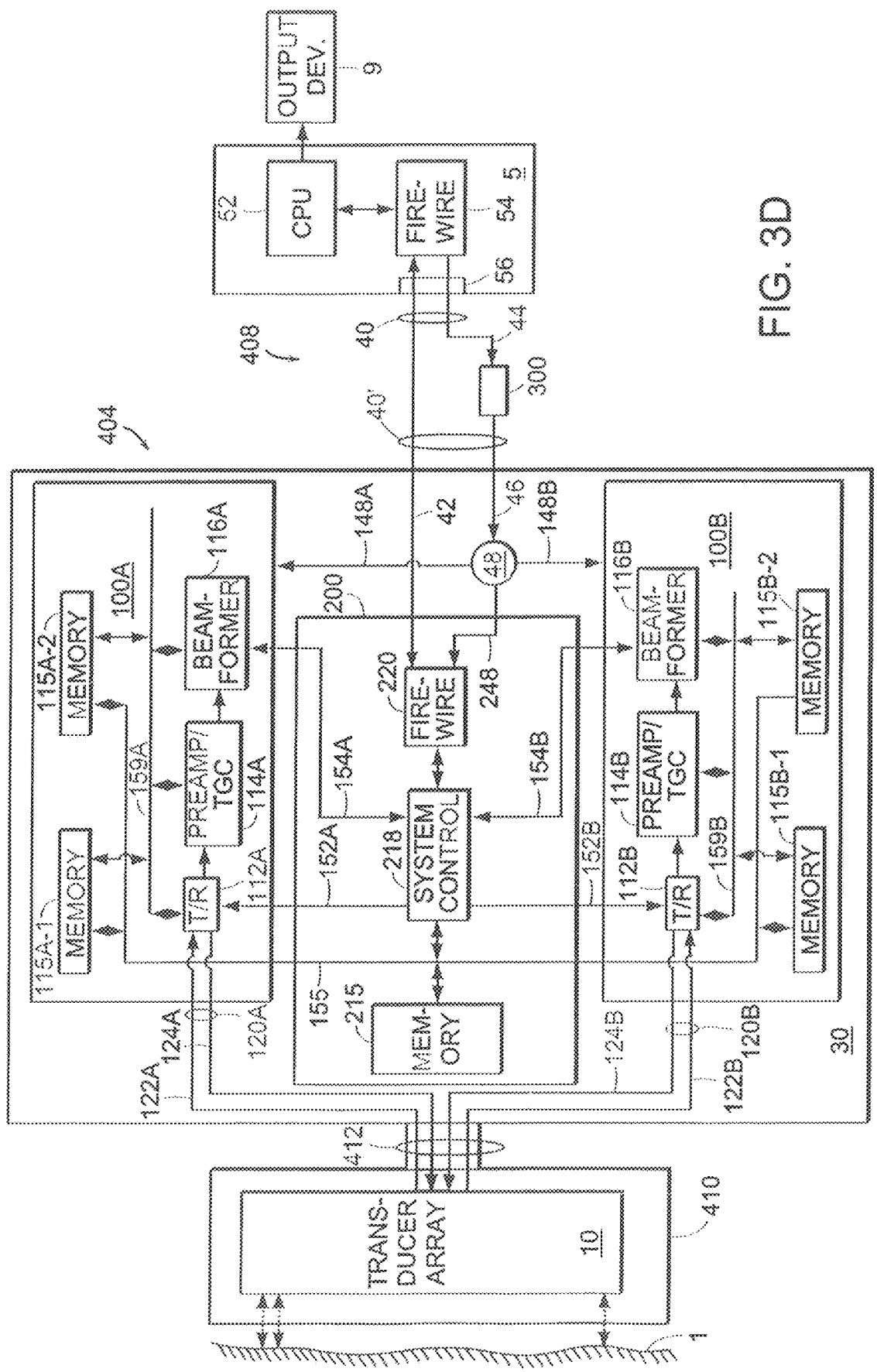
FIG. 3D illustrates an alternate embodiment in which the probe housing is separated from the interface housing by a cable.

FIG. 3D illustrates an alternate embodiment in which the transducer array 10' is located in a separate probe housing 410 connected to the interface housing 404 by a cable 412. Such a system is also illustrated in connection with FIG. 12. Note that another embodiment involves a probe housing in which certain circuit elements such as the transmit/receive circuitry and/or the preamp/TGC circuitry is included with the transducer army while the beamformer, system control and memory circuits remain in the interface. The system in FIG. 3D provides for the use of standard probes and a beamformer interface that weighs less than 10 lbs and which can be connected to a standard personal computer. The interface 404 has a volume of less than 1500 cm$^3$ and a weight that is preferably less than 5 lbs.

Figure 6:
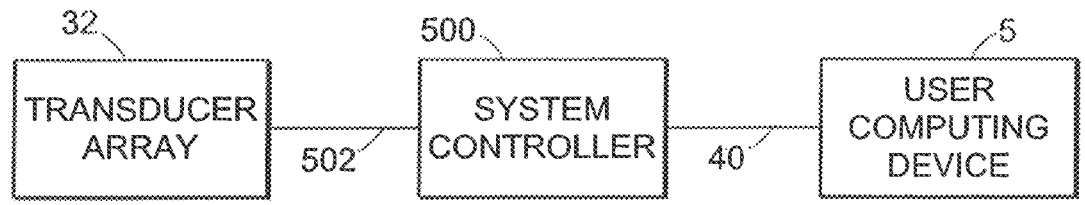
FIG. 6 shows a block diagram of an ultrasonic imaging system adapted for external application integration as defined by the present claims.

FIG. 6 shows a block diagram of another particular embodiment of an ultrasonic imaging system adapted for external application integration. Referring to FIG. 6, the transducer array housing 32 and associated circuitry are connected to a system controller 500 via an ultrasound (US) interface 502. The system controller 500 is connected to a host user computing device 5 such as a PC via a standard interface 40 which is a predetermined communication link, such as an IME 1394 interface, also known as FireWire. The US data therefore, is transmitted to a user computing device 5 via the standard interface 40, relieving the need for specialized components to be employed in the user computing device 5. The user computing device 5 therefore provides an ultrasonic application server which may be integrated with an external application, as will be described further below.

The ultrasonic application server running on the user computer device 5, therefore, receives the US data, and makes it available to be invoked by an external application for further processing. The external application may be either local, and therefore running on the user computer device 5, or remote, and accessing the ultrasonic application server remotely.

Figure 7A:
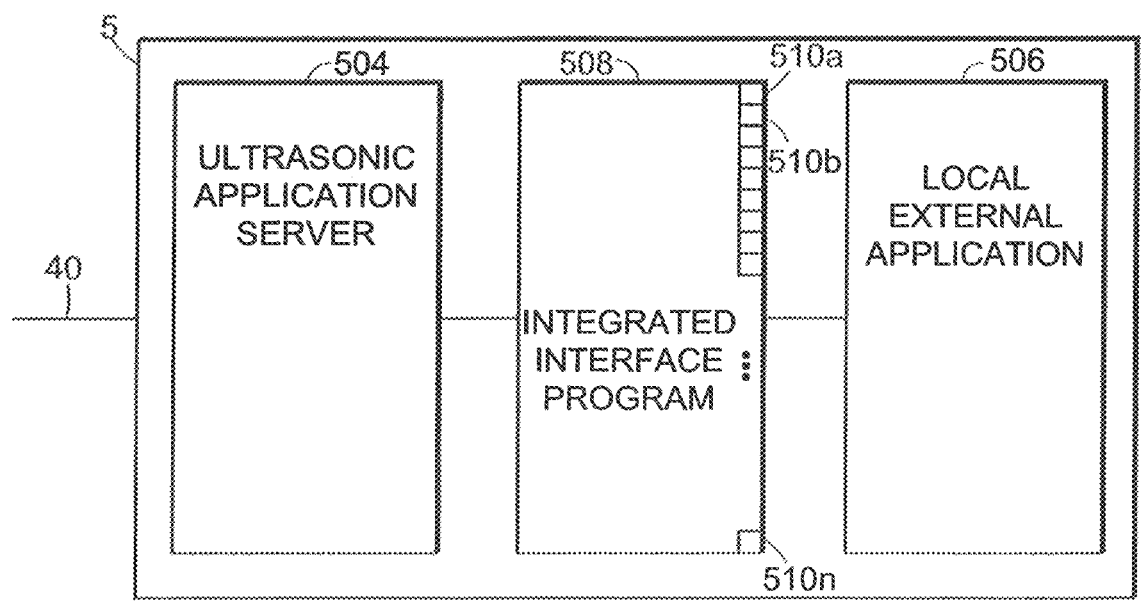
FIG. 7A shows an integrated interface program operable for use with a local external application.

FIG. 7A shows an integrated interface program operable for use with a local external application. Referring to FIG. 7A, the ultrasonic server application 504 is running on the user computing device 5. A local external application 506 is also running on the user computing device 5, and transmits to and from the ultrasonic server application 504 via an integrated interface program 508. The integrated interface program 508 contains a series of predetermined entry points 510a . . . 510n corresponding to operations which the ultrasonic application server 504 may perform on behalf of the local external application 506. The local external application 506 sends a command, which includes an instruction and optional parameters as defined by the predetermined entry points 510. The local external application 506 transmits the command to the ultrasonic server application 504 by invoking the entry point 510n in the integrated interface program which corresponds to intended operation. The entry point may be invoked by procedure or function call via a stack call, message transmission, object passing, or other suitable interprocess communication mechanism. In a particular embodiment, Windows® messages may be used.

The command is received by the ultrasonic server application 504 via the desired entry point 510n from the integrated interface program 508, and is processed. The ultrasonic server application 504 executes a result corresponding to the desired function, and transmits the result back to the external application 506 via the integrated interface program 508, typically by similar interprocess communication mechanisms employed in transmitting the corresponding command. The operations performed by the ultrasonic application server may include the following as referenced in Table 15:

TABLE 15

| OPERATION | DESCRIPTION |
| --- | --- |
| Freeze Image | Freeze active ultrasound data image; used to capture still frames |
| Resume Live | Obtain realtime ultrasound image |
| Export Frame | Export a frame of ultrasound image data in a format as determined by the parameters |
| Application Status | Return a status code of a previous operation |
| Initialize | Initialize Ultrasonic Application Server to begin receiving commands from an external application |
| Exit Application | Disconnect external application from the Ultrasonic Application Server | and may also include others by defining an entry point in the integrated interface program 508 and a corresponding operation in the ultrasonic server application 504.

The result received by the local external application 506, therefore; may be employed and analyzed by any functions provided by the local external application 506. The local external application 506 may be extended and modified to provide desired functions without modifying the ultrasonic application server 504 or the integrated interface program 508. Further, additional entry points 510n to other operations provided by the ultrasonic server application 504 may require only modification of the integrated interface program 508. Further, multiple external applications may access the integrated interface program 508 by computing the proper instructions and parameters of the commands as defined by the integrated interface program 508.

In particular embodiments, the external application is operable to process 2 dimensional and 3 dimensional radiation therapy data, fetal image data, cardiac image data, and image guided surgery data. Such applications are employed in the medical field by operators such as surgeons to provide visual feedback about medical information. For example, fetal image data is used to view a fetus in utero. By employing multidimensional data to provide a visual image, conditions such as birth defects, treatable ailments, gender, size, and others can be determined. Similarly, radiation therapy data may be employed to simultaneously display information about the direction and intensity of radiation treatment, and a visual image of the treatment area. Such visual image data may also be employed in image guided surgery, to indicate the location of a surgical instrument. Such information is particularly useful in contexts such as brain surgery, where it may not be possible to expose the afflicted area.

Figure 7B:
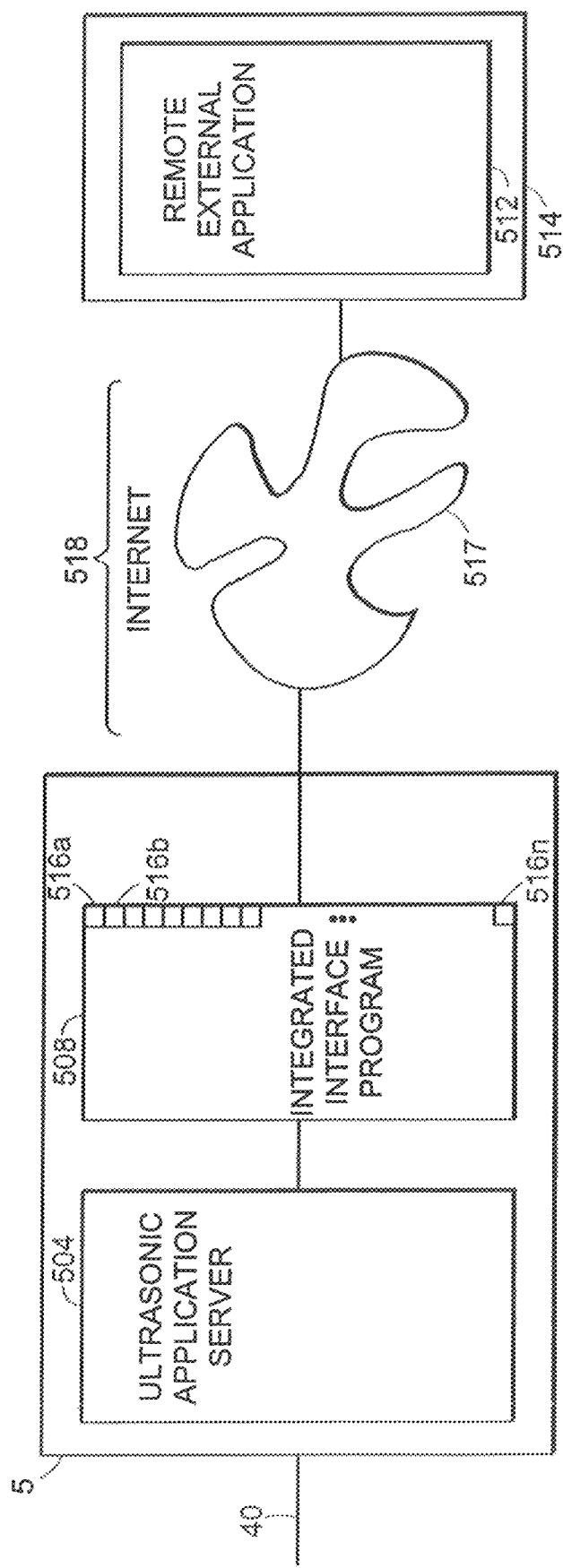
FIG. 7B shows an integrated interface program operable for use with a remote external application.

FIG. 7B shows an integrated interface program 508 operable for use with a remote external application. In such an embodiment, a remote external application 512 is running on a remote computing device 514 such as a PC, and is connected to the user computing device 5 via a public access network 517 such as the Internet via a communication link 518. The integrated interface program 508 includes connection points 516a . . . 516n such as remote procedure call (RPC) points or other inter-node communication mechanism. In a particular embodiment the connection points are sockets in accordance with the TCP/IP protocol.

Similar to the local external application 506; the remote external application 512 is operable to compute a command corresponding to an intended operation in the ultrasonic application server 504. The connection points 516n are generally operable to receive a command transmitted from the remote external application 512. The ultrasonic application server 504 sends a result corresponding to the command, and transmits the result back to the remote external application 512 via the integrated interface program 508 by an inter-node communication mechanism-such as that used to transmit the command. Further, the same integrated interface program could have both entry points 510n, generally to be accessed by the local external application 506, and connection points 516n, generally accessible by the remote external application 512.

Figure 8:
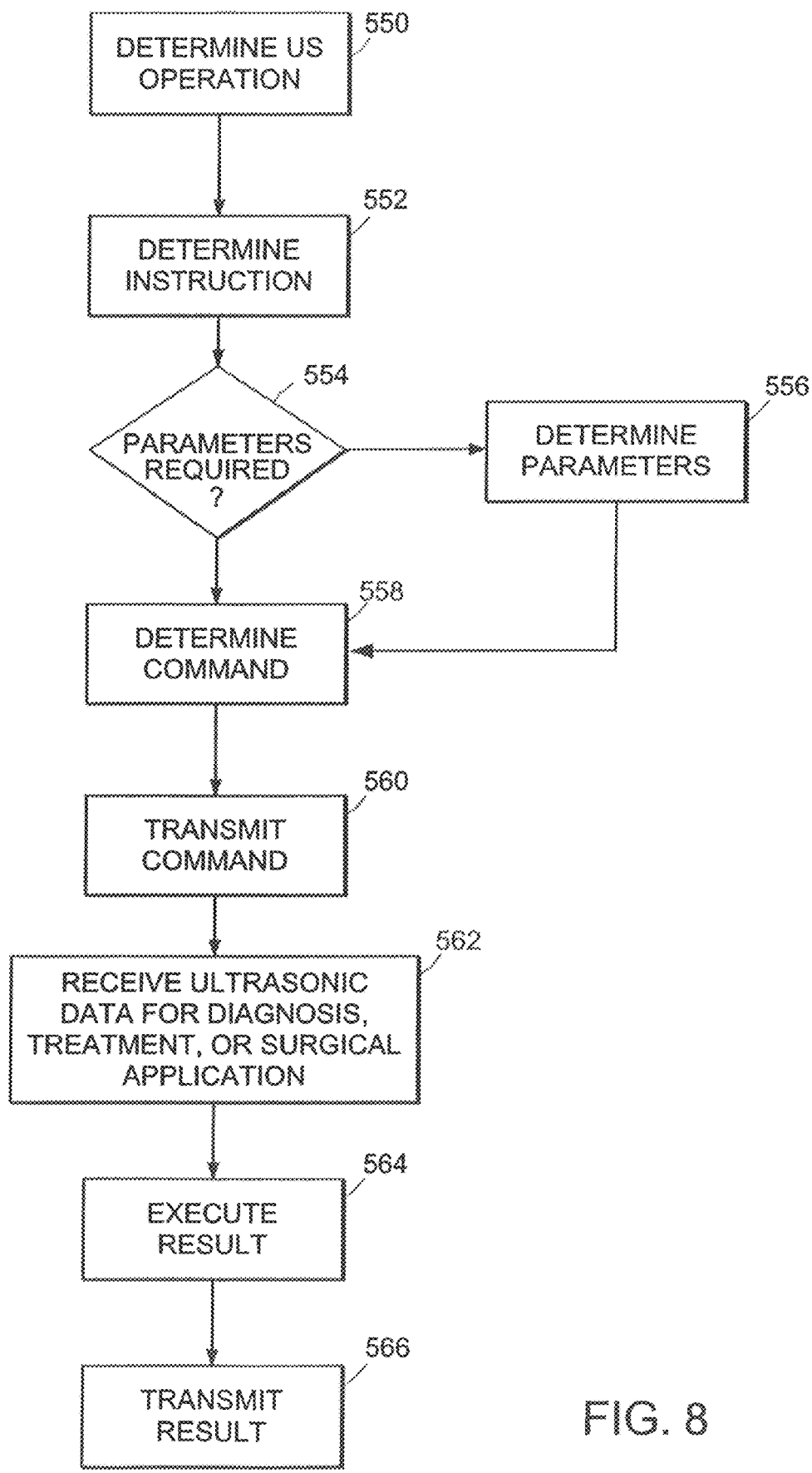
FIG. 8 shows a flowchart of external application integration as defined herein.

FIG. 8 shows a flowchart of external application integration. Referring to FIGS. 6, 7A, 7B and 8, an external application determines a desired US operation to be employed in processing and/or analysis, as depicted at step 550. The operation may provide data, and may cause a certain result or state change, or a combination. The external application determines the instruction corresponding to this operation, as shown at step 552, as defined by the integrated interface program. The external application then determines if any parameters are required for the operation, as disclosed at step 554. If parameters are required, the external application determines the parameters, as depicted at step 556. If no parameters are required, execution continues. The external application determines a command including the instruction and any required parameters, corresponding to the desired US operation, as shown at step 558. The command is transmitted to the ultrasonic application server via the integrated interface program, as disclosed at step 560. The transmission may be by any suitable method, such as those described above and others, depending on whether the external application is local or remote.

Ultrasonic data is received by the ultrasonic server application 504 via the standard communication interface 40 indicative of ultrasonic image information, as depicted at step 562. As described above, the ultrasonic data is received via a test probe disposed in contact with the subject, or patient, for viewing such visual information as radiation therapy data, fetal image data, cardiac image data, and image guided surgery data. Information such as the ultrasonic application server 504 executes a result corresponding to the command from the ultrasonic data as disclosed at step 564. Thus step 564 may involve control signals being generated to define or re-define a region of interest in which radiation is to be directed for treatment. The ultrasonic application server 504 then transmits the computed result to the external application viathe integrated interface program 508, as shown at step 566. Note that it is expected that many successive command and results are computed, and the ultrasonic data is concurrently sent in an iterative manner over the standard communication interface 40.

In another particular embodiment, the integrated application program includes both entry points for local external applications, and connection points for remote external applications. The instructions and parameters corresponding to the entry points are known to the local external application, and the instruction and parameters corresponding to the connection points are known to the remote external application. Further, there may be both an entry point and a connection point operable to invoke the same operation in the integrated application server. In such an embodiment, a semaphore or reentrancy mechanism is employed in the ultrasonic application server to avoid deadlock or simultaneous attempts to invoke the same operation. Both the local and remote external applications invoke the ultrasound application server via the integrated interface program 508 (FIGS. 7A and 7B).

Figure 9:
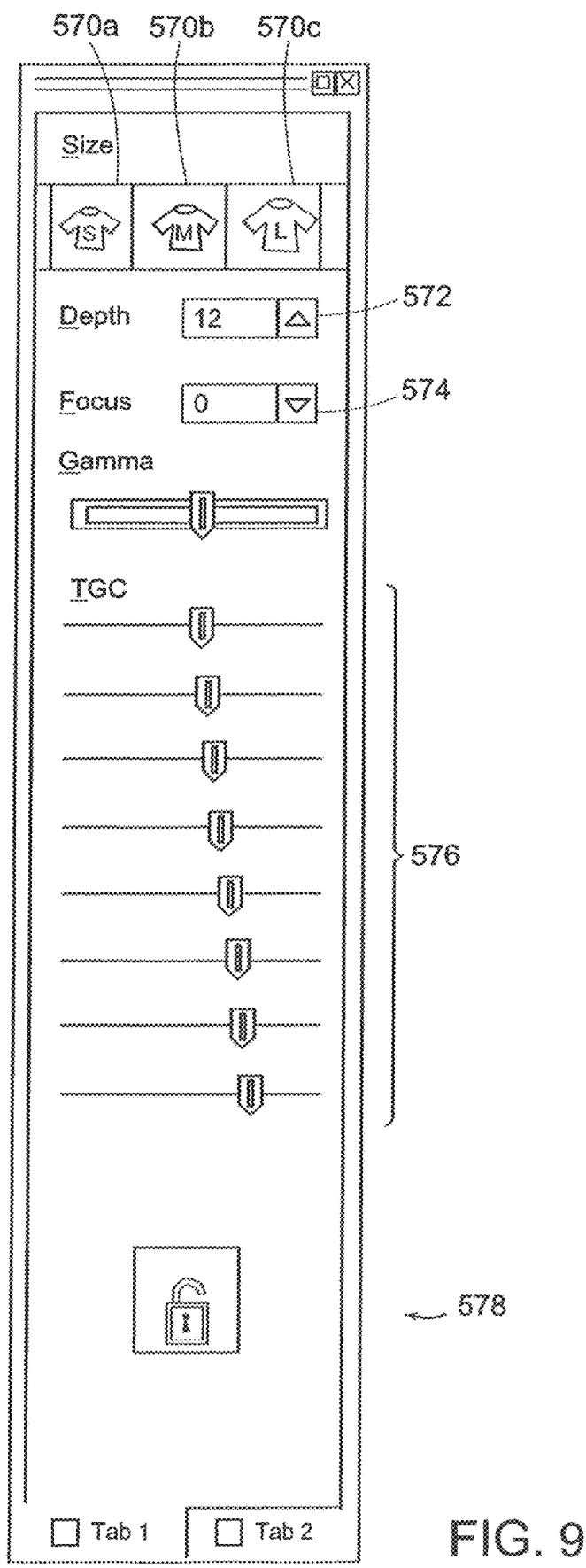
FIG. 9 shows a graphical user interface (GUI) for use with the ultrasonic imaging system as defined herein.

The ultrasonic application server also includes a graphical user interface for manipulating operations without accessing the external application. Referring to FIG. 9, a control bar 578 of a top level GUI screen is shown. The control bar allows manipulation of tools affecting image settings of the display via image control presets. The image settings are controlled for each of three sizes small 570*a*, medium 570*b*, and large 570*c*. For each size, the image settings within that size may be controlled, including depth 572, focus 574, and time gain compensation 576. Each of these settings may be saved under a user defined name for later recall. The user clicks on a save button and is prompted to enter a file name. Each of the three sets of image settings corresponding to the size settings 570*a*, 570*b*, and 570*c* is then stored corresponding to the file name, and may be recalled by the user at a later time.

Those skilled in the art should readily appreciate that the programs defining the operations and methods defined herein are deliverable to a user computing device and a remote computing device in many forms, including but not limited to a) information permanently stored on non-writeable storage media such as ROM devices, b) information alterably stored on writeable storage media such as floppy disks, magnetic tapes, CDs, RAM devices, and other magnetic and optical media, or c) information conveyed to a computer through communication media, for example using baseband signaling or broadband signaling techniques, as in an electronic network such as the Internet or telephone modem lines. The operations and methods may be implemented in a software executable by a processor or as a set of instructions embedded in a carrier wave. Alternatively, the operations and methods may be embodied in whole or in part using hardware components, such as Application Specific Integrated Circuits (ASICs), state machines, controllers or other hardware components or devices, or a combination of hardware, software, and firmware components.

Figure 10:
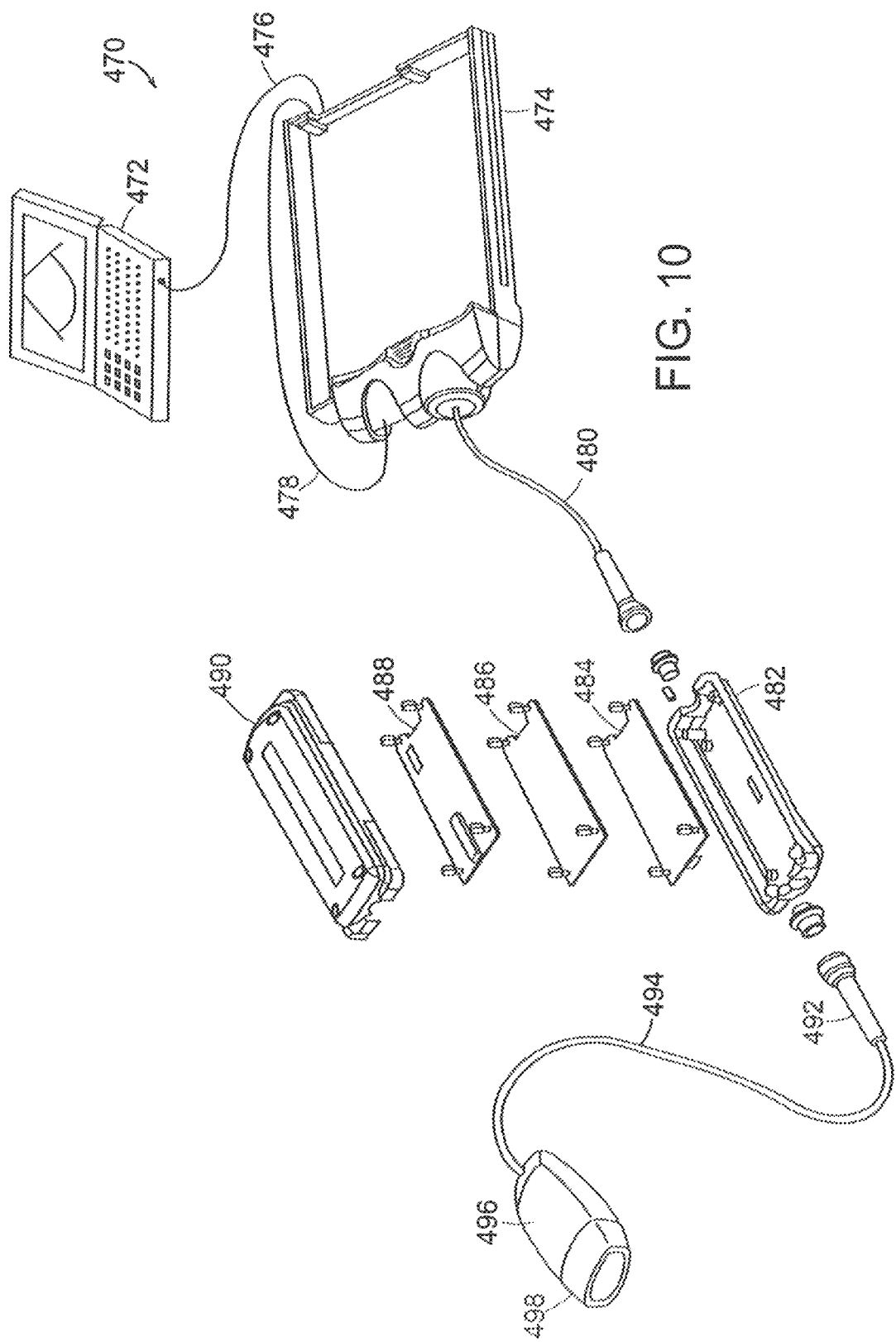
FIG. 10 is a preferred embodiment of a portable ultrasound system in accordance with the invention.

FIG. 10 illustrates a preferred embodiment of a portable ultrasound system 470 in accordance with the invention. A personnel computer 472 such as a laptop, a hand-held computer or a desktop workstation can provide power and a standard interface (e.g. IEEE 1394 or USB) to a housing 474 along cable 476. Housing 474 includes a DC-DC converter to deliver power along cable 480 to interface housing (482, 490). This interface housing has two or three circuit boards 484, 486, 488 as described previously. A standard transducer housing 496 with transducer array 498 is connected to the interface housing along cable 494 and connector 492. The beamformer integrated circuit mounted on circuit board 486 requires steering data, the transmit circuitry requires data to provide proper transmit focus and the TGC must have gain level information for a given depth.

Figure 11:
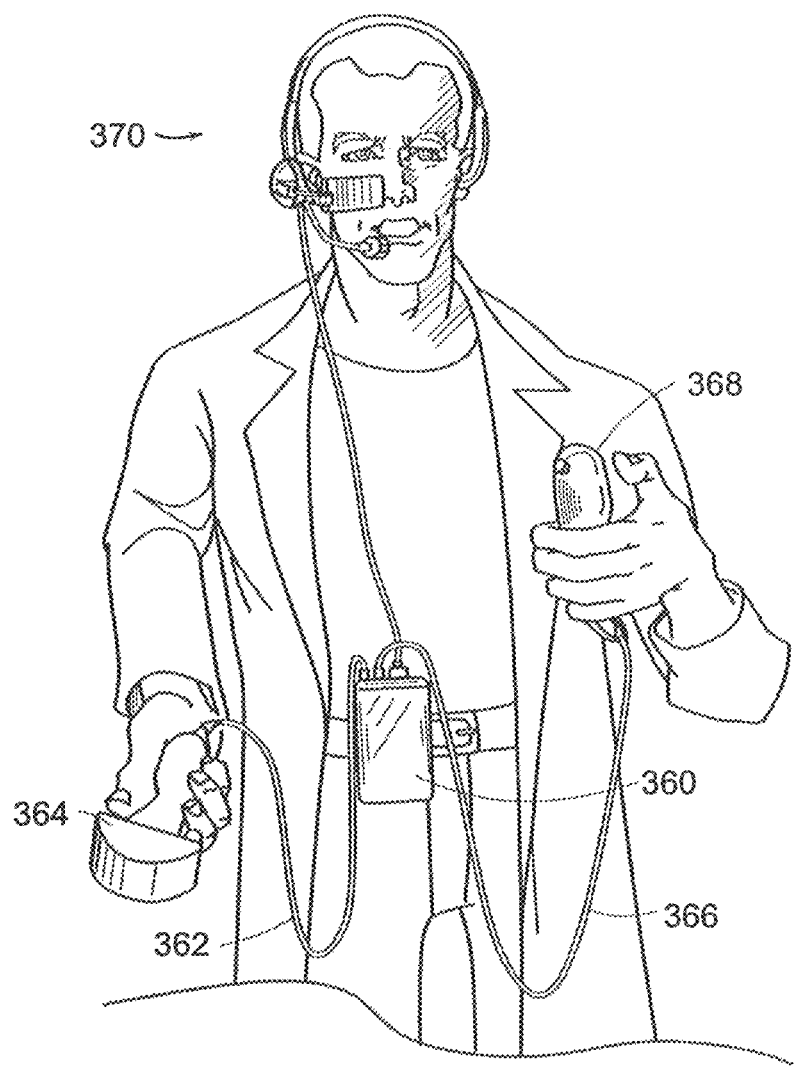
FIG. 11 illustrates a wearable or body mounted ultrasound system in accordance with the invention.

FIG. 11 illustrates a wearable ultrasound imaging system that can include a belt mounted computer 360 or interface connected big cable 362 to hand-held probe 364, a second hand-held unit 368 that can include various controls including a mouse control and buttons to freeze the image displayed or to store a particular image in electronic memory. The unit 368 can be connected by wireless (RF or infrared) connection or by cable 366 to housing 360. The computer 360 can be connected to a desktop, laptop or hand-held display or can be connected by cable to a headmounted display system 370 that includes a microphone, a pair of speakers for audio and a high resolution display positioned adjacent the user's eye.

Figure 12:
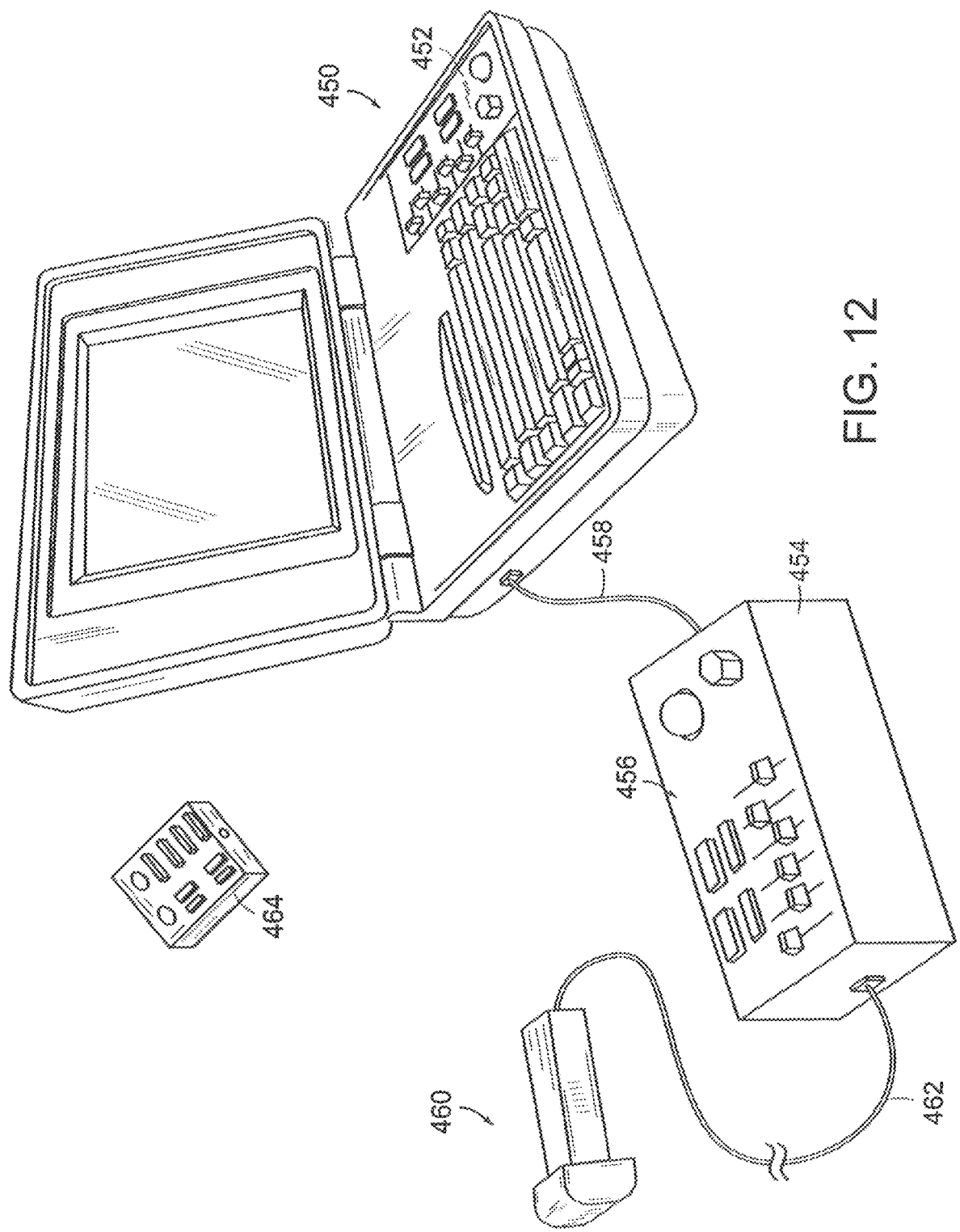
FIG. 12 illustrates an interface system using a standard communication link to a personal computer.

Another preferred embodiment is illustrated in FIG. 12 in which a laptop computer 450, having a flat panel display and a standard keyboard, has been programmed to perform scan conversion, doppler processing etc. on a beamformed representation of the region of interest that has been transmitted from interface housing 454 along a standard communications link such as cable 458 that conforms to the IEEE 1394 FireWire standard or the USB 2.0 standard, for example. The computer 450 and/or the interface can optionally include a control panel 452, 456, that can be used to control the study being conducted. A preferred embodiment of the interface housing 454 is controlled solely by the personnel computer 450 and provides for the use of standard transducer array probes that can be interchangeably attached to the interface housing 454 with a cable. Alternately, an additional remote controller 464 can be used to control system operation. The interface 454 can house the circuit boards on which the beamformer, memory, system controller and digital communication circuits are mounted. The interface 454 is connected to the hand-held probe 460 with a cable that is preferably between two feet and six feet in length, however longer lengths can be used. The transmit/receive and/or the preamplifier/GC circuits can be in the probe housing 460 or in the interface housing 454. The computer can also be configured for gigabit Ethernet operation and for transmitting video and image data over networks to remote systems at clinics or hospitals. The video data can also be sent to a VCR or standard video recorder or video camera with an IEEE 1394 part for recording on videotape. The VCR or video camera can be controlled using the computer.

Returning to FIG. 1, the host 5 can be a desktop, laptop palmtop or other portable computer executing software instructions to display ultrasound images. In addition to real-time B-mode ultrasound images for displaying soft-tissue structures in the human body, Doppler ultrasound data can be used to display an estimate of blood velocity in the body in real time. Three different velocity estimation systems exist: color-flow imaging (CFI), power-Doppler and spectral sonogram.

The color-flow imaging modality interrogates a specific region of the body, and displays a real-time image of mean velocity distribution. The CF's are usually shown on top of the dynamic B-mode image. To determine the direction of blood flow, different colors indicate velocity toward and away from the transducer.

While color flow images display the mean or standard deviation of the velocity of reflectors (i.e., blood cells) in a given region, power Doppler (PD) displays a measurement of the amount of moving reflectors in the area, similar to a B-mode image's display of the total amount of reflectivity. A PD image is an energy image in which the energy of the flow signal is displayed. These images give no velocity information but only show the location of flow.

The spectral Doppler or spectral sonogram modality utilizes a pulsed-wave system to interrogate a single range gate and displays the velocity distribution as a function of time. This sonogram can be combined with a B-mode image to yield a duplex image. Typically, the top side of the display shows a B-mode image of the region under investigation, and the bottom shows the sonogram. Similarly, the sonogram can also be combined with the CFI image to yield a triplex image. Thus, the time for data acquisition is divided between acquiring all three sets of data. Consequently, the frame rate of the complex image is generally decreased, compared to either CFI or duplex imaging.

A pulsed-Doppler processor for color-flow map applications is now described. Color Doppler (CD) or color-flow imaging combines, in a single modality, the capabilities of ultrasound to image tissue and to investigate blood flow. CD images consist of Doppler information that can be color-encoded and superimposed on a B-mode gray-scale image.

Color-flow imaging is a mean velocity estimator. There are two different techniques in computing the mean velocity. First, in a pulsed Doppler system fast fourier transformer (FFTs) can be used to yield the velocity distribution of the region of interest, and both the mean and variance of the velocity profile can be calculated and displayed as a dolor flow image. The other approach uses a one-dimensional auto correlation.

An estimate of the mean velocity in the range gate gives an indication of the volume flow rate. Given that the frequency of the reflected, range-gated signal is proportional to the flow velocity, the spatial mean velocity is determined by the mean angular frequency.

$$\bar{\omega} = \frac{\int_{-\infty}^{+\infty} \omega P(\omega) d\omega}{\int_{-\infty}^{+\infty} P(\omega) d\omega} \tag{1}$$

Here, $P(\omega)$ is the power-spectral density of the received, demodulated signal. The inverse Fourier transform of the power-spectral density is the autocorrelation:

$$R(\tau) = \int_{-\infty}^{+\infty} P(\omega) \exp(j\omega\tau) d\omega \tag{2}$$

The derivative of the autocorrelation with respect to $\tau$ is:

$$\dot{R}(\tau) = \int_{-\infty}^{+\infty} P(\omega) \exp(j\omega\tau) d\omega \tag{3}$$

Substituting Eqs. (2) and (3) into Eq. 1 yields:

$$\bar{\omega} = \frac{\dot{R}(0)}{jR(0)} \tag{4}$$

Therefore, the mean velocity estimator can be reduced to an estimation of the autocorrelation and the derivative of the autocorrelation. The estimator given by the proceeding expression can be calculated when data from two returned lines are used, i.e., $$\bar{\omega} = -f_{prf} \arctan(\Phi) \tag{5}$$

where $$\Phi = \frac{\frac{1}{N_c-1} \sum_{i=0}^{N_c-2} y(i+1)x(i) - x(i+1)y(i)}{\frac{1}{N_c-1} \sum_{i=0}^{N_c-2} x(i+1)x(i) + y(i+1)y(i)} \tag{6}$$

$f_{prf}$ is the pulse repetition frequency, and $N_e$, are the number of lines used in autocorrelation estimator. In practice, more then 2 lines are used to improve the signal-to-noise ratio. Data from several RF lines are needed in order to get useful velocity estimates by the auto-correlation technique. Typically, between 8 and 16 lines are acquired for the same image direction. The lines are divided into range gates throughout the image depths and the velocity is estimated along the lines.

For duplex imaging, the CFI pulses are interspersed between the B-mode image pulses. For CFI pulses, it is known that a longer duration pulse train gives an estimator with a lower variance, however, good spatial resolution necessitates a short pulse train. Consequently, a separate pulse train must be used for the B-mode image, because the CFI pulse train is too long for high-resolution, gray-scale images.

For color-flow imaging, CFI, the velocity estimator is given by Eq. (5). This can be computed by serial processing, since the arrival of samples for a new line results in the addition of the new data to an already calculated sum. Four multiplications, three additions, and a subtraction are performed for each range gate and each new line. Stationary echo cancellation is also performed for each new sample. A filter with $N_e$, coefficients necessitates $2N_e$ multiplications and additions per gate and line.

Assuming that all data samples are used for CFI imaging, the total number of multiplications and additions per second is $$N_{ops} = (2N_e + 2)Mf_0 \tag{7}$$

where $Mf_0$ is the number of data samples per second. This is a conservative value since B-mode lines are interspersed with CF imaging lines causing time to be lost switching between modes. It follows that $$N_{ops} = \eta(nN_e + 2)Mf_0 \frac{N_c - N_b}{N_c} \tag{8}$$

where $N_e$, is the number of CFI lines per estimate, $N_B$ is the number of B-mode image lines interspersed between CF lines, and η denotes the effective time spent on acquiring useful data.

For a CFI system using 8 lines per estimate, an echo cancellation filter with 4 coefficients and an 8 times-oversampled 41 MHZ pulse, one B-mode line is interspersed between CFI lines and 80% of the time is consumed acquiring data. Using Eq. (7), the number of calculations per second is $N_{ops}=172\lambda 10^6$. This is within the capability of a current Pentium-class laptop computer. Thus, all of the CFI signal processing can be performed in software using a state-of-the-art microprocessor.

While Color Flow Imaging (CF) has-been an effective diagnostic tool in clinical cardiovascular applications, Power Doppler (PD) imaging provides an alternative method of displaying the blood stream in the insonified regions of interest. While CF imaging displays the mean or standard deviation of the velocity of reflectors (e.g., blood cells) in a given region, PD displays a measurement of the density of moving reflectors in the area, similar to the B-mode image's display of reflectivity. Thus, Power Doppler is akin to a B-mode image with stationary reflectivity suppressed. This is particularly useful for viewing moving particles with small cross-sectional scattering, such as red blood cells.

Power Doppler displays the integrated Doppler power instead of the mean frequency shift as used for color Doppler imaging. As discussed in the previous section, the color-flow mapping is a mean-frequency estimator that is expressed as $$\overline{\omega} = \frac{\int_{-\infty}^{+\infty} \omega P(\omega) d\omega}{\int_{-\infty}^{+\infty} P(\omega) d\omega} \quad (9)$$

where $\overline{\omega}$ represents mean-frequency shift and $P(\omega)$ is the power-spectral density of the received signal. The inverse Fourier transform of the power-spectral density is the auto-correlation:

$$R(\tau) = \int_{-\infty}^{+\infty} P(\omega) \exp(j\omega\tau) d\omega \quad (10)$$

The total Doppler power can be expressed as the integral of the power-spectral density over all angular frequencies, $$pw = \int_{-\infty}^{+\infty} P(\omega) d\omega \quad (11)$$

By observing the similarities between Eq. (2) into (10), it follows that the 0th lag of the auto-correlation function can be used to compute the integrated total Doppler power.

$$R(0)=\int P(\omega)\exp(j\omega 0)d\omega=\int P(\overline{\omega})d\omega=pw \quad (12)$$

In other words, the integrated power in the frequency domain is the same as the integrated power in the time domain and hence the power Doppler can be computed from either the time-domain or the frequency-domain data. In either case, the undesired signals from the surrounding tissue, such as the vessel walls, should be removed via filtering. This calculation is also referred toas a Wall filter.

In a preferred embodiment, the PD can be computed in software running on a microprocessor; similar to the computation of the CFI processing described above. Parallel computation units, such as those in the Intel Pentium™ and Pentium II's MMX coprocessors; allow rapid computation of the required functions. A Digital Signal Processor (DSP) can also be used to perform this task. For either case, a software implementation permits the flexibility to change and investigate digital signal processing algorithms and transmitting signals that achieve the best performance as region of interest changes.

The above showed that the frequency content of the Doppler signal is related to the velocity distribution of the blood. It is common to devise a system for estimating blood movement at a fixed depth in tissue. A transmitter emits an ultrasound pulse that propagates into and interacts with tissue and blood. The backscattered signal is received by the same transducer and amplified. For a multiple-pulse system, one sample is acquired for each line or pulse emitted. A display of the distribution of velocities can be made by Fourier transforming the received signal and showing the result. This display is also called a sonogram. Often a B-mode image is presented along with the sonogram in a duplex system, and the area of investigation, or range gate, is shown as an overlay on the B-mode image. The placement and size of the range gate is determined by the user. In turn, this selects the epoch for data processing. The range gate length determines the area of investigation and sets the length of the emitted pulse.

The calculates spectral density is displayed on a screen with frequency on the y-axis and time on the x-axis. The intensity of a pixel on the screen indicates the magnitude of the spectrum; thus, it is proportional to the number of blood scatterers moving at a particular velocity.

The range gate length and position are selected by the user. Through this selection, both emitted pulse and pulse repetition frequency are determined. The size of the range gate is determined by the length of the pulse. The pulse duration is $$T_p = \frac{2l_g}{c} = \frac{M}{f} \quad (13)$$

where the gate length is $l_g$ and M is the number of periods. The gate duration determines how rapidly pulse echo lines can be acquired. This is referred to as the pulse-repetition frequency or $$f_{prf} \leq \frac{c}{2d_0}, \quad (14)$$

where $d_0$ is the distance to the gate. For example, a 4 period, 7 M HZ pulse is used for probing a blood vessel lying at a depth of 3 cm with a 10 ms observation time.

The gate length is computed as $$l_g = 0.44 \text{ mm}. \quad (15)$$

The pulse-repetition frequency is $$f_{prf} \leq \frac{c}{2d_0} \approx 25 \text{ KHz.} \quad (16)$$

The total number of independent spectral lines is $N=T_{obs}f_{prf}=250$. It follows that the maximum detectable velocity is $$v_{max} = \frac{f_{prf}}{2}\frac{c}{2f_0} = 1.4 \text{ m/s.} \qquad (17)$$

Using a 256-point FFT to computethe Fourier transform, the total number of multiplications/additions per second required for the preceding example is less than 10 MOPs/s. In a preferred embodiment, the sonograph computation can be carried out in software running on a microprocessor (similar to the computation of the CFI processing described above). Parallel computation units, such as those inside the Intel Pentium™ and Pentium II's MMX coprocessors, allow rapid computation of the required FFT functions. All three velocity estimation systems can be implemented in software on current microprocessors, such as the Intel Pentium, or digital signal processors (DSP).

Methods employing contrast agents have been developed to enhance certain-imaging methods. Stabilized microbubbles are used for ultrasound contrast imaging because of their unique acoustic properties compared to biological tissues. They present superior backscattering and nonlinear behavior, and fragility upon exposure to ultrasound. A number of ultrasound imaging modalities have been created to exploit these features.

In fundamental B-Mode imaging, the transmitting and receiving frequencies are the same. The echogenicity of blood is significantly increased with the administration of a contrast material. Gas microbubbles scatter sound much more intensely than an equivalent size liquid or solid particle owing to the acoustic impedance mismatch (particularly the difference in compressibility) between the gas and the surrounding tissue or blood. This effect will be observed in Doppler and M-Mode imaging techniques as well. One disadvantage of using fundamental B-Mode for contrast imaging is that the level of the echoes created by the bubbles is similar to the level of the echoes resulting from the biological tissues.

A technique using the second harmonic relies on the fact that bubbles generate harmonics of the transmitted frequency at a level much higher than the harmonics generated by the tissues. By creating images from the signal received at twice the transmitted frequency, high image contrast is achieved between regions with and without bubbles. A problem with this imaging modality is that a short pulse (typically used in B-mode imaging) has a broad bandwidth and the transmitting and receiving frequencies overlap, contaminating the harmonic image with the fundamental frequency. To alleviate this problem, the pulse length is increased to achieve a narrow bandwidth, however, at the expense of decreasing the axial resolution of the image.

The pulse inversion method (also called wideband harmonic imaging or dual pulse imaging), solves the problem of overlapping frequencies observed with the second harmonic technique. Each scan line is formed by summing the signals received from two ultrasound pulses, where the second pulse is inverted and slightly delayed relative to the first. This procedure cancels the response of all linear scatters (if there is no tissue movement between the two pulses) while enhancing the effects of nonlinear scatterers. Because there is delay between the two pulses, any bubble displacement adds an additional signal, resulting in velocity-dependent enhancement.

Because most ultrasound contrast agents are destroyed by ultrasound irradiation, intermittent or gated imaging techniques have been used. By acquiring an image frame at each cardiac cycle (or after several cardiac cycles), ultrasound exposure is reduced, increasing the longevity of the contrast agents in the region of interest on the image. Another benefit of intermittent imaging is the filling of vascular space during the off-cycle. The degree of filling produces enhancement that is directly related to blood volume of blood flow, since the higher-flow rate, the greater the number of bubbles that enters the region of interest, and thus the greater the fractional blood volume.

The stimulated acoustic emission method (also known as transient response imaging) typically involves color Doppler with the transmitting power set high to ensure bubble disruption with the first pulse. When the bubbles collapse, a broadband acoustic signal is generated. Since ultrasound Doppler systems compare the backscattered signal with respect to a "clean" reference signal, this loss of frequency correlation caused by the bubble collapse is interpreted by the machine as a random Doppler shift, resulting in a mosaic of colors at the location of the microbubbles.

A preferred embodiment of the invention employs a spatial filter in providing a power doppler image, for example. This spatial or high pass filter can also be used effectively with a contrast agent to further differentiate between blood flow and the surrounding vessel or artery. First the power is computed and a two pulse canceller is employed. The ratio of the power of the signal before and after the filter provides a data set yielding clear images of moving fluid within the body.

A preferred embodiment of the invention employs a spatial filter in providing a power doppler image, for example. This spatial or high pass filter can also be used effectively with a contrast agent to further differentiate between blood flow and the surrounding vessel or artery. First the power is computed and a two pulse canceller is employed. The ratio of the power of the signal before and after the filter provides a data set yielding clear images of moving fluid within the body.

Figure 13:
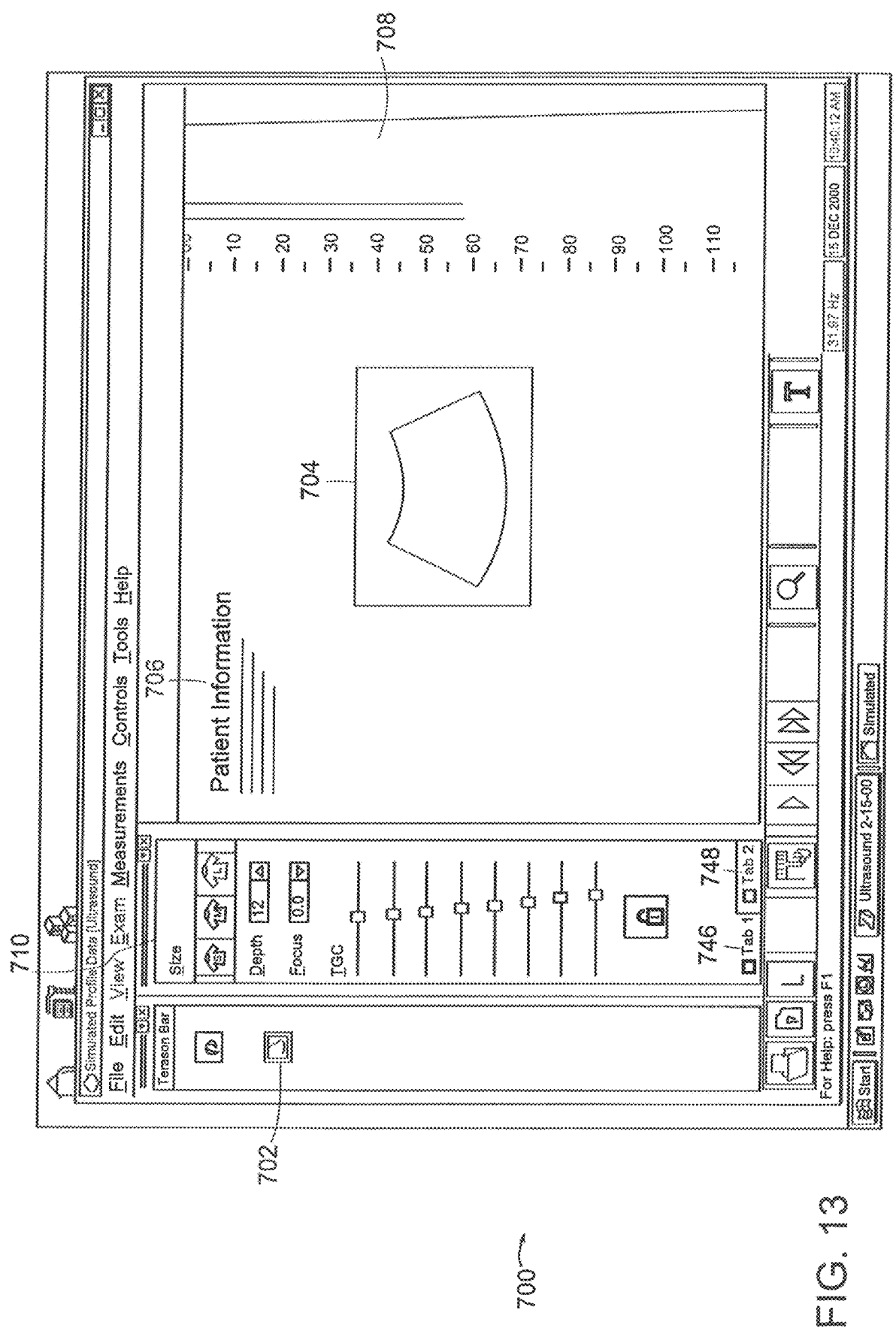
FIG. 13 shows the top-level screen of a graphical user interface (GUI) for controlling the ultrasonic imaging system.

FIG. 13 shows the top-level screen of a graphical user interface (GUI) for controlling the ultrasonic imaging system. Referring to FIG. 13, ultrasonic image data gathered by the hand-held probe is displayed and manipulated by the ultrasonic imaging system using this screen. A selection bar 702 allows the operator to select the active focus areas of the screen. An image area 704 displays the ultrasonic image of the subject area. A patient information area 706 displays information about the subject from whom ultrasonic data is being gathered. A Time Gain Compensation area 708 provides feedback about time gain compensation, described further below. A control bar 710 allows qualitative and quantitative selection of ultrasonic imaging operations, as will be described further below with respect to FIGS. 15A and 15B.

Figure 14:
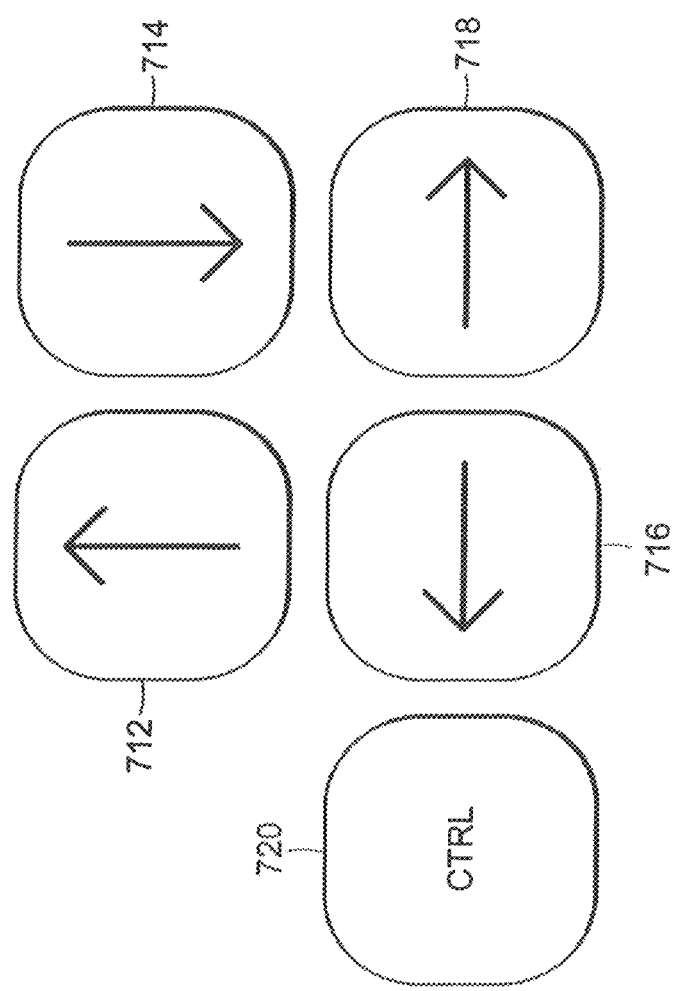
FIG. 14 shows a unitary control keypad for use in conjunction with the GUI of FIGS. 15A-15B.

FIG. 14 shows the unitary, directional keypad which provides a single operating position from which to control the ultrasonic imaging operations. Referring to FIG. 14, an up arrow key 712 and a down arrow key 714 allow a user to scroll through the qualitative ultrasonic imaging operations of the system, as will be described further below. A left arrow key 716 and a right arrow key 718 allow a user to select quantitative parameters corresponding to the ultrasonic imaging operation selected. As described above, the quantitative parameters may be in a range of discrete values, or may span a continuum. A control key 720, employed in conjunction with the up arrow key 712 or down arrow key 714 allows an operator to toggle between two control tabs depicted in FIGS. 15A and 15B, as will be described further below. Since all keys employed in controlling and selecting the ultrasonic imaging operations are accessible from a common operating position, an operator may focus on the ultrasonic image of the subject and on the hand-held probe, and need not be distracted by unwieldy controls. Traditional directional keypads allow only directional control to be applied by the directional keypads, and do not allow both qualitative and quantitative selection of operations from a common, unitary operating position accessible by a single hand.

Figure 15A:
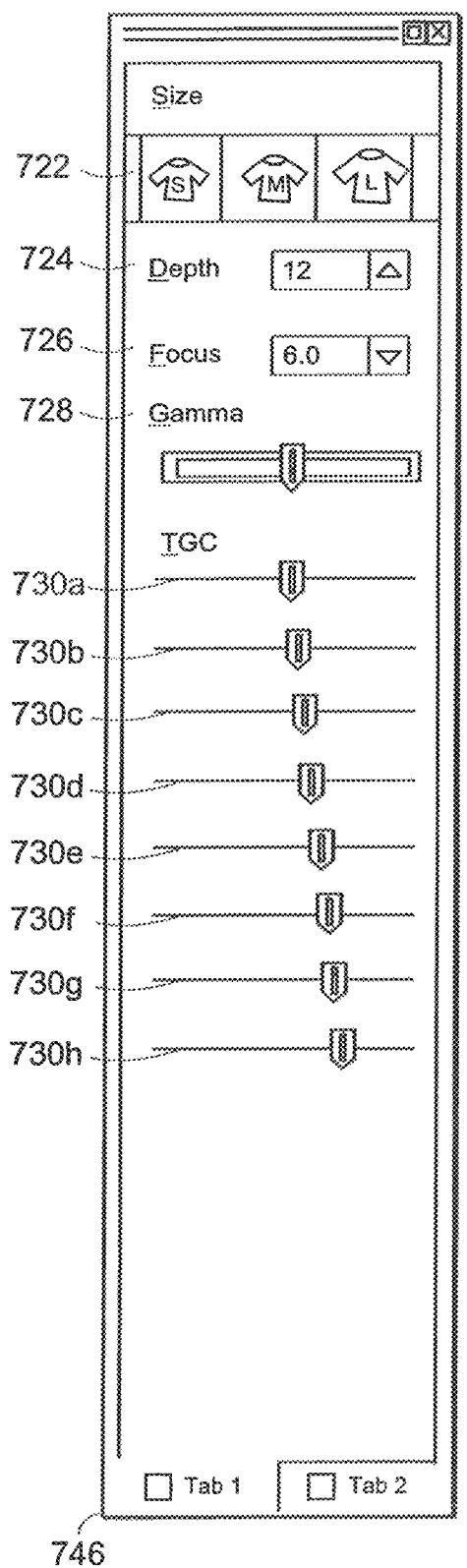
FIG. 15A shows a graphical user interface (GUI) for controlling the scanning operations of the ultrasonic imaging system.
Figure 15B:
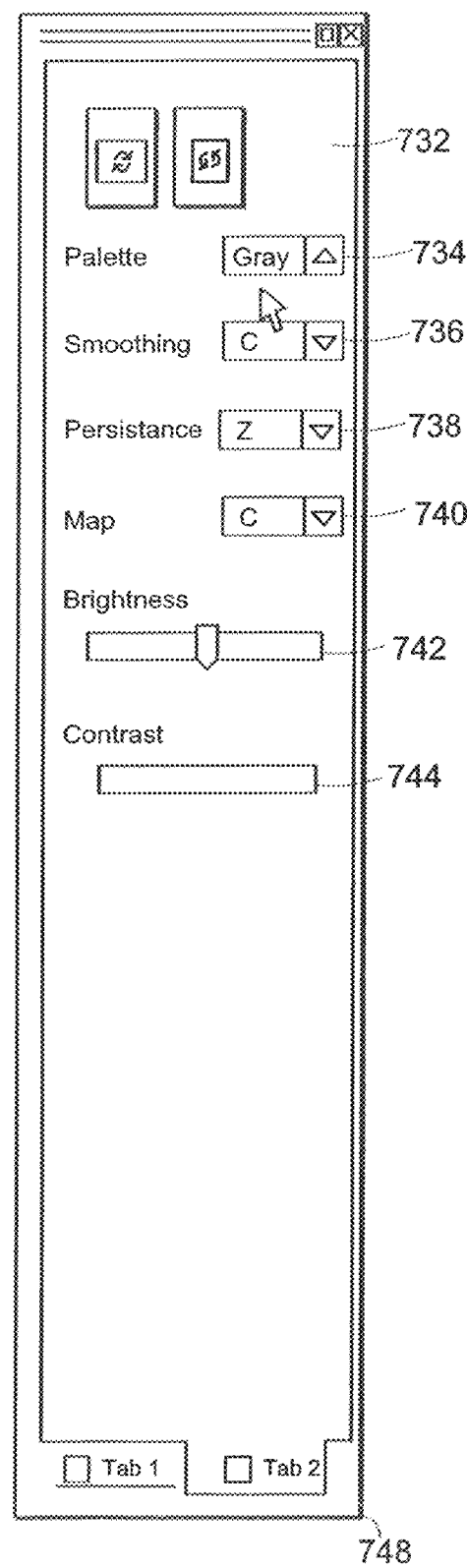
FIG. 15B shows a graphical user interface (GUI) for controlling the processing operations of the ultrasonic imaging system.

FIGS. 15A and 15B show qualitative and quantitative selection of ultrasonic imaging operations via invoking the unitary directional keypad of FIG. 14. Referring to FIG. 15A, ultrasonic imaging operations applicable to scanning are shown. The scanning operations are directed active acquisition of real-time, dynamic ultrasonic image data, and are typically applied as the hand-held probe is manipulated over the subject imaging area. A size operation 722 sets a series of predetermined defaults for other ultrasonic imaging operations. A small, medium, or large subject may be selected via the left and right arrow keys 716, 718 (FIG. 14). A depth operation 724 allows selection of a depth parameter via the arrow keys 716, 718. Focus is controlled by a focus 726 operation. Gain 728 control adjusts the TGC for all TGC settings 730a-730h. TGC operations 730a-730f adjusts amplification of return signals at varying depth, ranging from the least depth 730a to greatest depth 730h, via the arrow keys 716-718.

Referring to FIG. 15B, ultrasonic imaging operations applicable to processing are shown. The processing operations may be applied to static real-time or frozen images. An inversion operation is controlled by the inversion 732 selection, and rotates the image via the arrow keys 716, 718 (FIG. 14). Palate, smoothing, persistence, and mapping 734, 736, 738 and 740, respectively are selected via the up and down arrow keys 712, 714, and parameters selected via the arrow keys 716, 718 (FIG. 14). Brightness and contrast scales are selected via sliders 742 and 744, respectively, and are changed using arrow keys 716, 718.

Figure 16:
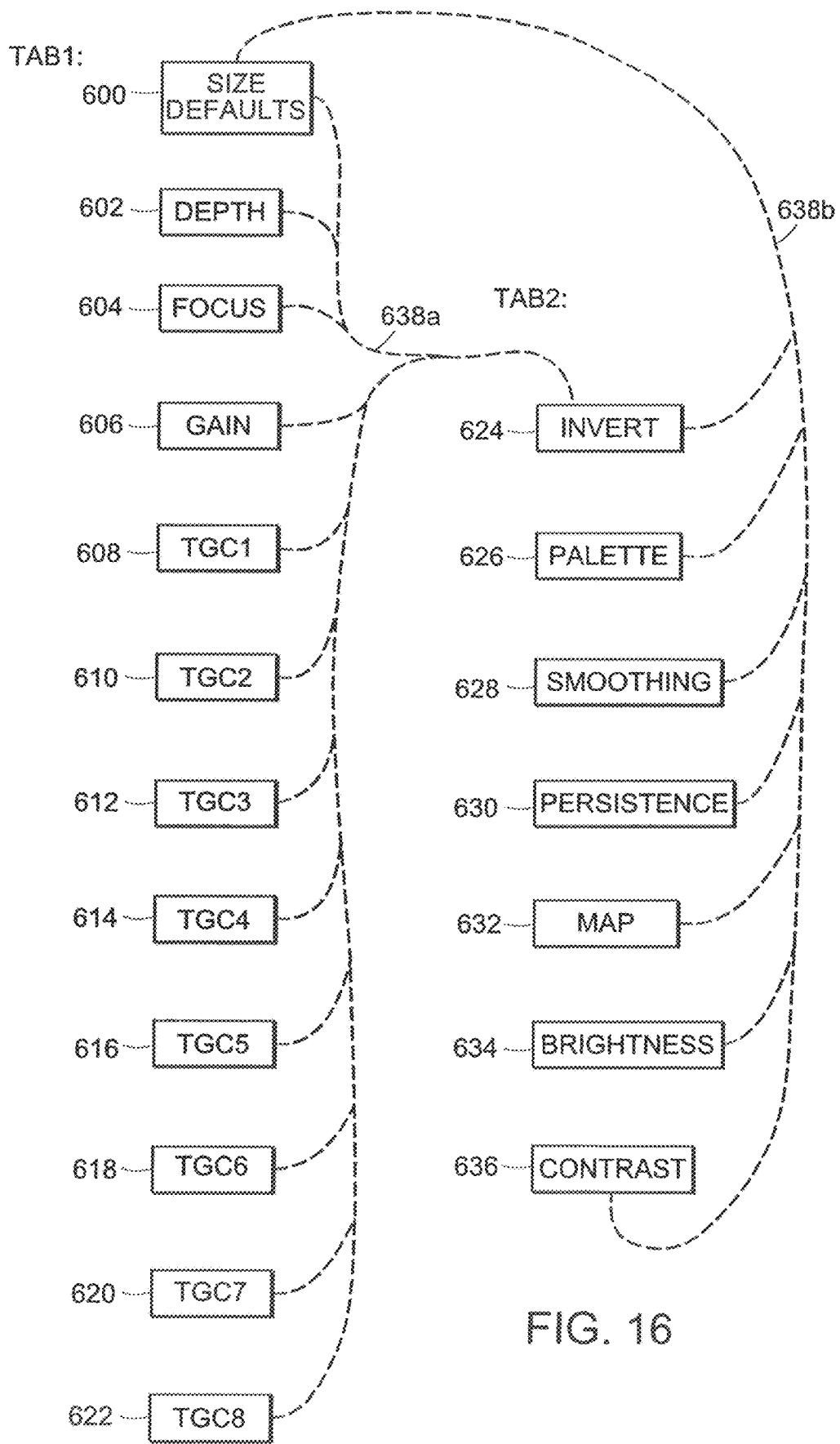
FIG. 16 shows a state diagram corresponding to the GUI of FIGS. 15A-15B.

FIG. 16 shows a state diagram depicting transition between the ultrasonic imaging operations depicted in FIGS. 15A and 15B. Referring to FIGS. 1, 14, and 16, the Tab 746 operations are selected via the up and down arrow keys 712, 714 and transition according to the following state sequence: size 600, depth 602, focus 604, Gain 606 and TGC degrees 608, 610, 612, 614, 616, 618, 620 and 622. Similarly, the Tab 2 operations are selected according to the following sequence: invert 624, palette 626, smoothing 628, persistence 630, map 632, brightness 634, and contrast 636. As indicated above, selection of operations may be toggled between Tab 1 746 and Tab 2 748 using control key 720 and arrow keys 712, 714.

The scanning operations shown in FIG. 15A are displayed on Tab 1746, as shown in FIG. 13. The processing operations shown in FIG. 15B are displayed and selected on Tab 2, as shown in FIG. 13. Referring again to FIG. 14, control is toggled between Tab 1 746 and Tab 2 748 using a combination of the control key 720 and either the up or down arrow keys 712, 714, as shown by dotted lines 638a and 638b.

In general the use of medical ultrasound systems requires the user to have significant training and regular practice to keep skills at a high level. Another embodiment of the invention involves providing the user with an intuitive and simple way to use the interface, and with the abilityto quickly and automatically set imaging parameters based on a software module. This enables general medical personnel with limited ultrasound experience to obtain diagnostic-quality images without having to adjust the controls. The "Quick Look" feature provides the user with a very simple mechanism of image optimization. It allows the user to simply adjust the image so as to obtain appropriate diagnostic image quality with one push of one button.

The benefits of programmed image parameters are many. The user no longer is required to adjust multiple controls in order to obtain a good image. Exams may be performed in a shorter period of time as a result. The use of this feature also results in more uniform images, regardless of the skills and expertise of the user. This approach is advantageous when performing exams under adverse circumstances such as emergency medical procedures performed in ambulances or remote locations.

The procedure involves the use of predefined histograms. Separate histograms are provided for different anatomical structures that are to be examined. The user chooses a structure, similar to the existing method of choosing a preset. Once the structure is chosen, the user places the transducer on the area of interest in the scanning window. At that time, pressing the selected control button triggers the system to adjust the system contrast and brightness control values so that histogram of the gray levels in the image closely matches the corresponding pre-defined histogram for that structure. The result is an image of diagnostic image quality that is easily recreated.

The procedure is highly dependent upon the brightness and contrast controls. As a result, a preferred embodiment provides an independent control which allows the user to adjust for ambient lighting changes. In many applications the programmed parameters gets the user very close, but they may choose to fine tune the contrast and brightness.

Figure 17A:
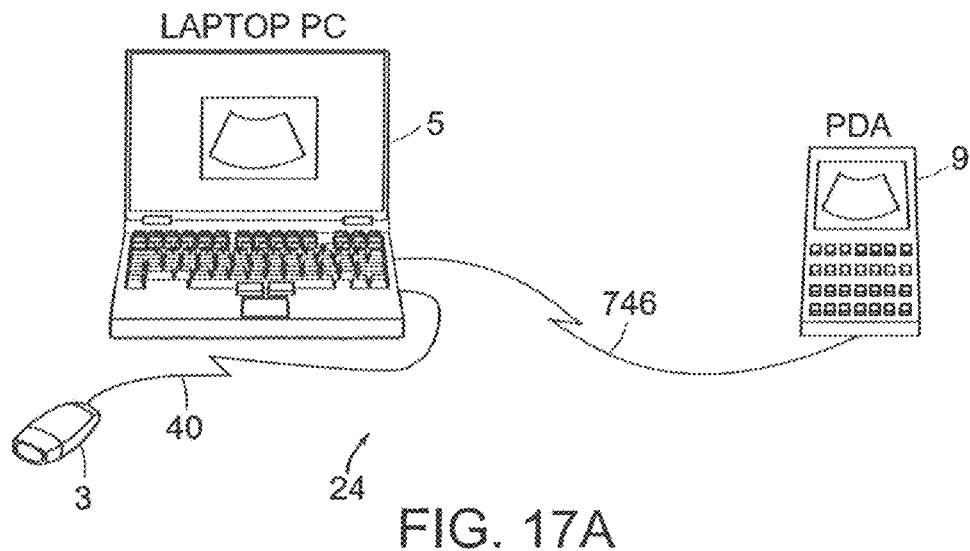
FIG. 17A is a block diagram illustrating an ultrasound imaging system with wired and wireless communication.

Referring to FIG. 17A, the integrated probe system 24 includes the front end probe 3, the host computer 5, and a portable information device such as a personal digital assistant (PDA) 9. The PDA 9, such as a Palm Pilot device, or other hand-held computing device is a remote display and/or recording device 9. In the embodiment shown, the front end probe 3 is connected to the host computer 5 by the communication link 40 that is a wired link. The host computer 5, a computing device, is connected to the PDA 9 by a communication link or interface 46 that is wireless link 46.

In that the integrated ultrasound probe system 24 in the embodiment described has a Windows®-based host computer 5, the system can leverage the extensive selection of software available for the Windows® operating system. One potentially useful application is electronically connecting ultrasound systems allowing physicians to said and receive messages, diagnostic images, instructions, reports or even remotely controlling the front-end probe 3 using the system.

The connections through the communication links or interfaces 40 and 746 can be either wired through an Ethernet or wireless through a wireless communication link such as, but not limited to, IEEE 802.11a, IE 802.11b, Hyperlink or HomeRF. FIG. 17A shows a wired link for the communication link 40 and a wireless link for the communication link 746. Alternative embodiments and protocols for wired links are described above with respect to FIG. 1. It is recognized that other wired embodiments or protocols can be used.

The wireless communication link 746 can use various different protocols, such as, an RF link which may be implemented using all or parts of a specialized protocol, such as the IEEE 1394 protocol stack or Bluetooth system protocol stack. IEEE 1394 is a preferred interface for high bandwidth applications such as high quality digital video editing of ultrasonic imaging data. The Bluetooth protocol uses a combination of circuit and packet switching. Slots can be reserved for synchronous packets. Bluetooth can support an asynchronous data channel, up to three simultaneous synchronous channels, or a channel which simultaneously supports asynchronous data and synchronous voice. Each synchronous channel support a 64 kb/s synchronous (voice) channel in each direction. The asynchronous channel can support maximal 723.2 kb/s asymmetric, or 433.9 kb/s symmetric.

The Bluetooth system consists of a radio unit, a link control unit, and a support unit for link management and host terminal interface functions. The link controller caries out the baseband protocols and other low-level link routines.

The Bluetooth system provides a point-to-point connection (only two Bluetooth units involved), or a point-to-multipoint connection. In the point-to-multipoint connection, the channel is shared among several Bluetooth units. Two or more units sharing the same channel form a piconet. One Bluetooth unit acts as the master of the piconet, whereas the other units act as slaves. Up to seven slaves can be active in a piconet.

The Bluetooth link controller has two major states: STANDBY and CONNECTION, in addition, there are seven substates, page, page scan, inquiry, inquiry scan, master response, slave response, and inquiry response. The substates are interim states that are used to add new slaves to a piconet.

The link may also be implemented using, but not limited to, Home RF, or the IEEE 802.11 wireless LAN specification. For more information on the IEEE 802.11 Wireless LAN specification, see the Institute of Electrical and Electronic Engineers (IEEE) standard for Wireless LAN incorporated herein by reference. IEEE standards can be found on the World Wide Web at the Universal Resource Locator (URL) www.ieee.org. For example, hardware supporting IEEE-standard 802.11b provides a communications link between two personal computers at 2 and 11 Mbps. The frequency bands allocated for transmission and reception of the signals is approximately 2.4 GHz. In comparison, IEEE standard 802.11a provides 54 Mbps communications. The frequency allocation for this standard is around 5 GHz. Recently, vendors, such as Proxim, have manufactured PC Cards and access points (basestations) that use a proprietary data-doubling, chipset, technology to achieve 108 Mbps communications. The chip that provides the data doubling (the AR5000) is manufactured by Atheros Communications. As with any radio system, the actual data rate maintained between two computers is related to the physical distance between the transmitter and receiver.

The wireless link 746 can also take on other forms, such as, an infrared communications link as defined by the Infrared Data Association (IrDA). Depending on the type of communication desired (i.e., Bluetooth, Infrared, etc.) the host computer 5 and the remote display and/or recording device 9 each has the desired communication port.

Figure 17B:
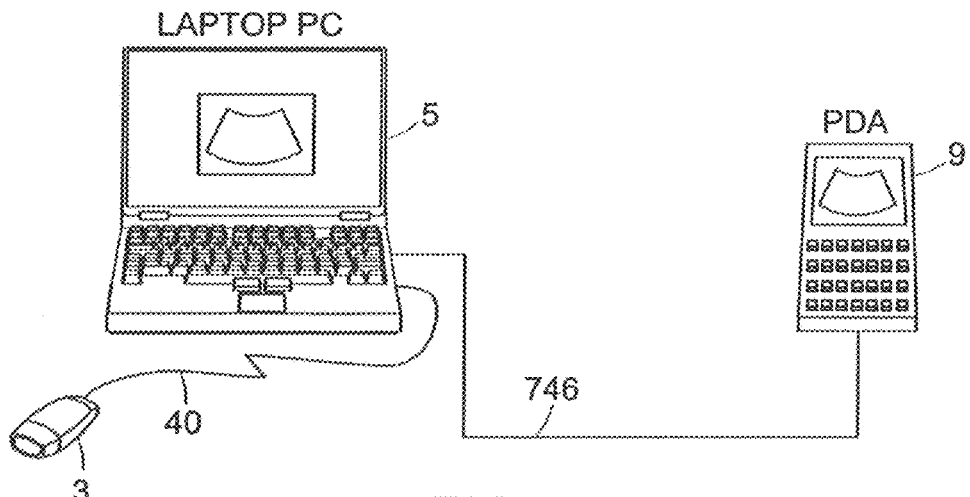
FIG. 17B is a block diagram illustrating an ultrasound imaging system with wireless and wired communication.

FIG. 17B shows the communication link 40 between the probe 3 and the host computer 5 as a wireless link. The communication link 746 between the host computer 5 and the PDA 9 is shown as a wired link.

Figure 17C:
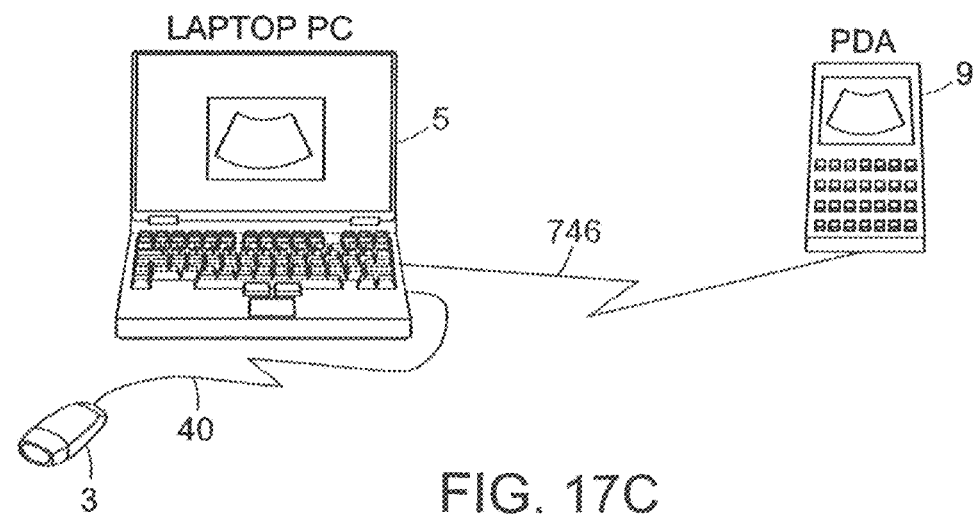
FIG. 17C is a block diagram illustrating an ultrasound imaging system with wireless communication.

The integrated probe system 24 of FIG. 17C has wireless links for both the communication link 40 between the probe 3 and the host computer 5 and the communication link 746 between the host computer 5 and the PDA 9. It is recognized that wired and wireless links can both be used together or in the alternative, can be exclusively wired links or wireless links in a system 24.

Figure 18:
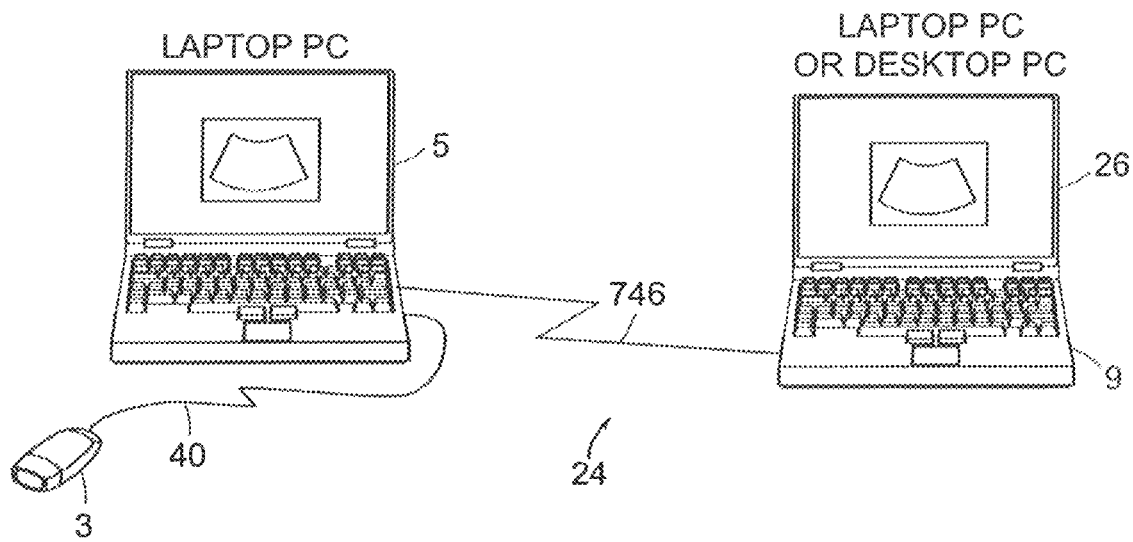
FIG. 18 is a block diagram illustrating an ultrasound imaging system with a remote or secondary controller/viewer and wireless communication.

The remote display and/or recording device 9 of the integrated probe system 24 of FIG. 18 is a remote computing system 26. The remote computing system 26 in addition to having remote display and/or recording capability can also remotely control the probe 3. The communication link 746 is shown as a wireless link. The communication link 40 between the probe 3 and the host computer 5 is shown as a wired link.

An example of a remote control system includes using a wearable computer (such as the one manufactured by Xybernaut Corporation), a pair of high-speed, wireless PC Cards (such as those provided by Proxim) and the ultrasound program and the probe 3. A portable-networked ultrasound system can be configured weighing less than 2.5 pounds. Using a program similar to Microsoft® NetMeeting, a real-time connection between a remote PC and the wearable computer can be established. The remote host can monitor all interactions with the wearable computer, including real-time ultrasound imaging (at display rates up to approximately 4 frames per second). NetMeeting can also be used to "take control" of the wearable computer and manage the ultrasound session from the remote personal computer in real time. In addition, images and iterative executable software instructions that are archived to the hard disk on the wearable computer can be transferred at 108 Mbps to the host computer. With this technology, real time ultrasound diagnoses can be performed and relayed to a remote sight at speeds that rival a hardwired 100 million bits per second (Mbps) local area network (LAN).

Figure 19:
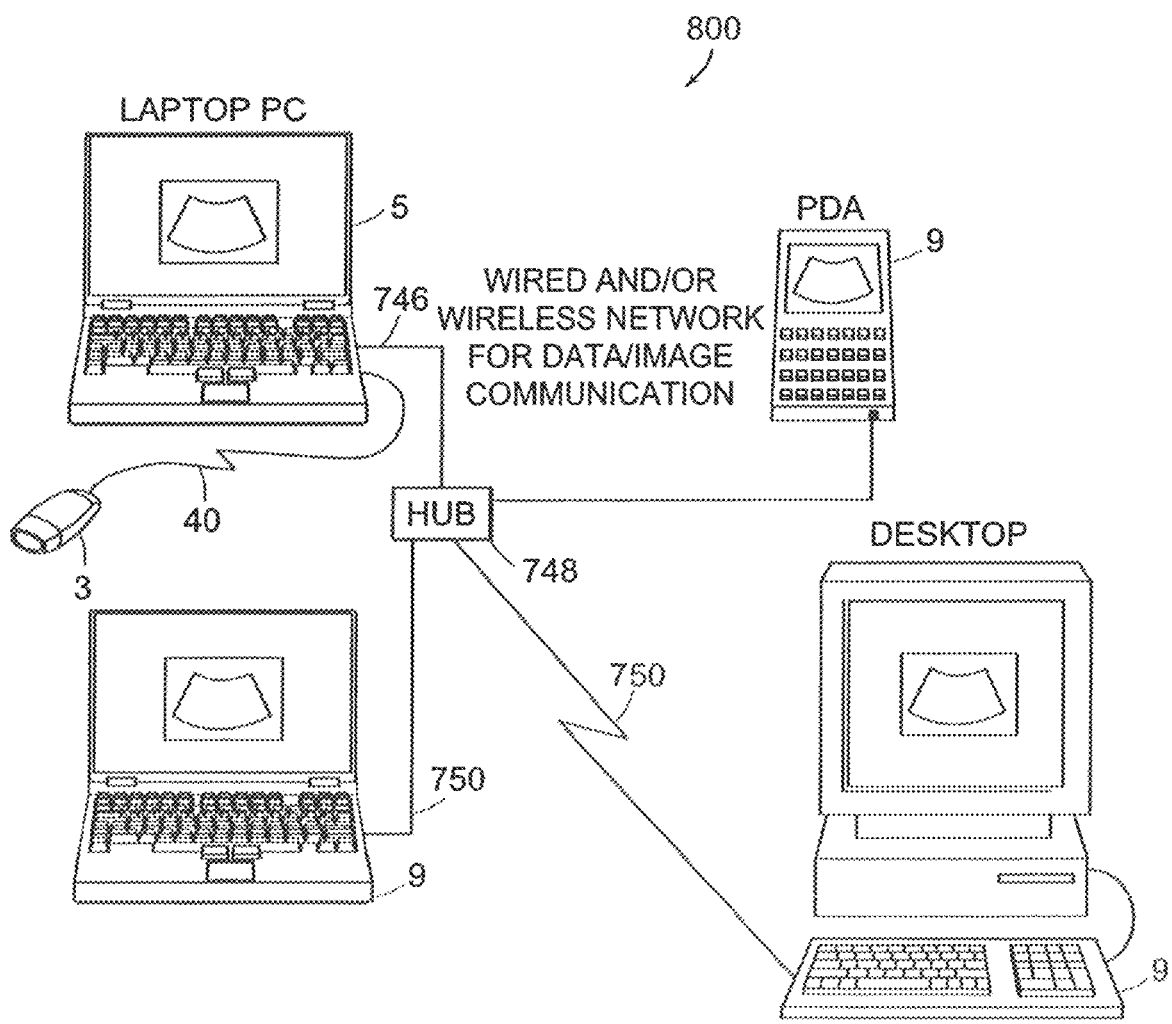
FIG. 19 is a block diagram illustrating an ultrasound imaging system with wired and wireless network communication capability.

FIG. 19 illustrates an integrated probe system 800 that has a hub 748 for connecting a plurality of remote devices 9 to the host computer 5. The communication link 750 from the hub 748 to the remote devices are shown both as wireless and wired links. It is recognized that a completely wired network such as a LAN or Ethernet can be used. In the alternative, with a wireless transceiver and port in each of the computers (remote device) 9, a wireless Network/Communication system can readily be established. With the recent advent of high-speed wireless standards, such as IEEE 802.11a, the communications between the remote and local machines can rival that of a wired, 100 Mbps local area network (LAN). Another alternative is using a Bluetooth system to form a piconet.

The increasing use of combined audio-visual and computer data is leading to greater need for multimedia networking capabilities and solutions are beginning to emerge that are included in preferred embodiments of the present invention. Standardization of multimedia networking is underway, and TE 1394 is emerging as the leading contender, capable of interfacing with a number of audio-visual (AV), computer and other digital consumer electronics and providing transmission bandwidth of up to 400 Mbps.

Preferred embodiments use TEE 1394 technology which uses a wireless solution for the transmission of 1394 protocols over IEEE 802.11, the emerging standard for wireless data transmission in the corporate environment and increasingly in the home as well In a preferred embodiment IEEE 1394 is implemented as a Protocol Adaptation Layer (PAL) on top of the 802.11 radio hardware and Ethernet protocols, bringing together a convergence of these important technologies. This protocol adaptation layer enables the PC to function as a wireless 1394 device. The engineering goal is for real delivered IEEE 1394 bandwidth sufficient for the transmission of a single high-definition MPEG2 video stream (or multiple standard-definition MPEG2 video streams) from one room in a facility to another.

Preferred embodiments of the present invention include the use of wireless transmission of IEEE 1394 at 2.4 GHz using Wi-LAN's Wideband Orthogonal Frequency Division Multiplexing (W-OFDM) technology. This development establishes W-OFDM, the most bandwidth-efficient wireless transmission technology, as one of the technologies capable of providing data rates necessary for in-home multimedia networking.

The Wireless IEEE 1394 system includes an MPEG-2 data stream generator, which feeds a multiple transport stream into a Set Top Box (STB) such as provided by Philips Semiconductors. The STB converts this signal to an ME 1394 data stream and applies it to the W-OFDM radio system such provided by Wi-LAN™. The radio transmitter then sends the IBM 1394 data stream over the air to the corresponding W-OFDM receiver in the host computer, for example. On the receive side, the IEEE 1394 signal is demodulated and sent to two STBs, which display the content of the different MPEG-2 data streams on two separate TV monitors. Using EM 1394 as the interface for the wired part of the network optimizes the entire system for transmission of isochronous information (voice, live video) and provides an ideal interface to multimedia devices in the facility. W-OFDM technology is inherently immune to the effects of multipath. Like all modulation schemes, OFDM encodes data inside a radio frequency (RF) signal. Radio communications are often obstructed by occurring noise, stray and reflected signals. By sending high-speed signals concurrently on different frequencies, OFDM technology offers robust communications. OFDM-enabled systems are highly tolerant to noise and multipath, making wide-area and in-home multi-point coverage possible. Additionally, as these systems are very efficient in use of bandwidth, many more high-speed channels are possible within a frequency-band. W-OFDM is a cost-effective variation of OFDM that allows much larger throughputs than conventional OFDM by using a broad frequency band. W-OFDM further processes the signal to maximize the range. These improvements to conventional OFDM result in the dramatically increased transmission speeds.

OFDM technology is becoming increasingly more visible as American and European standardization committees are choosing it as the only technology capable of providing reliable wireless high data rate connections. European terrestrial digital video broadcasting uses OFDM and the IEEE 802.11 working group recently selected OFDM in its proposed 6 to 54 Mbps wireless LAN standard. The European Telecommunications Standards Institute is considering W-OFDM for the ETSI BRAN standard. Detailed information on Wi-LAN™ can be found on the Web at http//www.wi-lan.com/Philips Semiconductors, a division of Royal Philips Electronics, headquartered in Eindhoven, The Netherlands. Additional information on Philips Semiconductors can be obtained by accessing its home page at http://www.semiconductors.philips.com/.

Further, NEC Corporation's wireless transmission technology based on the IEEE 1394 high-speed serial bus capable of 400 megabits (Mbps), at transmission ranges of up to 7 meters through interior walls and up to 12 meters by line-of-sight may also be used in preferred embodiments. This embodiment uses 60 GHz millimeter wavelength transmissions, which does not require any kind of license, with the amplitude shift keying (ASK) modulation scheme and the development of a low cost transceiver. This embodiment incorporates an echo detection function in NEC's PD72880 400 Mbps long-distance transmission physical layer device, to prevent the influence of signal reflections, a significant obstacle to stable operation of IEEE 1394 over a wireless connection.

Wireless IEEE 1394 can play an important role in bridging the PC to clusters of interconnected IEEE 1394 devices, which can be in another room in the facility. Three example applications are sourcing video or audio stream from a PC, providing internet content and connectivity to a IEEE 1394 cluster, and provide command, control and configuration capabilities to the cluster. In the first embodiment, the PC may provide data to someone in another room in a facility. In the second embodiment, the PC may provide an avenue for 1394 enabled devices to access the Internet. In the third embodiment, the PC plays the role of orchestrating activities in the 1394 clusters and routing data within the clusters and over bridges—though the actual data does not flow through the PC.

Figure 20:
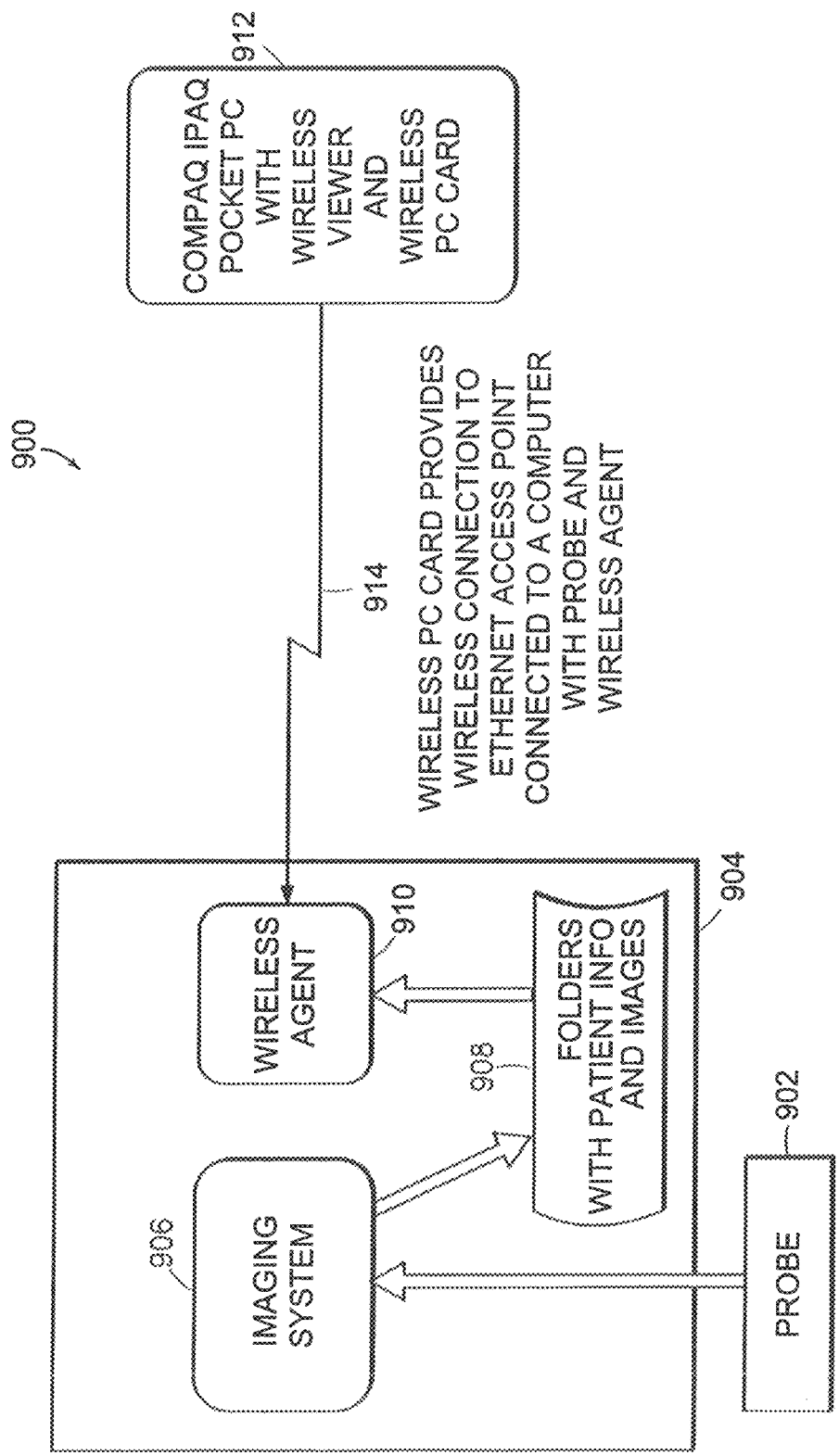
FIG. 20 is a diagram illustrating further details of the architecture of the ultrasound imaging system in accordance with a preferred embodiment of the present invention.

FIG. 20 is a diagram showing the provision of wireless access to the images created by a preferred embodiment ultrasound imaging system and the associated architecture. The imaging system 906 exports patient information and images to files in corresponding folders. Executable software instructions have all functionality required to implement the ultrasonic imaging methods described hereinbefore.

The wireless agent 910 serves to detect patient directories and image files and opens a port for wireless clients to get connection thereto. Upon establishing a connection it sends back to the client list of patients and corresponding images. For example, the wireless agent 910 may include data interface circuitry which may include a first port such as a RF interface port.

The wireless viewer 912 residing on a handheld side can establish connection to the wireless agent 910 and retrieve patient and image information. Upon user selection of the patient and image it initiates file transmission from the wireless agent. Upon receiving an image the Viewer 912 displays this image along with patient information. The image gets stored on the handheld for future use. The handheld user can view images retrieved in previous sessions or can request new image transmission.

Figure 24:
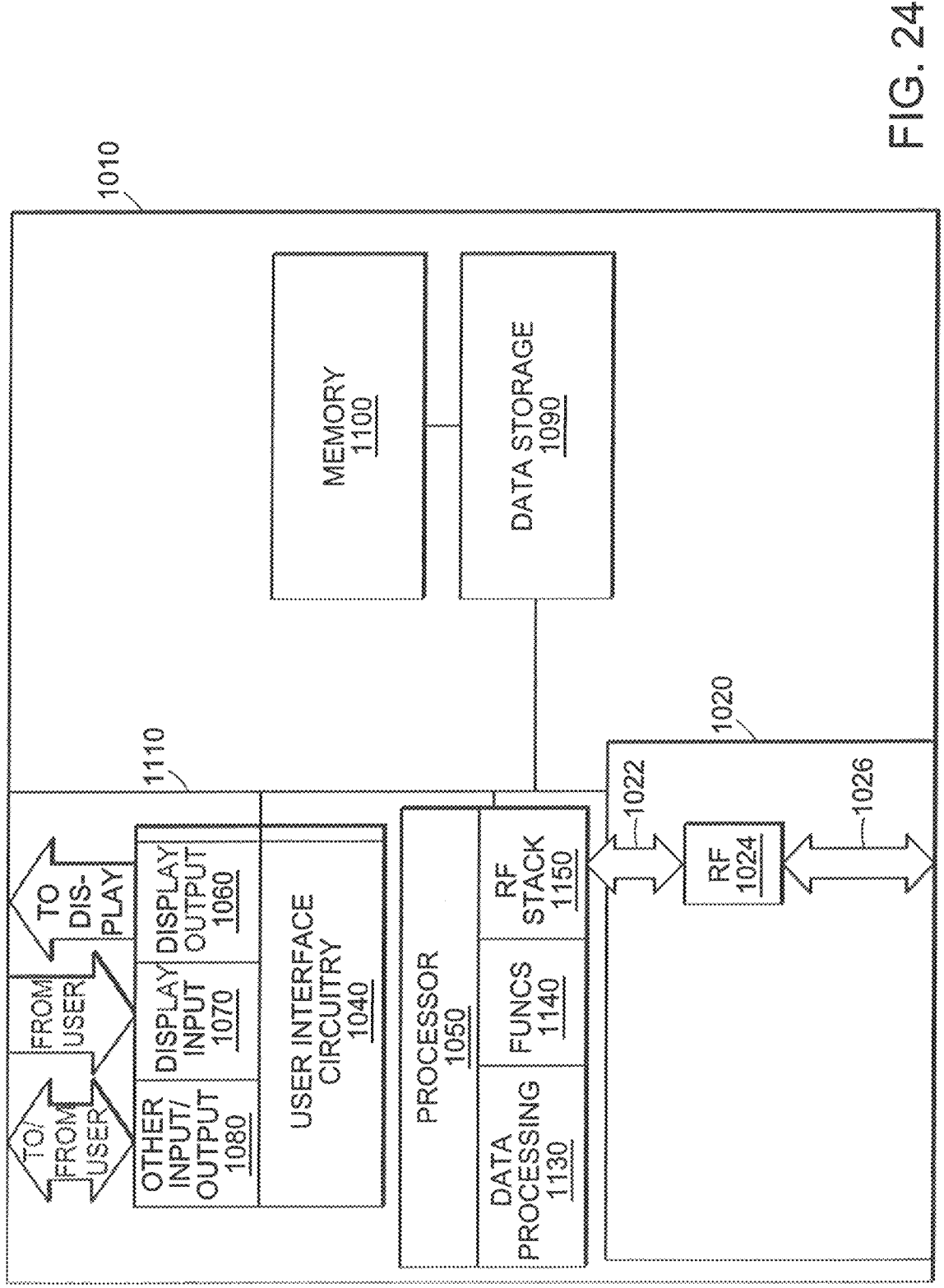
FIG. 24 is a block diagram illustrating a personal digital assistant (PDA) in communication with the host computer or probe system in accordance with preferred embodiment of the present invention.

FIG. 24 is a block diagram illustrating a portable information device 1010 such as a personal digital assistant (PDA) or any computing device according to an exemplary embodiment of the present invention. The link interface or data interface circuitry 1020 illustrates, but is not limited to, one link interface for establishing a wireless link to another device. The wireless link is preferable an RF link, defined by IEEE 1394 communications specifications. However, the wireless link can take on other forms, such as the infrared communications link as defined by the Infrared Data Association (IrDA). The PDA includes a processor 1050 that is capable of executing an RF stack 1150 that communicates with a data interface circuitry 1020 through bus 1110. The processor 1050 can execute data processing 1130 or funcs 1140. The processor 1050 is also connected through bus 1110 to user interface circuitry 1040, data storage 1090 and memory 1100. The user interface circuitry 1040 connects to a display output 1060, display input 1070, and other input/output 1080.

The data interface circuitry 1020 includes a port such as the RF interface port. The RF link interface may include a first connection 1022 which includes radio-frequency (RF) circuitry 1024 for converting signals into radio-frequency output and for accepting radio-frequency input. The RF circuitry 1024 can send and receive RF data communications via a transceiver that establishes communication port 1026. RF communication signals received by the RF circuitry 1024 are converted into electrical signals and relayed to the RF stack 1150 in processor 1050 via bus 1110. The radio interface 1024, 1026 and the link between the laptop PC (host computer) and the PDA may be implemented by, without limitation, IEEE 1394 specifications.

Similarly, the PC host computer has a RF stack and circuitry to be able to communicate to the remotely located image viewer. In a preferred embodiment, the remote image viewer may be used to monitor and/or control the ultrasonic imaging operations, not just display the resultant imaging data.

The current market offers a lot of different options related to wireless connectivity. In a preferred embodiment, spread-spectrum technology Wireless LAN is used. Among wireless LAN solutions the most advanced is the 802.11b standard. Many manufacturers offer 802.11b compliant equipment. Compatibility with the selected handheld is the major criteria in a specified class of wireless connectivity options.

The handheld market offers various handheld devices as well. For imaging purposes it is very important to have high quality screen and enough processing power to display an image. Considering these factors, in a preferred embodiment, a Compaq® iPAQ® is used, in particular a Compaq® iPAQ® 3870 is used. A wireless PC card compatible with the handheld is used such as Compaq's® Wireless PC Card WL110 and corresponding Wireless Access Point.

Figure 21:
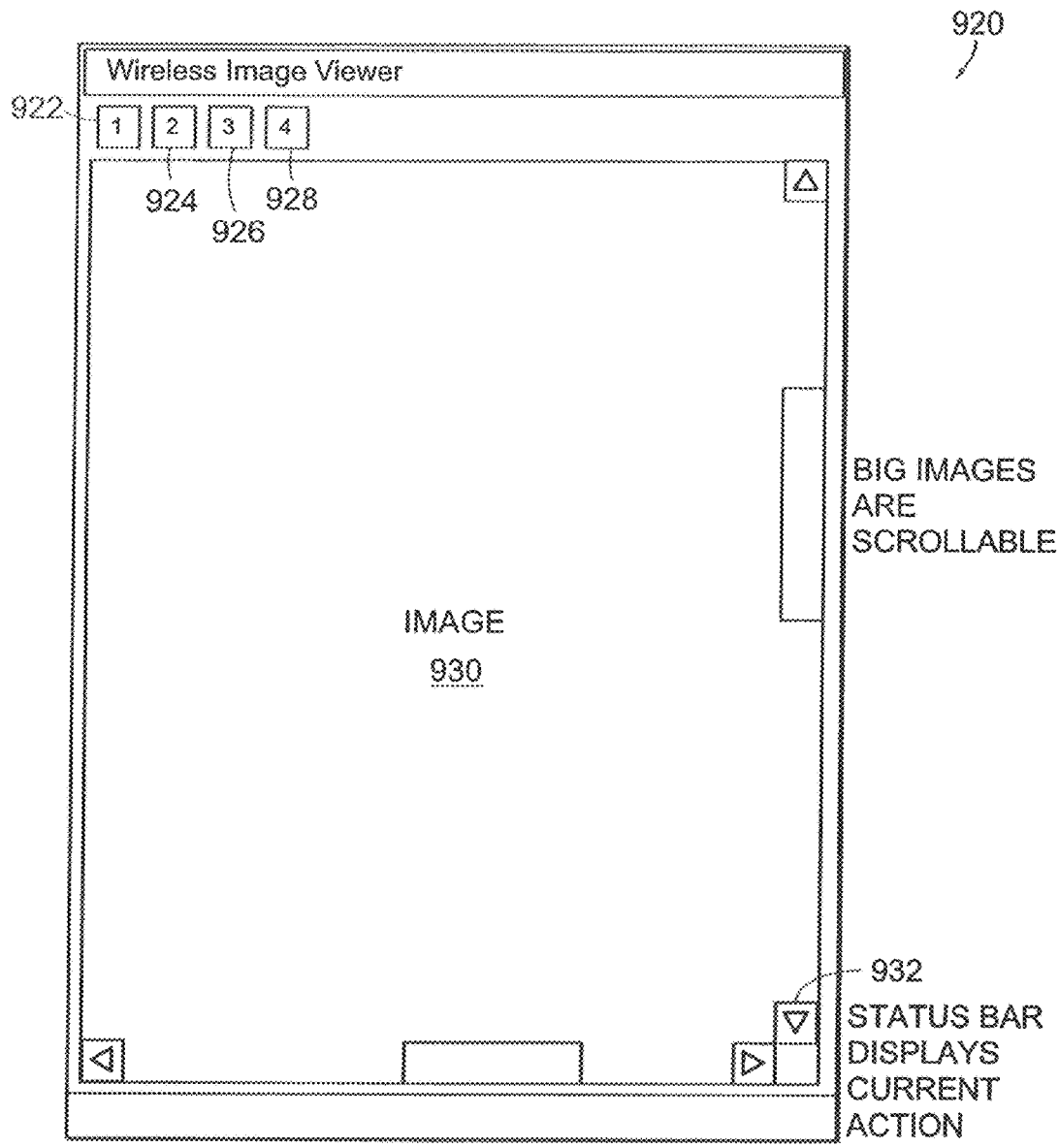
FIG. 21 is a diagram of a wireless viewer graphical user interface in accordance with a preferred embodiment of the present invention.

FIG. 21 illustrates the image viewer 920 in communication with the personal computer in a preferred embodiment or the probe in an alternate embodiment. The image viewer has user interface buttons 922, 924, 926, 928 that allow the user to interface with the ultrasonic imaging system computer or probe in accordance with preferred embodiments of the present invention. In a preferred embodiment, a communicating interface such as button 922 allows the user to initiate a connection with the ultrasonic imaging application. Similarly, button 924 is used to terminate an established connection with the ultrasonic imaging application. A button 926 functions as a selection button that is used to provide a list of patients and corresponding images that are selectable. These images are either stored locally or remotely. If selected, the image that may be stored remotely is transmitted to the viewer. The selected image is displayed on the viewer 930.

Additional communication interface buttons such as button 928 functions as an options button which may, but is not limited to, allow changing configuration parameters such as an internet protocol (IP) address.

Figure 22:
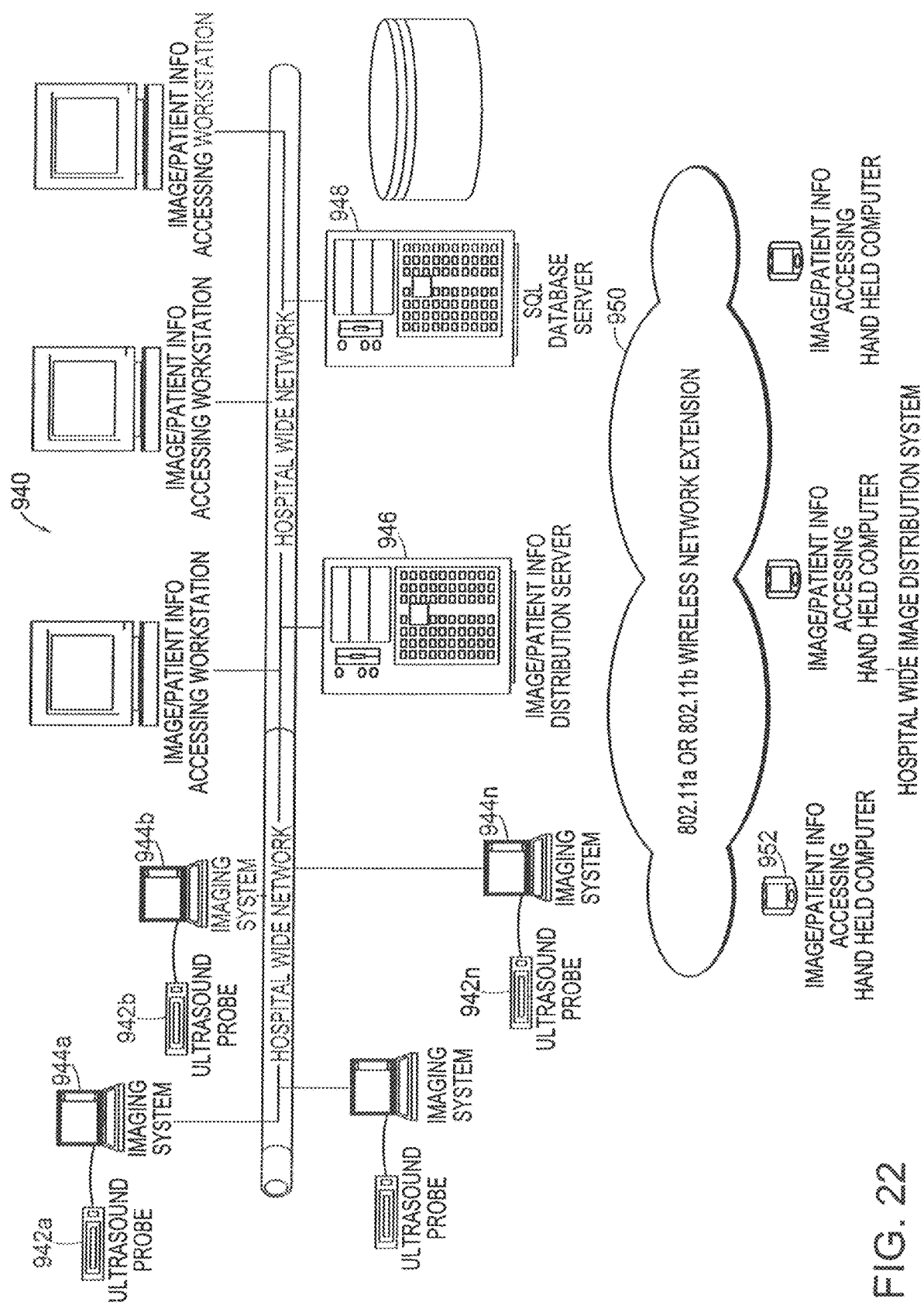
FIG. 22 is a diagram of a facility wide ultrasound image distribution system in accordance with a preferred embodiment of the present invention.

FIG. 22 is a diagram illustrating a preferred embodiment ultrasound image collection and distribution system 940 including four major software components. The main hardware element of the system is ultrasound probe 942a-944n. The probe in communication with the laptop computer 944a-944n allows generation of the ultrasound images and related patient information and submits images and information to an image/patient information distribution server 946. The distribution server utilizes an SQL database server 948 to store and retrieve images and related patient information. The SQL server provides distributed database management. Multiple workstations can manipulate data stored on the server, and the server coordinates operations and performs resource-intensive calculations.

Image viewing software or executable instructions may be implemented in two different embodiments. In a first embodiment, a full stationary version of the Image Viewer as described in FIG. 21 may reside on a workstation or laptop computer equipped with high bandwidth network connection. In a second embodiment, a light weight version of the Image Viewer may reside on a small PocketPC handheld 952 equipped with IEEE 802.11b and/or IEEE 802.11a compliant network card. The PocketPC image viewer implements only limited functionality allowing basic image viewing operations. The wireless network protocols 950 such as IEEE 802.11 may be used to transmit information to a handheld or other computing devices 952 in communication with a hospital network.

This preferred embodiment describes the ultrasound imaging system to cover hospital wide image collecting and retrieving needs. It also provides instant access to non-image patient related information. In order to provide inter-hospital information exchange, image distribution servers have the ability to maintain connectivity with each other across wide area networks.

Figure 23:
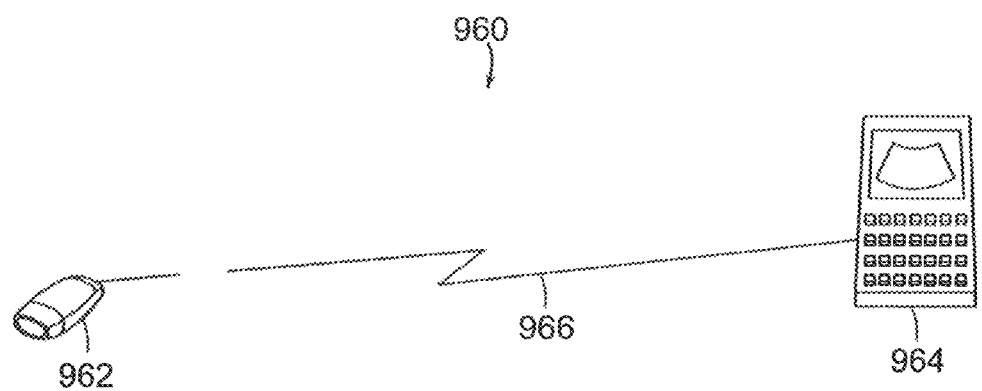
FIG. 23 is a diagram illustrating an ultrasound imaging system in accordance with a preferred embodiment of the present invention.

In another preferred embodiment 960 shown in FIG. 23, the probe 962 may directly communicate with a remote computing device such as a PDA 964 using a wireless communication link 966. The communication link may use the IEEE 1394 protocol. The probe and the PDA both have an RF stack and circuitry described with respect to FIG. 24 to communicate using wireless protocols. The probe includes a transducer array, beamforming circuitry, transmit/receive module, a system controller and digital communication control circuitry. Post processing of the ultrasonic image data including scan conversion is provided in the PDA.

A preferred embodiment of the microminiaturized PC enabled ultrasound imaging system runs on an industry standard PC and Windows® 2000 operating system (OS). It is therefore network ready which makes it ideal for telemedicine solutions while being cost efficient. It provides open architecture support embedded and thus integrated with third party applications. The preferred embodiment includes an enhanced Application Programming Interface (API), common interface, export support for third party applications, such as, but not limited to, for example, radiation therapy planning, image guided surgery, integrated solutions, for example, calculations, three-dimensional and reporting packages. The API provides a set of software interrupts, calls, and data formats that application programs use to initiate contact with network services, mainframe communication programs, telephone equipment or program-to-program communications. Software based feature enhancements reduce hardware obsolescence and provide efficient upgrades.

Further, the preferred embodiment includes system-on-chip integrated circuits (ICs) which run on PCs and have a large channel count, large dynamic range; high image quality, full feature sets, broad diagnostic coverage, minimal supply chain requirements, simplified design for easy testing and high reliability, and very low maintenance costs. As previously described herein, the preferred embodiment includes a PC based design which is intuitive, has a simple graphical user interface, is easy to use and train with, which leverages PC industry know-how, robust electronics, high quality displays and low manufacturing costs. It also provides support of software controlled communications with other applications, which are embedded applications that allows patient data, scanner image, Current Procedural Terminology (CPT) code management, which is a numeric coding system by which physicians record their procedures and services, physician's plan, outcome assessment reports, all on an integrated PC. The reforms to the health care system have been applying pressure to lower costs, highlight the need for first visit/in-field diagnosis, data storage and retrieval solutions which when combined with technology innovations such as, for example, data storage and retrieval based on the Digital Imaging and Communications in Medicine (DICOM) standard, broadband and Picture Archiving and Communications-Systems (PACS) drives, changes in patient record storage and retrieval and transmission, innovations in lower cost/handheld devices for ultrasound data acquisition, all which enable the preferred embodiment of the present invention. The DICOM standard aids the distribution and viewing of medical images such as, for example, ultrasound, Magnetic Resonance Images (MRIs), and CT scans. Broadband is a wide area network term that refers to a transmission facility providing bandwidth greater than 45 Mbps. Broadband systems are generally fiber optic in nature.

A preferred embodiment of the present invention provides image acquisition and end-user application, for example, radiation therapy, surgery, angiography, all applications executed on the same platform. This provides low cost, user friendly controls through a common software interface. The ultrasound system has scalable user interfaces for advanced users and has an intuitive Windows® based PC interface. A preferred embodiment of the ultrasound system also provides an enhanced diagnostic ability due to the features of one-stop image capture, analysis, storage, retrieval and transmittal capability for the data and images. A high image quality is provided by a 128 channel bandwidth. Besides ease of use, the ultrasound system also provides patient access at any time, any location and using any tool. Point of care imaging is provided with a 10 ounce probe in accordance with a preferred embodiment of the present invention. The data storage and retrieval abilities are based on the DICOM standard and are compatible with off-the-shelf third party analytical and patient record systems. The ultrasound system in accordance with a preferred embodiment also provides immediate image transfer ability using, but not limited to, for example, electronic mail, LAN/WAN, DICOM and Digital Imaging Network-Picture Archiving and Communications Systems (DINPACs). The choices to display the images captured include, but are not limited to, a desktop computer, a laptop computer, wearable personal computers and handheld devices such as personal digital assistants.

Figure 25A:
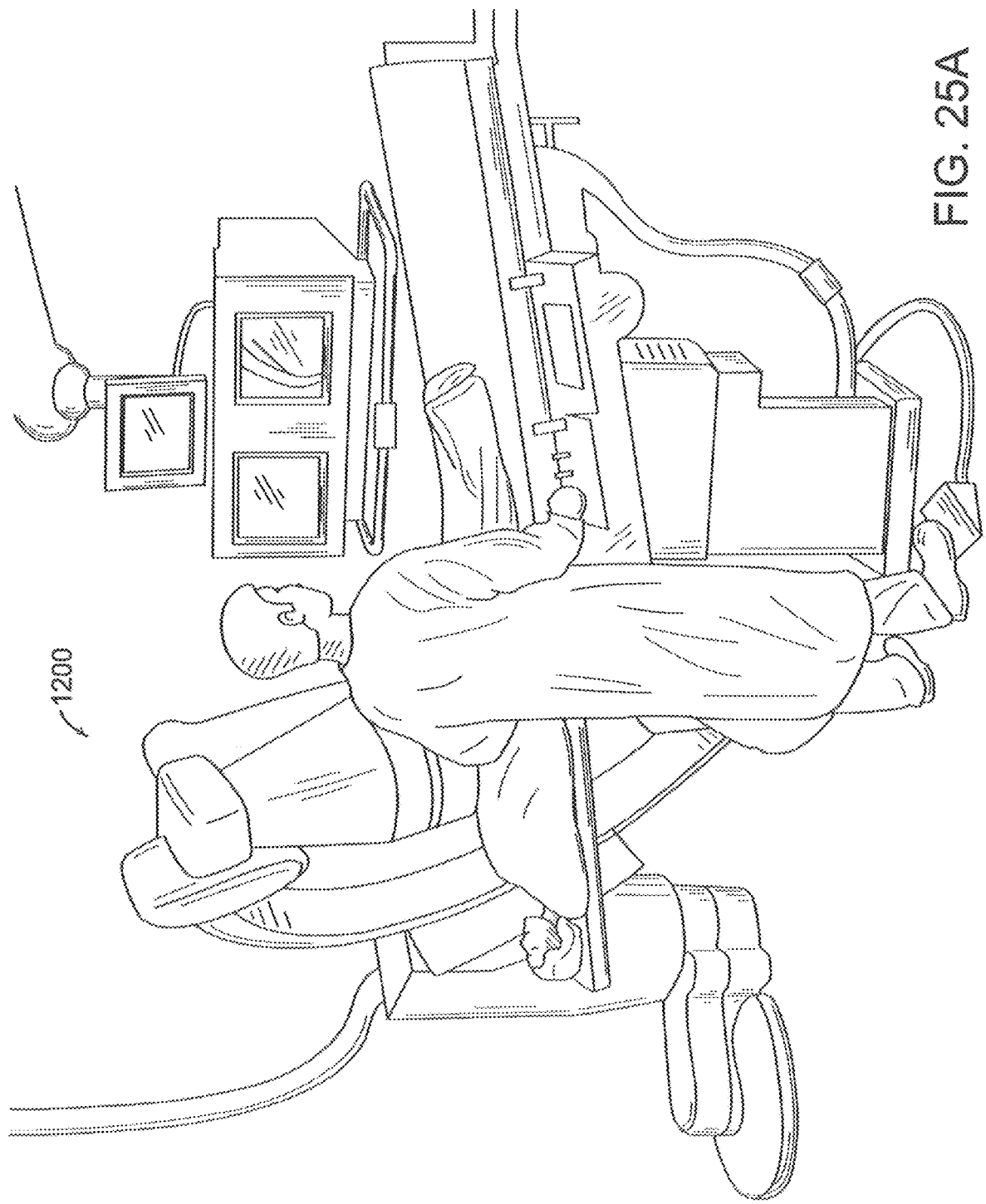
FIGS. 25A-25C illustrate an ultrasound system in accordance with a preferred embodiment of the present invention integrated with an angiography system, a high frequency image of the carotid artery with directional power doppler and an image of the carotid artery with simultaneous quantitative spectral doppler, respectively.
Figure 25B:
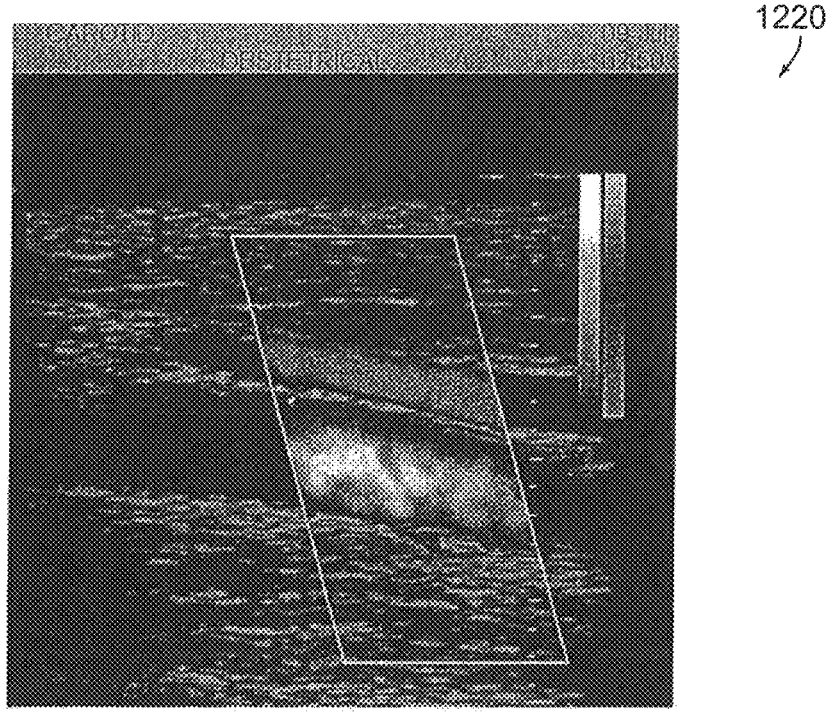
Figure 25C:
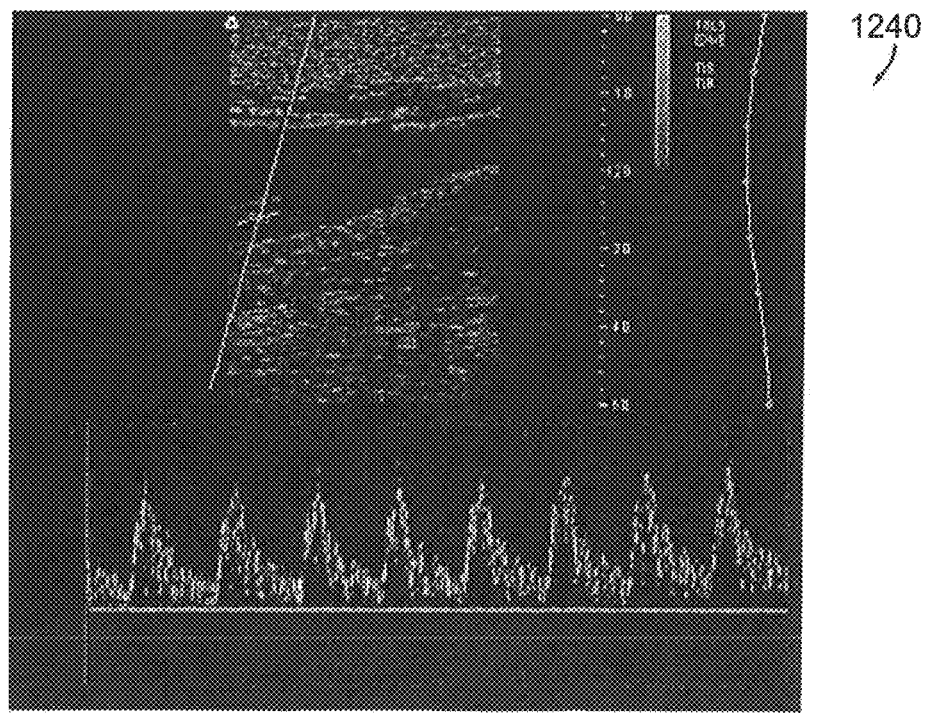

FIGS. 25A-25C illustrate an ultrasound system 1200 in accordance with a preferred embodiment of the present invention integrated with an angiography system, a high frequency image 1220 of the carotid artery with directional power doppler and an image 1240 of the carotid artery with simultaneous quantitative spectral doppler, respectively. During an acute coronary syndrome, multiple atherosclerotic plaques typically rupture, suggesting that the syndrome is associated with overall coronary instability. Intravascular ultrasound with the system of the present invention can evaluate the entire coronary circulation. Ultrasonographic screening reduces mortality from abdominal aortic aneurysms. The ultrasound system of a present invention provides easy guidance and confirmation of aortic arch placement, helps the rapid delivery of cold perfusate into the aortic arch, hypothermic preservation of the brain, heart, and spinal cord. Further, sensor monitoring for critical flow/temperature/physiological data can be provided. Automatic computer controlled flow-temperature adjustments can be facilitated along with exsanguination control and blood pressure management using the embodiment of the present invention. Preferred embodiments use a touch screen display.

Figure 26A:
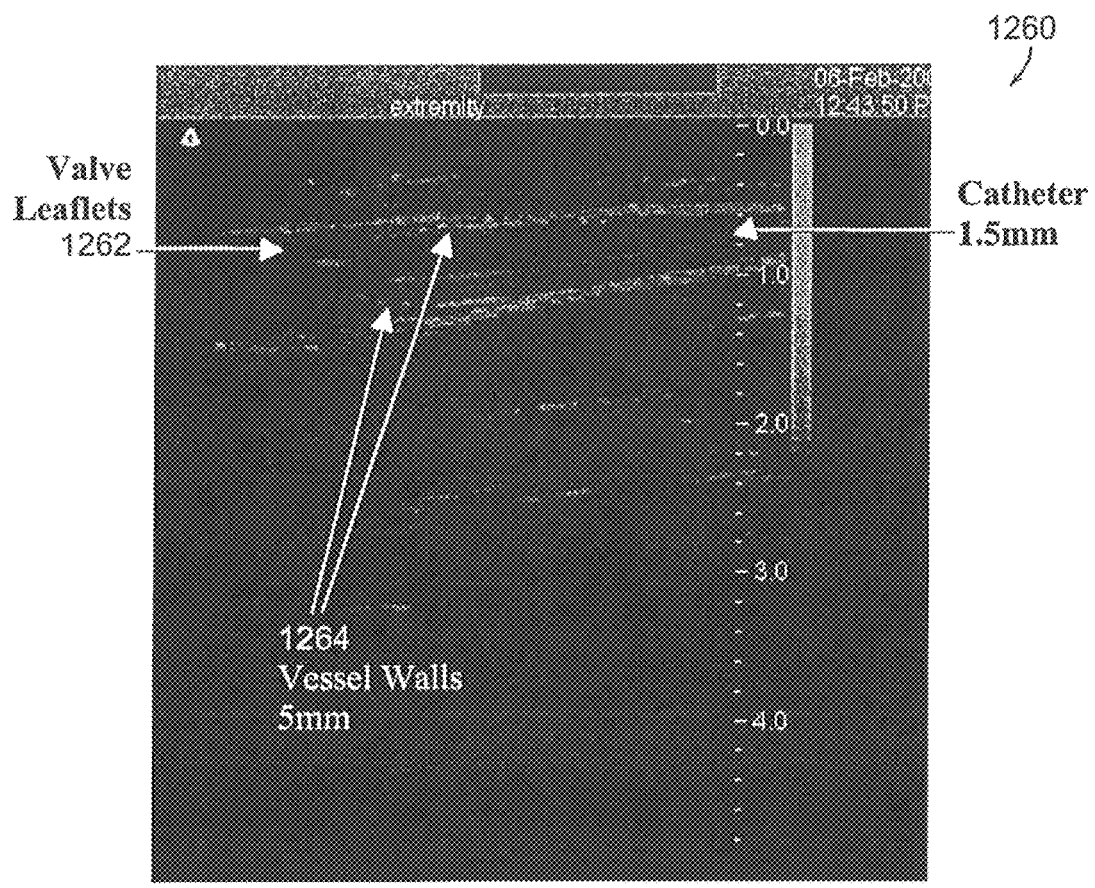
FIGS. 26A and 26B illustrate an ultrasound image of vessel walls in accordance with a preferred embodiment of the system of the present invention and a catheter used with the system, respectively.
Figure 26B:
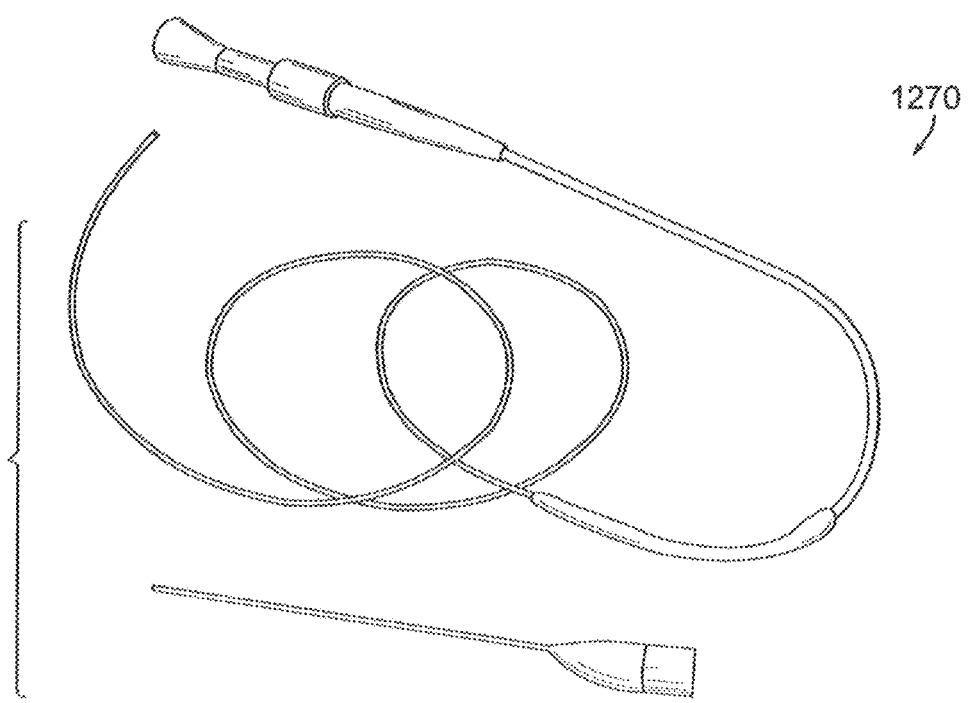

In an alternate preferred embodiment, the ultrasound system ensures accurate vessel localization. FIGS. 26A and 26B illustrate an ultrasound image 1260 of vessel walls 1264 and valve leaflets 1262 in accordance with a preferred embodiment of the system of the present invention and a catheter placement 1270 used with the system. Surgeons can use the ultrasonic system for catheter or line placements for both guidance and confirmation of placement. In preferred embodiments, the image file or raw RF data is directly accessed using a direct digital memory access. Thus, the ultrasound system provides real-time RF data output.

In an alternate embodiment, the ultrasound system of the present invention contributes to accurate surgical planning and imaging by providing neuro-navigation during neuro-surgery.

Figure 27B:
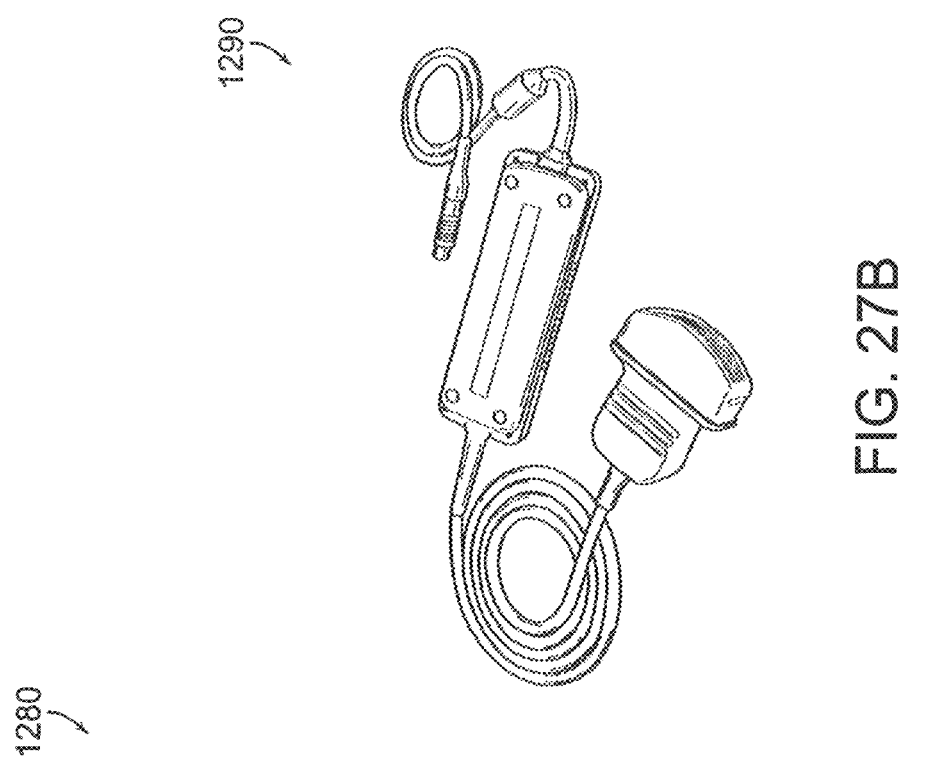
FIGS. 27A and 27B illustrate a radiation planning system integrating the ultrasound system in accordance with preferred embodiments of the present invention and the probe of the ultrasound system, respectively.
Figure 27A:
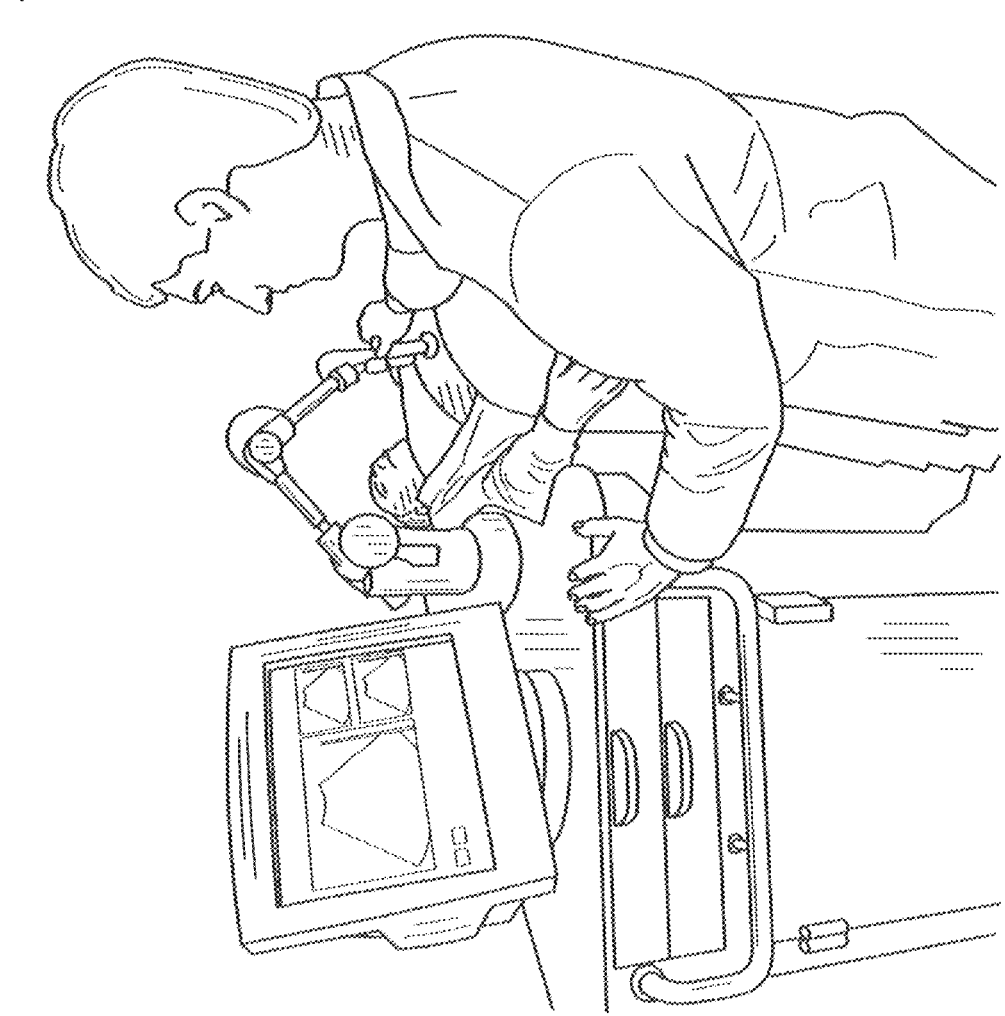

In an alternate embodiment, the ultrasound system of the present invention assists in radiation therapy by helping in planning and treatment phases. FIGS. 27A and 27B illustrate a radiation planning system 1280 integrating the ultrasound system in accordance with a preferred embodiment of the present invention and the probe 1290 of the ultrasound system, respectively. The ultrasound image can be integrated in the display.

Figure 28A:
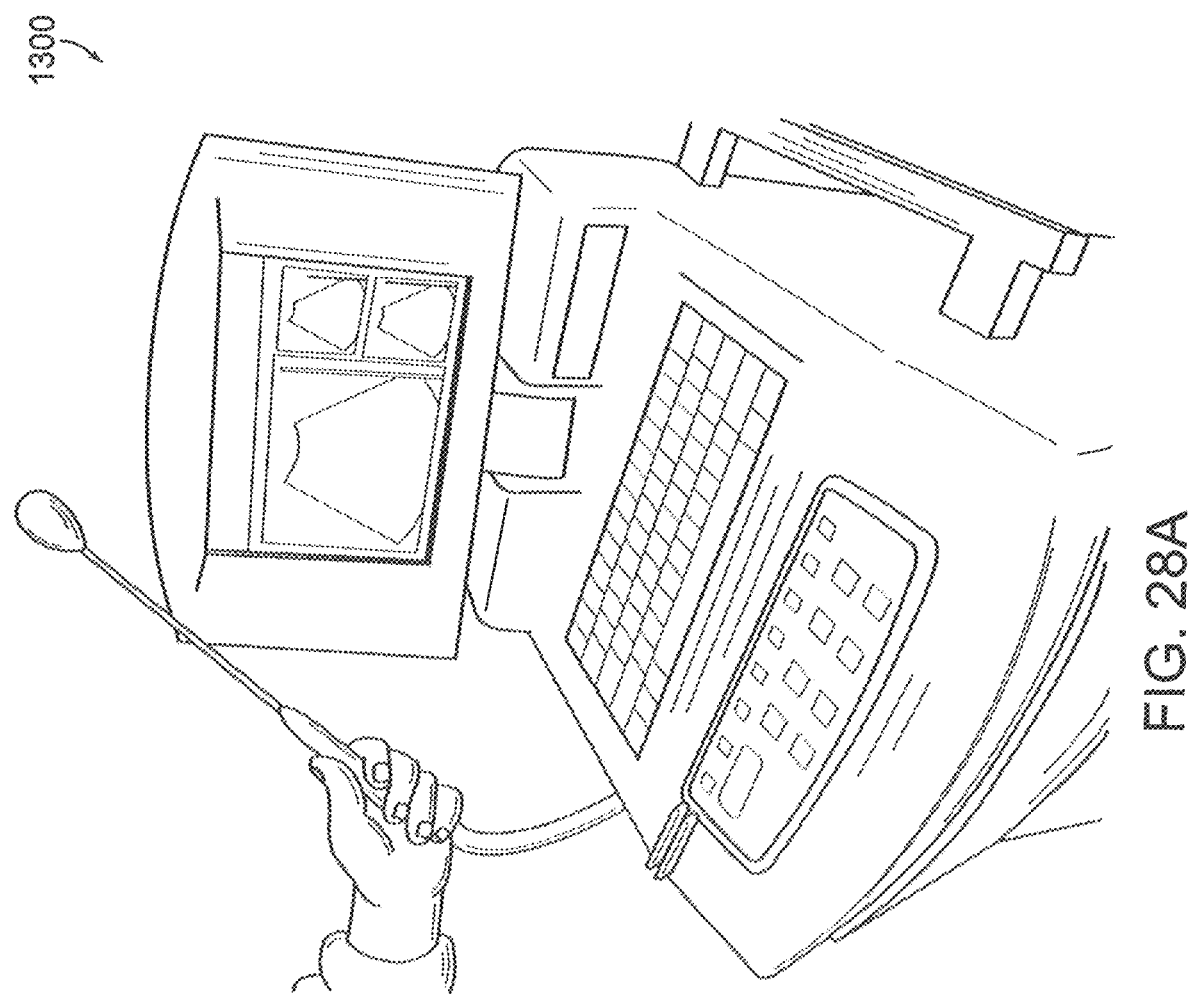
FIGS. 28A and 28B illustrate an ultrasonic imaging system for cryotherapy in accordance with a preferred embodiment of the present invention and a probe used in the system, respectively.
Figure 28B:
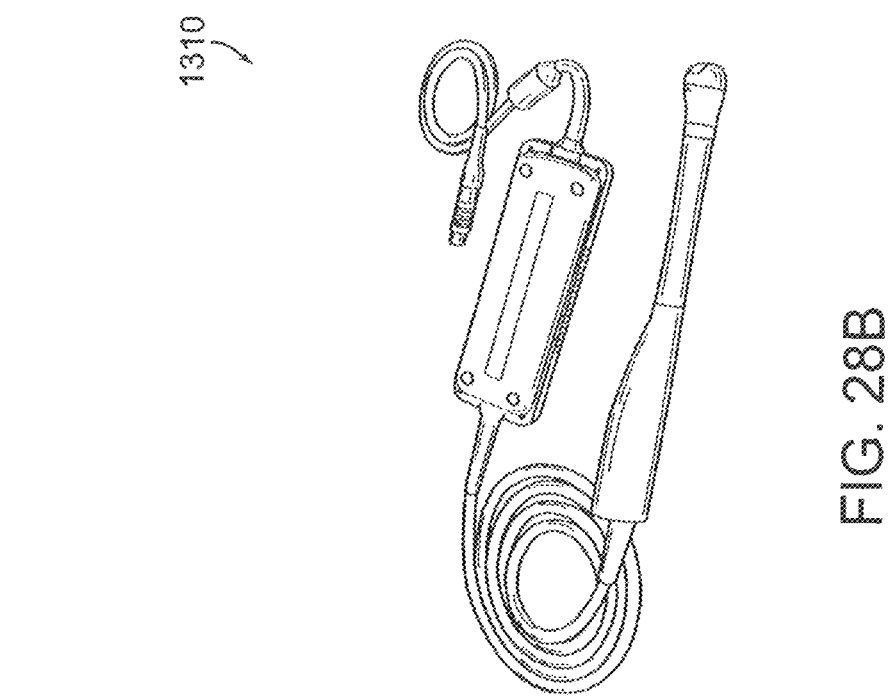

FIGS. 28A and 28B illustrate an ultrasonic imaging system 1300 for cryotherapy in accordance with a preferred embodiment of the present invention and a probe 1310 used in the system, respectively. In prostate cancer patients with limited disease, percutaneous ultrasound-guided cryosurgery applied focally can spare one neurovascular bundle and thus preserve potency without compromising cancer control. The cryotherapy can be used for urological surgery also. Preferred embodiments of the present invention provide multi-plane images with processing instructions that easily switch between planes in real time. At least two orthogonal transducer arrays having 64 or 128 elements can be used.

FIGS. 29A-29B are exploded views illustrating a robotic imaging and surgical system 1320 integrating the ultrasound system in accordance with a preferred embodiment of the present invention. FIG. 29C is a diagram illustrating a robotic imaging and surgical system integrating the ultrasound system 1320 in accordance with a preferred embodiment of the present invention. The system ensures appropriate vessel harvesting. The operating surgeon uses the ultrasound system 1322 to visualize the forceps and cautery controls. The surgeon is seated across the room from the patient 1326 and peers into a monitor 1324 and manipulates the robot with controls such as, for example, joystick-like hand controls. The robotic arms slip through the small, for example, nickel-size incisions between the ribs. A camera, forceps and a cautery 1328 are used to free up the mammary artery and attach it to the heart. The smaller incisions due to ultrasonic image guided surgery results in lower trauma to patients, less post-operative pain, less patient morbidity and shorter recovery times.

Further, image-guided surgery benefits from the provision of real-time RF data output in accordance with preferred embodiments of the system. In contrast to raw RF data, processed data includes data compression processing which masks differences between bone and tissue. RF data emphasizes the reflectivity and thus the differences between bone and tissue. Thus, the output data from the beamformer can be formatted and provided to enhance surgical imaging. This is enabling for surgeries such as, for example, hip and pelvic replacements.

In addition, computer enhanced image guided surgery further benefits a patient as it combines the dexterity of open surgery with low patient trauma.

In another preferred embodiment, an ultrasound system can be used for pacemaker placement surgery and monitoring. A three-dimensional ultrasound can be integrated into the systems for providing direct access to digital data via a shared memory.

Figure 30:
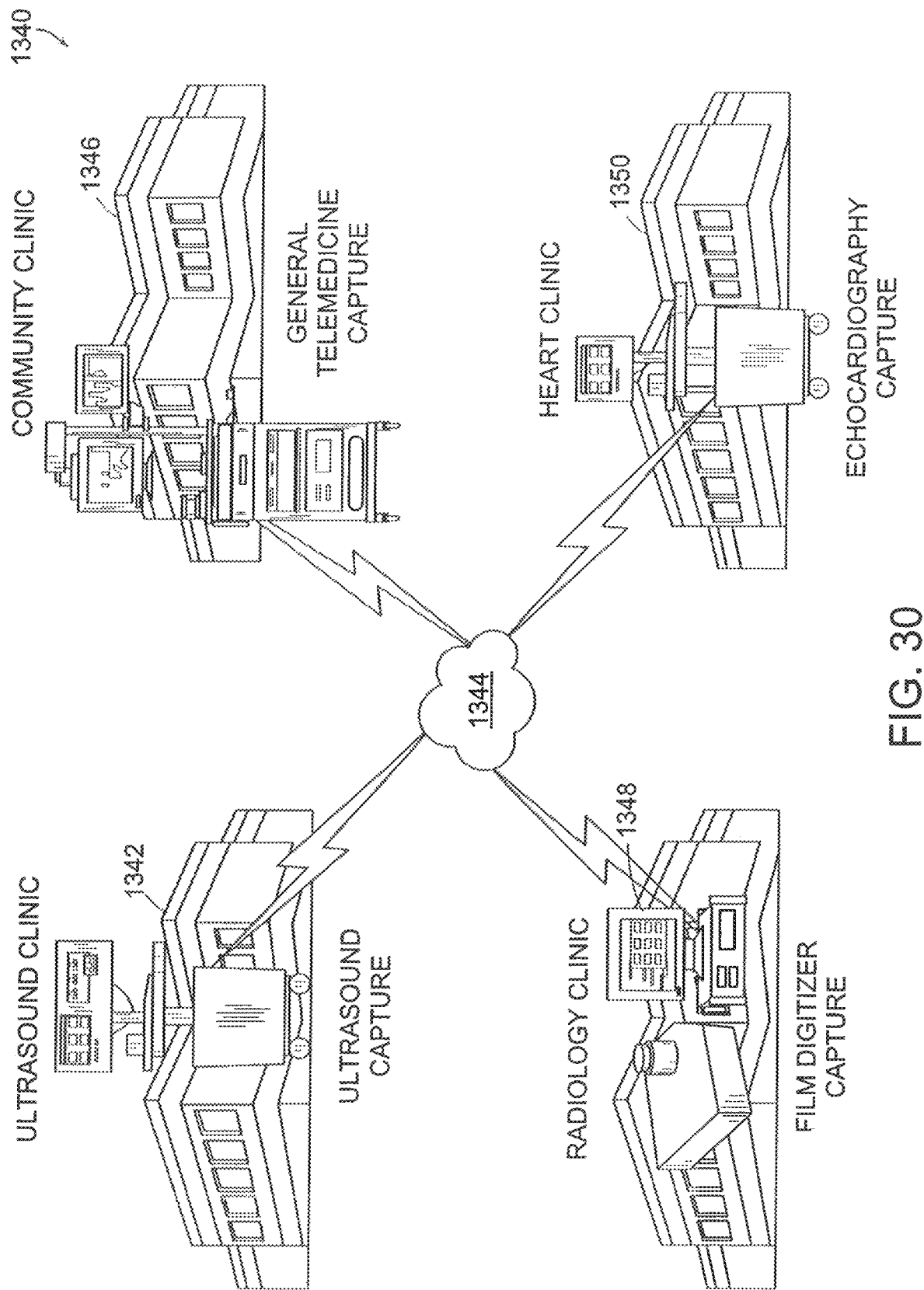
FIG. 30 is a schematic diagram illustrating an imaging and telemedicine system integrating the ultrasound system in accordance with a preferred embodiment of the present invention.

FIG. 30 is a schematic diagram 1340 illustrating an imaging and telemedicine system integrating the ultrasound system in accordance with a preferred embodiment of the present invention. Preferred embodiments of the system output the real-time RF digital data or the front-end data. General telemedicine capture 1346, echocardiography capture 1350, film digitizer capture 1348, and ultrasound capture 1342 are connected from different physical locations through a network 1344.

Figure 31B:
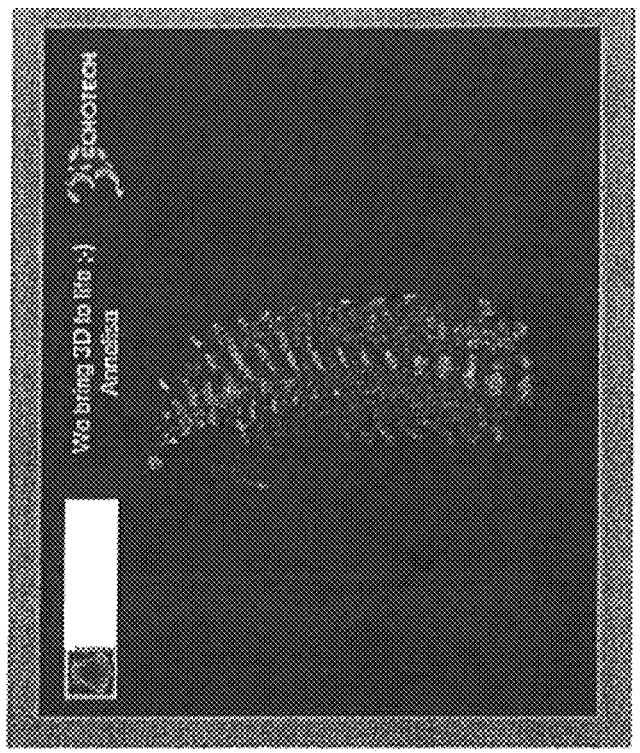
FIGS. 31A and 31B are three-dimensional images from fetal imaging obtained from an ultrasound system in accordance with a preferred embodiment of the present invention.
Figure 31A:
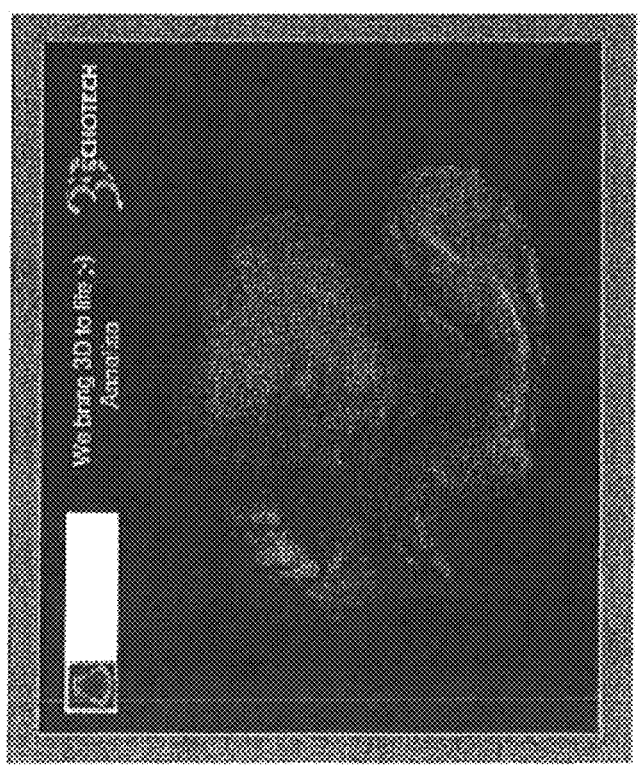

FIGS. 31A and 31B are three-dimensional images 1360 and 1370, respectively, from fetal imaging obtained from an ultrasound system in accordance with a preferred embodiment of the present invention. Preferred embodiments for fetal imaging use the streaming data. Using an RF transmitter in the ultrasound probe the location of each frame of data can be provided thus allowing for spatial registration. Three-dimensional alignment is provided by looking at the frame locations.

In a preferred embodiment, the ultrasound imaging system provides an elastographic image of a tissue's elastic properties both in-vitro and in-vivo. Ultrasound elastography is an imaging technique whereby local axial tissue strains are estimated from differential ultrasonic speckle displacements. These displacements are generated by a weak, quasi-static stress field. The resultant strain image is called an elastogram. Most pathological changes are associated with changes in tissue stiffness. Palpation is an effective method for lesion detection and evaluation. Many cancers (breast, prostate) are isoechoic, and hence difficult to detect by ultrasound alone.

Elastography uses the principle by which a small compression (strain) of the tissue results in a small compression of the signal (similar to frequency modulation.) Ultrasound elastography conveys new and clinically important tissue information. The tradeoffs among engineering and elastographic image parameters are now reasonably well understood. Elastography can operate in hypoechoic areas, for example, shadows. Reliable small elastic contrast exists among normal soft-tissue components, good carrier-to-noise ratio (CNR) allows its visualization. Pathology generally exhibit large elastic contrast. Areas that can benefit from the elastography include breast, prostate, vasculature, small parts and treatment monitoring.

Currently, breast cancer is the most frequent cancer in women. Every ninth woman in the U.S. is affected during her lifetime. It is well known that palpation of the breast is a very helpful mean to detect conspicuous lesions. Although a lot of effort is put into screening method for breast cancer, in the majority of cases the patient herself is the first who notices palpable changes in her breast during self-examination. Although it can support the diagnostics of breast tissue, there is still a need for an imaging modality that can provide a direct measure of material parameters related to tissue elasticity such as Young's modulus. Concerning breast imaging, the elasticity tensor can be reconstructed three-dimensionally using magnetic resonance imaging. A semi-quantitative measure of elasticity with ultrasound has recently become a real-time imaging modality. As described hereinbefore, the strain imaging or elastography method is helpful to describe mechanical properties of tissue in vivo. Elastography compares ultrasonic radio frequency (RF) data of an object before and after the application of a slight compression step. Time delays between the pre- and post-compression RF signals can be estimated and converted to mechanical displacement in the axial direction. The derivative of axial displacement leads to axial strain as a semi-quantitative measure of elastic properties.

The quality of strain images or elastograms is limited by noise due to signal decorrelation in the time delay estimation. One method to minimize this source of error is to apply motor-driven compression plates and to use multi-compression averaging. Another method is to correct for lateral displacements by interpolating A-lines two-dimensionally. For breast imaging, initial clinical results have been published, which indicate that ultrasound elastography has the potential for improving differential diagnosis of benign and malignant breast lesions. Preferred embodiments of the present invention ultrasound systems can be used for ultrasound elastography and provide elastograms which can be used to diagnose benign and malignant lesions.

In accordance with a preferred embodiment, when the suspect lesion is found, a slight compression can be applied to the breast and a palpation performed with the transducer including both compression and relaxation. Usually the system is able to store the last two compression cycles in a cine-buffer of the ultrasound system, including approximately 80 images. In the conventional B-mode it is only possible to record demodulated echo data, i.e., gray-scaled imaged data. In order to acquire RF data for elastography at the same time, a color-mode-window of 20×40 mm, i.e., 20 mm depth and 40 mm width can be used. The RF data from the color-mode window, which is usually used to calculate flow parameters, can be recorded as IQ-data (base-band data). Prior to the off-line calculation of strain images, the limited bandwidth of color-mode RF data is compensated for. The ultrasound system is reprogrammed to use broadband transmit pulses and broadband receive filter for the color-mode. After performing time delay estimation on every two successive frames of an IQ-data series, a series of time-delay images or axial displacement images is obtained, respectively.

The purpose of imaging elastic tissue properties using ultrasound elastography is to support the detection, localization and differential diagnosis of lesions. Strain imaging is a semi quantitative method. Therefore, it is definitely possible to evaluate elastograms qualitatively. A qualitative method for the evaluation of ultrasound elastograms uses a gray-scaled colormap. The appearance (visualization, brightness, margin) and size of each lesion on the elastogram in comparison to the B-mode image, in order to distinguish breast tissues is used. However, the results of a qualitative image analysis depend on the choice of the colormap and image scaling, respectively.

As described hereinbefore, the ultrasound systems of the present invention are used in minimally invasive surgery and robotic surgery methods including biopsy procedures, catheter introduction for diagnostic and therapeutic angiography, fetal imaging, cardiac imaging, vascular imaging, imaging during endoscopic procedures, imaging for telemedicine applications and imaging for veterinary applications, radiation therapy, and cryotherapy, without limitation. The embodiments use computer based tracking systems and CT and MR images to pinpoint the precise location of the target areas. Alternative preferred embodiments of ultrasound systems can at lower cost and using smaller footprint devices provide images just prior, during, and just after the procedure. Preferred embodiments overcome the need of requiring a separate ultrasound appliance to be wheeled into the procedure room and a method to move images from the ultrasound to the device that is tracking position and registering targets against previously captured CT and MR images. A preferred embodiment of the ultrasound system provides a fully integrated solution, since it can run its' ultrasound application on the same platform as any third party application that is processing the images. The system includes a streaming video interface, an interface between a third party application and the system's ultrasound application. A key component of this system allows the two applications to run on the same computer platform (using the same operating system (OS)) such as, for example, Windows® based platform, other platforms such as Linux® can also be used and thus providing a seamless integration of the two applications. The details of the software interface to move images from the system's ultrasound application to another application are described herein below.

Preferred embodiments include control and data transfer methods that allow a third party Windows® based application to control, for example, a portable Windows® based ultrasound system by running the ultrasound application as a background task, sending control commands to the ultrasound application and receiving images (data) in return. Further, the embodiment configures a portable ultrasound Windows® based application as a server of live ultrasound image frames supplying another Windows® based application that acts as a client. This client application receives these ultrasound image frames and processes them further. In addition, an alternate embodiment configures the portable ultrasound Windows® based application as a server, interacting with a third party client application via two communication mechanisms, for example a component object model (COM) automation interface used by third party, hereinafter referred to interchangeably as external or a client to startup and control the portable ultrasound Windows® based application and a high-speed shared memory interface to deliver live ultrasound images.

A preferred embodiment includes and configures a shared memory interface to act as a streaming video interface between a portable Windows® based Ultrasound application and another third party Windows® based application. This streaming video interface is designed to provide ultrasound images to a third party client in real-time.

A preferred embodiment allows the third party Windows® based application to control the flow rate of images from the portable ultrasound Windows® based application through the shared memory interface within the same PC platform and the amount of memory required to implement this interface. These controls consist of a way to set the number of image buffers, the size of each buffer and the rate of image transfer. This flow rate control can be set for zero data loss thus ensuring that every frame is delivered to the third party Windows® based application from the ultrasound system, or minimum latency thus delivering the latest frame generated by ultrasound system to the third party Windows® based application first.

A preferred embodiment formats the ultrasound image frame such that probe, spatial, and temporal information can be interpreted by the third party Windows® based application as it retrieves the images (generated by the portable ultrasound Windows® based application) from the shared memory interface. The actual image data passed between the server (i.e. portable ultrasound application) and the client application (third party Windows® based application) is a Microsoft® device independent bitmap (DIB) with 8 bit pixels and a 256 entry color table. The image frame also contains a header that provides the following additional information, for example, but not limited to, Probe Type, Probe Serial Number, Frame Sequence Number, Frame Rate, Frame Timestamp, Frame Trigger Timestamp, Image Width (in pixels), Image Height (in pixels), Pixel Size (in X and Y), Pixel Origin (x, y location of the first pixel in image relative to the Transducer Head, and Direction (spatial direction along or across each line of the image).

Further, the preferred embodiment controls the shared memory interface used to transfer ultrasound images between a Windows® based portable ultrasound system and a third party Windows® based system through the use of ActiveX® controls. The Windows® based portable ultrasound application contains an ActiveX® control that transfers a frame into the shared memory and sends out a Windows® Event (that includes a pointer to the frame just written) to the third party Windows® based application. This third party application has a similar ActiveX® control that receives this Event and pulls the image frame out of shared memory.

The graphical user interface includes one or more control programs, each of which is preferably a self-contained, for example, client-side script. The control programs are independently configured for, among other functions, generating graphical or text-based user controls in the user interface, for generating a display area in the user interface as directed by the user controls, or for displaying the processed streaming media. The control programs can be implemented as ActiveX® controls, as Java™ applets, or as any other self-contained and/or self-executing application, or portion thereof, operable within a media gateway container environment and controllable through the web page.

Ultrasonic content can be displayed within a frame in the graphical user interface. In an embodiment, the program generates an instance of an ActiveX® control. ActiveX® refers to a set of object-oriented programming technologies and tools provided by Microsoft® Corporation of Redmond, Wash. The core part of the ActiveX® technology is the component object model (COM). A program run in accordance with the ActiveX® environment is known as "component," a self-sufficient program that can be run anywhere in the network, as long as the program is supported. This component is commonly known as an "ActiveX® control." Thus, an ActiveX® control is a component program object that can be re-used by many application programs within a computer or among computers in a network, regardless of the programming language with which it was created. An ActiveX® control runs in what is known as a container, which is an application program utilizing the COM program interfaces.

One advantage of using a component is that it can be re-used by many applications, which are known as "component containers." Another advantage is that an ActiveX® control can be created using one of several well-known languages or development tools, including C++, Visual Basic, or PowerBuilder, or with scripting tools such as VBScript. ActiveX® controls can be downloaded as small executable programs, or as self-executable code for Web pages animation, for example. Similar to ActiveX® controls, and suitable for the client-side scripts, are applets. An applet is typically a self-contained, self-executing computer program written in Java™, a web-based, object-oriented programming language promulgated by SUN Microsystems Corporation of Sunnyvale, Calif.

The control programs can be stored and accessed locally at the client system, or downloaded from the network. Downloading is typically done by encapsulating a control program in one or more markup language-based files. The control programs can also be used for any commonly-needed task by an application program running in one of several operating system environments. Windows®, Linux® and Macintosh® are examples of operating system environments that can be used in preferred embodiments.

A preferred embodiment of the Ultrasound Imaging System has specific software architecture for the image streaming capabilities. This Ultrasound Imaging System is an application that controls the Ultrasound Probe of a preferred embodiment and allows to obtain and display visual images for medical purposes. The Imaging System has it's own graphical user interface. This interface has reach in features and is conveniently organized to provide maximum flexibility working with the separate images as well as streams of images. Some of the possible medical applications require developing of graphical user interfaces with significantly different features. This involves integration of the Imaging System into other more complicated medical system. The preferred embodiment allows exporting imaging data in a highly effective and convenient fashion for original equipment manufacturers (OEMs) to have direct access to imaging data.

The quality of the Image Streaming solution in accordance with a preferred embodiment is measured by the following criteria such as, data transfer performance. Imaging data consume significant amount of memory and processor power. Large number of separate image frames are required to produce live medical video patient examination. It becomes very important to minimize data coping operations in a process of transferring data from one process generating video data to a process consuming video data. The second criteria includes industry standard imaging format. Since applications consuming video imaging data are intended to be developed by third party companies data can be represented in industry standard formats. A third criteria is convenience. Imaging data may be presented by means of a programming interface that is convenient to use and does not require additional learning.

Further, the criteria includes scalability and extendibility. Streaming data architecture may be easily extendable to accommodate new data types. It may provide basic framework for future multiplication of video streams targeting more then one data receiving process.

The image streaming architecture of the preferred embodiment provides methods of data transportation between two processes. The image streaming architecture defines operational parameters regulating data transferring process, and describes the mechanism of transferring parameters between processes. One of the methods to transfer operational parameters from a third party client application to the imaging system of a preferred embodiment is by using existing COM interface.

In a preferred embodiment, the image transferring architecture intensively uses object-oriented programming methodology and inter-processing capabilities of the Microsoft Windows® operating system. Object-oriented methodology provides a necessary foundation allowing an architectural solution that satisfies the necessary requirements. It also lays ground for future enhancements and extensions making modification relatively simple and backward compatible.

Video imaging data represent complicated data structures with mutual interferences between different data elements. It also permits and often requires different interpretation of the same data elements. The preferred embodiment of the following image transferring architecture includes a shared memory for physical data exchange. For example, Windows® shared memory is a fast and economical way to exchange data between processes. Further, the shared memory can be subdivided into separate sections of a fixed size in certain embodiments. Each section can then be at a minimum a controllable unit. In addition, the imaging data can be abstracted as objects. Each frame of the imaging data can be represented by a separate object. The objects can then be mapped to the sections of the shared memory.

Preferred embodiments can include the locking-unlocking of a section-object. The programming API notification mechanism used is an event-driven mechanism. Event-driven mechanisms are implementation based on C++ pure-virtual functions.

In a preferred embodiment, the image transferring architecture consists of three layers: an application programming interface (API) layer, a programming interface implementation and shared memory access layer, and a physical shared memory layer. The application programming interface layer provides two different C++ class library interfaces to applications on a client and server side. All the associated sequence of instructions that belongs to the application itself is part of this layer as well. Application derived classes and their implementation are the key elements of application programming interface layer. The server which is the imaging data provider side uses, for example, Object Transmitter class and related derived and base classes. The client which is the imaging data consumer side uses an Object Factory class, for example, and related derived and base classes. The programming interface implementation layer provides two different Dynamic Link Libraries (DLLs) implementing classes for the applications. This layer maps objects of the classes associated with the application to an internal implementation of objects accessing the shared memory physical system object. This layer allows the hiding of all implementation specific member variables and functions from the scope of the application. Thus, the application programming interface layers become uncluttered, easy to understand and use. The server side application can use, for example, ObjectXmitter.DLL, while the client side application can use, for example, ObjectFactory.DLL.

The physical shared memory layer represents the operating system object implementing shared memory functionality. It also describes the structure of the shared memory, it's segmentation, and memory controlling blocks.

With respect to the organization of the shared memory since shared memory is intended to be used for interprocess communications the operating system specifies a unique name at the time of its creation. In order to manage the shared memory, other interprocess communications (IPC) system objects are required. They need to have unique names as well. To simplify a unique name generation process only one base is required. All other names are derived from the base one by an implementation code. Thus, the application programming interface requires the specification of only one base name for the logical shared memory object. The same unique name can be used by both the server side of the application and the client side of the application.

The server side of the application is responsible for the creation of shared memory creation. In a process of creation, it has to specify not only unique name of the shared memory but other configuration parameters. These parameters include, but are not limited to, segments count which specifies the number of segments to be allocated, segment size and operational flags. There are three such flags in a preferred embodiment. The first one specifies the segment submission and retrieval order. It can be one of, Last In First Out (LIFO), First In First Out (FIFO), or Last In Out (LIO). LIO is a modification of the usual LIFO in such a way that whenever at the time when a new frame arrives, if it finds frames that were ready for retrieval, but yet not locked for retrieval, they are erased. The second flag specifies shared memory implementation behavior under a condition when a new segment allocation is requested but there is no segment available. Typically it may happen when receiving application process data slower then submitting the application. This flag may allow deleting one of the previously allocated segments. If it does not allow deleting one of the previously allocated segments, it reports an exceptional condition back to the application. Using this flag application may automatically select overwriting of data in a shared memory or it may control the data overwrite process itself. The third flag can be used only when the second one allows overwriting segments in a shared memory. It specifies how to select a segment to be overwritten. By default, shared memory implementation deletes the youngest or the most recently submitted data segment. Alternatively, the oldest segment can be selected for overwrite process.

Figure 32:
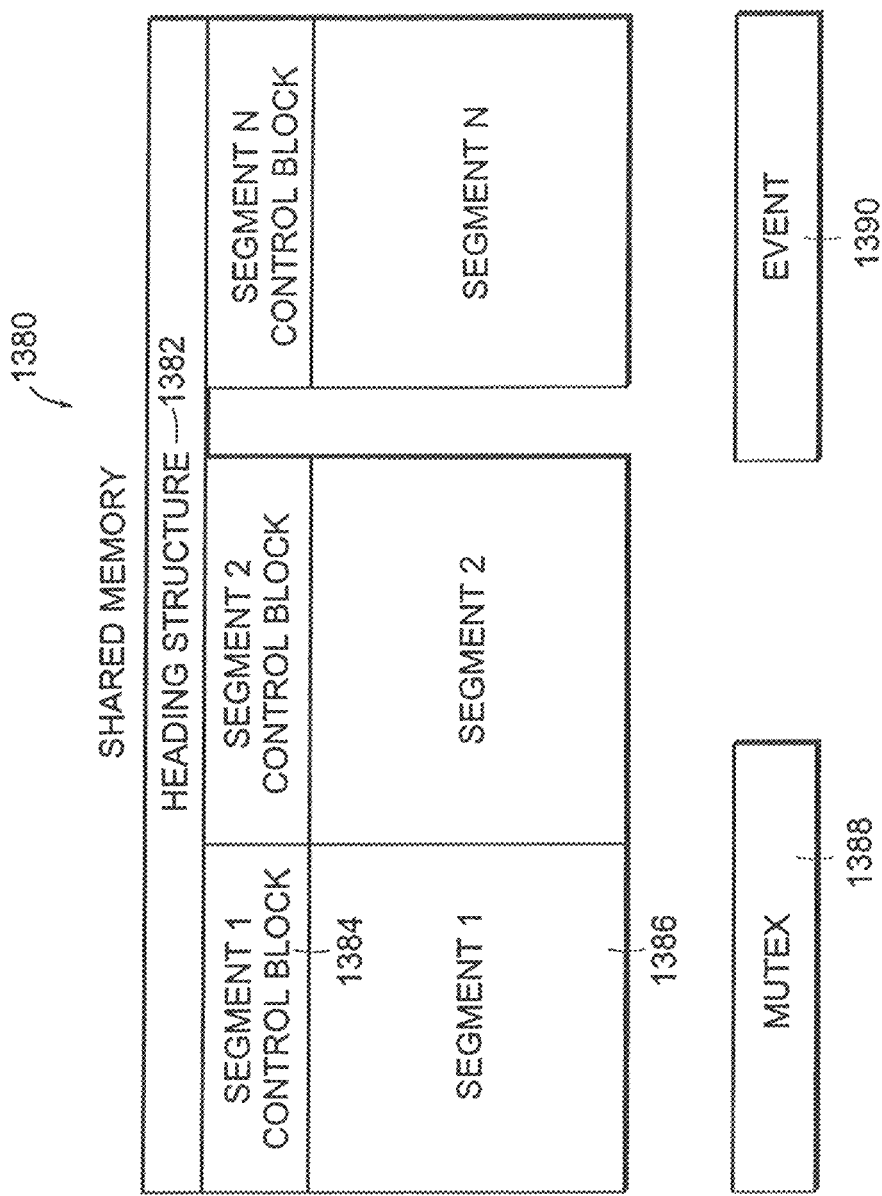
FIG. 32 is a block diagram illustrating the structure of the physical shared memory in accordance with a preferred embodiment of the present invention.

At the time of the creation of the shared memory it's physical layout is initialized. Since the operating system does not allow address calculation in a physical shared memory data pointers are not used within shared memory. All addressing within the shared memory controlling blocks 1384 and segments is implemented in terms of relative offsets from the Virtual Origin (VO). With the offset zero from the VO, the shared memory heading structure is allocated. It contains all the parameters listed herein above. FIG. 32 is a block diagram 1380 illustrating the structure of the physical shared memory.

Immediately after the allocation of the shared memory heading structure 1382 follows the creation of array of headers for every memory segment. The memory segment header contains the occupied size of the segment, unique tag of the class of the object mapped to the segment, and the segment state. Each segment can be in one of four states: unused where the segment is available for allocation, locked for write where the segment is mapped to an object of a specific class and currently is being formed, written, wherein the segment is mapped to an object of a specific class and available for retrieval, and locked for read, wherein the segment is mapped to an object of a specific class and currently is in a process on data retrieval. Since every segment has its own state it is possible for the application to lock more than one segment for object forming and object retrieval. This allows the system to have flexible multi-threaded architecture on both the server and client sides of the application. Further, the ability to have more than one segment in a "written" state provides a "buffering" mechanism nullifying or minimizing performance difference of the applications on the server and client sides.

The last element in a physical shared memory layout contains memory segments 1386. The logical shared memory besides physical shared memory contains a physical system mutex 1388 and system event 1390. The physical mutex provides mutual exclusive access to physical shared memory. The physical event is of a manual control type. It stays at the level "high" all the time when at least one of the segments has a "written" state. It goes to the level "low" only when there is no single segment in a "written" state. This mechanism allows to retrieve "written" objects from the shared memory without passing control to an operating system within the same time-slice allocation for the thread.

In a preferred embodiment; the object transmitting programming interface consists of three classes: namely, AObjectXmitter, USFrame, and BModeFrame. The AObjectXmitter class allows the initiation of an object transferring service specifying desired operational parameters. Once the AObjectXmitter class object is instantiated the initialized objects of USFrame and BModeFrame classes can be created. The USFrame class constructor requires a reference to an object of the AObjectXmitter class. The first action that has to be accomplished upon instantiation of the USFrame object is to establish association of the object with one of the segments in the shared memory. The function Allocate( ) maps an object to an unused shared memory segment and locks this segment for the current object usage. At the time of mapping an object a bitmap size may be provided by an application. The provided size represents only the size required for bitmap data not including the memory size required for other data elements of the object.

The BModeFrame class is a class derived from the USFrame class. It inherits all the methods and functionality that the base class has. The only additional functionality provided by BModeFrame class is additional methods allowing to provide information related specifically to the BMode operation.

After the USFrame or BModeFrame class object has been instantiated and mapped to the shared memory segment the application can fill all desired data elements of the object. It is not necessary to provide a value for every data element. At the time when an object is being mapped to the shared memory segment, all data elements of the object are being initialized with default values. The only data elements that are not initialized upon mapping are bitmap data elements. When the server side of the application has provided all desired data elements it can hand over the object to the client side of the application by calling a method, for example, Submit( ).

The USFrame or BModeFrame object can be reused by means of subsequent remapping and resubmitting. Alternatively, it can be deleted and a new one can be created when it is appropriate for an application. Since object instantiation does not require any interprocess-communication mechanisms, it is as simple as memory allocation for an ordinary variable.

There are at least two advantages of the architecture of the preferred embodiment. Since the ObjectXmitter class does have knowledge about the USFrame or BModeFrame class, it is very easy to introduce additional classes similar or directly or indirectly derived from the USFrame class. This allows to produce future versions of Object Transmitting Programming Interface without requiring any modifications to the code or sequence of instructions that was developed for existing embodiments. Further, Object Transmitting Programming Interface classes do not have any member variables. This provides two more benefits of the interface. The first one is that these classes are COM object interface oriented and can be directly used for the COM object interface specification and implementation. The second benefit is that these classes effectively hide all implementation specific details making the interface very clear, easy to understand and use.

The Object Transmitting Programming Interface is implemented by the ObjectXmitter.DLL. For every object created by the application there is a mirroring implementation object being created by the code residing in the ObjectXmitter.DLL. Since every programming interface class has corresponding mirroring class in implementation modifications are facilitated and extend currently to specified image types. This can be accomplished by the creation of the corresponding mirroring classes in the implementation DLL. Implementation objects are responsible for handling of the shared memory and the mapping of programming interface objects. An embodiment of the present invention includes the DLL allowing instantiate of only one ObjectXmitter class object using only one communication channel with the one client application. Object Transmitting implementation transmits not only object data but provides additional information describing the object type transferred.

The Object Factory Programming Interface consists of three classes: AObjectFactory, USFrame, and BModeFrame. The class AObjectFactory contains three pure virtual member functions. This makes this class an abstract class that cannot be instantiated by an application. It is required from the application to define its own class derived from the AObjectFactory class. There is no need to define any "special" class derived from the AObjectFactory class. Since the application intends to process images that would be received, the chances that it will have a class processing images are very high. An image processing class can very well be derived from AObjectFactory class.

The class derived from an AObjectFactory class has to define and implement only pure virtual functions such as, for example, OnFrameOverrun( ), OnUSFrame( ), and OnBModeFrame( ). For instance, a derived class can be defined as follows:

```
Class ImageProcessor: public AObjectFactory {
public:
  ImageProcessor(void);
  ~ImageProcessor(void);
virtual unsigned long OnFrameOverrun(void);
virtual unsigned long OnBModeFrame( const BModeFrame * frame);
virtual unsigned long OnUSFrame( const USFrame *frame);
};
```

Upon instantiation of an object of the class ImageProcessor base class member function Open( ) can be called. This function provides a shared memory name that matches to the shared memory name being used by the server side of application. Function Open( ) connects the client application to the server application via a specified shared memory.

At any moment after opening the shared memory, the application can expect a call on a virtual function OnFrameOverrun( ), OnUSFrame( ), and OnBModeFrame( ). Every invocation of OnUSFrame( ) function carries as an argument an object of USFrame class type. Every invocation of OnBModeFrame( ) function carries as an argument an object of BModeFrame class type. There is no need for an application to instantiate an object of USFrame or BModeFrame class. USFrame and BModeFrame objects are "given" to an application by underlying implementation on an AObjectFactory class.

The only action that application needs to accomplish is to process received frame and to release the "given" object. The application does not attempt to delete a frame object, as deletion is done by an underlying implementation. Member function Release( ) of USFrame object is called only when all data processing is done by the application and USFrame object or object of the derived class is no longer needed by the application.

Once the application has received an object of a class USFrame or BModeFrame it can retrieve imaging data and process them appropriately. The application needs to be aware that it does processing of the frame object data in a separate thread and make sure that processing function is written using a thread-safe programming technique. Since any of the pure virtual functions are being called within a separate thread created by the implementation DLL none of the subsequent calls are possible before virtual function returns control back to the calling thread. This means that as long as the application has not returned control to implementation created thread any new frames cannot be received by the application. Meanwhile the server side of the application can continue to submit extra frames. This eventually causes the shared memory to overflow and prevents any new frame transmission.

All the time when the application processes frame data it keeps shared memory resources locked from subsequent remapping. The more frames not released by the application the less shared memory segments are available for Object Transmitting Interface on the server side of the application. If framing objects are not being released with an appropriate speed ratio eventually all memory segments of the shared memory are locked by the client application. At that time the image transmitting application stops sending new frames or overwrites frames that are not locked yet by the receiving application. If all the segments were locked by the receiving application the transmitting application does not even have an option to overwrite existing frames.

The function OnFrameOverrun( ) is called when the Frame Overrun is raised by the servicing application. This condition is raised any time when the servicing application makes an attempt to submit a new frame and there is not any available shared segments to map an object to. This condition can be cleared only by the client side of application by means of calling function ResetFrameOverrun( ). If this function is not called by the client application the Frame Overrun condition is raised and OnFrameOverrun( ) pure virtual function is called again.

The Object Factory Interface has the same advantages that were outlined herein above in describing the Object Transmitting Interface. In addition to these advantages, it implements an event-driven programming method that minimizes programming effort and maximizes execution performance. At the same time there are functions such as, for example, USFrames( ), BModeFrames( ), GetUSFrame( ), and GetBModeFrame( ). These functions can be used to implement less efficient "polling" programming methods.

The Object Factory Programming Interface is implemented by the ObjectFactory.DLL. This DLL retrieves an object class type information as well as object related data from the shared memory. It creates an object of the type that is used by the transmitter. The Object factory implementation maps newly created objects to the corresponding data. Object factory implementation has a separate thread that fires newly generated and mapped object via pure virtual function event. The application "owns" this object for the duration of processing and by calling Release( ) function indicates that the object is no longer needed by the application. The factory implementation releases resources allocated for the object locally as well as shared memory resources.

Figure 33:
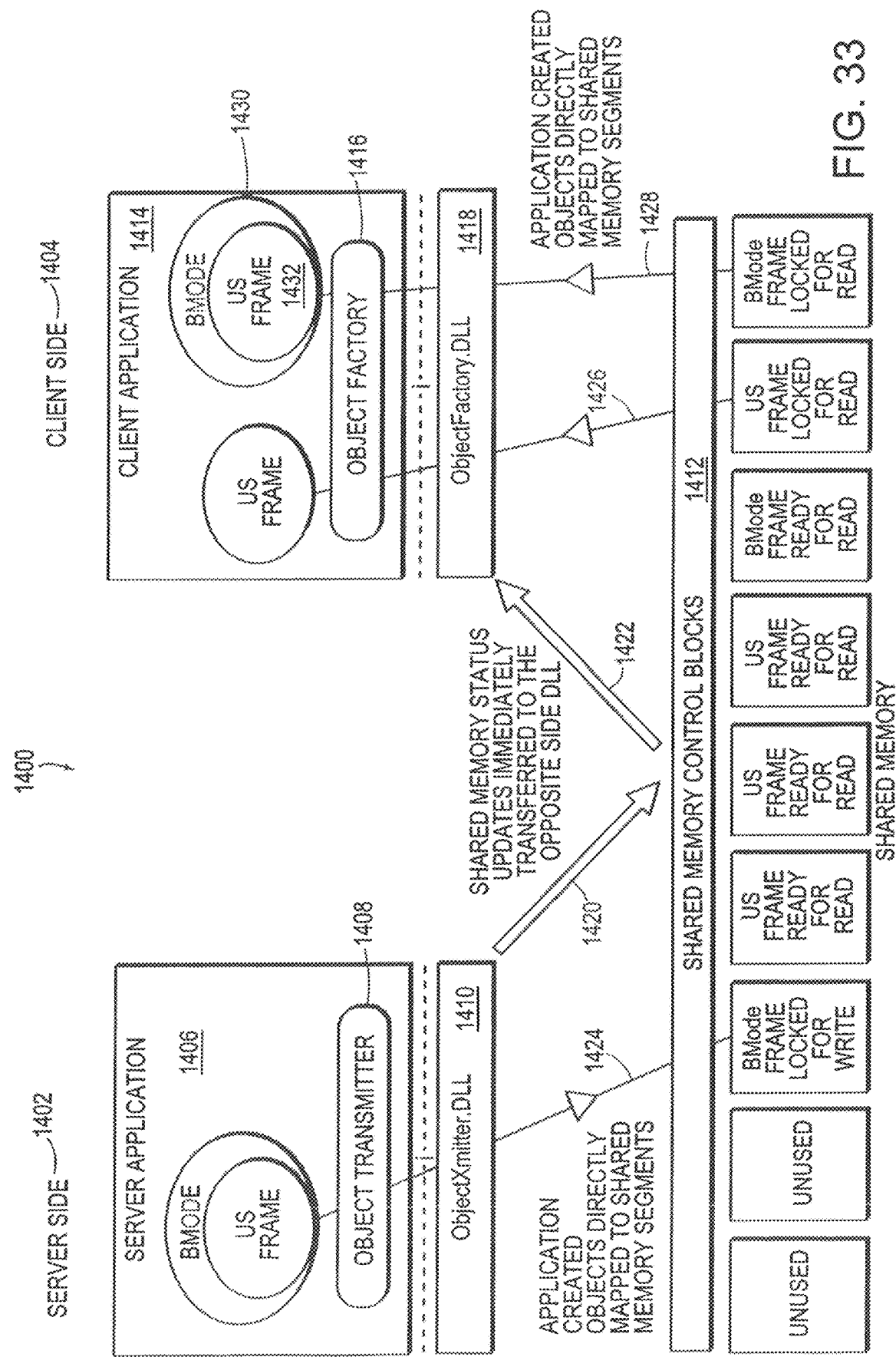
FIG. 33 is a schematic block diagram of the processing flow between the server side, the client side and the shared memory control in accordance with a preferred embodiment of the present invention.

The processing flow described herein above is pictorially represented in the block diagram FIG. 33. Preferred embodiments, include the ease of code maintenance and feature enhancement for the image transferring mechanism. The Object Transferring and Object Factory Interfaces as well as their implementations allow such modifications to be made at a relatively low development cost. With respect to Object Modification, the shared memory implementation is completely independent from the transferred data types. Thus, any type modification does not require making any changes to the underlying code controlling shared memory. Since transferred data is encapsulated within classes of a particular type the only action that is needed to modify transferring an object is to modify the corresponding class defining such object. Since objects represent a class derivation tree any modification of the base class causes appropriate change of every object of the derived classes. Such modifications of the object types do not affect application code not related to modified object classes.

The new types of objects can be introduced by deriving a new class from one of the existing classes. A newly derived class can be derived from the appropriate level of the base classes. An alternative way to create a new object type is by the creation of a new base class. This method may have the advantage in the case when a newly defined class differs from existing ones significantly.

With respect to multiple Object Transferring Channels, alternate preferred embodiments, can support more than one AObjectXmitter class object and more then one corresponding communication channel. It also can be extended in such a way that it allows communication channels transmitting objects in opposite directions. This allows the application to distribute imaging data to more then one client application. It can accept incoming communication controlling image creation and probe operation.

Further, wireless and remote image streaming channels can be accommodated in preferred embodiments. A same Object Transmitting Programming Interface can be implemented to transfer images not via the shared memory but via the high-speed wireless communication network such as, for example, ISO 802.11a. It also can be used to transfer images across a wired Ethernet connection. Remote and wireless image streaming assumes that the recipient computing system can differ in performance. This makes the selection of a model of the recipient's device one of the important factors for the successful implementation.

The streamed imaging included in preferred embodiments thus utilizes a shared-memory client-server architecture that provides high bandwidth with low overhead.

The Ultrasound Imaging System software application of a preferred embodiment is used as a server of live ultrasound image frames by a client application. This client-server relationship is supported by two communications mechanisms as described hereinabove. A COM automation interface is used by the client application to start-up and control the ultrasound imaging system application. A high-speed shared-memory interface delivers live ultrasound images with probe identification, spatial and temporal information from the application to the client application.

Complexities of the shared-memory implementation are encapsulated for the client application in a simple ActiveX® COM API (TTFrameReceiver). The shared-memory communications have flexible parameters that are specified by the client application. Queue order, number of buffers, buffer size and overwrite permission are all specified by the client when opening the image frame stream. The queue order mode can be specified as First-In-First-Out (FIFO), Last-In-First-Out (LIFO) and Last-In-Out (LIO). In general, the FIFO mode is preferred when zero data loss is more important than minimum latency. The LIO mode delivers only the most recent image frames and is preferred when minimum latency is more important than data loss. The LIFO mode can be used when minimum latency and minimum data loss are both important. However, in the LIFO mode, frames might not always be delivered in sequential order and a more complicated client application is required to sort them after they are received. Overwrite permission, when all of the shared-memory buffers are full, is specified as not allowed, overwrite oldest and overwrite newest.

Each image frame contains a single ultrasound image, probe identification information, pixel spatial information and temporal information. The image format is a standard Microsoft® device independent bitmap (DIB) with 8-bit pixels and a 256-entry color table.

The TTFrameReceiver ActiveX® control provides two schemes for receiving frames. The first scheme is event driven. A COM event, FrameReady, is fired when a frame has been received. Following the FrameReady event, the image and associated data can be read using the data access methods of the interface. After image and other data have been copied, the client releases the frame by calling the ReleaseFrame method. The next FrameReady event does not occur until after the previous frame is released. In another embodiment, the client can poll for the next available frame using the WaitForFrame method.

In a preferred embodiment, both the client application and the server application are executed on the same computer. The computer can be running the Microsoft® Windows® 2000/XP operating system, for example, without limitation. The client application (USAutoView) can be developed using Microsoft® Visual C++ 6.0 and MFC. The source code can be compiled, for example, in Visual Studio 6.0. The server side COM Automation interface and the TTFrameReceiver ActiveX® control may be compatible with other MS Windows® software development environments and languages.

In an embodiment of the present invention, the name of the server side COM automation interface (ProgID) is, for example, "Ultrasound.Document" and the interface is registered on the computer the first time the application is run. The dispatch interface can be imported into a client application from a type library.

In a preferred embodiment, automation interface is extended to support frame streaming with the addition of different methods such as void OpenFrameStream(BSTR* queueName, short numBuffers, long bufferSize, BSTR* queueOrder, short overwritePermission). The Opens frame stream transmitter on the server side; opens the shared-memory interface to the client application, queueName is a unique name of the shared-memory "file" and is the same name that is used when opening the receiver, numBuffers is the number of buffers in the shared-memory queue, bufferSize is the size of each buffer in the shared-memory queue in bytes wherein the buffer size is 5120 bytes larger than the largest image that can be transmitted, queueOrder "LIO", "FIFO", or "LIFO", overwritePermission is 0 for overwrite not allowed, 1 for overwrite oldest, or 2 for overwrite newest. Note, OpenFrameStream must be called before opening the TTFrameReceiver control.

The next additional methods include void CloseFrameStream( ) which closes the_frame stream transmitter on the server side, void StartTransmitting( ), which tells the server side to start transmitting ultrasound frames, void StopTransmitting( ), which tells the server side to stop transmitting ultrasound frames, and short GetFrameStreamStatus( ), which gets the status of the frame stream transmitter. It is important to check that the stream transmitter is open before opening the TTFrameReceiver. The COM automation interface is non-blocking and the OpenFrameStream call cannot occur at the instant it is called from the client application.

In a preferred embodiment, the TTFrameReceiver ActiveX® Control is the client application's interface to the live ultrasound frame stream. Frame Stream Control Methods include boolean Open(BSTR name), which opens the frame stream receiver. The frame stream receiver cannot be opened until after the frame stream transmitter on the server has been opened. It also includes boolean Close( ), which closes the frame stream receiver, long WaitForFrame(long timeoutms), which wait for a frame to be ready or until end of timeout period, and boolean ReleaseFrame( ) which release the current image frame. The current frame can be released as soon as all of the desired data has been copied. The next frame cannot be received until the current frame is released. The return values of the other data access functions are not valid after the current frame is released until the next FrameReady event.

Data Access Methods in a preferred embodiment for the image includes long GetPtrBitmapInfo( ), which gets a pointer to the header (with color table) of the DIB that contain the image. The ultrasound image is stored as a standard Microsoft® device independent bitmap (DIB). BITMAPINFO and BITMAPINFOHEADER structures can be cast to the returned pointer as needed. Memory for the BITMAPINFO structure is allocated in shared-memory and may not be de-allocated; instead, ReleaseFrame( ) can be called to return the memory to the shared-memory mechanism. Further methods include long GetPtrBitmapBits( ), which gets a pointer to the image pixels. The returned pointer can be cast as needed for use with the Microsoft® DIB API. Memory for the bitmap pixels is allocated in shared-memory and may not be de-allocated; instead, ReleaseFrame( ) is called to return the memory to the shared-memory mechanism.

The methods related to probe identification include short GetProbeType( ), which gets the defined ultrasound probe type being used, BSTR GetProbeType( ), which gets the defined probe name, long GetProbeSN( ), which gets the serial number of the probe being used.

With respect to temporal information, the methods include short GetSequenceNum( ), which gets the sequence number of the current frame. The sequence number is derived from an 8-bit counter and thus repeats every 256 frames. It is useful for determining gaps in the frame sequence and for re-ordering frames received when using the LIFO buffer order mode. Further, double GetRate( ), gets the frame rate when combined with the sequence number, provides precise relative timing for the received frames, BSTR GetTimestamp( ), which gets a timestamp for the current frame which provides an absolute time for the current frame that may be useful when synchronizing to external events. The resolution is approximately milliseconds. Timestamps can be averaged and used in conjunction with rate and sequence number to achieve higher precision. Lastly, with respect to temporal information, the methods include BSTR GetTriggerTimestamp( ), which gets a timestamp for the start of ultrasound scanning wherein the ultrasound probe is stopped when "freezing" the image. The trigger timestamp is recorded when live imaging is resumed.

Spatial Information in preferred embodiments has the following methods, short GetXPixels( ), which get the width of the image in pixels; short GetYPixels( ), which gets the height of the image in pixels; double GetXPixelSize( ), which gets the size of each pixel in the x-direction, (x-direction is defined to be horizontal and parallel to each image line); and double GetYPixelSize( ), which gets the size of each pixel in the y-direction. The y-direction is defined to be vertical and perpendicular to each image line. Further, double GetXOrigin( ), which get the x-location of the first pixel in the image relative to the transducer head and double GetYOrigin( ), which gets the x-location of the first pixel in the image relative to the transducer head. The positive y-direction is defined to be away from the transducer head into the patient. Another method includes short GetXDirection( ), which gets the spatial direction along each line of the image. The positive x-direction is defined to be away from the probe marker. The short GetYDirection( ), gets the spatial direction across each line of the image. The positive y-direction is defined to be away from the transducer head into the patient.

The spatial position of any pixel in the image relative to the transducer head can easily be calculated as follows:
PX=OX+NX*SX*DX
PY=OY+NY*SY*DY
wherein,
P=the position of the pixel relative to the transducer head,
O=the origin
N=the index of the pixel in the image,
S=the pixel size
D=the direction of the pixel.

Further, events in a preferred embodiment, void FrameReady( ) is used when a frame is ready and data can be read. The handler copies data from the data access methods and then calls ReleaseFrame( ). It is recommended that any kind of indefinite processing, for example, function that invokes message loops be avoided in the handler. Further, void FrameOverrun( ) is used when the server is unable to send a frame or a frame has to be overwritten in the buffers because the buffers are full. This only applies to the FIFO and LIFO modes, since the LIO automatically releases old buffers. This event is usefully for determining whether the client application is reading frames quickly enough and whether the number of buffers allocated is sufficient for the latency of the client.

In a preferred embodiment, USAutoView is a sample client application that automates the server side and displays live ultrasound image frames. It has functions to demonstrate starting and stopping the server side, hiding and showing the server side, toggling between showing and not showing graphics on the image, freezing and resuming the ultrasound acquisition, loading a preset exam, changing the designated patient size, changing the image size, spatial information, and inverting the image.

Figure 34:
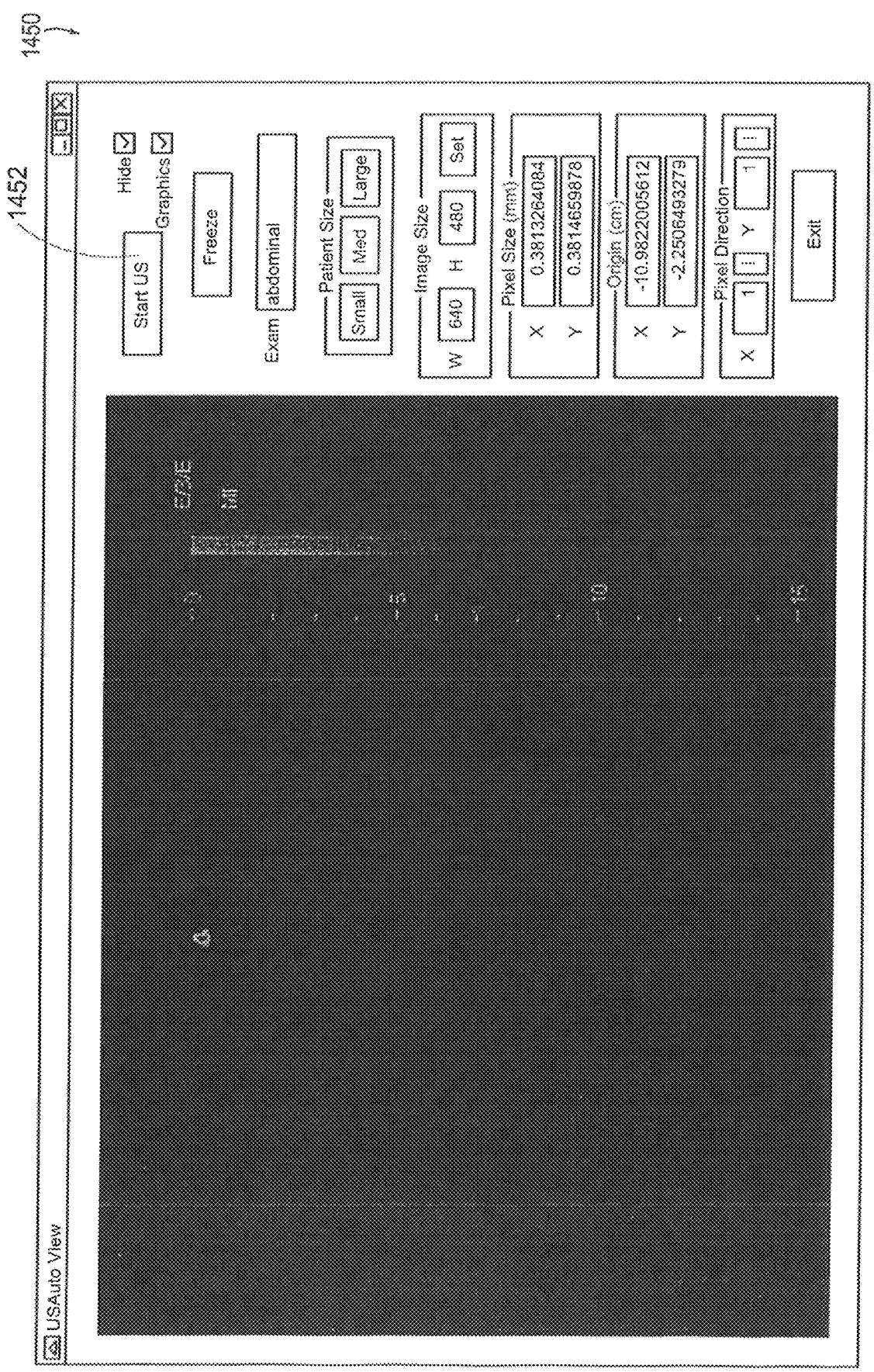
FIG. 34 is a view of a graphical user interface of the Autoview user interface in accordance with a preferred embodiment of the present invention.

FIG. 34 is a view of a graphical user interface 1450 used for a USAutoView UI in accordance with a preferred embodiment of the present invention. The graphical user interface includes a Start US button 1452. The USAutoView program is a Windows® dialog application with three ActiveX® components. TTFrameReceiver which supplies ActiveX® interface to receive ultrasound frames, TTAutomate which encapsulates automation of the server side and TTSimpleImageWnd which is the image display window. CUSAutoViewDlg is the main dialog. It manages the automation of the server side through the TTAutomate control, receiving ultrasound frames through TTFrameReceiver and image display through TTSimpleImageWnd. The OnStartUS( ) method of CUSAutoViewDlg calls the TTAutomate and TTFrameReceiver methods needed to start or stop automation and data transmission from the server side.

The method OnFramnReady( ) handles the FrameReady event from TTFrameReciever. It copies the desired data from TTFrameReceiver and then releases the frame with TTFrameReceiver's ReleaseFrame( ) method. It avoids any functions that perform indeterminate processing, such as functions that invoke message loops.

TTAutomate is an ActiveX® control that encapsulates automation functions for the server side. The native COM Automation interface of the server side is non-blocking and requires waiting with GetStatusFlags to coordinate functions. TTAutomate wraps each function in the required wait loops. The wait loops allow Windows® messages to be processed so that the client application's user interface thread does not become blocked while waiting. Although automation methods in TTAutomate cannot return until the function has been completed, other Windows® messages are still processed before the function is completed. It is recommended to prevent multiple concurrent calls from message handlers to TTAutomate methods, as coordination with the server side is generally non-reentrant. Source code for this control is included in the USAutoView workspace. It may be reused or modified as desired.

TTSimpleImageWnd is an ActiveX® control that provides a display window for device independent bitmaps (DIB's). The two properties of the display interface are long DIBitmapInfo and long DIBits. DIBitmapInfo corresponds to a pointer to a block of memory that contains the BITMAPINFO structure for the DIB. DIBits corresponds to a pointer to a block of memory that contains the image pixels. To load a new image, the DIBitmapInfo is set to the pointer to the bitmap info of the DIB. Then DIBits is set to the pointer to the bitmap bits. When DIBits is set, the pointer that was set for DIBitmapInfo is expected to still be valid and both the bitmap info and bitmap bits are copied internally for display on the screen. Both DIBitmapInfo and DIBits are set to zero to clear the image. Source code for this control is included in the USAutoView workspace. It may be reused or modified as desired.

The preferred embodiments of the present invention include a plurality of probe types. For example, the probes include, but are not limited to, a convex-linear transducer array operating between, 2-4 MHz, a phased-linear transducer array operating between 2-4 MHz, a convex-linear endocavity transducer array operating between 4-8 MHz, a linear transducer array operating between 4-8 MHz and a linear transducer array operating between 5-10 MHz.

Preferred embodiments of the portable ultrasound system of the present invention provide high resolution images such as the following during an examination: B-mode, M-mode, Color Doppler (CD), Pulsed Wave Doppler (PWD), Directional Power Doppler (DirPwr) and Power Doppler (PWR). Once the system software is installed the probe device is connected into a desktop or laptop. The probe can be an industry standard transducer connected to a 28 oz. case that contains the system's beamforming hardware. If the probe is connected to a laptop, then a 4-pin FireWire cable is connected to a IEEE 1394 serial connection located on a built-in MediaBay®. However, if the probe is connected to a desktop, the computer may not be equipped with a MediaBay®. One can connect the probe using an External DC Module (EDCM) connector. Before connecting the probe, one needs to make sure that the FireWire is connected on both the right and left sides of the computer.

In an embodiment, the EDCM is designed to accept a 6-pin IEEE 1394 (also referred to as FireWire) cable at one end and a Lemo connector from the probe at the other end. The EDCM accepts an input DC voltage from +10 to +40 Volts. Further, the system, in an embodiment, can be connected to a host computer with IEEE 1394. The 6-pin IEEE 1394 input to the EDCM can originate from any IEEE 1394 equipped host computer running, for example, the Windows® 2000 operating system. An external IEEE 1394 hub may also be necessary to provide the requisite DC voltage to the EDCM. In a host computer equipped with IEEE 1394, there are one of two types of IEEE 1394 connectors; a 4-pin or a 6-pin. The 6-pin connector is most often found in PC-based workstations that use internal PCI-bus cards. Typically, the 6-pin connector provides the necessary DC voltage to the EDCM. A 6-pin-male to 6-pin-male IEEE 1394 cable is used to connect the host computer to the EDCM.

The 4-pin connector is found in laptop computers that do not contain a MediaBay® in accordance with a preferred embodiment or provide a DC voltage output. When using this connector type, an external IEEE-1394 hub can be used to power the EDCM and the probe.

When power is not provided from the host computer, an external IEEE-1394 hub can be used between the host computer and the EDCM. The hub derives its power from a wall outlet and is connected using a medical-grade power supply that conforms to the IEC 60601-1 electrical safety standard.

To connect the hub to the host computer, a 4-pin-male to 6-pin-male or 6-pin-male to 6-pin-male IEEE cable is required. The appropriate connector (4-pin or 6-pin) is inserted into the host computer and the 6-pin connector into the hub. The hub is then connected to the EDCM using a 6-pin-male to 6-pin-male IEEE 1394 cable. An IEEE 1394 hub is only necessary when the host computer cannot supply at least +10 to +40 DC volts and 10 watts power to the EDCM. If the host computer can supply adequate voltage and power, a 6-pin-male to 6-pin-male IEEE 1394 cable can be used to connect the computer directly to the EDCM.

Figure 35:
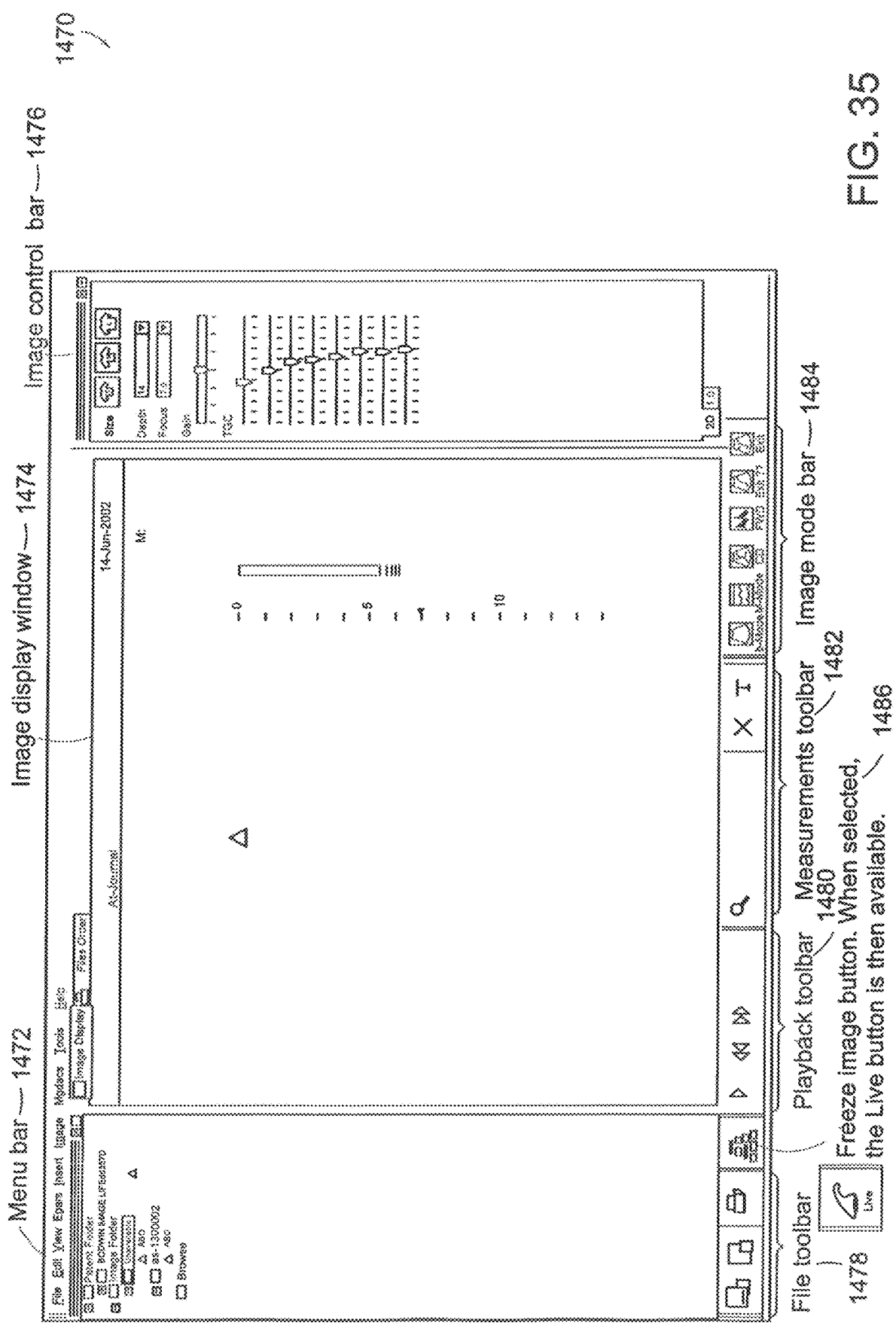
FIG. 35 illustrates a view of a main screen display of a graphical user interface in accordance with a preferred embodiment of the present invention.

FIG. 35 illustrates a view of a main screen display of a graphical user interface 1470 in accordance with a preferred embodiment of the present invention. When the user starts the system in accordance with the present invention the main screen displays. To help the user navigate, the main screen can be considered as four separate work areas that provide information to help one perform tasks. These include a menu bar 1472, an image display window 1474, an image control bar 1476, and tool bars 1478, 1480, 1482, 1484, 1486.

In order to resize windows and regions the user can click the small buttons in the upper right of the window to close, resize, and exit the program. A user interface or button closes the window but leaves the program running (minimizing the window). A system button appears at the bottom of the screen, in the area called the taskbar. By clicking the system button in the taskbar the window re-opens. Another interface button enlarges the window to fill the entire screen (called maximizing), however, when the window is at its largest, the frame rates may decrease. Another interface button returns the window to the size that it was before being enlarged. The system program can be closed by another interface button.

Figure 36A:
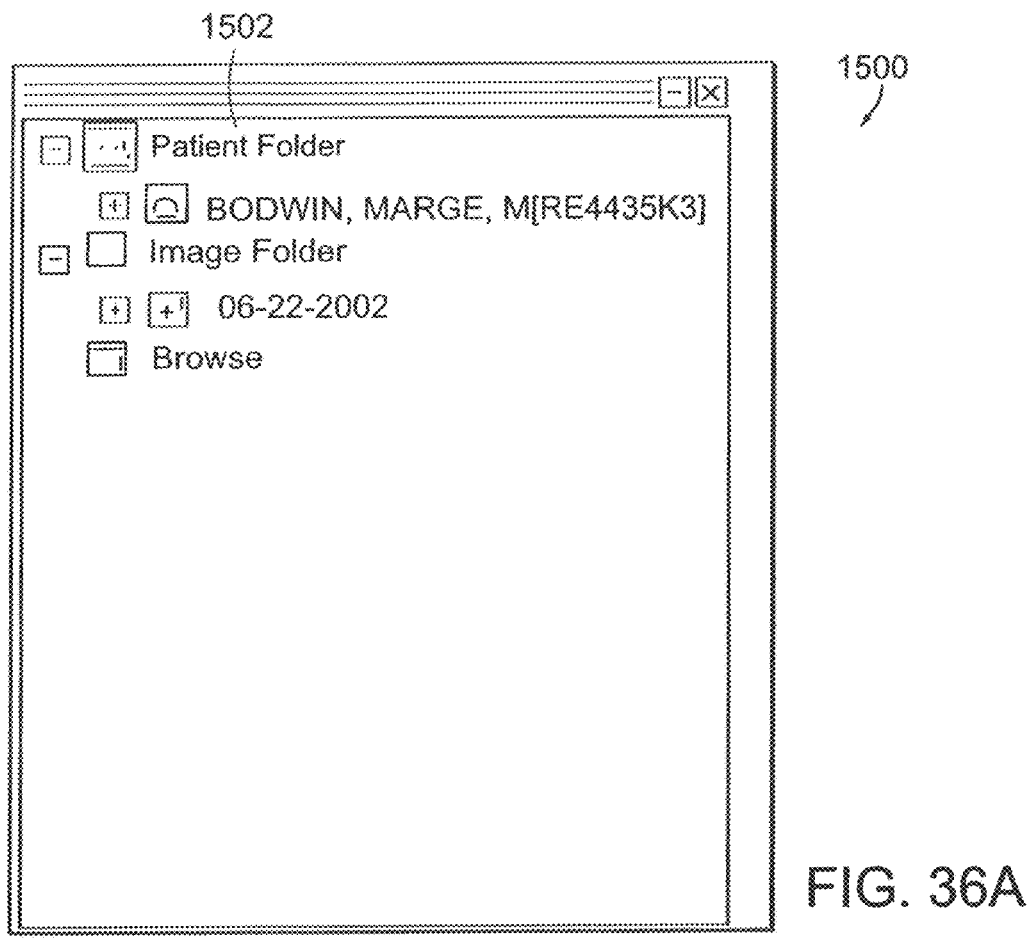
FIGS. 36A-36C are views of a graphical user interface showing the icons used to control the size of windows, and creation of floating windows in accordance with a preferred embodiment of the present invention.
Figure 36B:
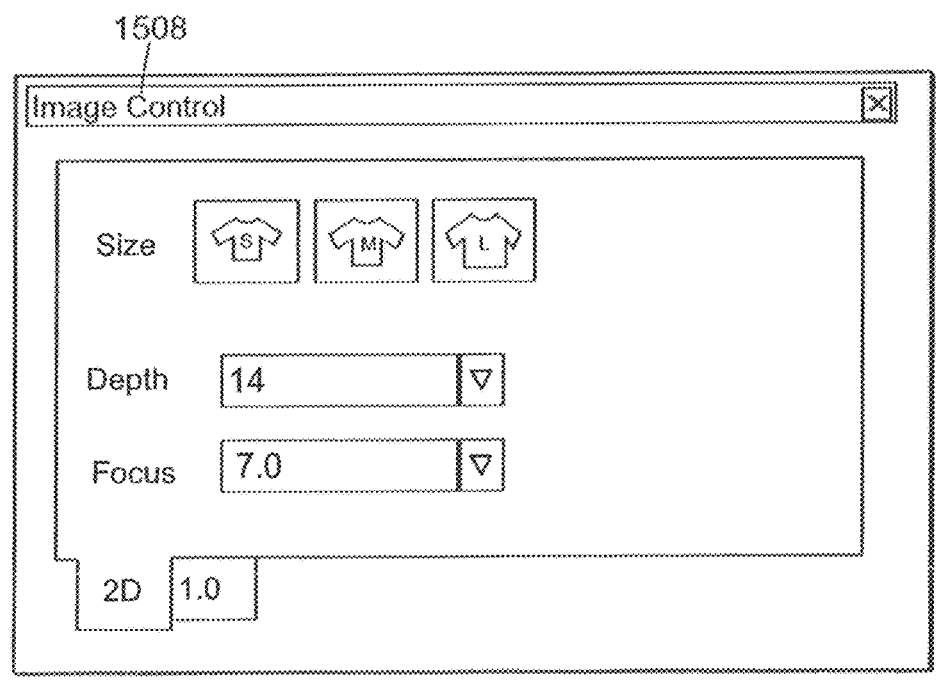
Figure 36C:
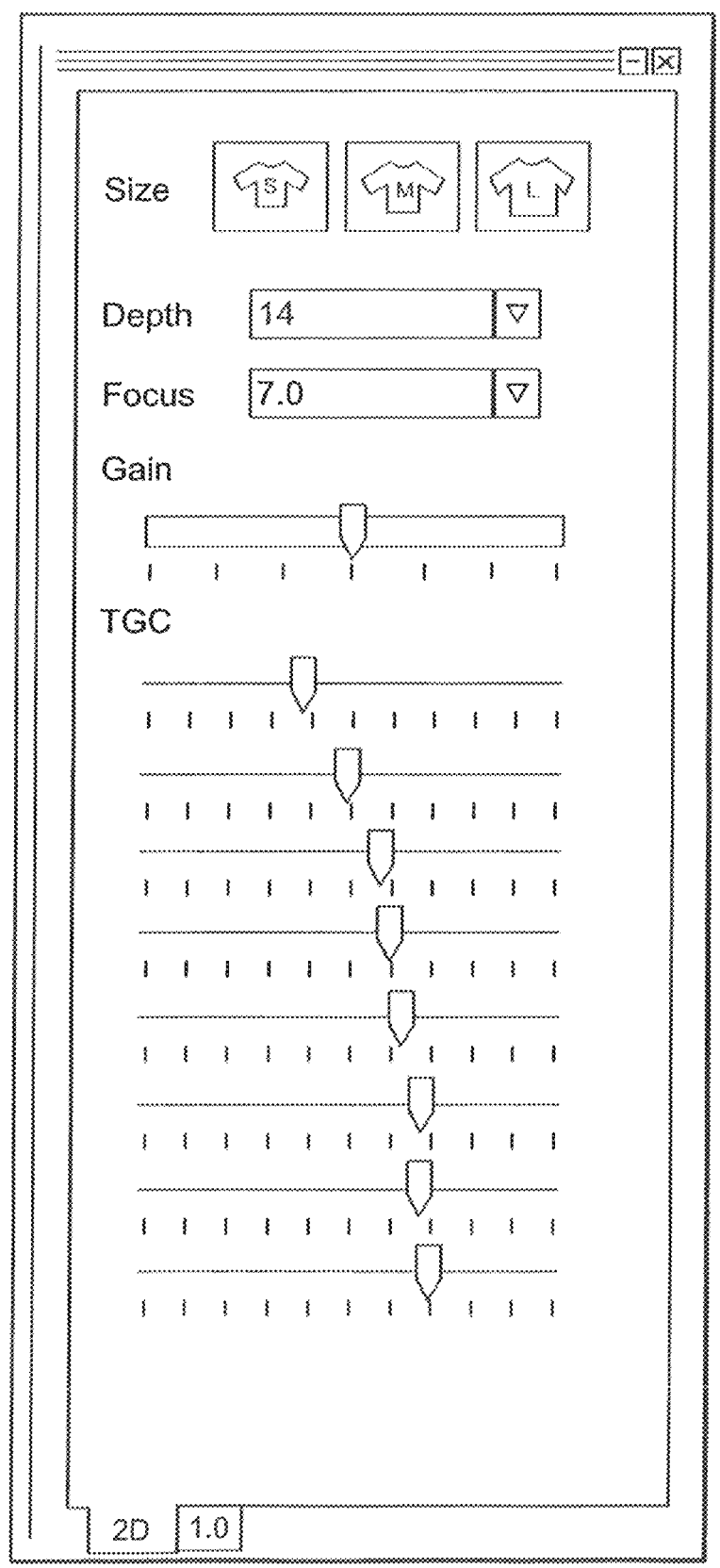

The user can increase or decrease the width of each region of the application to meet one's needs. For example, to make the Explorer window more narrow, the cursor is placed at either end of the region and by clicking and dragging the new desired size is obtained. One can re-position the size and location of each region so that they become floating windows. To create floating windows, the user simply clicks one's mouse on the double-edged border of the specific region and drags it until it appears as a floating window. To restore the floating window back to original form, one double-clicks in the window. These functionalities are depicted in FIGS. 36A-36C which are views in a graphical user interface in accordance with a preferred embodiment of the present invention.

Figure 37A:
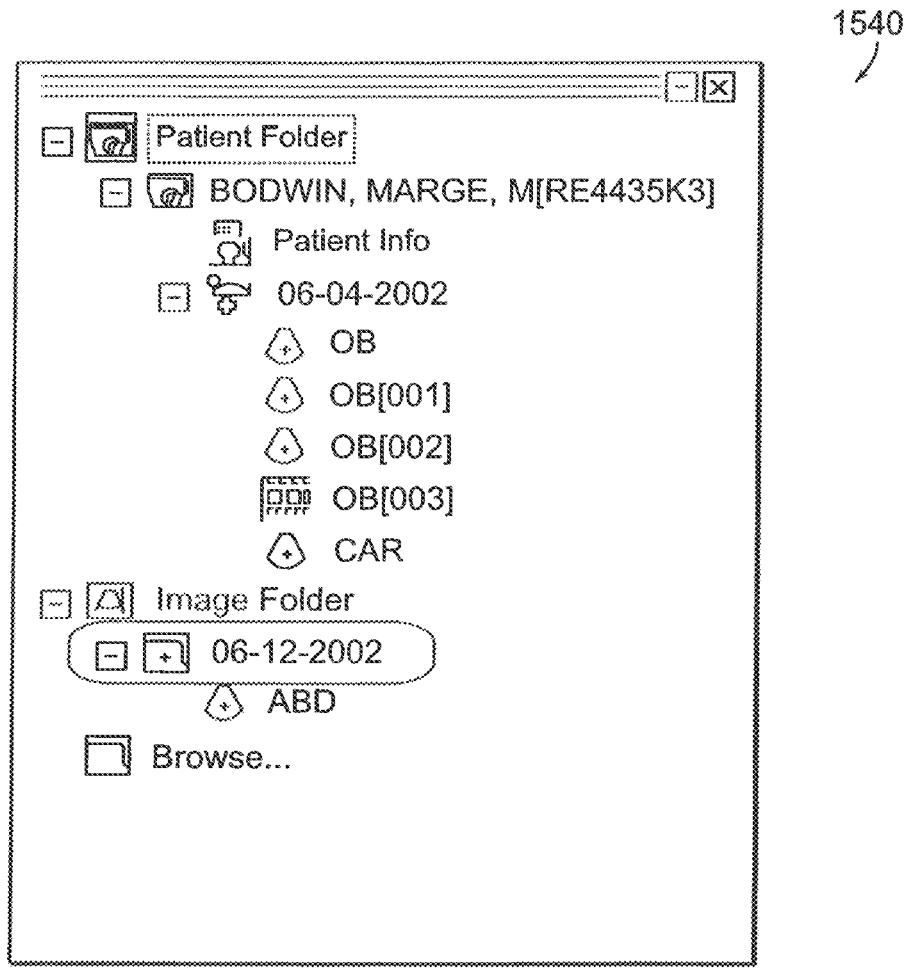
FIGS. 37A and 37B are views of a graphical user interface illustrating a patient folder and an image folder directory in accordance with a preferred embodiment of the present invention.
Figure 37B:
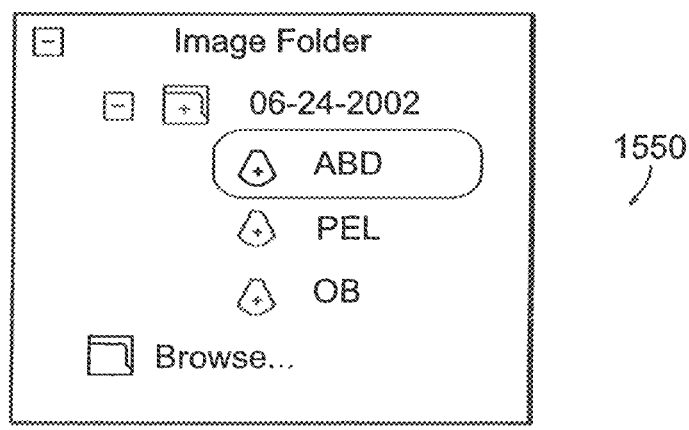

The Explorer window provides the nested level file directory 1500 for all patient folders the user creates images that are created and saved. The folder directory structure 1502 includes the following, but is not limited to, patient folder, and an image folder. The patient folder directory is where patient information files are stored along with any associated images. The image folder directory contains images by date and exam type. The images in this directory are not associated with a patient and are created without patient information. FIGS. 37A-37B illustrate the patient folder 1540 and image folder 1550 in accordance with a preferred embodiment of the present invention. The menu bar at the top of the screen provides nine options one can use to perform basic tasks. To access a menu option simply click the menu name to display the drop-down menu options. The user can also access any menu by using its shortcut key combination.

The Image display window provides two tabs: Image Display and Patient Information. The user clicks on the Image Display tab to view the ultrasound image. The image is displayed in the window according to the control settings that are defined. Once the image is saved, when the user retrieves it again, the category, date and time of the image is also shown in the Image Display window. The Patient Info tab is used to enter new patient information which is later stored in a patient folder. The user can access this tab to also make modifications and updates to the patient information.

Figure 38:
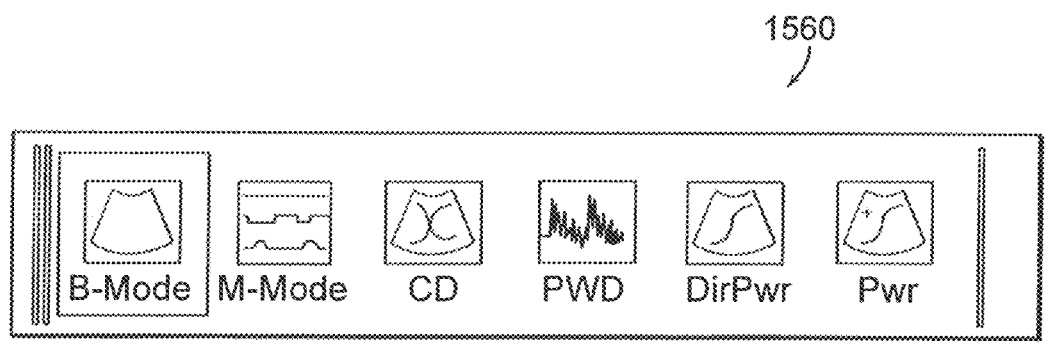
FIG. 38 illustrates a tool bar in a graphical user interface in accordance with a preferred embodiment of the present invention, whereby different modes of imaging can be selected.

The Image Mode bar 1560 is illustrated in FIG. 38 in accordance with a preferred embodiment of the present invention. It provides six control modes the user can choose from when performing an examination. The modes include B-Mode which is a brightness mode providing a standard two-dimensional display in real time, an M-Mode which is used to display motion along a line depicted in the B-mode image as a function of time, and CD mode which is Color Doppler tab that displays, in real time, a two dimensional image of blood flow overlaid to the B-mode image. The hues in the color palette indicate mea n flow velocity, and the different colors indicate the direction of blood flow.

Further, Pulsed-Wave Doppler (PWD) mode displays a line in the B-mode image, which contains the sample size and location of interest. The pulsed Doppler waveform depicts the instantaneous velocity of flow within that sample, as a function of time.

The Directional Power Doppler (DirPwr) mode, displays, in real time, a two-dimensional image of blood flow overlaid to the B-mode image. The hues in the color palette indicated the density of red blood cells. Brighter hues indicate greater density. The different colors indicate the direction of blood flow.

The Power Doppler (Pwr) mode displays, in real time, a two-dimensional image of blood flow overlaid to the B-mode image. The hues in the color palette indicate the density of red blood cells. Brighter hues indicate greater density. It should be noted that directional information is not provided. Power Doppler is not subject to aliasing. It is generally more sensitive to low flow than Color Doppler or Directional Power Doppler.

When a user is in the process of performing the ultrasound, which can be referred to as viewing a live image, the user chooses the control mode they wish to use to view the image. The tabs available in the Image Control bar 1508, 1520 compliment the specific mode the user selects from the Image Mode bar. FIG. 38 illustrates the tool bar in the graphical user interface in accordance with a preferred embodiment of the present invention.

Figure 39:
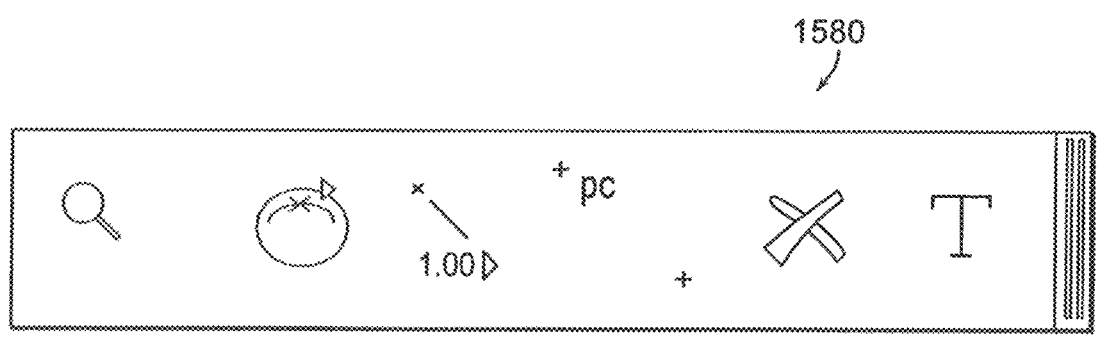
FIG. 39 illustrates a measurement tool bar in a graphical user interface in accordance with a preferred embodiment of the present invention.

FIG. 39 illustrates a measurement tool bar 1580 in a graphical user interface in accordance with a preferred embodiment of the present invention. The Measurements toolbar provides the following buttons: a zoom button that lets a user magnify the selected region of the image of interest, an ellipse button lets one perform real and ellipse measurements on the image, a measure distance button that performs distance measurements on an image, an SD button that provides cursors for measurement of the systolic and diastolic portions of the pulse Doppler waveform, and a delete button that removes a selected measurement or the last measurement made, a text button that lets one enter text on live or frozen images.

Figure 40:
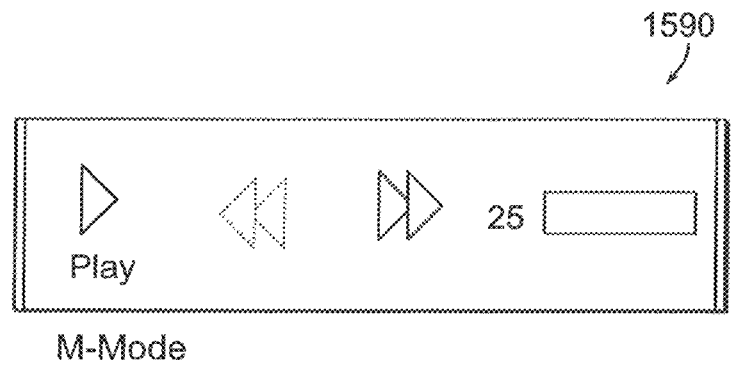
FIG. 40 illustrates a playback tool bar in a graphical user interface in accordance with a preferred embodiment of the present invention.

FIG. 40 illustrates a playback toolbar 1590 in a graphical user interface in accordance with a preferred embodiment of the present invention. The Playback toolbar 1590 provides the following buttons: a play button that lets one play and pause loops of data. The user can play or pause up to sixty frames of loop information. The flip side of this button is a Pause Loop which lets the user pause the loops of date in Play mode. Further, a previous button that lets a user return to the previous frame during Playback Mode, a next image button that allows a user to advance to the next frame during Playback Mode, a status indicator button that shows graphically and numerically the frame number being viewed.

Figures 41A, 41B:
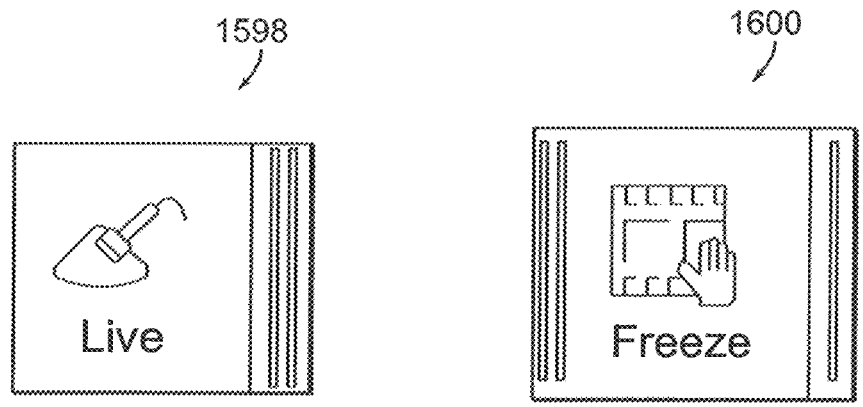
FIGS. 41A and 41B illustrate Live/Freeze interface buttons in a graphical user interface in accordance with a preferred embodiment of the present invention.

The Live/Freeze buttons 1598/1600 that are used during a scan to record the examination or save the image to a file are illustrated in FIGS. 41A and 41B in accordance with a preferred embodiment of the present invention. The live button 1598 provides a real-time image display, while the freeze button 1600 freezes the image during the scan to allow the user to print or save to a file.

Figure 42:
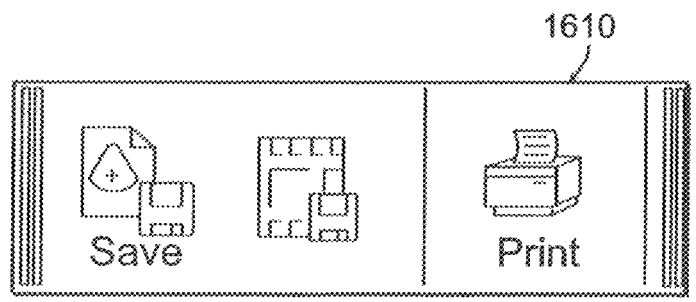
FIG. 42 illustrates a file tool bar in a graphical user interface in accordance with a preferred embodiment of the present invention.

FIG. 42 illustrates the file toolbar 1610 in a graphical user interface of a preferred embodiment. The file toolbar 1610 provides the following buttons: a save button saves the current image to a file, a save Loop button that saves the maximum allowed number of previous frames as a Cine loop, and a print button that lets the user print the current image.

The preferred embodiments of the present invention also provide an online help system from the system program, that provides information grouped as contents, index and search.

The preferred embodiments of the present invention provides the steps a user needs to take to set up and modify information relating to a new patient in the system program. The user can enter new patient information so that pertinent exam history can be retained when a patient is scanned. A patient folder is created when one sets up a new patient which stores the patient information. All examination images for the patient are stored in this folder and are viewable by accessing the system Explorer window.

FIG. 43 illustrates a view of a patient information screen 1620 in a graphical user interface of a preferred embodiment. The Patient Information screen 1620 is accessible by selecting the Patient Information tab from the main system window. Several fields in the Patient Information screen 1620 provide drop-down arrows. The drop-down arrows displays a list box of choices for a field when selected. The choices available in the list box are created based on new data the user enters into a field for patients each time they perform an exam. For example, FIG. 44 illustrates patient information screen 1640 where one can enter a new comment or choose a previously entered comment available from the list box in the Comment field. In the examination location and clinical information fields, one can enter new data or choose a value from a list box displaying existing names or locations.

Figure 45:
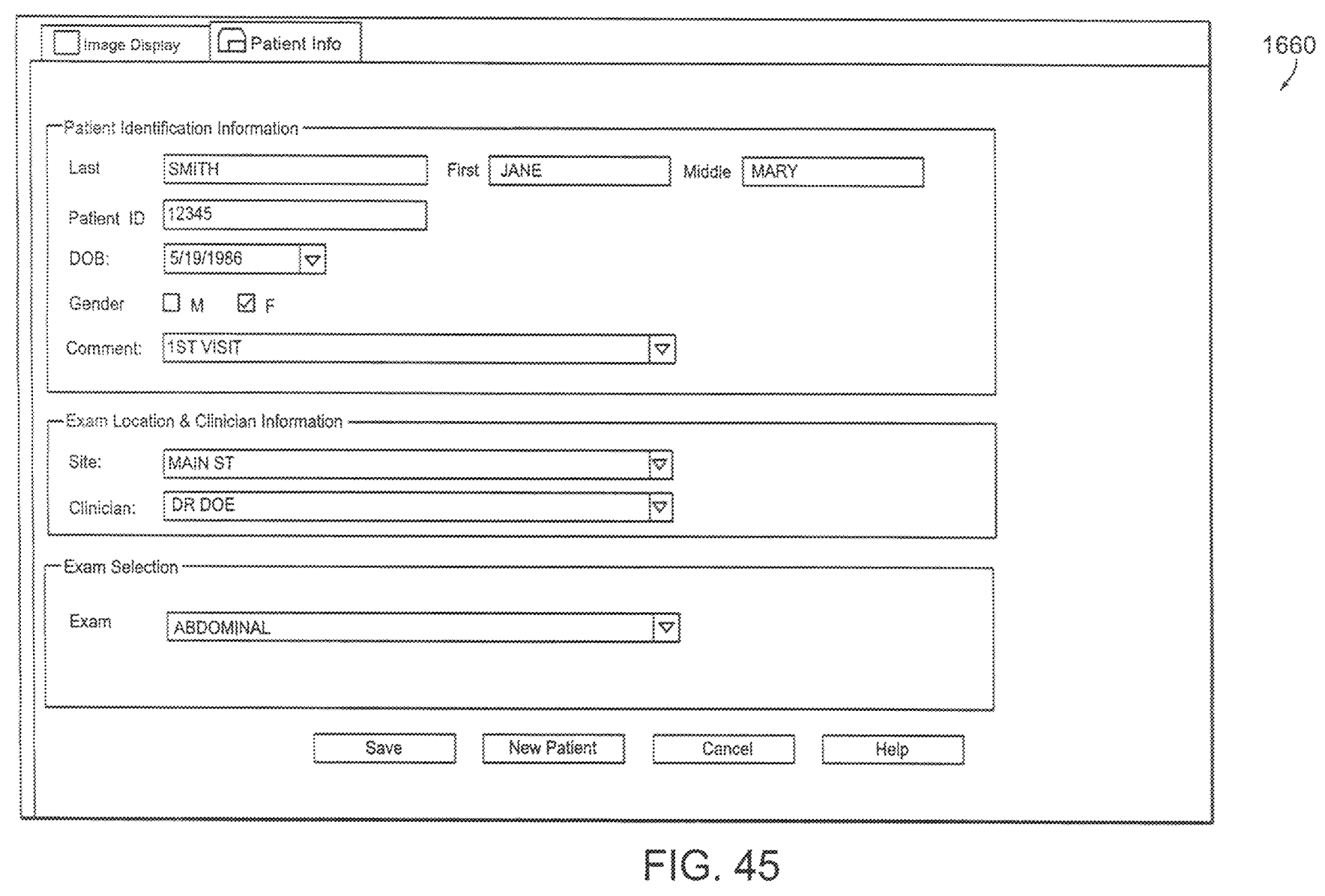

FIG. 45 illustrates further interface buttons in a patient interface screen 1660. The interface buttons provide the following functions: a save button lets a user save new or modified patient information, a new Patient button clears the Patient Information screen so the user can add a new patient, a cancel button stops the performing function and reverts back to last saved data, and a help button provides access to the online system Help. If previous data was entered for the last patient, when one clicks on a New Patient the data is eliminated from the screen. A dialog box displays prompting one to save the data. If the user chooses Yes, the data is saved. If the user chooses No, the screen is cleared with no changes saved. If one chooses Cancel, the operation is cancelled.

To view the data in the file, the user locates the specific patient information folder and clicks to select the Patient Information file. The data appears again in the Patient Information screen. If the user clicks the Cancel button while entering new patient information, the data is lost and cannot be retrieved.

FIG. 45 also illustrates a view of a screen for adding a new patient in a graphical user interface of a preferred embodiment. When adding a new patient, the user can enter information in the fields that display in the Patient Information screen. When the user is finished adding new patient information, a Patient Information file is created that resides in the system directory. The Patient Information file is stored in the patient folder. Any associated images for a patient are also stored in the same directory. The Patient Information tab can be chosen in the image area to enter new patient information. Further, the New Patient button can be chosen at the bottom to clear all previous information entered from the last patient.

In the examination (exam) selection field, the user can choose the exam type they want for this examination. Each time one performs an examination on the specific patient, the user can choose the new examination type. The information is stored as part of the image filename. Further, to save a new patient that has been added, the user clicks on Save. The patient information is saved in the Patient Information file and displays in the system Explorer window next to the patient folder for the patient. Important patient information the user entered in the Patient Information tab is displayed in the Image Display screen. To view the patient information, one clicks the Image Display tab. The patient information is shown across the top of the screen and is saved with scanned images one creates for the patient. The user, be it a clinician or an ultrasound technician, for example, can update information for an existing patient. First they need to retrieve the appropriate file and then make their changes.

Ultrasound is primarily an operator-dependent imaging technology. The quality of images and the ability to make a correct diagnosis based on scans depends upon precise image adjustments and adequate control settings applied during the exam. The user can optimize the image quality during a patient exam while using any of the six image modes available in the system software. A two-dimensional (2D) image control setting tab that provides adjustments for size depth, focus, as well as time gain compensation is available for each of the six modes. An image quality (IQ) control setting that allows the user to further adjust the image for clarity is also available for each of the six modes.

Preferred embodiments of the present invention, provide B-mode and M-mode images. The B-mode (Brightness mode) tab provides two-dimensional image adjustments that allow the user to control the size, depth, focus, and overall image gain as well as TGC (Time Gain Compensation). The user can further manipulate the image quality by selecting from various palettes, smoothing, persistence settings and maps offered in the Image Quality tab menu. B-mode is selected when the user wants to view only a two-dimensional display of the anatomy. The B-mode provides the standard image mode options necessary for an ultrasound using the 2D and IQ (image control) settings. To select the B-mode for image display, the user chooses the B-mode button from the image mode bar, or from the Modes menu.

Figure 46:
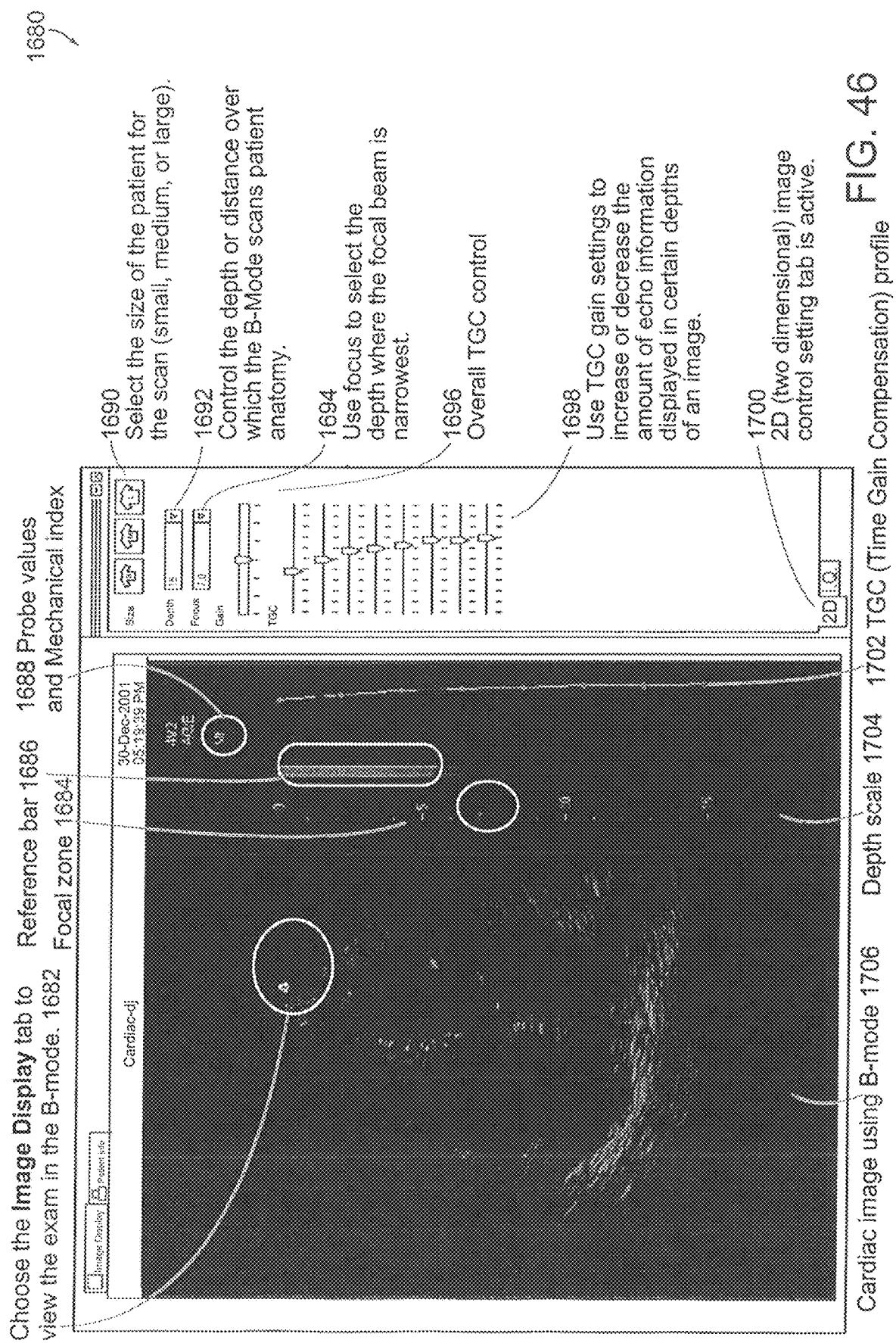
FIG. 46 illustrates an image in the B-mode including the controls provided by a graphical user interface in the B-mode in accordance with a preferred embodiment of the present invention.

FIG. 46 illustrates an image in the B-mode including the controls 1690, 1692, 1694, 1696, 1698, 1700 provided by a graphical user interface 1680 of a preferred embodiment. Choose the image display tab to view the exam in the B-mode 1682. The cardiac image 1706 is displayed with depth scale 1704, time gain compensation (TCG) profile 1702, reference bar 1686, focal zone 1684, probe values and mechanical index 1688. FIGS. 47A-47H illustrate the different control interfaces for adjusting a B-mode image in the graphical user interface of the preferred embodiment. For adjusting size, the user can choose the parameters for the scan that meet the size of the patient, or structured anatomy. For example, the user clicks the T-shirt button 1720 that matches the patient size for small, medium, or large (or for superficial, moderately deep, and deep areas of interest). In the alternative, the user can access the size option from the Image menu 1728 and choose the size from the drop-down list. Selection of the appropriate scan size can provide the user with fast and easy baseline settings. Other B-mode settings such as Gain, Focus and Depth have been optimized according to the T-shirt size in a preferred embodiment. All controls return to default settings when a new T-shirt size is selected. This feature makes it easy for the user to reset multiple parameters.

With respect to adjusting depth, the user can control the field of view for the scanned image by using depth control 1740. If they want to capture deeper structures, they increase the depth. If there is a large part of the exam display that is unused or not necessary at the bottom of the screen, the user decreases the depth. To select the depth, the user clicks on the down arrow next to the Depth field label, and chooses a value from the list 1760 of available options. The available depth option depends on the probe that the user is working with. To decrease the depth, the user chooses a lower value from the depth list box 1760. Or, in the alternative, the user can access the depth option from the Image menu and choose depth from the drop-down list.

The depth control adjusts the user's field of view. It increases one's field of view to see larger or deeper structures. Depth control also decreases the user's field of vision to enlarge the display of structures near the skin line. After adjusting Depth, the user may want to adjust the TGC and focus control settings.

With respect to adjusting focus, the user can change the position of the focal zone to specify a location for the optimal area of focus. A graphic caret is positioned on the depth scale to represent the focal zone. To adjust the focus, the user clicks on the down-arrow next to the Focus label 1780 to view the list box, or selects Focus from the Image menu. The list of values displayed in the menu can be chosen. The available focal position options depend on the probe being used. The Focus optimizes the image by increasing the resolution for a specific area.

With regard to adjusting Gain, the users increase or decrease the amount of echo information displayed in an image. Adjusting Gain may have the effect of brightening or darkening the image if sufficient echo information is generated. To adjust the Gain in a preferred embodiment, the user slides the bar 1790 illustrated in FIG. 47F to the right to increase, or to the left to decrease the level. Gain allows the user to balance echo contrast so that cystic structure appear echo-free and reflecting tissue fills in.

Figure 47A:
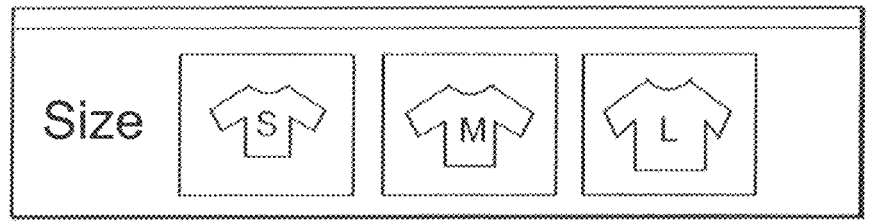
Figure 47B:
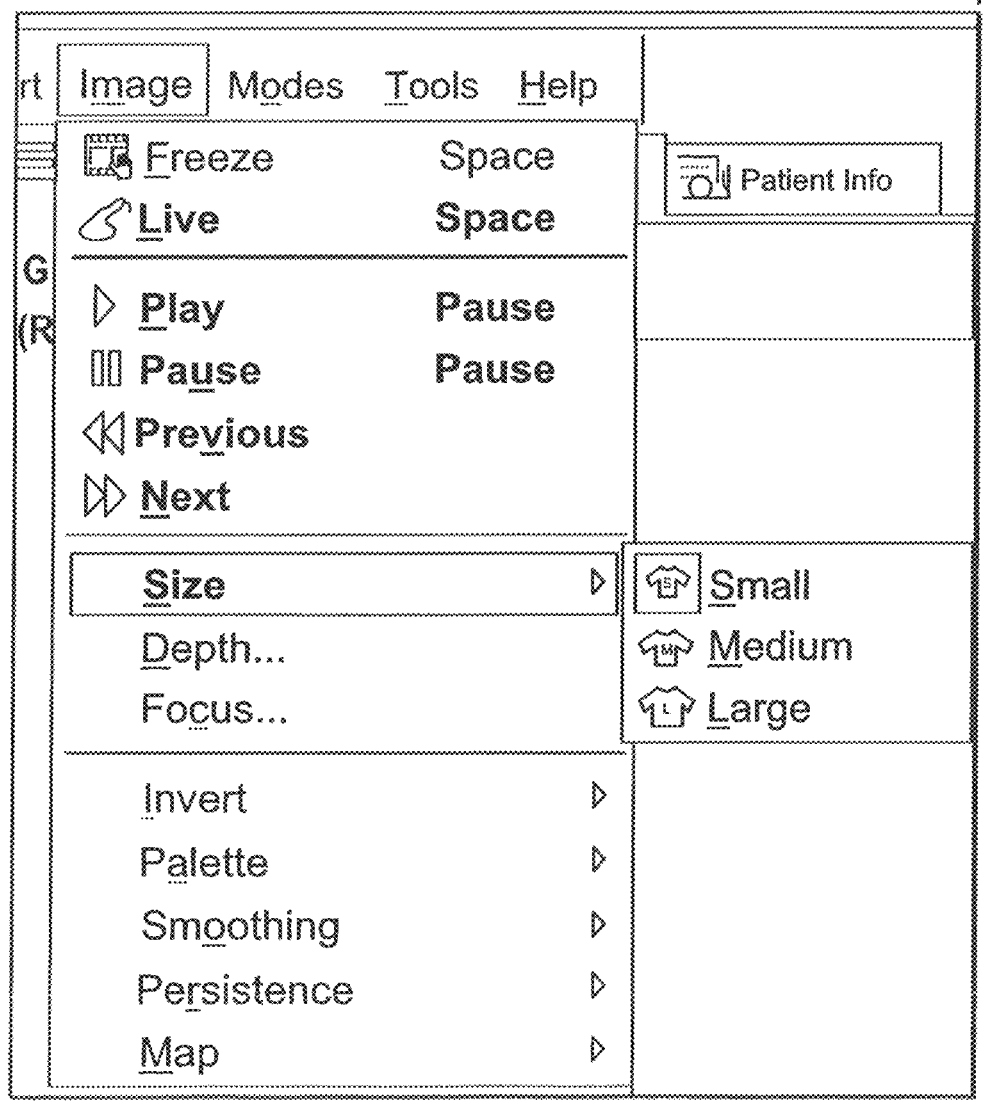
Figure 47D:
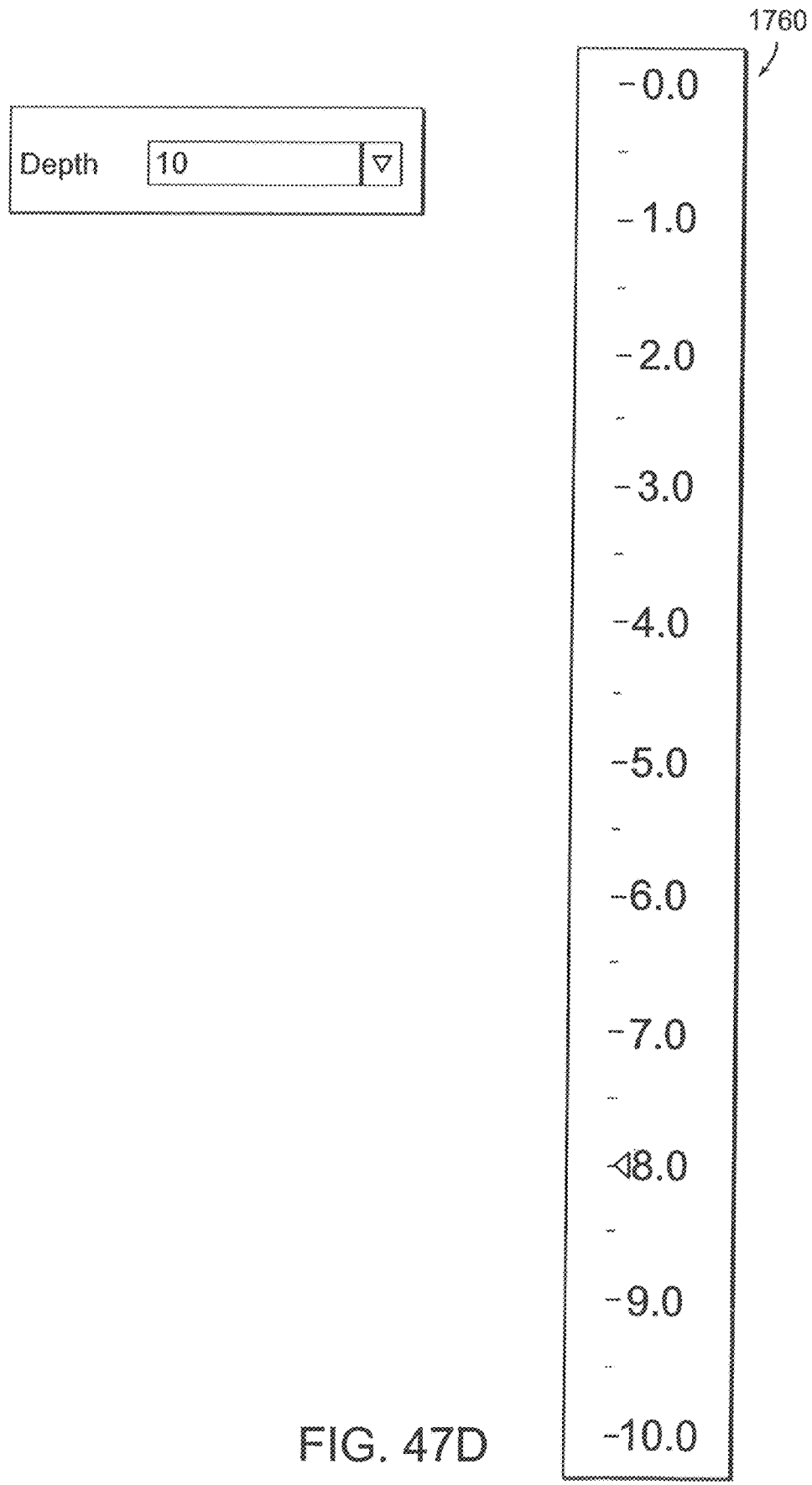
Figure 47E:
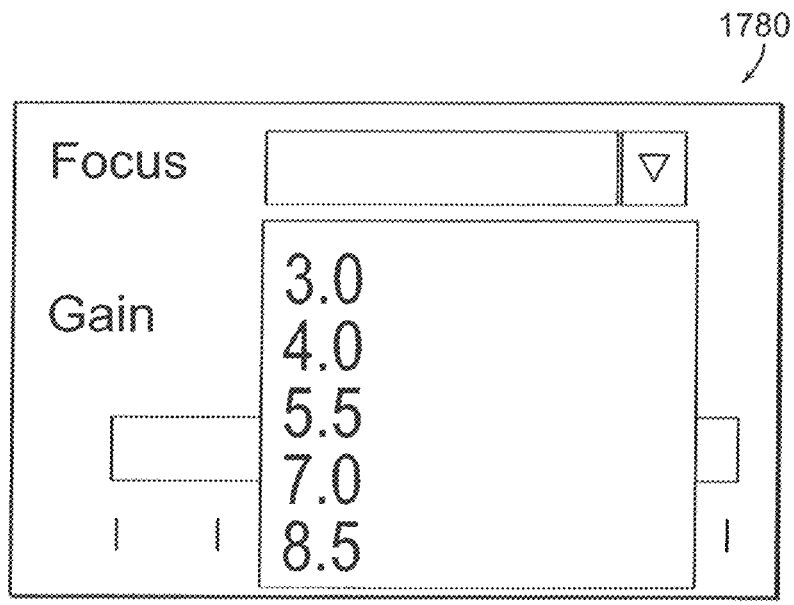
Figure 47F:
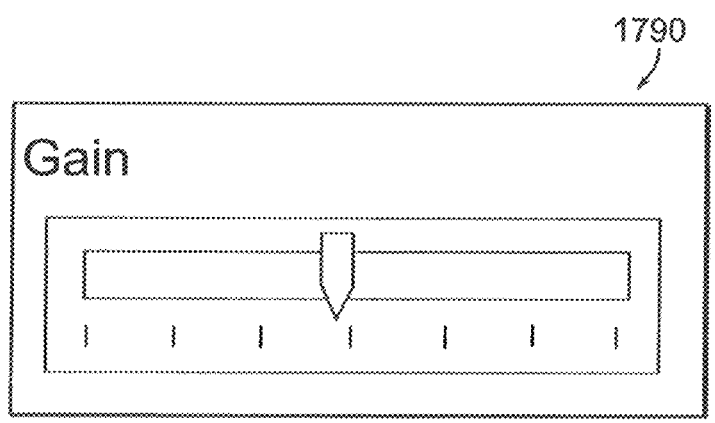
Figure 47G:
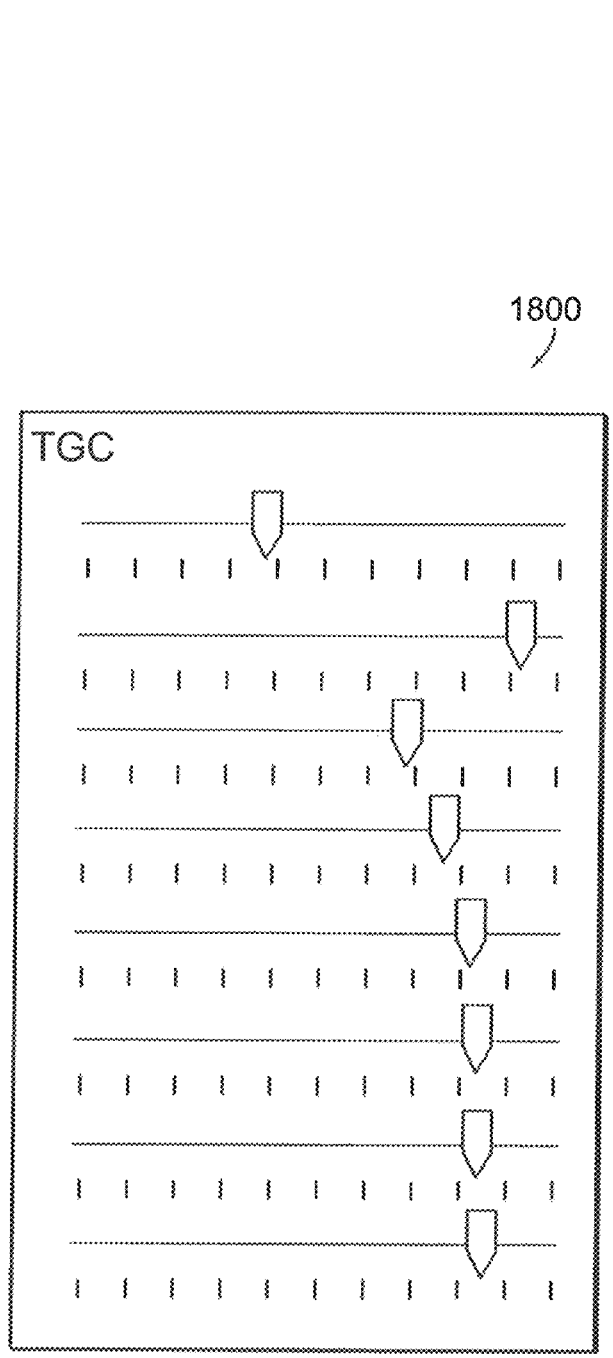
Figure 47H:
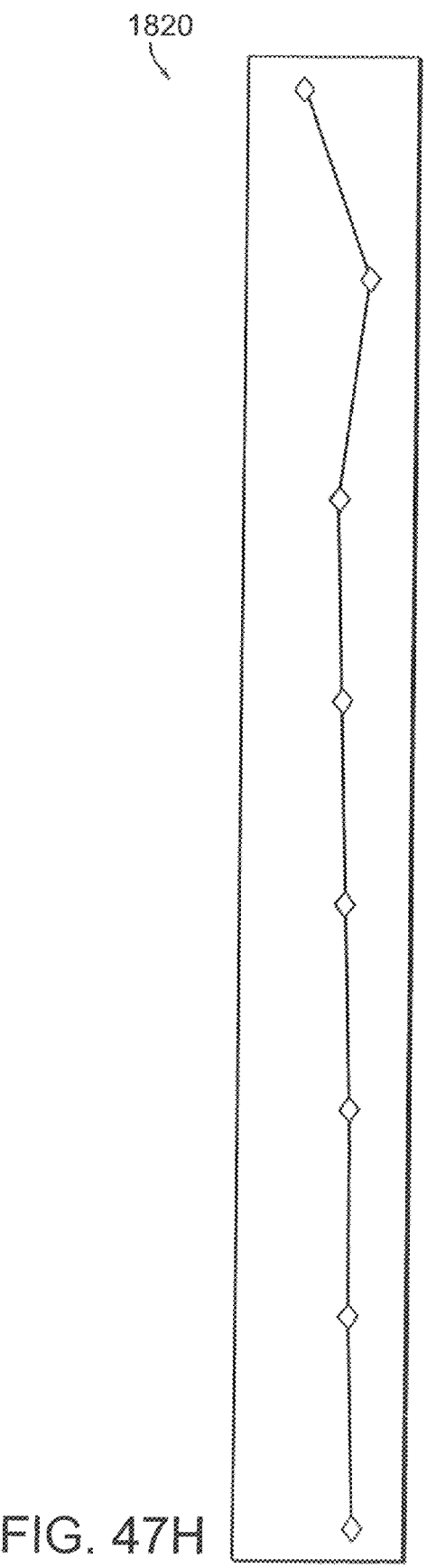

With respect to adjusting TGC, or the Time Gain Compensation, a slider illustrated in FIG. 47C adjusts how the control amplifies returning signals to correct for the attenuation caused by tissues at increasing depths. Each of the eight TGC slider bars 1800 are spaced proportionately to the depth. Depending on the adjustments, the TGC curve 1820 on the image display illustrated in FIG. 47H shows the values that match the TGC control. When a user changes the depth, the TGC is rescaled across the new depth range. The TGC is used to balance the image so that the brightness of echoes is the same from near field to far field.

Figure 48:
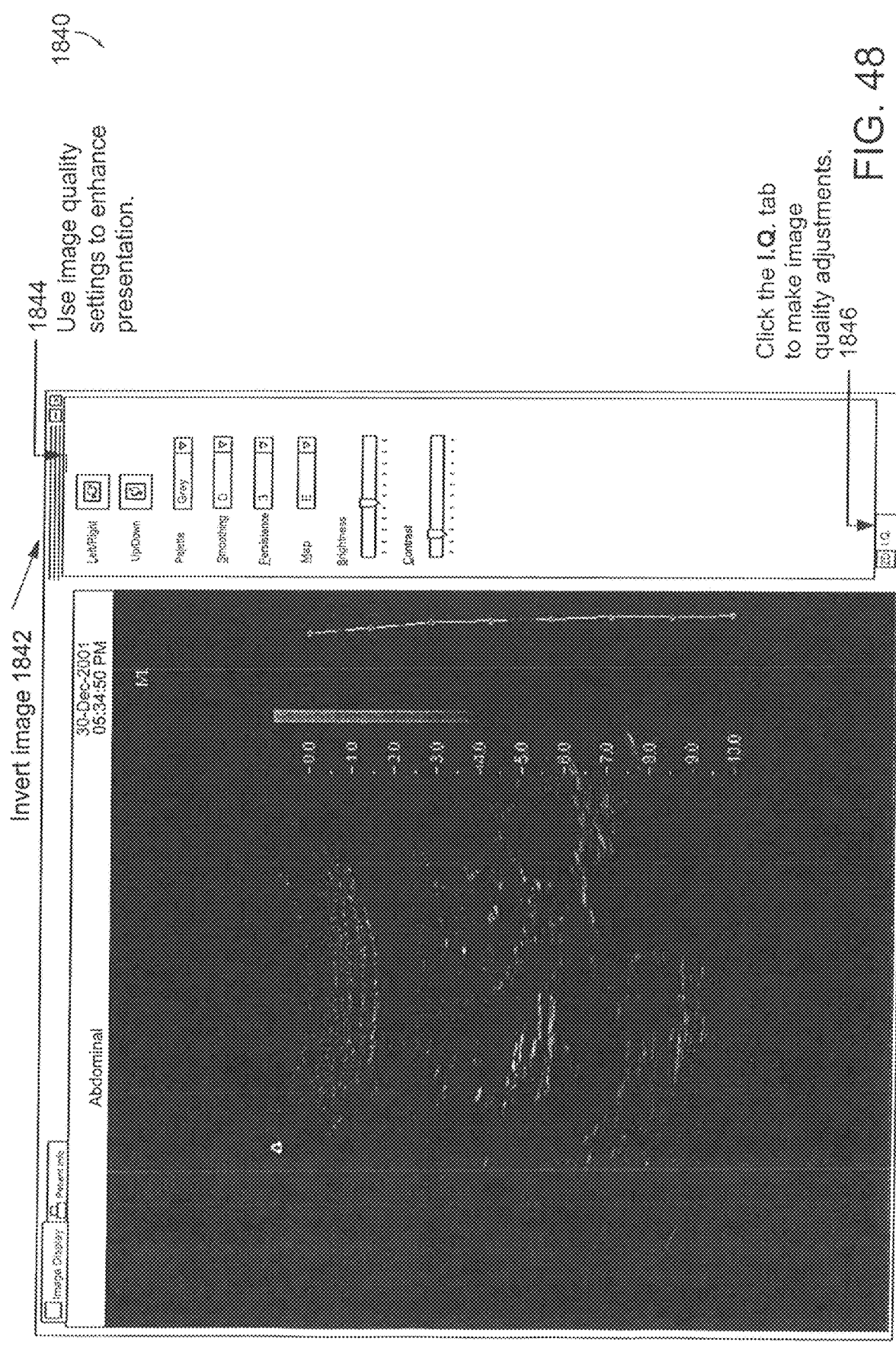
FIG. 48 illustrates the image quality control setting provided in the B-mode image option in accordance with a preferred embodiment of the present invention.

FIG. 48 illustrates the image quality control setting 1844 provided in the B-mode image 1840 option in a preferred embodiment. To select the I.Q. (image quality) control setting, the user clicks the I.Q. tab 1846 at the bottom of the image control bar, or accesses the Image menu. The user can invert 1842 the scanned image to the left or right by clicking on the Left/Right button. Further, the user can also invert the image in the top to bottom direction by clicking on the Up/Down button. It is appropriate to refer to the display to confirm the orientation of the image.

In addition, the palette can be adjusted by the user. The user can choose from a palette color range to define the reference bar, or the user can choose to use the default conventional gray scale display. The down-arrow next to the Palette field label can be clicked or selected to view the list box of color choices. The color the user wants can be chosen. The color scald changes to the new color and is represented in the image display. The gray palette is the most frequently used palette. To determine if another palette will improve visualization of the anatomy, the user can cycle through the available options. The anatomy that is being imaged has an effect on which palette is most advantageous.

With respect to image smoothing, the user can select from a range of A to E smooth image display. The user can click on the down-arrow next to the Smoothing field label to view the list box of values. The value displays in the probe information and is the first value in A/4/E. Increasing the smoothing increases the amount of interpolation between scan lines which makes the image appear smoother. It also decreases the frame rate. The opposite is true when the user decreases the amount of smoothing.

For image persistence, the user selects from a range of 0 to 4 to define the amount of image frame averaging is desired. By clicking on the down-arrow next to the Persistence field label the user views the list box of values. The value displays in the probe information and is the second value in A/4/E. When the persistence rate is high, the image appears less speckled and smoother. However, increasing the persistence rate also increases the possibility that the image appears to be blurred if the tissue is moving when the user freezes the image. When the persistence is low, the opposite is true.

With respect to an image map, the user can select from a range of A to F in the Map label field to change gray levels. The user clicks on the down-arrow next to the Map field label to view the list box of values. The value displays in the probe information and is the third value in A/4/E. Adjusting the map can assist in closely viewing certain anatomical features or to detect subtle pathologies.

To adjust the brightness of the image tone of the display, the user does so by defining the brightness range. By adjusting the brightness control to the right, the brightness of the image is increased. By adjusting the brightness control to the left, the brightness is decreased. Increasing the brightness increases the overall brightness of the image. The brightness is adjusted to correspond with map and contrast values.

The contrast of the image tone of the display is adjusted by defining the contrast range. By adjusting the contrast control to the right, the contrast of the image is increased. By adjusting the contrast control to the left, the contrast is decreased. Increasing the contrast decreases the amount of levels of gray in the image and makes the image contrast more. The opposite is true when the user decreases the contrast. It is recommended to adjust contrast to correspond and compliment the brightness and map value.

Figure 49:
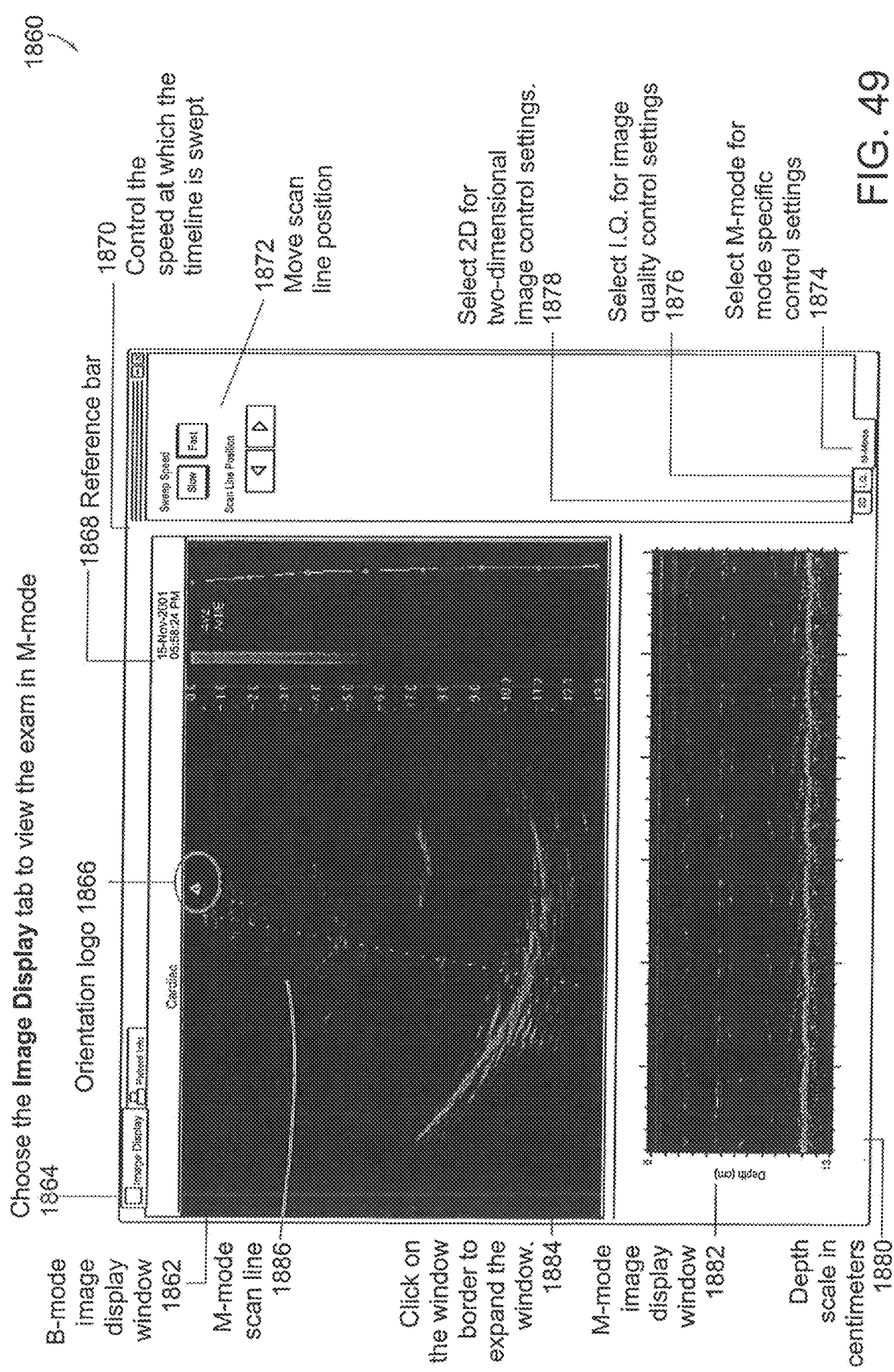
FIG. 49 illustrates an M-mode image and the controls provided to adjust the M-mode image in accordance with a preferred embodiment of the present invention.

FIG. 49 illustrates the M-mode image 1860 option in accordance with a preferred embodiment of the present invention. The M-mode 1860 (motion mode) provides a display format and measurement capability that represents tissue displacement (motion) occurring over time along a single vector. The M-mode is used to determine patterns of motion for objects within the ultrasound beam. Typically, this mode is used for viewing motion patterns of the heart. When a user chooses M-mode for the image display the user can view the image in B-mode 1862 at the top of the screen with an orientation logo 1866 as well as view the M-mode depth scale 1880 in the window at the bottom of the screen.

To select the M-mode for image display, the user chooses the M-mode button 1864 from the image mode bar. The following image control settings can be used to make adjustments to image display: 2D-Two dimensional 1878, I.Q.-Image quality 1876, an M-mode.

To select the M-mode image control setting, the user clicks the M-mode tab 1874 at the bottom of the image control bar. To adjust the sweep, you can change the speed at which the timeline is swept. To increase the speed, in the Sweep Speed field 1870, the user clicks the Fast button. To decrease the speed, the user clicks the Slow button. One can also access speed by right-clicking in the M-mode window. As necessary, the M-mode display is optimized by adjusting the Depth, Focus, Gain and TGC controls on the 2D tab 1878 of the Image Control bar. The user can also adjust the image quality by selecting the IQ tab 1876 in the Image Control bar. To adjust the size of the 2D and M-mode image display, the user clicks on the horizontal bar 1884 between the two images and drags to the new appropriate window size. Changing the Sweep Speed 1870 can affect the thermal index (TI) and/or mechanical index (MI).

To adjust the scan line position in the B-mode window, the user can click on the left or right arrows next to the Scan Line Position label 1872. The scan line 1886 moves accordingly to the left or the right. The M-mode cursor line can be moved manually.

During a scan, live images are recorded by frame. Depending upon the mode the user selects, a certain amount of frames are recorded. For example, the B-mode allows the capture of up to 60 frames in a Cine loop. When the user freezes a real-time image during a scan, all movement is suspended in the image display area. The freezed frame can be saved as a single image file or an entire image loop dependent upon the mode.

The ultrasound images can be magnified and text annotation can be added to the image area. Further, measurements accompanying ultrasound images can be added to supplement other clinical procedures available to the attending physician. The accuracy of measurements is not only determined by the system software, but also by the use of proper medical protocols by the users. The user can create measurements for Distance, Ellipse, or Peak Systole/End Diastole-depending upon the mode you are using.

Images and loops can be exported in formats that can be viewed by others who do not have the system software. The preferred embodiment of the present invention can electronically mail (e-mail) an image and loop files or include them as graphics in other applications. The user can export images to one of the following graphic file formats: Bitmap (.bmp), and DICOM (.dcm). The user can export loops to one of the following graphic file formats: Tagged Image File Format (.tif), DICOM (.dcm). The Obstetrical measurement generated by the preferred embodiments of the system can easily be exported to the R4 Obstetrical reporting package.

Examination types in preferred embodiments are considered presets that contain standard image control settings. The system provides the user with a wide variety of exam types. The exam types automatically optimize multiple parameters one can use during a scan. The examination types available depend on which probe is being used. Although several probes may provide the same examination type, the preset image control parameters are unique to the characteristics of each probe. Each examination type contains three T-shirt presets: Small, Medium, and Large. The T-shirt icons, also interfaces represent predefined parameters for image control settings used with small, medium and large patients, or for superficial, moderately deep and deep areas of interest.

The image settings that can be optimized for each size using a two dimensional graphical interface include: depth, focus, gain, and TGC. The image setting controls that are optimized for each examination type using the image quality graphical user interface includes: left/right, up/down, palette, smoothing, persistence, map, brightness and contrast. The image setting controls that are optimized for each examination type using the M-mode graphical user interface include: sweep speed 1870, scan line position 1872, and B-mode to M-mode display ration 1884. The image setting controls that are optimized for each examination type using the Pulsed Wave Doppler (PWD) interface include: sweep speed, velocity display, PRF (Pulse repetition frequency), wall filter, steering angle, invert, correction angle, sample volume size, gain, baseline, and sound volume.

Further, the image setting controls that are optimized for each examination type using the Color Doppler (CD) graphical user interface include: scan area, PRF (Pulse repetition frequency), wall filter, steering angle, invert, color gain, priority, persistence, baseline, high spatial resolution, and high frame rate. The image setting controls that are optimized for each examination type using the Direction Power Doppler (DirPwr) interface include: scan area, PRF (Pulse repetition frequency), wall filter, steering angle, invert, gain, priority, persistence, baseline, high spatial resolution, and high frame rate. The image setting controls that are optimized for each examination type using the PWR interface include: scan area, PRF (Pulse repetition frequency), wall filter, steering angle, gain, priority, persistence, high spatial resolution, and high frame rate.

Although the user can use the preset examination types available with the probe, the user can also create customized exam types based on the presets. Customized exam types can include specific modifications to the preset image control setting parameters. The user can select a customized exam type for future use without having to perform the exact settings again. Any examination type can be customized to include the specific control settings the user wishes to use.

Certain embodiments include diagnostic ultrasound images being displayed on a display monitor away from the operator's hands. Larger ultrasound imaging systems have the display integrated in the main operator console. The operator is accustomed to turning his/her head between his/her hand holding the probe or scan head, the system console and display, or he/she keeps his/her eyes on the display and manipulates the scan head without looking at the patient. This does not work well for some medical procedures in which the operator is performing visually intensive operations at the same location on the patient where the scan head is. Therefore, it is very beneficial to locate the display proximate to the operator's hands. Therefore, in alternate preferred embodiments, a visor mounted display is a workable alternative, but is deemed uncomfortable for some operators.

A preferred embodiment integrates the display on the hand-held scan head, thus allowing the operator to easily view the image and operate the probe or scan head, as well as perform operations in the same local area with the other hand. The data/video processing unit is also compact and portable, and may be placed close to the operator or alternatively at a remote location. Optionally, in another embodiment, a display is also integrated into the data/video processing unit. The processing unit also provides an external monitor port for use with traditional display monitors.

Figure 50:
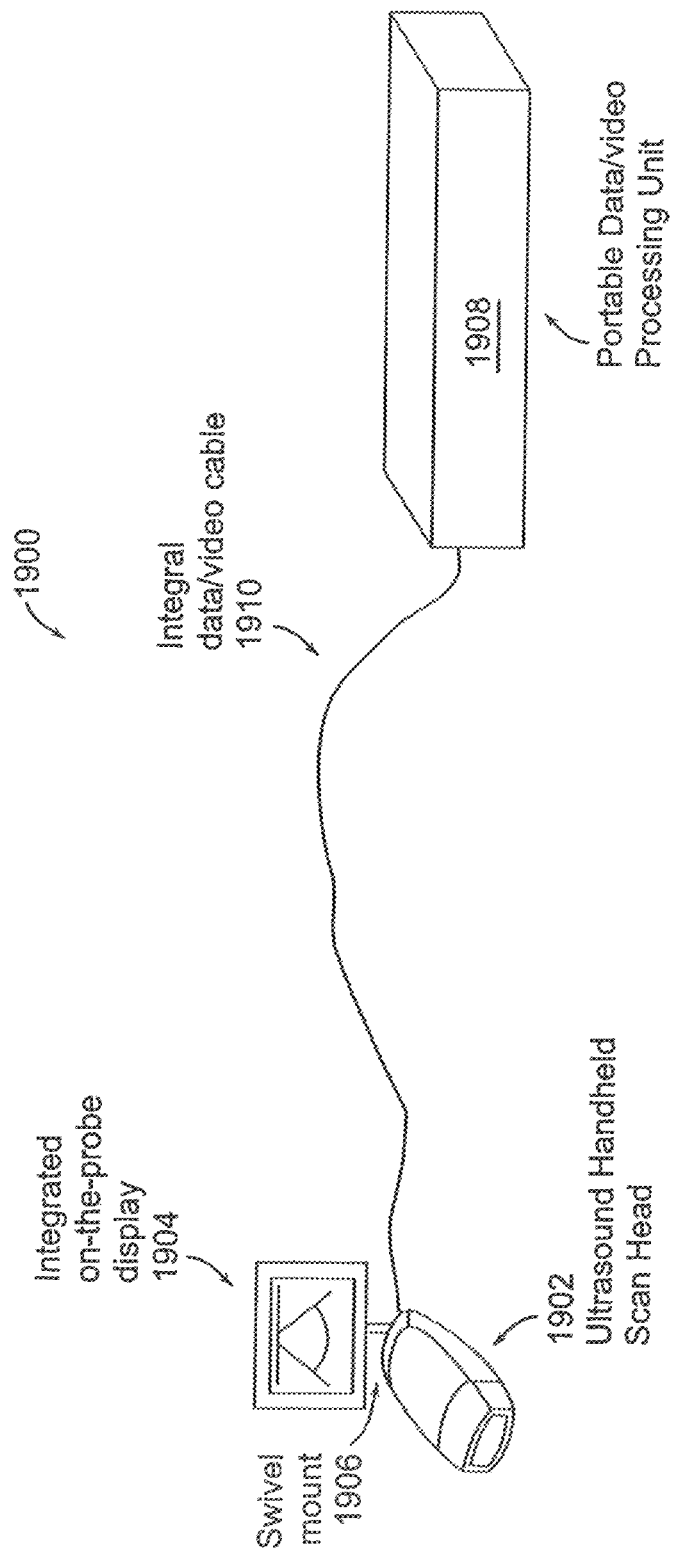
FIG. 50 illustrates a portable ultrasound imaging system including a hand-held probe with an integrated display in accordance with a preferred embodiment of the present invention.
Figure 51:
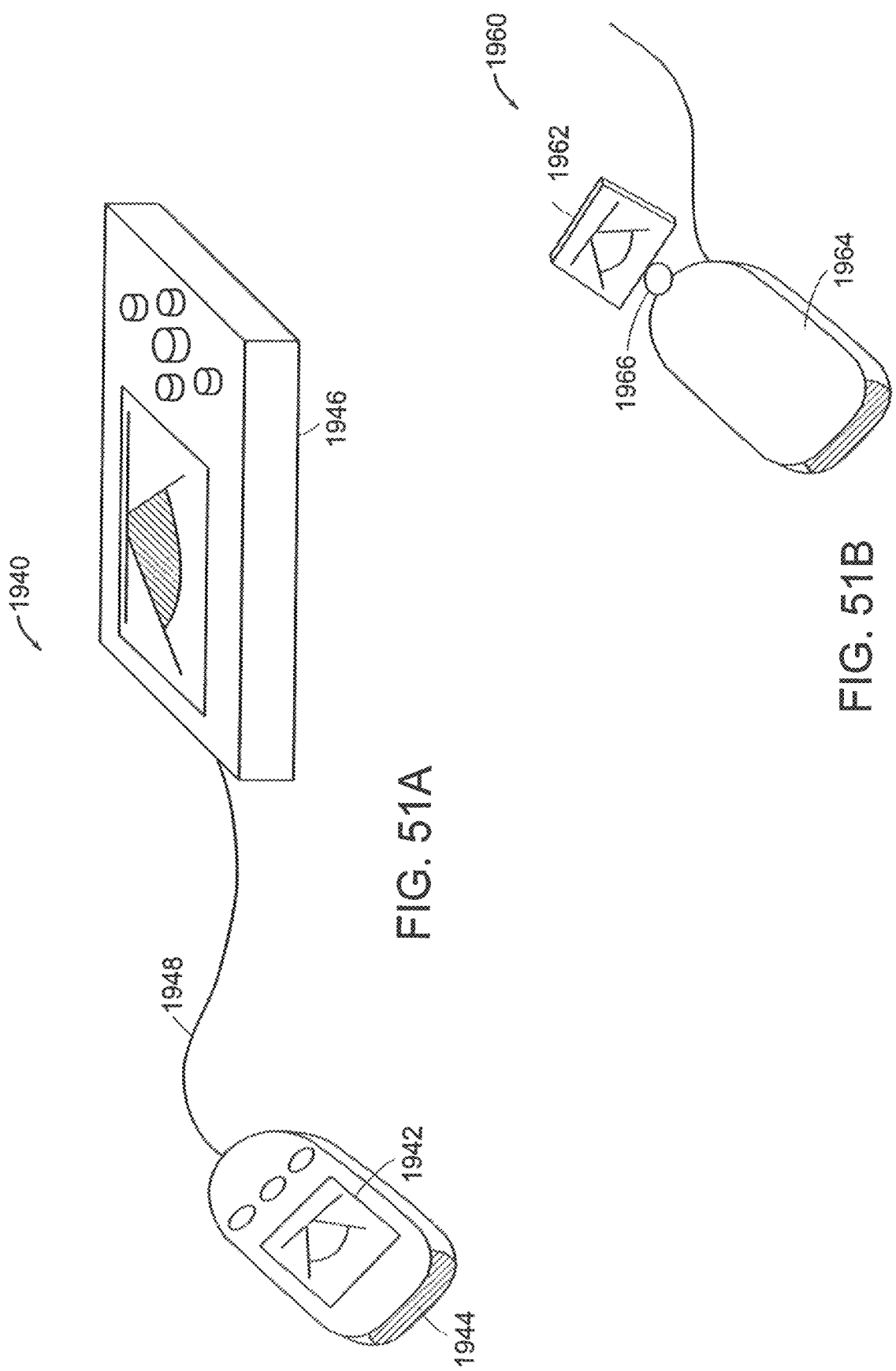
FIGS. 51A and 51B are embodiments illustrating a hand-held scan head having a display unit integrated on the scan head housing or the display unit being attached to the scan head, respectively, in accordance with the present invention.

FIG. 50 illustrates a preferred embodiment of a portable ultrasound imaging system 1900 including a hand-held scan head with integrated display and a portable processing unit. The hand-held scan head assembly 1902 comprises an ultrasound transducer and a compact video display 1904 attached to a swivel mount 1906. The display unit 1942 can be integrated into the hand-held scan head 1944 either directly on the scan head housing as illustrated in FIG. 51A, or the display unit 1962 can be mounted onto the scan head 1964 via a mechanical swivel assembly 1966 as illustrated in system 1960 in FIG. 51B, which may be permanently attached or detachable. Alternatively, the display can be mounted on the interface 1908 in close proximity to the probe. The interface 1908 and scan head 1902 can connect with an integral data/video cable 1910. The interface can use a system such as that shown in FIG. 3D, for example, that is modified to have a video cable and power running alongside the Firewire connection from the processor housing 5.

The on-the-probe display unit 1940 such as shown in FIG. 51A can be a 2.5 inch to 6.4 inch color LCD panel display 1942, with a screen resolution ranging from a quarter VGA (320×240 pixels) to full VGA (640×480 pixels). The video data delivered to the display may be composite video via a thin coaxial cable, or digital VGA using Low Voltage Differential Signaling (LVDS) via four coaxial or twisted-pair wires. The display may be powered by battery in the unit, or by DC-power supplied by the portable data/video processing unit 1946 via power wires from the processing unit.

In a preferred embodiment, the video and power wires for the display are integrated with the transducer data wires for the scan head to form a single cable assembly 1948 that connects the hand-held scan head to the portable data/video processing unit.

Figure 53A:
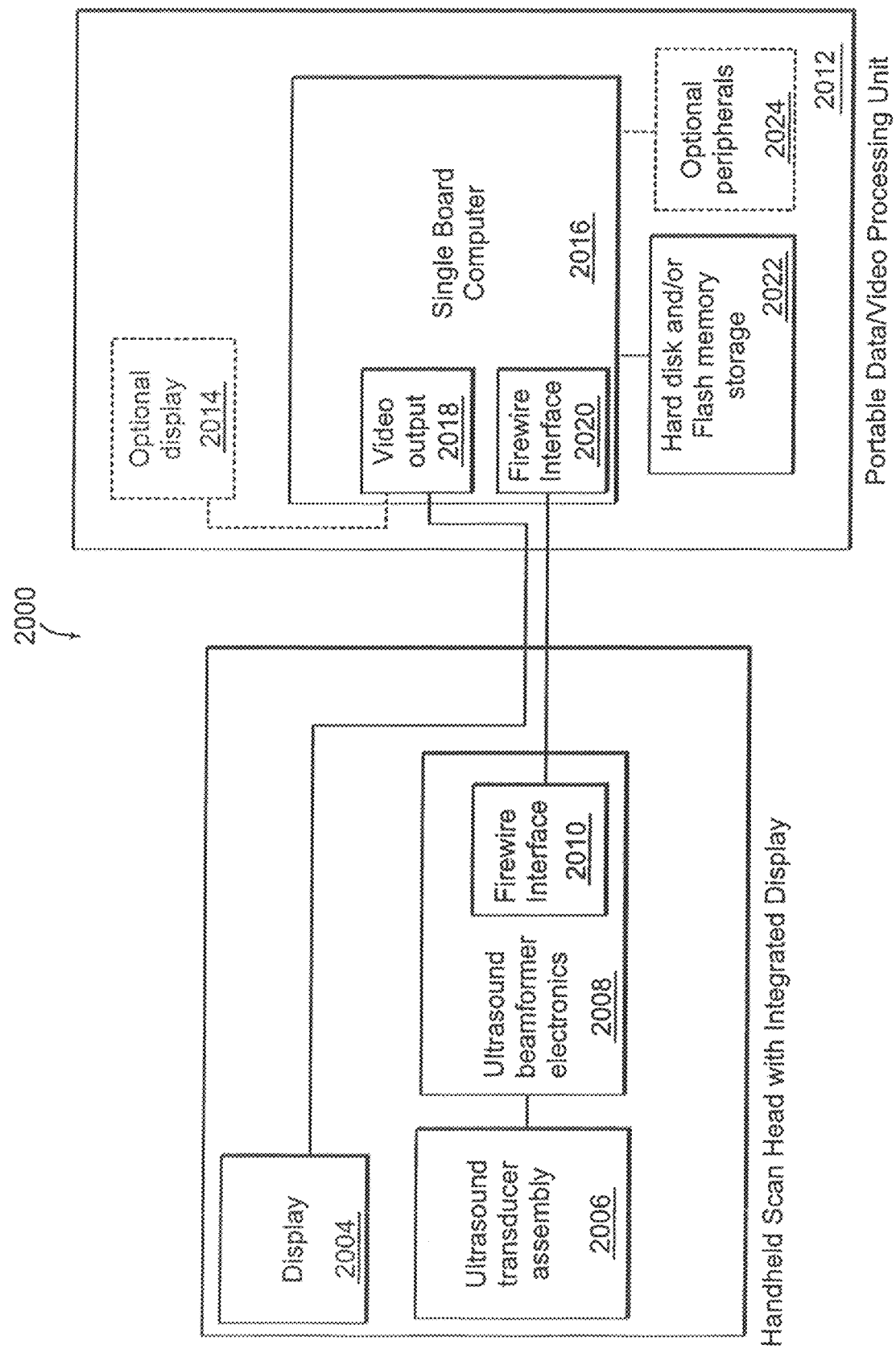
FIGS. 53A and 53B illustrate alternate preferred embodiments wherein the beamformer electronics are housed either in the hand-held scan head assembly or in the processing unit, respectively, in accordance with the present invention.

The data/video processing unit 1908 is compact and portable. In a preferred embodiment, the beamformer electronics 2008 and transducer assembly 2006 is an integral part of the hand-held scan head assembly 2000, and the scan head communicates with the processing unit 2012 via a Firewire (IEEE 1394) interface 2010, 2020 as illustrated in FIG. 53A. Processing unit 2021 can include single board computer 2016, video output 2018, Firewire interface 2020, hard disk and/or flash memory storage 2022, optional display 2014, and optional peripherals 2024.

Figure 52:
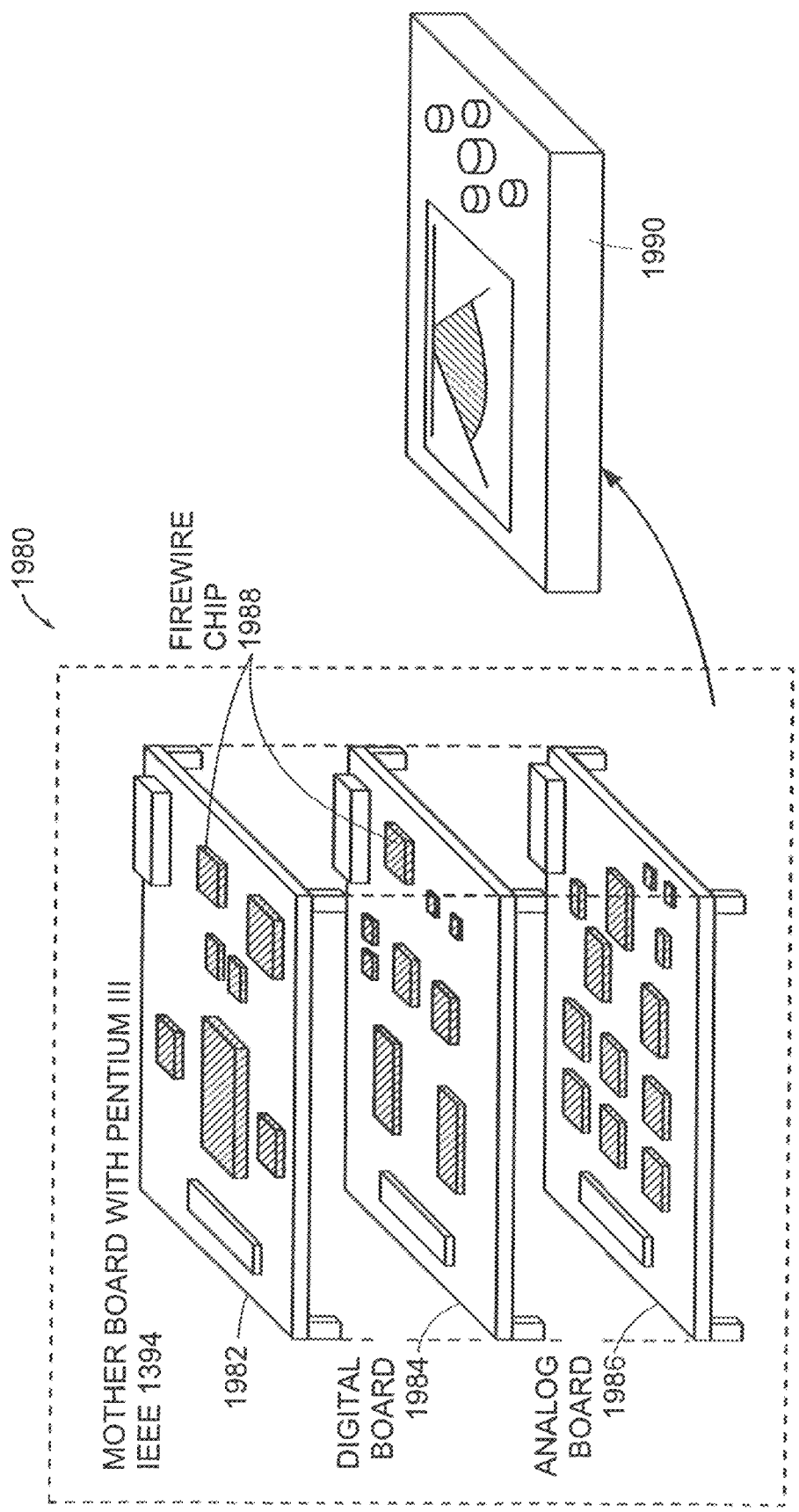
FIG. 52 illustrates the single board computer and beamformer circuits that form the processing unit in accordance with a preferred embodiment of the present invention.
Figure 53B:
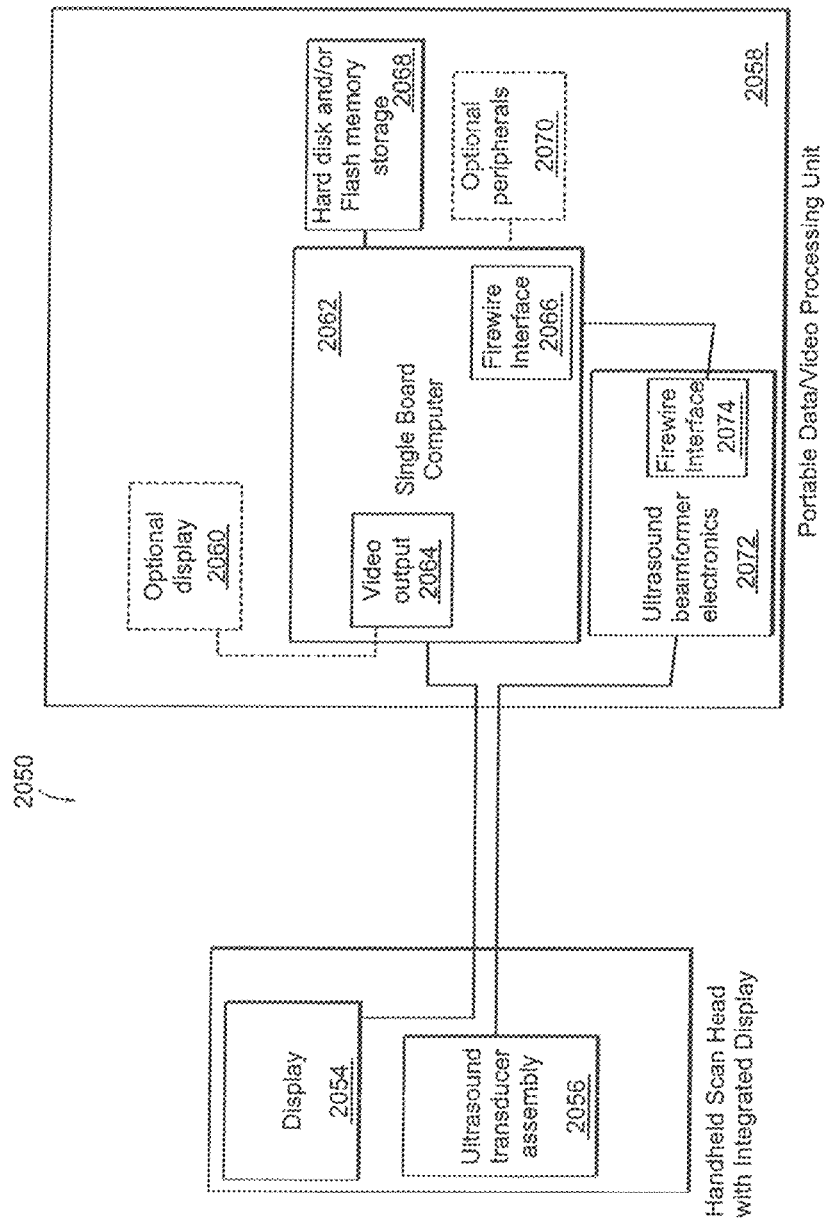

In another preferred embodiment of the system 2050, the beamformer electronics 2072 is moved inside the processing unit 2058 to further reduce the size and weight of the hand-held scan head as illustrated in FIG. 53B. Processing unit 2058 can include optional display 2060, single board computer 2062, video output 2064, Firewire interface 2066, hard disk and/or flash memory storage 2068, optional peripherals 2070, and ultrasound beamformer electronics 2072. The ultrasound beamformer electronics 2072 can include Firewire interface 2074. The processing unit 1980 in this configuration comprises of a compact single board 1982 computer and the beamformer electronics in a housing 1990 as illustrated in FIG. 52. The beamformer electronics includes a digital processing printed circuit board 1984 and an analog processing printed circuit board 1986. The beamforming electronics communicates with the single board computer via a Firewire (IEEE 1394) interface 1988, 2074, 2066.

In an embodiment, the compact single board computer has a printed circuit board size of a 5¼ inch disk drive or a 3½ inch disk drive. One embodiment of the present invention uses a NOVA-7800-P800 single board computer in a 5¼ inch form factor, with a low power Mobile Pentium-III 800 MHz processor, 512 Mbytes of memory, and has on board interface ports for Firewire (IEEE 1394), LAN, Audio, IDE, PCMCIA and Flash memories.

For some dedicated applications, the entire system includes the hand-held scan head with an integrated display and the portable data/video processing unit, can be operated without any controls other than power on/off. For other applications, the system is equipped with an optional operator interface such as buttons and knobs, either on the processing unit, or integrated in the scan head, or both. The processing unit provides an additional video output to drive an external monitor, or optionally an integrated display on the processing unit itself.

When an external monitor is attached to the processing unit, and/or an integrated monitor is available on the processing unit, the hand-held scan head display may be used in a View-Finder mode wherein the operator uses the smaller hand-held display to locate the region of interest, and uses the larger monitor to observe more detailed images either in real time, or capture-then-review manner.

There are different methods to realize trapezoidal scan format using Linear Arrays. A first method is to perform conventional rectangular linear scanning over the center of the array and scan a portionof a sector field at each end of the array. A second approach is to activate groups of elements of the transducer successively such that the transmitted beams form a sector scan field having the origin point located behind the transducer array.

Figure 54:
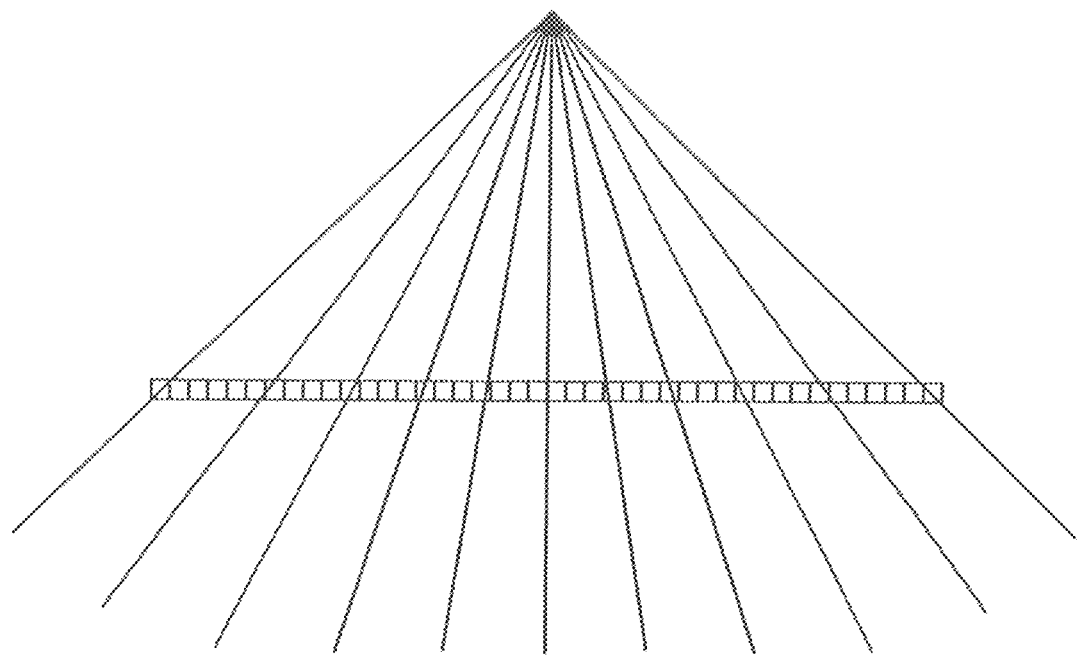
FIG. 54 illustrates a trapezoidal scan format using a uniform angular increment with non-uniform tangential increment.
Figure 55:
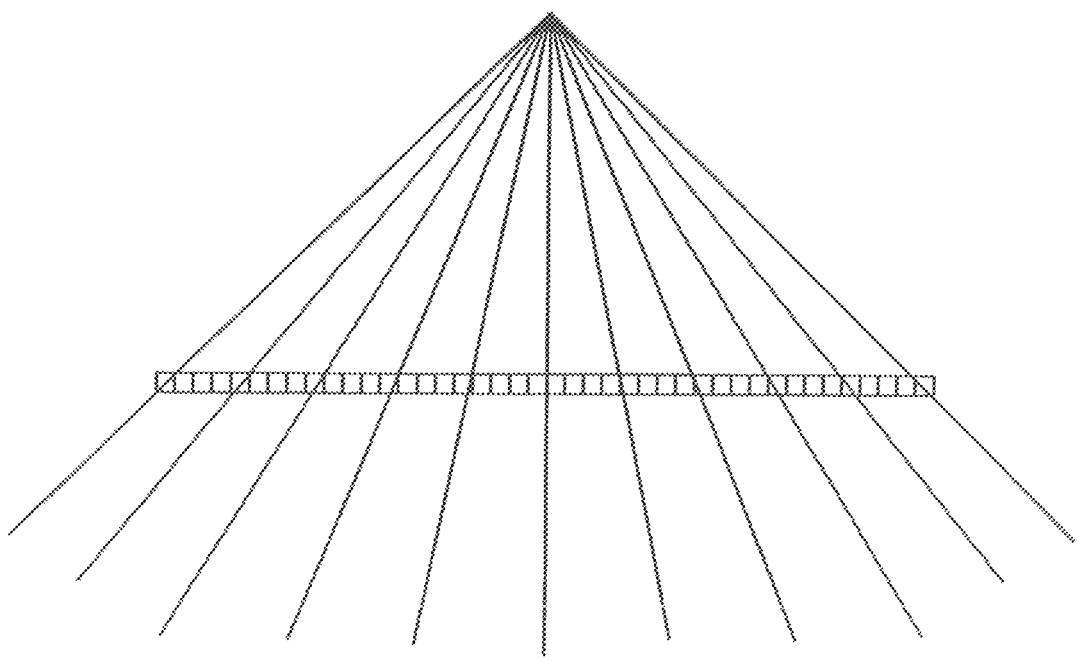
FIG. 55 illustrates a trapezoidal scan format using uniform tangential increment with non-uniform angle increment.

The second approach has only one coordinate system, thus it simplifies the scan conversion. It also creates a more uniform image over the whole field of view. However, because all the beams originate from one point, it is difficult to have both steering angle and scan-position (tangential) increments be uniform as illustrated in FIGS. 54 and 55, respectively. The uniform angular increment approach has higher scan line density in the center of the array than on the side, so the images on the side are more degraded. The scan line density of the constant tangential increment approach is uniform, but almost every line has larger steering angle than the uniform angular increment, which degrades the image quality especially in the near field.

Figure 56:
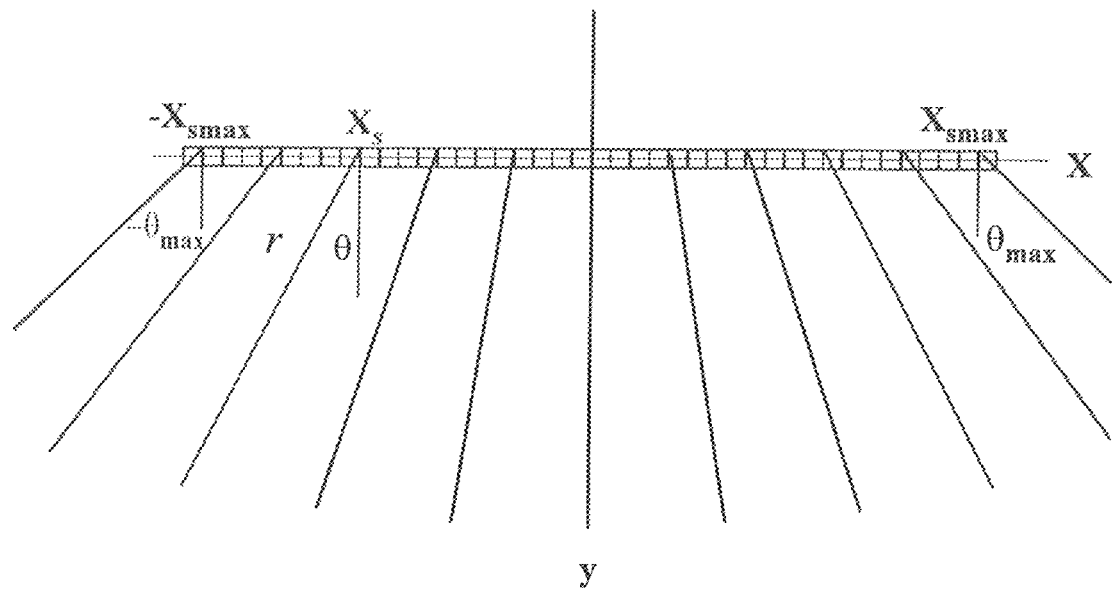
FIG. 56 schematically describes preferred embodiments for generating trapezoids scan formats in accordance with the present invention.

A preferred embodiment creates trapezoidal image scans using an extension of the two methods. The steered angle of each scan line is determined by a monotonic function of the scan position as illustrated in FIG. 56, or vice versa, which can be written as $\theta=f(x_s)$ or $x_s=g(\theta)$. By choosing different functions $f(x_s)$ or $g(\theta)$, one can get different scan patterns. Three different approaches include the following:

1. Even scan line space and uniform steered angle increment.

If one defines the function $\theta=f(x_s)=\lambda x_s$ and has the scan line position be evenly spaced in the face of the transducer, one can have both even scan line space uniform steered angle increment. The scan conversion between the two coordinate systems, i.e. scan coordinate system $(x_s, r)$ or $(\theta, r)$, and display screen coordinate system $(x,y)$ is given as follows:

1.1 Scan position $x_s$ and radius r to raster image coordinate $(x,y)$ $$x=x_s+r\sin(\lambda x_s)$$

$$y=r\cos(\lambda x_s)$$

1.2 raster image coordinate $(x,y)$ to scan position $x_s$ and radius r

The $x_s$ can be calculated by solving the following equation $$y\tan(\lambda x_s)+x_s-x=0$$

after $x_s$ has been calculated, $$r=\frac{r}{\cos(\lambda x_s)}$$

This method involves a solution using a numerical method, and is computationally expensive. Two alterative ways are as follows:

2. Even scan line space with adjustable steering angle.

The scan lines are even space located at the front face of the tranducer. The steered angle is defined as $$\theta=\arctan\left(\frac{x_s}{\beta-\alpha|x_s|}\right)$$

where $$\beta=\frac{x_{smax}}{\tan\theta_{max}}+\alpha x_{max}$$

By adjusting a parameter, $\alpha$, one can control the steering angle of each scan line. The scan conversion between the two coordinate systems, i.e. scan coordinate system $(x_s, r)$, and display screen coordinate system $(x,y)$ is given as follows:

2.1 Scan position $x_s$ and radius r to raster image coordinate $(x,y)$ $$x=x_s+r\sin\left(\arctan\left(\frac{x_s}{\beta-\alpha|x_s|}\right)\right)$$

$$y=r\cos\left(\arctan\left(\frac{x_s}{\beta-\alpha|x_s|}\right)\right)$$

2.2 raster image coordinate $(x,y)$ to scan position $x_s$ and radius r $$x_s=\frac{2xb}{y+b+\alpha|x|+\sqrt{(y+b+\alpha|x|)^2-4\alpha b|x|}}$$

$$r=\sqrt{x^2+(y+b-\alpha|x_s|)^2}-\sqrt{l^2+(b-\alpha|x_s|)^2}$$

Figure 57:
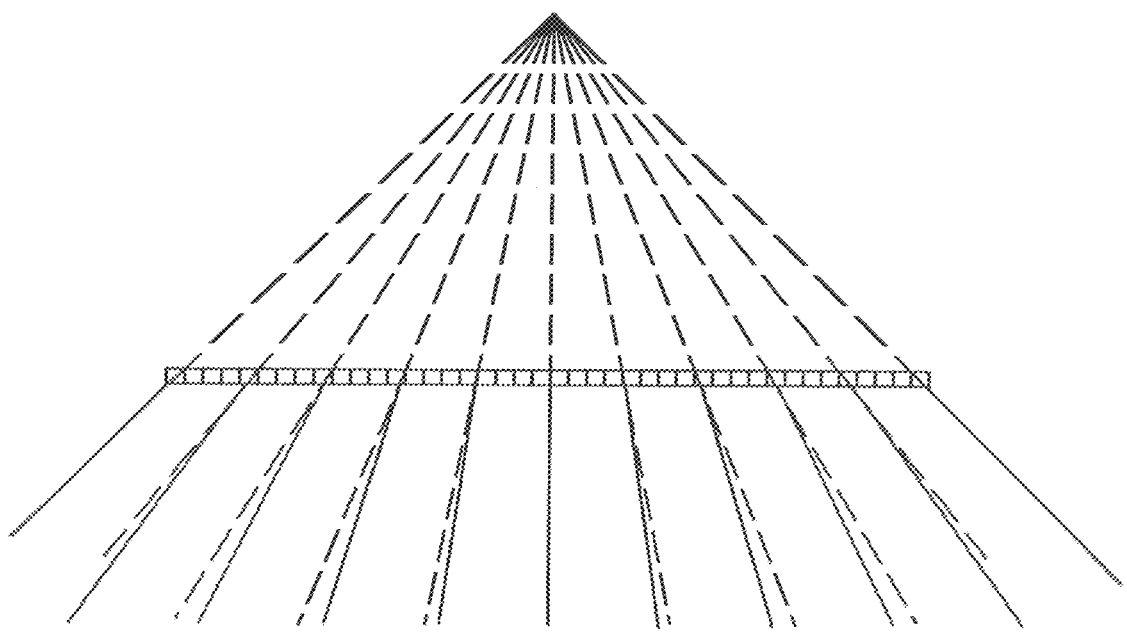
FIG. 57 illustrates the steering angle comparison wherein the solid line equals even scan line space with adjustable steering angle ($\alpha$–0.5), dashed line equals uniform tangential increment.
Figure 58:
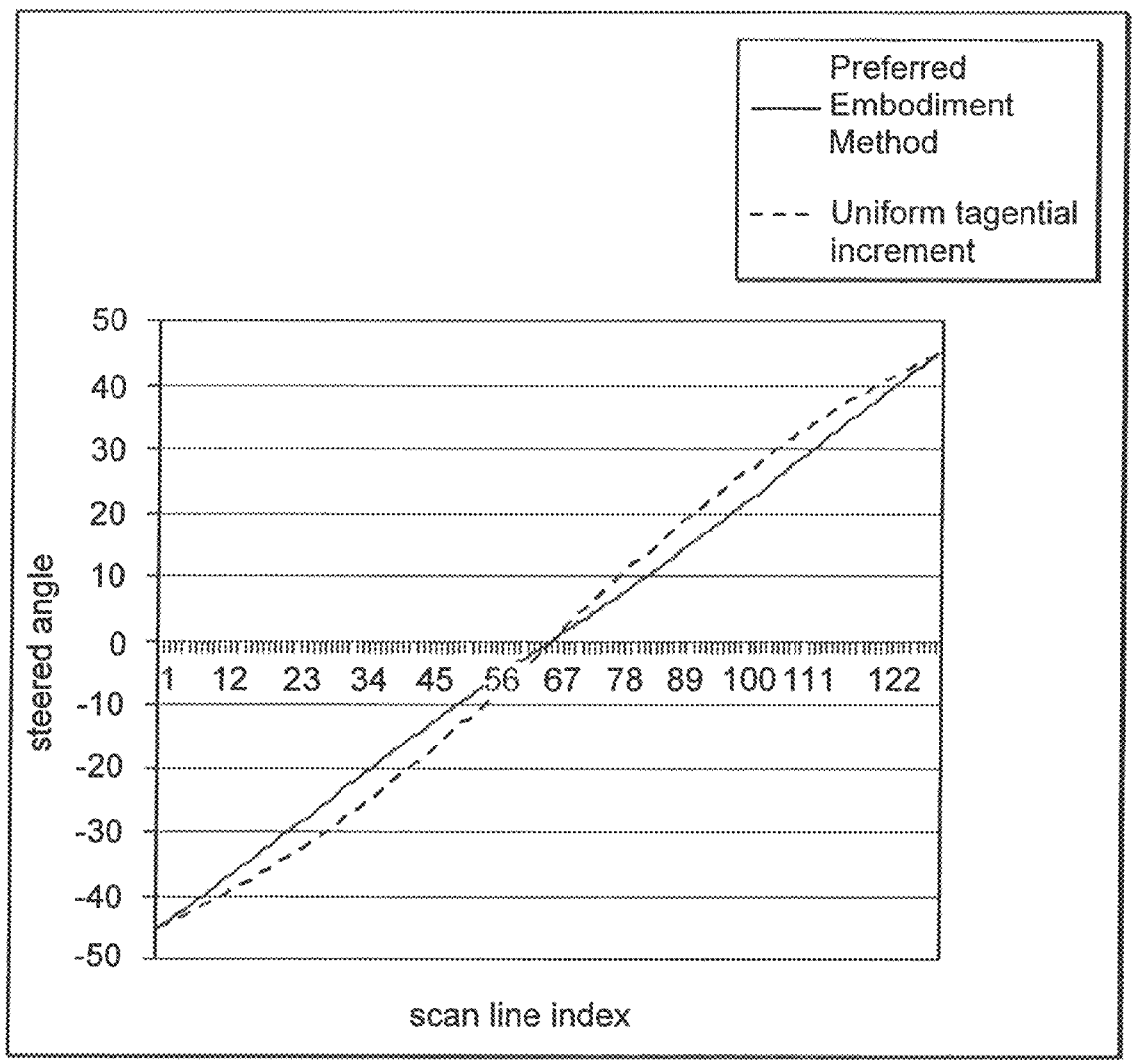
FIG. 58 illustrates the steering angle as a function of scan line for the uniform scan line position approach.

FIG. 57 shows a comparison of the steering angle using the method of the preferred embodiment and the uniform tangential increment approach. Note that at every beam position, the steering angle using the preferred embodiment approach is smaller than the uniform tangential approach (better near field). FIG. 58 shows more clearly that the preferred embodiment approach can have uniform tangential increment and also nearly uniform steering angle increments.

3. Uniform steering angle increment with adjustable scan position.

The third method to increment the steering angle uniformly, and adjust each scan line position by the following function:

$$x_s = (\beta - \alpha|\tan\theta|)\tan\theta$$

where $$\beta = \frac{x_{smax}}{\tan\theta_{max}} + \alpha\tan\theta_{max}$$

3.1 Scan angle $\theta$ and radius r to raster image coordinate (x,y).

$$x = \left(r + \frac{\beta - \alpha|\tan\theta|}{\cos\theta}\right)\sin\theta$$

$$y = r\cos\theta$$

3.2 Raster image coordinate (x,y) to scan angle $\theta$ and radius r.

$$\theta = \arctan\left(\frac{2x}{y + \beta + \sqrt{(y+\beta)^2 - 4\alpha|x|}}\right)$$

$$r = \frac{y}{\cos\theta}$$

The claims should not be read as limited to the described order or elements unless stated to that effect. Therefore, all embodiments that come within the scope and spirit of the following claims and equivalents thereto are claimed as the invention.

While this invention has been particularly shown as described with references to preferred embodiments thereof it will be understood by those skilled in the art that various changes in form and details may be made therein without departing from the scope of the invention.

What is claimed is:

1. A method for ultrasonic imaging of an invasive medical probe procedure, the invasive medical probe being inserted into a body, the method comprising:
    positioning an ultrasound transducer probe relative to a body, the ultrasound transducer probe being connected to a battery powered, handheld, portable ultrasound imaging device including a data processor, a beamforming device, and a touchscreen display with a graphical user interface for unitary operator control, and a segmented shared memory wherein the battery powered handheld ultrasound imaging device is configured to perform Doppler processing;
    inserting an invasive medical probe into the body;
    performing an ultrasound imaging operation with the battery powered, handheld, portable ultrasound imaging device in response to imaging parameters received from an external application using an external networked server that is connectable to the segmented shared memory, the ultrasound imaging operation generating an ultrasound image of a portion of the body using the ultrasound transducer probe during insertion of the invasive medical probe into the body; and
    guiding the insertion of the invasive medical probe into the body using one or more images generated by the ultrasound imaging operation and displayed on the touchscreen display wherein the one or more images are communicated to the segmented shared memory and transmitted to the external networked server during the ultrasound imaging operation.

2. The method of claim 1, further comprising confirming placement of the invasive medical probe in the body based on the imaging operation.

3. The method of claim 1, further comprising displaying, on the display, an image of the invasive medical probe during the insertion of the invasive medical probe into the body.

4. The method of claim 1, further comprising receiving, from the external application, a request for at least one ultrasound operation; and
    executing, in an ultrasound application server operating on the battery powered handheld ultrasound imaging device, a result corresponding to the request.

5. The method of claim 4, wherein the request comprises an instruction and at least one parameter.

6. The method of claim 4, wherein the request conforms to a communication interface.

7. The method of claim 4, wherein the request includes an operation selected from the group consisting of freeze live data, fetch live data, export image, exit, initialize, and get status.

8. The method of claim 1, wherein the performing step comprises transmitting data using an integrated interface program.

9. The method of claim 8, wherein the performing step comprises transmitting data using the integrated interface program with a standard communication protocol.

10. The method of claim 9, wherein the protocol is a transmission control protocol.

11. The method of claim 1, wherein the ultrasound imaging operation comprises generating one or more image frames, each image frame including an ultrasound image, identification information corresponding to the ultrasound probe, pixel spatial information and temporal information.

12. The method of claim 8, wherein the integrated interface program includes a plurality of entry points into an ultrasound application server operating on the battery powered handheld ultrasound imaging device, the entry points operable to access each of at least one ultrasound operation included in the ultrasound application server.

13. The method of claim 1, wherein ultrasound image data is transmitted in real-time during the insertion of the invasive medical probe into the body.

14. The method of claim 8, wherein the integrated interface program provides a streaming video interface for transmitting the ultrasound image data in real time.

15. The method of claim 8, wherein the integrated interface program provides a segmented shared memory interface between the ultrasound imaging application and the external application.

16. The method of claim 1, wherein an ultrasound application and the external application are configured to run on an operating system.

17. The method of claim 8, further comprising controlling a rate at which the ultrasound image data is transferred across the integrated interface program with the external application.

18. The method of claim 17, wherein controlling the rate of transfer of the ultrasound image data comprises controlling a number of image buffers and/or a size of one or more image buffers used for buffering the ultrasound image data during transmission with the external application.

19. The method of claim 17, wherein the rate of transfer of the ultrasound image data is controlled to minimize latency so that the ultrasound image data is transferred from a non-ultrasound application in the order in which the data is generated with the ultrasound imaging application.

20. The method of claim 17, wherein the rate of transfer of the ultrasound image data is controlled to eliminate data loss.

21. The method of claim 1, wherein an ultrasound image comprises spatial and temporal information.

22. The method of claim 1, wherein an ultrasound application and the external application are run on a networked computer connected to the external networked server.

23. The method of claim 1, wherein an ultrasound application is run on the processor of the handheld ultrasound imaging device and the external application is run on a networked computer connected to the external networked server.

24. The method of claim 8, wherein the integrated interface program is adapted to transmit information pertinent to data selected from the group consisting of radiation therapy, fetal images, cardiac images, and image-guided surgery.

25. The method of claim 8, further comprising transmitting ultrasound image data generated by the imaging via the integrated interface program from the ultrasound application server to a second external application.

26. The method of claim 25, wherein the external application and the second external application access the integrated interface program using a standard predetermined platform.

27. The method of claim 1 further comprising adjusting a brightness level of an imaged feature.

28. The method of claim 1 further comprising adjusting a pulse transmission frequency of the ultrasound probe.

29. The method of claim 1 wherein the step of inserting the invasive medical probe comprises inserting a catheter into the body.

30. The method of claim 1 wherein the step of inserting the invasive medical probe comprises inserting a biopsy device.

31. The method of claim 1 wherein the step of inserting the invasive medical probe comprises inserting a forceps.

32. The method of claim 1 wherein the ultrasound transducer probe and the battery powered handheld ultrasound imaging device weighs less than 10 pounds.

33. The method of claim 1 further comprising connecting the ultrasound transducer probe to the handheld ultrasound imaging device with a cable.

34. The method of claim 1 further comprising imaging an angiography procedure.

35. The method of claim 1 wherein the imaging operation comprises an ultrasound imaging guided surgical procedure.

36. The method of claim 1 further comprising performing a cryotherapy procedure.

37. The method of claim 1 further comprising transmitting an image frame header having probe information.

38. The method of claim 1 further comprising receiving data from an external networked computer device.

39. A system for ultrasonic imaging of an invasive medical probe procedure comprising:
  an ultrasound transducer probe having a transducer array;
  a battery powered, handheld, portable ultrasound imaging device including a data processor, a shared memory and a touchscreen display with a graphical user interface for unitary operator control of an ultrasound imaging operation, the battery powered, handheld, portable ultrasound imaging device performing Doppler processing and being in operable communication with the ultrasound transducer probe;
  a beamforming device that receives signals from the transducer array, the beamforming device being connected to a controller that controls ultrasonic imaging to generate ultrasound images that are communicated to the shared memory; and
  a networked computer connected to an external server wherein the networked computer transmits image parameters for imaging of a medical procedure using an invasive medical probe to be inserted into a body, the image parameters being delivered to the battery powered handheld ultrasound device that performs an imaging procedure to generate the ultrasound images of the body and the invasive medical probe on the touchscreen display and wherein the ultrasound images stored in the shared memory are transmitted to the networked computer during the imaging procedure.

40. The system of claim 39 wherein the invasive medical probe comprises a catheter.

41. The system of claim 39 wherein the touchscreen display comprises a liquid crystal touchscreen display.

42. The system of claim 39 wherein the ultrasound transducer probe is connected to the ultrasound imaging device with a cable, the ultrasound transducer probe including the beamforming device and the controller.

43. The system of claim 39 wherein the battery powered, handheld, portable ultrasound imaging device includes the beamforming device and the controller.

44. The system of claim 39 wherein each of the ultrasound images comprises an image frame including a header that includes a probe type and a frame rate.

* * * * *